(12) United States Patent
Wang et al.

(10) Patent No.: US 12,227,811 B2
(45) Date of Patent: Feb. 18, 2025

(54) PRIMER GROUP FOR SIMULTANEOUS DETECTION OF 15 PORCINE PATHOGENS THROUGH HIGH-THROUGHPUT TARGETED AMPLICON SEQUENCING AND USE THEREOF

(71) Applicant: China Agricultural University, Beijing (CN)

(72) Inventors: Shaolin Wang, Beijing (CN); Yang Zuo, Beijing (CN); Zhangqi Shen, Beijing (CN); Lei Zhou, Beijing (CN); Jun Han, Beijing (CN); Jianzhong Shen, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 18/509,322

(22) Filed: Nov. 15, 2023

(65) Prior Publication Data
US 2024/0167106 A1 May 23, 2024

(30) Foreign Application Priority Data

Nov. 18, 2022 (CN) .......................... 202211450766.0

(51) Int. Cl.
| | | |
|---|---|---|
| *C12Q 1/68* | (2018.01) | |
| *C12Q 1/6874* | (2018.01) | |
| *C12Q 1/6888* | (2018.01) | |
| *C12Q 1/70* | (2006.01) | |
| *C12Q 1/6844* | (2018.01) | |

(52) U.S. Cl.
CPC ........... *C12Q 1/701* (2013.01); *C12Q 1/6874* (2013.01); *C12Q 1/6888* (2013.01); *C12Q 1/6844* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2012/0107355 | A1* | 5/2012 | Harris | C12N 15/86 |
| | | | | 435/235.1 |
| 2013/0064839 | A1* | 3/2013 | Harris | C12N 7/00 |
| | | | | 435/6.12 |
| 2023/0119678 | A1* | 4/2023 | Inoue | C12Q 1/701 |
| | | | | 435/6.12 |

FOREIGN PATENT DOCUMENTS

| | | |
|---|---|---|
| CN | 108220479 A | 6/2018 |
| CN | 112831604 A | 5/2021 |

(Continued)

OTHER PUBLICATIONS

Fan Qing, et al., Development of a GeXP Assay for Simultaneous Differentiation of 8 Pathogens of Bovine Infectious Diseases, Acta Veterinaria at Zootechnica Sinica, 2017, pp. 1920-1931, vol. 48 No. 10.

(Continued)

*Primary Examiner* — Aaron A Priest
(74) *Attorney, Agent, or Firm* — Bayramoglu Law Offices LLC

(57) ABSTRACT

A primer group for simultaneous detection of 15 porcine pathogens through high-throughput targeted amplicon sequencing and use thereof are provided. The primer group for simultaneous detection of 15 porcine pathogens through high-throughput targeted amplicon sequencing includes: primers having nucleotide sequences set forth in SEQ ID NO: 1 to SEQ ID NO: 302. The nucleotide sequences of pathogenic target genes are set forth in SEQ ID NO: 303 to SEQ ID NO: 344. The primer group of the present invention is used for amplicon sequencing detection analysis method for 42 target genes of 15 porcine respiratory pathogens, has the technical advantages of rapidness, high efficiency, high targeting, strong specificity, and the like, and is suitable for (Continued)

| Host & Transmission | Types | Targeted genes | Pathogens |
|---|---|---|---|
| | | 8 | African swine fever virus ASFV |
| | | 2 | porcine respiratory and reproductive syndrome virus PRRSV(NA/EU) |
| | | 2 | pseudorabies virus PRV |
| | | 2 | porcine circovirus PCV (2/3) |
| | | 2 | classical swine fever virus CSFV |
| | | 2 | foot and mouth disease virus FMDV |
| | | 3 | swine influenza A virus swIAV |
| | | 2 | Haemophilus parasuis HPS |
| | | 2 | Pasteurella multoctica Pm |
| | | 2 | Actinobacillus pleuropneumoniae APP |
| | | 2 | Streptococcus suis S.suis |
| | | 2 | Eperythrozoon suis E.suis |
| | | 2 | Toxoplasma gondii T.gondii |
| | | 2 | Mycoplasma hyorhinis Mhr |
| | | 2 | Mycoplasma hyopneumonia Mhp | rapid and accurate simultaneous diagnosis of multiple pathogens of diseased pigs in pig farms.

5 Claims, 5 Drawing Sheets

Specification includes a Sequence Listing.

(56) References Cited

FOREIGN PATENT DOCUMENTS

| | | | | |
|---|---|---|---|---|
| CN | 112852937 A | 5/2021 | | |
| CN | 112852938 A | 5/2021 | | |
| WO | WO-2005049851 A2 * | 6/2005 | ............ | G06F 19/20 |
| WO | WO-2020073810 A1 * | 4/2020 | ............ | C12Q 1/686 |

OTHER PUBLICATIONS

Yiming Li, et al., Multiplexed Target Enrichment Enables Efficient and In-Depth Analysis of Antimicrobial Resistome in Metagenomes, Microbiology Spectrum, 2022, vol. 10, Issue 6.

Dinah Henritzi, et al., Rapid detection and subtyping of European swine influenza viruses in porcine clinical samples by haemagglutinin- and neuraminidase-specific tetra-and triplex real-time RT-PCRs, Influenza and Other Respiratory Viruses, 2016, pp. 504-517, vol. 10.

* cited by examiner

| Host & Transmission | Types | Targeted genes | Pathogens |
|---|---|---|---|
| | | 8 | African swine fever virus ASFV |
| | | 2 | porcine respiratory and reproductive syndrome virus PRRSV(NA/EU) |
| | | 2 | pseudorabies virus PRV |
| | | 2 | porcine circovirus PCV (2/3) |
| | | 2 | classical swine fever virus CSFV |
| | | 2 | foot and mouth disease virus FMDV |
| | | 3 | swine influenza A virus swIAV |
| | | 2 | Haemophilus parasuis HPS |
| | | 2 | Pasteurella multoctica Pm |
| | | 2 | Actinobacillus pleuropneumoniae APP |
| | | 2 | Streptococcus suis S.suis |
| | | 2 | Eperythrozoon suis E.suis |
| | | 2 | Toxoplasma gondii T.gondii |
| | | 2 | Mycoplasma hyorhinis Mhr |
| | | 2 | Mycoplasma hyopneumonia Mhp |

FIG. 3

PRIMER GROUP FOR SIMULTANEOUS DETECTION OF 15 PORCINE PATHOGENS THROUGH HIGH-THROUGHPUT TARGETED AMPLICON SEQUENCING AND USE THEREOF

CROSS REFERENCE TO THE RELATED APPLICATIONS

This application is based upon and claims priority to Chinese Patent Application No. 202211450766.0, filed on Nov. 18, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBRZBC153_Sequence Listing.xml, created on Oct. 26, 2023, and is 379,175 bytes in size.

TECHNICAL FIELD

The present invention relates to the technical field of high throughput of target gene detection, and in particular, to a primer group for simultaneous detection of 15 porcine pathogens through high-throughput targeted amplicon sequencing and use thereof.

BACKGROUND

Amplicon sequencing is a high-targeting method, and the general idea is to target-capture a target region, then perform next generation sequencing (NGS) and analyze a sequencing result by designing primers near the conserved region of a target gene, performing PCR amplification and further performing sequencing analysis on an amplification product, thereby obtaining corresponding information.

Amplicon sequencing mainly comprises 16S rDNA sequencing, 18S rDNA sequencing, ITS sequencing, target region amplicon sequencing, and the like. At present, the amplicon sequencing is mainly applied to analysis of a metagenomics sample, and a sequence of a specific hypervariable region of 16S/18S/ITS determined by a second-generation high-throughput sequencing platform is used to reflect the differences between species of environmental samples in the classification of bacteria, fungi, and archaea, so that the microbial composition in the environments such as ocean, soil, and intestinal excrement is studied. In addition, few studies apply amplicon sequencing to pathogen detection, however, there is no related design for detecting porcine respiratory pathogens at present.

The respiratory diseases of pigs are mainly caused by single or mixed infection of viruses, bacteria and other pathogens, and the diagnosis methods of the pathogens generally comprise nucleic acid detection, antigen detection, and the like. Generally, most of detection means are single aiming at a certain pathogen, and the simultaneous rapid and accurate diagnosis of a plurality of pathogens cannot be implemented. In addition, at present, the most extensive fluorescent quantitative detection means for detecting the epidemic diseases in the pig farms can only detect 3 to 5 pathogens at most, however, the fluorescent quantitative detection means is only a simple diagnosis of pathogenic genes, and cannot further detect pathogenic gene mutations on the basis of disease diagnosis so as to discover a new mutant pathogen.

SUMMARY

An objective of the present invention is to provide a primer group for simultaneous detection of 15 porcine pathogens through high-throughput targeted amplicon sequencing, which is used for amplicon sequencing detection analysis method for 42 target genes of 15 porcine respiratory pathogens, has the technical advantages of rapidness, high efficiency, high targeting, strong specificity, and the like, and is suitable for rapid and accurate simultaneous diagnosis of multiple pathogens of diseased pigs in pig farms.

In order to achieve the above objective, the present invention provides the following technical solution.

The present invention provides a primer group for simultaneous detection of 15 porcine pathogens through high-throughput targeted amplicon sequencing, which comprises primers having nucleotide sequences set forth in SEQ ID NO: 1 to SEQ ID NO: 302, the primer group is used to amplify pathogenic target genes, the pathogenic target genes are as follows:

| Pathogen name | Target gene | Sequence No. |
| --- | --- | --- |
| African swine fever virus | ASFV-p72 | SEQ ID NO: 303 |
| | ASFV-p54 | SEQ ID NO: 304 |
| | ASFV-EP402R | SEQ ID NO: 305 |
| | ASFV-MGF505-1R | SEQ ID NO: 306 |
| | ASFV-MGF505-2R | SEQ ID NO: 307 |
| | ASFV-MGF360-13L | SEQ ID NO: 308 |
| | ASFV-MGF360-14L | SEQ ID NO: 309 |
| | ASFV-K205R | SEQ ID NO: 310 |
| Porcine reproductive and respiratory syndrome virus | PRRSV-NA-orf6/M | SEQ ID NO: 311 |
| | PRRSV-NA-orf7/N | SEQ ID NO: 312 |
| | PRRSV-EU-orf6/M | SEQ ID NO: 313 |
| | PRRSV-EU-orf7/N | SEQ ID NO: 314 |
| Pseudorabies virus | PRV-gE | SEQ ID NO: 315 |
| | PRV-gB | SEQ ID NO: 316 |
| Porcine circovirus | PCV2-cap | SEQ ID NO: 317 |
| | PCV2-rep | SEQ ID NO: 318 |
| | PCV3-cap | SEQ ID NO: 319 |
| | PCV3-rep | SEQ ID NO: 320 |
| Classical swine fever virus | CSFV-5'UTR | SEQ ID NO: 321 |
| | CSFV-E2 | SEQ ID NO: 322 |
| Foot and mouth diseases virus | FMDV-3D-1C2B(polyprotein) | SEQ ID NO: 323 |
| | FMDV-5'UTR | SEQ ID NO: 324 |
| Swine influenza A virus | swIAV-M | SEQ ID NO: 325 |
| | swIAV-H1 | SEQ ID NO: 326 |
| | swIAV-H3 | SEQ ID NO: 327 |
| Haemophilus parasuis | HPS-vtaA | SEQ ID NO: 328 |
| | HPS-infB | SEQ ID NO: 329 |
| Pasteurella multocida | Pm-plpE | SEQ ID NO: 330 |
| | Pm-kmt1 | SEQ ID NO: 331 |
| Actinobacillus pleuropneumoniae | APP-omlA | SEQ ID NO: 332 |
| | APP-apxIVA | SEQ ID NO: 333 |
| Streptococcus suis | S.suis-gdh | SEQ ID NO: 334 |
| | S.suis-recN | SEQ ID NO: 335 |
| | S.suis-gapdh | SEQ ID NO: 336 |
| Eperythrozoon suis | E.suis-ppa | SEQ ID NO: 337 |
| | E.suis-g1 | SEQ ID NO: 338 |
| Toxoplasma gondii | T.gondii-B1 | SEQ ID NO: 339 |
| | T.gondii-RE | SEQ ID NO: 340 |
| Mycoplasma hyorhinis | Mhr-p37 | SEQ ID NO: 341 |
| | Mhr-16SrRNA | SEQ ID NO: 342 |
| Mycoplasma hyopneumoniae | Mhp-p36 | SEQ ID NO: 343 |
| | Mhp-p102 | SEQ ID NO: 344; | nucleotide sequences of the pathogenic target genes are set forth in SEQ ID NO: 303 to SEQ ID NO: 344;

SEQ ID NO: 303:
atggcatcaggaggagcttttttgtcttattgctaacgatgggaaggccgacaagattatattggcccaagacttgctgaatagcaggatct ctaacattaaaaatgtgaacaaaagttatgggaaacccgatcccgaacccactttgagtcaaatcgaagaaacacatttggtgcatttttaa tgcgcattttaagccttatgttccagtagggtttgaatacaataaagtacgcccgcatacgggtaccccccaccttgggaaacaagcttacc tttggtattccccagtacggagactttttccatgatatggtgggccatcatatattgggtgcatgtcattcatcctggcaggatgctccgattc agggcacgtcccagatgggggcccatgggcagcttcaaacgtttcctcgcaacggatatgactgggacaaccaaacacccttagagg gcgccgtttacacgcttgtagatccttttggaagaccccattgtacccggcacaaagaatgcgtaccgaaacttggtttactactgcgaata ccccggagaacgactttatgaaaacgtaagattcgatgtaaatggaaattccctagacgaatatagttcggatgtcacaacgcttgtgcg caaattttgcatcccaggggataaaatgactggatataagcacttggttggccaggaggtatcggtggagggaaccagtggccctctcc tatgcaacattcatgatttgcacaagccgcaccaaagcaaacctattcttaccgatgaaaatgatacgcagcgaacgtgtagccatacca acccgaaatttcttcacagcattttcccgagaactctcacaatatccaaacagcaggtaaacaagatattactcctatcacggacgcaac gtatctggacataagacgtaatgttcattacagctgtaatggacctcaaacccctaaatactatcagcccctcttgcgctctggattaagtt gcgcttttggtttaatgagaacgtgaaccttgctattccctcagtatccattcccttcggcgagcgctttatccacataaagcttgcatcgca aaaggatttggtgaatgaatttcctggactttttgtacgccagtcacgttttatagctggacgccccagtagacgcaatatacgctttaaacc atggtttatcccaggagtcattaatgaaatctcgctcacgaataatgaactttacatcaataacctgtttgtaaccccctgaaatacacaaccctt tttgtaaaacgcgttcgcttttcgctgatacgtgtccataaaacgcaggtgacccacaccaacaataaccaccacgatgaaaaactaatgt ctgctcttaaatggcccattgaatatatgtttataggattaaaacctacctggaacatctccgatcaaaatcctcatcaacaccgagattggc acaagttcggacatgttgttaacgccattatgcagcccactcaccacgcagagataagctttcaggatagagatacagctcttccagacg catgttcatctatatctgatattagcccgttacgtatccgatcacattaccattattaaaaacatttccgtaactgctcatggtatcaatcttat cgataaatttccatcaaagttctgcagctcttacataccttccactacggaggcaatgcgattaaaaccccgatgatccgggtgcgatg atgattacctttgctttgaagccacgggaggaataccaacccagtggtcatattaacgtatccgagcaagagaattttatattagttggga cacggattacgtggggtctatcactacggctgatcttgtggtatcggcatctgctattaactttcttcttcttcagaacggttcagctgtgctg cgttacagtacctaa;

SEQ ID NO: 304:
atggattctgaattttttcaaccggtttatccgcggcattatggtgagtgtttgtcaccagtcactacaccaagcttcttctccacacatatgta tactattctcattgctatcgtggtcttagtcatcattatcatcgttctaatctatctattctcttcaagaaagaaaaaagctgctgctattgagga ggaagatatacagtttataaatccttatcaagatcagcagtgggtagaagtcactccacaaccaggtacctctaaaccagctggagcga ctacagcaagtgtaggcaagccagtcacgggcagaccggcaacaaacagaccagcaacaaacaaaccagttacggacaacccagt tacggacagactagtcatggcaactggcgggccggcggccgcacctgcggccgcgagtgctcctgctcatccggctgagccttaca cgacagtcactactcagaacactgcttcacaaacaatgtcggctattgaaaatttacgacaaagaaacacctatacgcataaagacctag aaaactccttgtaa;

SEQ ID NO: 305:
atgataatacttattttttttaatattttctaacatagtttttaagtattgattattgggttagttttaataaaacaataatttttagatagtaatatta ctaatgataataatgatataaatggagtatcatggaattttttaataattcttttaatacactagctacatgtggaaaagcaggtaacttttgtg aatgttctaattatagtacatcaatatataatataacaaataattgtagcttaactattttttcctcataatgatgtatttgatacaacatatcaagt agtatggaatcaaataattaattatacaataaaaattattaacacctgctactcccccaaatatcacatataattgtactaatttttttaataacatgt aaaaaaaataatggaacaaacactaatatatatttaaatataaatgatacttttgttaaatatactaatgaaagtatacttgaatataactggaata atagtaacattaacaattttacagctacatgtataattaataatacaattagtacatctaatgaaacaacacttataaattgtacttatttaacatt gtcatctaactattttatacttttttttaaattatattatattccattaagcatcataattgggataacaataagtattcttcttatatccatcata acttttttatctttacgaaaaagaaaaaaacatgttgaagaaatagaaagtccaccacctgaatctaatgaagaagaacaatgtcagcatgatgaca ccacttccatacatgaaccatctcccagagaaccattacttcctaagccttacagtcgttatcagtataatacacctatttactacatgcgtcc ctcaacacaaccactcaacccatttcccttacctaaaccgtgtcctccacccaaaccatgtccgccacccaaaccatgtcctccacctaa -continued accatgtccttcagctgaatcctattctccacccaaaccactacctagtatcccgctactacccaatatcccgccattatctacccaaaatat ttcgcttattcacgtagatagaattatttaa;

SEQ ID NO: 306:
atgttctctctccagaacttatgtcgaaaaacattacctaaccgtaaacttcctgaattttttgacgaatatatattacaactgctgggattata ctgggaaaaccatggaactattcaacgagcaggaaacaactgtgtgcttatacagcaacatacctcattcccgtaaatgaagccctga gaacagcagcatctgaagaaaattatgagatcgtgagccttttattagcgtgggaggggaacctttactatgctattatagggctctaga gggcaaccgccacgacttaattcgtaaatatgatgaccaaatcaaggaccatcatgaattctgccattcattgacgatccagtcatatttc acaaatgccatatcatgcggcaatgctttttgattgtatttatatcaagctgtaaaatatagtaagtttcgcgttcttctttactttaaacatag attagaggatgatttgcccttcactcatttacttattgaaaaggcatgtaaagatcataattatgaagttattaaatggatatatgaaaacctac atatctacaatatgatagatacctttgaatgtgctattgcccataaggatctacatctatattgtttggggtatagatttatatataacagaatcg tacccgataagtatcatcatttagatattcgcatgctttcaagcctacaactcctacataaggtggcagccaaaggatacttagattttatcct agaaaccttaaagtatgatcataataaagataatataaatattattctaacacaagctgcaacctataaccatagaaaaattttaatctatttca ttcctcaatcaacccacgcacagatagaacaatgtttactagtggcgataaaagcaaaatcttccaggaaaaccttgaacttactactgtct cacctaaaccttcctcatcaacctcatcaaaaaataagccattatgttgccacttacaattcaacaaatataataggcattctgagtatgcgg cggaaaaagaagatatatttagatatcatattgacaaaattgtaaaaaaagctattttaataagtttgtcgttcgatgtatggatacatttct ataaacccggaaagaatccttaaaatagccgcgcgaataaataggatgatgttagtgaaaaaaatatctgaacatgtttggaaaaatcat gcggttagacttaaataccttaaacatgcggtacacacgatgaagcataaagatgggaaaaatagactcatgaactttatctatgatcgct gttattaccatatgcaaggggaagaaatctttagcctcgcaagatttatgcaatccatcatgcaccaaagttgtttgacgttttttatgattgt tgtatcctagatacgatacgattcaaaagccttcttttagattgttcacatatcataggtaaaaacgctcatgatgctaccaatatcaacatcg tgaacaagtatatcggcaacctgtttgttatgggagttcttagcaaaaaagaaatcttacaggactatccatccatttattctaaacaatacat gccttag;

SEQ ID NO: 307:
atgttttcccttcaagacctttgccgaaagcatcttttttattcttcccgatgttttggcgagcatgtactacaacgattaggactgtattggag atgtcacggctcccttcaacgcataggagacgaccacatactcatacgacgggatctcatcctttccaccaacgaggccttaagaatgg cgggagaggaaggaaacaatgaagtagtaaagctcttgttactgtggaagggaaatcttcattacgccgtcataggagccttgcagggt gatcaatatgacctgatccataagtatgaaaaccaaatcggcgactttcatttatcttaccattgattcaagacgcgaatacgtttgaaaaa tgccacgctttagaacgttttgtggtgtttcatgtctgctaaaacatgctacaaaatacaacatgctcccctattctccaaaaataccaagaa gagctgtctatgagagcgtatcttcacgaaaccctatttgaactagcatgcctatggcagaggtatgatgtccttaaatggatagagcaaa ccatacatgtttacgacctaaagattatgtttaatattgccatctccaagagggatctgactatgtactccttaggatatattttccttttttgatag agggaacaccgaagctacgttgctaacgcaacatctcaagaagacagcggccaaagggctcctccactttgtgctagaaacgttaaaa tacggcggcaacatagataccgtcctgacccaagccgtaaagtacaatcatagaaaacttttagattattttctgcgtcaactacctcgtaa acatattgaaaaacttttgttgctggccgtgcaggaaaaggcttctaaaaaaacattgaacttactgttgtcacatttaaactactccgtgaa acgcatcaaaaaactaccgcgctatgtgatagagtacgagtccaccttggtgataaagattttattaaaaaaaagagtgaacctgatagat gccatgttggaaagatggtaagatattttctgcgacgaaagtgaggacgatcatggatgagctttcgattagtccggaaagagtcatta agatggctatacagaaaatgagaacggatatcgtaatccatacttcttatgtttgggaggatgatctagaacgtcttactcgtcttaaaata tggtatacaccataaagtacgaacatgggaaaaaatgttaattaaagtcatgcacggcatatacaaaaacttattatacggcgaaaggg aaaaagtcatgttttatttagccaagctctatgttgctcaaaacgcggccacccaattcagagacatttgtaaggactgttacaaactggat gtggcacggtttaaaccgcggtttaagcaactaatattagactgtttagaaattattactaaaaaatcttgctatagtatcctggaaatcttag aaaaacatatttatttccctgtttactatgaaagttatgactgaagaagaaaaaaacctatgtttagaaatattatataaagtaattcattataaa acaatacaatgttaa;

-continued

SEQ ID NO: 308:
atgtcgttgccgctctctctgcagaccctcgtcaaaaagacgatagccagccagtgtttgtcaatagatgaacactgcattttgaaatattg tggcctatggtggcatgatgctcctctcaagctttgtatggatcgtggccgaatacaaataaaatcaggattttaggagaagatatagac cttcgtgtggcattaataatagctgttaaggaaaacaactatagtctgataaagctctttacagagtggggcgcaaatatcaactatggttt gctttctatcaatacgaagcacatccgagagttgtgtagacagctaggcgccaaagaaactctagaggcaacgatattttccgtattttta ccaggataatgcacaataaaaccagcggcagtattattttgtgccatgaattttatgaataatcctattttagaaaacaaatttgttatacaa ttaaggggcttaatttataaaagactatggggctcatagaaataaaagaaacggacgagttaaatggtttactagtgaagtattggtacg ccaaagcagtacaatacgattgtaaggacgccatttgttttctagatgagaaatatacggatcttaatgaatggcgattaaaatgtctcctgt attataacaaaatatgagcttcatgagatgtaccacaaggaaaacatccaaatagacgtccatgacatgatatgtctggcttctaccaa ggataacaatccattaacaatatattactgttacgcgctgggggcaacatcaaccaagctatgcttacttcagtacaatattataacatcg gtaatatattttctgtatagatttgggtggtaatgcctttgaagagggtcgtgccatagcggaacaaaaaggttataatttctgagccatag tttggctttggatatttacagctcagatgcttccttgccactaaacttaaaggaccccgaagaaataagcagtttattaaaagattataaatca aaaaacttatccatcatttgggaatattctcataatatactatag;

SEQ ID NO: 309:
atgttgtctttacaaacgttggccaaaaaagttgtggcatgcaattatctttcaagtgactatgattatacgttgcagcgttttggtttgtggtg ggatttaggtcctattcacctatgtaacaattgtaagcaagttttttcgtataaacatttacagtgtttttctgaggatgatctttgtctcgaagc ggcgctagtaaaggccgtgaagagcgataatcttgaacttatacgtttatttgtggattggggcgcaaatcctgaatatgggcttatacgt gttcctgccgtgtatctaaagcggctgtgtgcggaactggggaggcttaacgcctgtatccgaaccccgtcttctggaaatttaaaagaa gtggccaggctaaaatcctgtgcaggagttctgctgggttatgacatgttttgtcataatccactcttggaaaccgtaactagaaccacttt agacacagttacgtacacctgttcaaacattccgttgacgggggatacggcgcaccacctattaacaaagttttggtttgccctggcatta cgacataattttacaaaggctattcactatttctataaaaggcataaaaatcacctctattgggggtagcttgtagcctttatttaataacatt tttgacatacacgagttgtgtcgtgaaaaagagatttgcatcagccctaatctgatgatgaaatttgcttgcttgcgggaaaaaaattacgc ggccatttattactgtcataggttgggggctagtctcgattatggcatgaatctttctatctataacaataatactttaaacatgtttttctgtatt gatttgggggctgccgatttttga;

SEQ ID NO: 310:
atggttgagccacgcgaacagttttttcaagacctgctttcagcagtggatcaacaaatggacactgtaaaaaatgacataaaagacatc atgaaagaaaaaacatcttttatggtgtcattcgaaaactttatagaacgttacgataccatggaaaaaaatattcaagaccttcagaataa gtacgaagaaatggcggccaaccttatgaccgtcatgacggatacaaaaattcagcttggagccattatcgcccaacttgagattctgat gataaatggcactccacttccggcaaaaaaacaacgattaaggaggctatgccctaccttcatcaaacacgaacaatgatcaaacg agtcctcccgcctcaggcaaaacaagtgaaacacctaaaaaaaatcccacgaatgcaatgttcttcacgcgtagcgaatgggcatcctc gaaaacttttcgagaaaagtttttaacaccagaaattcaggccatattggatgagcagtttgcaaacaagaccgggatcgaaagattgca tgccgagggtctttacatgtggagaacccaattctctgacgaacagaagaaaatggtcaaagagatgatgaagaagtaa;

SEQ ID NO: 311:
atggggtcgtctctagacgacttctgcaatgatagcacagctccacagaaggtgcttttggcgttttccattacctacacgccagtgatgat atatgctctaaaggtaagtcgcggccgactgctagggcttctgcaccttttgatctttctgaattgtgcttttaccttcgggtacatgacattc gtgcactttgagagcacaaatagggtcgcgctcactatgggagcagtagttgcacttctttggggagtgtactcagccatagaaacctg gaaattcatcacctccagatgtcgtttgtgcttgctaggccgcaagtacattctggcccctgcccaccacgtcgaaagtgccgcgggctt tcatccgattgcggcaaatgataaccacgcatttgtcgtccggcgtcccggctccactacggtcaacggcgcattggtgcccgggttga aaagcctcgtgttgggtggcagaaaagctgttaagcagggagtggtaaaccttgttaaatatgccaaataa;

SEQ ID NO: 312:
atgccaaataacaacggcagacagcaaaataaaaagaaggggatggccagccagtcaatcagctgtgccagatgctgggcaaaat tatcgcccagcagaaccagtccagaggtaagggaccggggaagaagaataagaatagaaaccggagaagcccccatttccctctag cgactgaagatgacgtcagacatcacttcaaccccagtgaacgacaattgtgcctgtcgtcaatccggactgcctttaaccaaggcgct -continued gggacttgcaccctgtcagactcagggagaataagttacactgtggagtttagtttgcctactcatcacactgtgcgcttgattcgcgcca cagcgtcaccctcagcatga;

SEQ ID NO: 313:
atgggaagcctagatgatttctgcttcgatcacaccgccgcacaaaagcttgtgctagcctttagcatcacatatacacctataatgatata cgccctcaaggtgtcacgcggccgactcctggggctgttgcacatcctgatatttctgaactgtgccttcacgttcggatacatgacatat gtgcattttgaatccaccaaccgtgtcgcactcactatgggggctgttgttgcccttctgtggggtatttatagcttcacagagtcatggaa gttcattacttccagatgcagattgtgttgcctaggccggcgatacattctggccctgcccaccacgtagaaagtgctgcaggtctccat tcaatcccagcgtctggtaaccgagcatacgctgtgagaaagcccggactaacatcagtgaacggcaccctagtaccagggcttcgg agcctcgtgttgggcggcaaacgagctgttaaacgaggagtggttaacctcgtcaagtatggccggtaa;

SEQ ID NO: 314:
atggccggtaagaaccagagccagaagaaaaggaaaaacacagctccaatggggaatggccagccagtcaatcaactgtgtcagtt gctgggtgcaatgataaagtcccagcgccagcaatctaggggaggacaggccaaaaagaaaaagcctgagaagccgcattttcccc tggccgctgaagatgacatccggcaccatctcacccagaccgaacgatccctttgcttgcaatcgatccagacggcttttaatcaaggc gcaggaactgcgtcgctttcatccagcgggaaggttggttttcaggttgagtttatgctgccggttgctcatacagtgcgcctgattcgcg tgacttctacatccgccagtcagggtgcaagttaa;

SEQ ID NO: 315:
atgcggccctttctgctgcgcgccgcgcagctcctggcgctgctggccctggcgctctccaccgaggccccgagcctctccgccgag acgaccccgggcccgtcaccgaggtcccgagtccctcggccgaggtctgggacgacctctccaccgaggccggcgacgatgacc tcaacggcgacctcgacggcgacgaccgccgcgcgggcttcggctcggccctcgcctccctgagggaggcgccccggcccatct ggtgaacgtgtccgagggcgccaacttcacccctcgacgcgcgcggcgacggcgccgtgctggccgggatctggacgttcctgccc gtccgcggctgcgacgccgtgtcggtgaccacggtgtgcttcgagaccgcgtgccacccggacctggtgctgggccgcgcctgcgt ccccgaggcccggagatgggcatcggcgactacctgccgcccgaggtgccgcggctccggcgcgagccgcccatcgtcacccc ggagcggtggtcgccgcacctgagcgtcctgcgggccacgcccaacgacacgggcctctacacgctgcacgacgcctcggggcc gcgggccgtgttctttgtggcggtgggcgaccggccgcccgcgccgcggacccggtgggccccgcgcgccacgagccccgctt ccacgcgctcggcttccactcgcagctcttctcgcccggggacacgttcgacctgatgccgcgcgtggtctcggacatgggcgactcg cgcgagaactttaccgccacgctggactggtactacgcgcgcgcgccccgcggtgcctgctgtactacgtgtacgagccctgcatct accaccgcgcgcgcccgagtgcctgcgcccggtggaccggcgtgcagcttcacctcgccggcgcgcgcggctggtggcgc gccgcgcgtacgcctcgtgcagcccgctgctcggggaccggtggctgaccgcctgccccttcgacgccttcggcgaggaggtgcac acgaacgccaccgcggacgagtcggggctgtacgtgctcgtgatgacccacaacggccacgtcgccacctgggactacacgctcgt cgccaccgcggccgagtacgtcacggtcatcaaggagctgacggccccggccccgggccccgggcacccgtggggccccggcg gcggcgacgacccgatctacgtggacggcgtcacgacgccggcgccgcccgcgcccgtggaacccgtacggccggacgacg cccgggcggctgtttgtgctggcgctgggctccttcgtgatgacgtgcgtcgtcggggggccgtctggctctgcgtgctgtgctccgg cgccgggcggcctcgcggccgttccgggtgccgacgcgggcgcggacgcacatgctctctccggtgtacaccagcctgcccacgc acgaggactactacgacggcgacgacgacgacgaggaggcgggcgtcatccgccggcggcccgcctccccggcggagacagc ggctacgaggggtcgtacgcgagcctggaccccgaggacgagttcagcagcgacgaggacgacgggctgtacgtgcgccccgag gaggcgccccgctccggcttcgacgtctggttccgcgatccggagaaaccggaagtga;

SEQ ID NO: 316:
atgcccgctggtggcggtctttggcgcgggccccgcgggcatcggcccgggcaccacggcggtgctggcctcggacgtctttggcc tgctccacaccacgctgcagctgcgcggggcgccgtcgcgctagcgctgctgctgctggcgctcgccgcgaccccgacgtgcggc gcggcggccgtgacgcgggccgcctcggcctcgcccgcgcccgggacgggcgccaccccagacgcgcttctccgcggaggagtc cctcgaggagatcgacggggccgtcaccccccggcccctcgaacgccccgacggcgagtacggcgacctggtcgcgcgcacggc cgtgcgcgcggccgcgaccgagcgggaccgcttctacgtctgcccgccgccgtccggctccacggtggtgcgcctggagcccgag caggcctgccccgagtactcgcaggggcgcaacttcacggagggatcgccgtgctcttcaaggagaacatcgccccgcacaagtt caaggcccacatctactacaagaacgtcatcgtcacgaccgtgtggtccgggagcacgtacgcggccatcacgaaccgcttcacgga ccgcgtgcccgtccccgtgcaggagatcacggacgtgatcgaccgccgcggcaagtgcgtctccaaggccgagtacgtgcgcaac aaccacaaggtgaccgccttcgactgcgacgagaacccgtcgaggtgggcctgcgcccctcgcgcctgaacgcgctcggcaccc gcggctggcacaccaccaacgacacctacaccaagatcggcgccgcgggcttctaccacacgggcacctccgtcaactgcatcgtc gaggaggtggaggcgcgctccgtgtaccc ctacgactccttcgccctgtccacggggga catcgtgtacatgtccccctt ctacggcc tgcgcgaggggg cccacggggagcacatcggcta cgcgcccgggcgcttccagcaggtggagcactactaccccatcgacctgga ctcgcgcctccgcgcctccgagagcgtgacgcgcaactttctgcgcacgccgcacttcacggtggcctgggactgggcccccaaga cgcggcgcgtgtgcagcctggccaagtggcgcgaggccgaggagatgatccgcgacgagacgcgcgacgggtccttccgcttcac gtcgcgggccctgggcgcctccttcgtcagcgacgtcacgcagctcgacctgcagcgcgtgcacctgggcgactgcgtcctccgcg aggcctcggaggccatcgacgccatctaccgcggcgctacaacaacacgcacgtgctggccggcgacaagcccgaggtgtacct cgcccgcggggg cttcgtggtggccttccgcccgctgatctcgaacgagctggcgcagctgtacgcgcgcgagctcgagcgcctcg gcctcgccgcgtcgtgggcccgcgctccccgcggccgccgtcgggcccggcgctccccggcccgggggacgcccgag ccgccggccgtcgacggcacggggcacctgcgcatcaccacgggctcggccgagtttgcgcgcctgcagttcacctacgaccacat ccaggcgcacgtgaacgacatgctgagccgcatcgcggccgcctggtgcgagctgcagaacaaggaccgcacccgtggggcga gatgtcgcgcctgaaccccagcgccgtggccacggccgcgctgggccagcgcgtctcggcgcgcatgctcggcgacgtgatggcc atctcgcggtgcgtggaggtgcgcggcggcgtgtacgttcagaactccatgcgcgtgcccggcgagcgcggcacgtgctacagccg cccgctggtgaccttcgagcacaacggcacgggcgtgatcgagggccagctcggcgacgacaacgagcctcatctcgcgcgac ctcatcgagccctgcaccggcaaccaccggcgctactttaagctgggcggcgggtacgtgtactacgaggactactgctacgtgcgc atggtggaggtgcccgagacgatcagcacgcgggtgaccctgaacctgacgctgctcaaggaccgcgagttcctgcccccc gaggt gtacacgcgcgaggagctcgccgacacggccctcctggactacagcgagatccagcgccgcaaccagctgcacgcgctcaagttct acgacattgaccgcgtggtcaaggtggaccacaacgtggtgctgctgcgcggcatcgccaacttcttccagggcctcggcgacgtgg gcgccgccgtcggcaaggtggtcctgggcgccacggggg ccgtgatctcggccgtcggcggcatggtgtccttcccgtccaacccc ttcggggcgctcgccatcgggctgctggtgctggccggcctggtcgcggccttcctggcctaccggcacatctcgcgcctgcgccgc aaccccatgaaggccctgtaccccgtcacgacgaaggcgctcaaggaggacggcgtcgaagaggacggcgtggacgaggccaa gctggaccaggcccgggacatgatccggtacatgtccatcgtgtcggccctcgagcagcaggagcacaaggcgcgcaagaagaac agcgggcccgcgctgctggccagccgcgtcggggcgatggccacgcgccgccggcactaccagcgcctcgagaacgaggaccc cgacgccctgtag;

SEQ ID NO: 317:
atgacgtatccaaggaggcgttaccgaagaagaagacaccgccccgcagccatcttggccagatcctccgccgccgcccctggct cgtccaccccgccaccgttaccgctggagaaggaaaaatggcatcttcaacacccgcctctcccgcaccttcggatatactgtcaag cgaaccacagtcagaacgccctcctgggcggtggacatgatgagattcaatattaatgactttcttcccccaggaggggg ctcaaaccc ccgctctgtgccctttgaatactacagaataagaaaggttaaggttgaattctggccctgctcccgatcacccagggtgacaggggag tgggctccagtgctgttatttta gatgataactttgtaacaaaggccacagccctcacctatgacccctatgtaaactactcctcccgccat accataacccagcccttctcctaccactcccggtactttaccccc aaacctgtcctagattccactattgattacttccaaccaaacaacaa aagaaaccagctgtggctgagactacaaactgctggaaatgtagaccacgtaggcctcggcactgcgttcgaaaacagtatatacgac caggaatacaatatccgtgtaaccatgtatgtacaattcagagaatttaattttaaagaccccccacttaacccttaa;

SEQ ID NO: 318:
atgcccagcaagaagagtggaagaagcggaccccaaccacataaaaggtgggtgttcacgctgaataatccttccgaagacgagcg caagaaaatacgggagctcccaatctccctatttgattattttattgttggcgaggaaggcaatgaggagggccgaacaccccacctac aggggttcgctaattttgtgaagaagcaaacttttaataaagtgaagtggtattttggtgcccgctgccacatcgagaaagcgaaaggaa cagatcagcagaataaagaatattgcagtaaagaaggcaacttactgatagaatgtggagctcctagatctcaaggacaacggagcga -continued cctctctaccgctgtgagtaccttgttggagagcggagtctggtgaccgttgcagagcagcaccctgtaacgtttgtcagaaatttccg cgggctggctgaacttttgaaagtgagcgggaaaatgcagaagcgtgattggaagacgaatgtacacgtcattatggggccacctgg gtgtggaaaaagcaaatgggctgctaattttgcagacccggaaaccacatactggaaaccacctagaaacaagtggtgggatggttac catggtgaagaagtggttgttattgatgacttttatggctggctgccgtgggatgatctactgagactctgtgatcgatatcctttgactgttg agactaaaggtggaactgtacctttttggcccgcagtattctgattaccagcaatcagaccccgttggaatggtactcctcaactgctgtc ccagctgtagaagctctctatcggaggattacttccttggtattttggaagaatgctacagaacaatccacggaggaagggggccagttc gtcacccttttccccccccatgccctgaatttccatatgaaataaattactga;

SEQ ID NO: 319:
atgagacacagagctatattcagaagaagaccccgcccaaggagacgacgacgccacagaaggcgctatgtcagaagaaaactatt cattaggaggcccacagctggcacatactacacaaagaaatactccaccatgaacgtcatttccgttggaaccccctcagaataacaagc cctggcacgccaaccacttcattacccgcctaaacgaatgggaaactgcaattagctttgaatattataagatactaaagatgaaagttac actcagccctgtaatttctccggctcagcaaacaaaaactatgttcgggcacacagccatagatctagacggcgcctggaccacaaac acttggctccaagacgacccttatgcggaaagttccactcgtaaagttatgacttctaaaaaaaaacacagccgttacttcaccccccaaa ccaattctggcgggaactaccagcgctcacccaggacaaagcctcttcttttttctccagacccaccccatggctcaacacatatgacccc accgttcaatggggagcactgctttggagcatttatgtcccggaaaaaactggaatgacagacttctacggcaccaaagaagtttggatt cgttacaagtccgttctctaa;

SEQ ID NO: 320:
gtccggagggaaagcccgaaacacaggtggtgttttacgataaacaactggaccccgaccgagtgggaatctattgtggagtgtgga ggcagtatagcgagataccttattatcggcaaagaggttggaaaaagcggtaccccacacttgcaagggtacgtgaatttcaagaaca aaaggcgactcagctcggtgaagcgcttacccggatttggtcgggcccatctggagccggcgagggggagccacaaagaggccag cgagtattgcaagaaagagggggattacctcgagattggcgaagattcctcttcgggtaccagatcggatcttcaagcagcagctcgg attctgacggagacgtcgggaaatctgactgaagttgcggagaagatgcctgcagtatttatacgctatgggcggggtttgcgtgattttt gcggggtgatggggtTgggtaaaccgcgtgattttaaaactgaagtttatgtttttattggtcctccaggatgcgggaaaacgcgggaag cttgtgcggatgcggctgcgcgggaattgcagttgtatttcaagccacgggggccttggtgggatggttataatggggagggtgctgtt attctggatgattttTatggGtgggttccatttgatgaattgctgagaattgggGacaggTacCctctgagggttcctgttaagggtgggttt gttaattttgtggctaaggtattatatattactagtaatgttgtaccggaggagtggtattcatcggagaatattcgtgGaaagttggaggcct tgtttaggaggttcactaaggttgtttgttgggggGagggggggtaaagaaagacatggagacagtgtatccaataaactattga;

SEQ ID NO: 321:
atggagttgaatcattttgaacttttatacaaaacaaacaaacaaaaaccaatgggagtggaggaaccggtatacgatgccacggggag gccattgtttggagacccgagtgaggtacacccacaatcaacactgaagctaccacatgatagggggagaggtaacatcaaaacaac actgaagaacctacctaggaaaggcgactgcaggagtggcaaccatctaggcccggttagtgggatatatgtaaagcccggccctgt cttttatcaggactacatgggcccggtctaccatagagcccctctagagttttttaacgaagcgcagttttgcgaggtgaccaaaaggata ggtagggtgacaggtagtgacggaaagctttaccatatatgtgtgcatcgatggttgcatactgctgaagctagccaagagggacga gccaagaaccctgaagtggattagaaatttcaccgactgtccattgtgggttaccagttgctctgatgatggcgcaagtggaagtaaaga gaagaagccagataggatcaacaaaggcaaattaaaaatagcccaaagagcatgagaaggacagcagaactaagccacctgac gctacgattgtagtggaaggagtaaatacaggttaaaaagaagggtaaagttaaaggaaagagtacccaagacggcctgtaccac aacaagaataaaccaccagaatctaggaagaaattagaaaaagccctattggcatgggcggtaatagcaattatgttgtaccaaccagt tgaagccgaaaatataactcaatggaacctgagtgacaacggcactaatggtatccagcatgctatgtaccttagaggggttagcagga gcttgcatgggatctggccggaaaaaatatgcaaaggagtccccacctacctggccacagacacggaactgaaagaaatacaggga atgatggatgccagcgaggggacaaactatacgtgctgtaagttacagagacatgaatggaacaaacatggatggtgtaactggtaca atatagaccccctggatacagttgatgaatagaacccaagcaaacttggcagaaggccctccggccaaggagtgcgctgtgacttgcag gtacgataaagatgctgacatcaacgtggtcacccaggccagaaacaggccaacaaccctgaccggttgcaagaaaggaaaaaattt -continued

```
ttcttttgcgggtacagttatagagggcccatgtaatttcaatgtttccgtggaggatatcttgtatggggatcatgagtgcggcagtttgctt caggacacggctctgtacctagtggatggaatgaccaacactatagagaatgccagacagggagcagcgagggtaacatcttggctc gggaggcaactcagcactgccgggaagaggttggagggtagaagcaaaacctggtttggtgcctatgccctatcgccttactgtaatg taacaagcaaaatagggtacatatggtacactaacaactgcaccccggcttgcctcccaaaaatacaaagataataggcccggaaa atttgacactaacgcggaagacggaaagattctccatgagatgggggtcacctatcagaatttctgctgctctctggttgttctgtctg acttcgcccctgaaacagccagcgcgttataccctcattttgcactacatgattcctcaatcccatgaagaacctgaaggctgcgacacaa accagctgaatctaacagtggaactcaggactgaagacgtaataccgtcatcagtctggaatgttggcaaatatgtgtgttagaccag actggtggccatatgaaaccaaggtggctttgttatttgaagaggcaggacaggtcgtaaaattagccttacgagcgctgagggatttaa ccagggtctggaatagcgcatcaaccacggcattcctcatctgcttgataaaagtattaagaggacagatcgtgcaaggtgtgatatgg ctgctactagtaactggggcacaaggccggctagcctgcaaggaagattacaggtacgcaatatcatcgaccaatgagatagggctac tcggggccgaaggtctcaccaccacctggaaagaatacaaccacgatttgcaactgaatgacgggaccgttaaggccatttgcgtggc aggttccttaaagtcatagcacttaatgtggtcagtaggaggtatttggcatcattgcataaggaggcttcactcacttccgtgacatttga gctcctgttcgacgggaccaacccatcaactgaggaaatgggagatgacttcgggttcgggctgtgcccgttcgatacgagtcctgttg tcaagggaaagtacaatacaaccttgttgaacggtagtgctttctatcttgtctgcccaataggtggacgggtgtcatagagtgcacag cagtgagcccaacaactctgagaacagaagtggtaaagaccttcaggagagacaagcccttccgcacagaatggattgtgcgacca ccacagtggaaaatggagatttattctactgtaagttgggggcaactggacatgtgtgaaaggtgaaccagtggtctacacgggggg gctagtaaaacaatgcagatggtgtggcttcgacttcaatgagcccgacggactcccgcactacccataggtaagtgcatcttggtaa atgagacaggttacagaatagtagattcaacggactgtaacagagatggcgttgtaatcagcacagatgggagtcatgagtgcttgatc ggtaacacaactgtcaaggtgcatgcatcagatgaaagactgggcccctgccatgcagacccaaagagattgtctctagtgcaggac ctgtaaggaaaacttcctgtacattcaactacgcaaaaactttgaagaacaagtactatgagcccagggacagctacttccagcaatatat gcttaagggcgagtatcagtactggtttgacctggacgtgactgaccgccactcagattacttcgcagaatttgtcgtcttggtagtggta gcactgttaggaggaagatatgtcctgtggctaatagtgacctacatagttctaacagaacaactcgccgctggtttaccattgggccag ggtgaggtagtgttgatagggaacttaattacccacacagacattggagtcgtagtatatttcttactactctatttggtcatgagggatgag cctataaagaaatggatactgctgctgttccatgctatgactaacaatccagtcaagaccataacagtggcattgcttatggttagtgggt tgccaagggtggaaagatagacggcggttggcagcggctgccagagaccagctttgacatccaactcgcgctgacagttatagtagt cgctgtgatgttactggcaaagagagatccaactactgtcccccttggttataacagtggcaaccctgagaacggctaagatgactaatgg acttagcacggatatagccatagctacagtgtcaacagcgttgctaacctggacctacattagtgactattatagatacaagacttggcta cagtaccttattagcacagtgacaggtatcttcttaataagggtactgaagggaataggtgagttggatttacacactccaaccttgccatc ttacagacccctcttcttcattctcgtgtacctcatttccactgcagtggtaacaagatggaatctggacatagccggattgctgttgcagtg tgtcccaaccctttgatggttttacgatgtgggcagacattctcaccctgatcctcatactgcccacttacgagctaacaaaactatattac ctcaaggaagtgaagactggggcagaaaagggctggttatggaagaccaacttcaagagggtaaacgacatatacgaagttgaccaa tctggtgaagggggttttacctttcccgtcaaaaaaaagacaagttcaataacaggtaccatgttgccattgatcaaagccatactcatca gctgcatcagtaataagtggcagttcatatatctattgtacttgatatttgaagtgtcttactacctccacaagaagatcatagatgaaatagc aggagggaccaacttcatctcaagacttgtagccgctttgatcgaagccaattgggcctttgacaacgaagaagttaggggtttaaaga agttcttcctgttgtctagtagggttaaagaactgatcatcaaacacaaagtgaggaatgaagtaatggtccactggtttggtgacgaaga ggtttatgggatgccaaagttggttggcttagtcaaggcagcaacattgagtaaaaataaacattgtattttgtgcaccgtctgtgaagaca gagagtggagaggagaaacctgcccaaaatgcgggcgttttgggccaccaatgacctgtggtatgaccctagccgactttgaagaaa aacattataagaggatctttttagagaggatcaatcagaagggccggttagagaggagtacgcagggtatctgcaatatagagccaga gggcaattattcctgaggaatctcccggtgctagcaacaaaagtcaagatgctcctggtcggaaatcttgggacggaggtgggagactt ggaacaccttggctgggtccttaggggggcctgccgtttgcaagaaggttaccgaacatgagaaatgcaccacatccataatggacaaa ttgactgctttttttcggtgttatgccaaggggcaccacacctagagcccctgtgagattccccacctctctcttaaagataagaaggggggtt
```

-continued ggaaactggctgggcgtacacacaccaaggtggcattagttcagtggaccatgtcacttgtgggaaagacttgctggtatgtgacacta tgggccggacaagggtcgtttgccaatcaaataataagatgacagatgagtctgagtatggagttaaaactgactccggatgcccgga aggagctaggtgttatgtgttcaacccagaggcagttaacatatcagggactaaaggagccatggtccacttacaaaaaactggagga gaattcacctgtgtgacagcatcaggaactccggccttctttgatctcaagaacctcaaaggctggtcagggctaccgatatttgaggca tcaagtggaagggtagtcggcagggtcaaggtcgggaagaatgaggactctaaaccaaccaagcttatgagtggaatacaaacagtc tccaaaagtaccacagacttgacagaaatggtaaagaaaataacgaccatgaacaggggagaattcagacaaataaccttgctacag gtgccggaaaaaccacggaactccctaggtcagtcatagaagagatagggaggcataagagagtcttggtcttgatccctctgagggc ggcagcagagtcagtataccaatatatgagacaaaaacatccaagcatcgcatttaacctgaggataggggagatgaaggaagggga catggccacagggataacctatgcttcatacggttacttctgtcagatgccacaacctaagttgcgagccgcgatggttgagtactccttc atatttcttgacgagtaccactgtgccaccccagaacaattggccatcatgggaaagatccacagattttcagagaacctgcgggtagta gccatgaccgcaacaccagcaggcacagtaacaaccacagggcagaaacacccatagaagaattcatagcccagaagtgatgaa aggggaagacttaggctcagagtacttggacattgctggactaaagataccagtagaggagatgaagagcaacatgctggttttttgtgc ccactaggaacatggcggtggagacagcaaagaaattgaaagctaagggttacaactcaggctactattatagtggagaggatccatc taacctgagggtggtaacgtcgcagtccccgtacgtggtggtggcaaccaacgcgatagaatcaggtgttactctcccggacttggatg tggttgtcgatacagggcttaagtgtgaaaagagaatacggctgtcacctaagatgcccttcatagtgacgggcctgaagagaatggct gtcacgattggggaacaagcccagagaaggggggagagttgggagagtaaagcctgggagatactacaggagtcaagaaactcccg ttggttctaaagattaccattatgatctactgcaagcacagaggtacggtattgaagatgggataaacatcaccaaatcctttagagagat gaactatgattggagcctttatgaggaggacagtctgatgattacacaattggaaatcctcaataatttgttgatatcagaagaactaccga tggcagtaaaaaatataatggccaggactgaccacccagaaccaattcagctggcgtacaacagctacgaaacacaagtgccagtgc tattcccaaaaataaagaatggagaggtgactgatagttacgataactataccttcctcaacgcaagaaaattgggggatgatgtaccc cttacgtgtatgccacagaggatgaggacttagcggtagagctactgggcttagactggccagaccctggaaaccaaggaaccgtag aggctggcagagcactaaaacaagtagttggtctatcaacagctgagaatgccctgttagtagccttattcggctatgtaggatatcagg cactttcaaagaggcatataccagtagtcacagatatatattcaattgaagatcacaggttggaagacaccacacacctacagtacgccc caaatgctatcaagacggaggggaaggagacagaattgaaggagctagcccaggggatgtgcagagatgtgtggaagctatgac caattatgcaagagagggtatccaattcatgaagtctcaggcactgaaggtgaaagaaaccccacttacaaagagacaatgaacact gtgactgactatgtaaagaaattcatggaggcgctggcagacagtaaagaagacatcttaagatatgggttgtgggggacgcacacag ccttatataagagcatcagtgccaggcttgggagtgagactgcgttcgctaccctggtcgtgaagtggctggcatttgggggggaatca atagcagaccatgtcaaacaagcggccacagacttggtcgtctactatatcatcaacagacctcagttcccaggagacacagagacac aacaggaaggaaggaaatttgtggccagcctactggtctcagctctagctacttacacatacaaaagctggaattacaataatctgtcca agatagttgaaccggctttggccactctgccctatgccgccacagctctcaaactattcgcccccactcgattggagagcgttgtcatatt gagtaccgcaatctacaagacctacctatcaatcaggcgcggaaaaagcgatggtttgctaggcacaggggttagtgcggctatggag atcatgtcacaaaatccagtatccgtgggcatagcagtcatgctaggggtagggccgtggcagcccacaatgcaatcgaggccagt gagcagaagagaacactactcatgaaagttttgtaaagaacttcttggaccaagcagccactgatgaattagtcaaggagagtcctga gaaaataataatggctttgtttgaagcagtgcagacagtcggtaaccctcttagactagtataccacctttatggagttttctataagggggtg ggaggcaaaagagttggcccaaaggacagccggtaggaaccttttcactttgataatgttcgaggctgtggaactactgggagtagata gtgaaggaaagatccgccagctatcaagtaattacatactagagctcctgtataagttccgtgacagtatcaagtctagcgtgagggaga tggcaatcagctgggccctgcccctttcagctgtgattggacaccgacggatgacagaatagggctcccccaagacaatttcctccaa gtggagacgaaatgccctgtggttacaagatgaaggcagttaagaattgtgctggagagctgagactcttggaggaggaaggctcat ttctctgcagaaataaattcgggagaggttcacggaactacagggtgacaaaatactatgatgacaatctatcagaaataaagccagtga taagaatggaagggcatgtggaactctactacaagggagccaccatcaaactggacttcaacaacagtaaaacaatactggcaaccg -continued ataaatgggagattgatcactccactctggtcagggtgctcaagaggcacacaggggctggatatcatgggcatacctgggcgaga
aaccgaactacaaacatctgatagagagggactgtgcaaccatcaccaaagataaggtttgttttctcaaaatgaagagagggtgtgca
tttacttatgacttatcccttcacaaccttacccgactgattgaattggtacacaagaataacttggaagacaaagagattcctgctgttacg
gttacaacctggctggcttacacgtttgtaaatgaagatatagggaccataaaaccagccttcggggagaaagtaacaccggagatgc
aggaggaaataaccttgcagcctgctgtagtggtggatacaactgacgtgaccgtgactgtggtaggggaagcccctactatgactac
agggagactccgacagcgttcaccagctcaggttcagacccgaaaggccaacaagtttttaaaactgggggtaggtgaaggccaata
ccccgggactaatccacagagggcaagcctgcacgaagccatacaaggtgcagatgagagaccctcggtgctgatattagggtctga
taaagccacctctaatagagtgaaaactgcaaagaatgtaaaggtatacagaggcagggacccactagaagtgagagatatgatgag
gaggggaaagatcctggtcatagccctgtctagggttgataatgctctattgaaatttgttgactacaaaggcacctttctaactagagag
accctagaggcattaagtttgggtaggcctaaaaagaaaaacataaccaaggcagaagcgcagtggttgctgtgcctcgaagaccaa
atggaagagctacccgattggttcgcagccggggaacccatttttctagaggctaacattaaacatgacaggtaccatctggtgggga
tatagctaatatcaaggaaaaagccaaacagttgggagctacagactccacaaagatatctaaggaggttggtgcaaaagtgtattctat
gaaactgagtaattgggtgatgcaagaagaaaataaacagggcaacctgaccccettgtttgaagagctcctgcaacagtgtccaccc
ggaggccagaacaaaactgcacatatggtctctgcttaccaactagctcaagggaactggatgccaaccagctgccatgtttttatggg
gaccatatctgccaggaggaccaagacccatccatatgaagcatacgtcaagttaagggagttggtagaggaacacaagatgaaaac
attgtgtcctggatcaagcctgggtaagcacaacgaatggataattggtaaaatcaaataccagggaaacctgaggaccaaacacatgt
tgaacccggcaaggtggcagagcaactgtgcagagagggacacagacacaatgtgtataacaagacaataggctcagtaatgaca
gctactggtatcaggttggagaagttgcccgtggttagggcccagacagacacaaccaacttccaccaagcaataagggataagatag
acaaggaagagaacctacaaacccgggtttacataagaaactaatggaagttttcaatgcattgaaacgacccgagttagagtcctcc
tacgatgccgtggaatgggaggaactggagagaggaataaacaggaagggtgctgctggtttctttgaacgcaaaaatatagggggaa
atattggattcagagaaaaacaaagtcgaagagattattgacaatctgaaaaaaggcagaaacatcaaatactatgaaaccgcgatccc
aaagaatgagaagagggacgtcaatgatgactggactgctggtgacttcgtggaagagaagaaacccagagtcatacaataccctga
agcaaaaacaaggctggccatcaccaaggtgatgtataagtgggtgaagcagaagccagtagttatacccgggtatgaagggaaga
cacctctattccaaattttttgacaaagtaaagaaggaatgggatcaattccaaaatccagtggcagtgagttttgacactaaggcgtggga
cacccaggtaaccacaaaagatttggagttgataaaggacatacaaaagtactatttcaagaagaaatggcataaatttattgacaccct
gaccatgcacatgtcagaagtacccgtaatcagtgctgatggggaagtatacataaggaaagggcaaagaggcagtggacaacctga
cacaagcgcaggcaatagcatgctaaatgtgttaacaatgatttacgccttctgcgaggccacgggagtaccctacaagagcttcgaca
gggggcaaaaattcatgtgtgtggggatgatggtttcctgatcacagaaagagctctcggtgagaaattcgcgagtaagggagtccag
atcctatatgaagctgggaagccccagaagatcactgaaggggacaagatgaaagtggcctaccaatttgatgatattgagttttgctcc
catacaccaatacaagtaaggtggtcagataacacttctagttacatgccggggagaaatacaaccacaatcctggctaaaatggccac
aaggttagattccagtggtgagaggggtaccatagcatatgagaaagcagtagcattcagcttcctgctgatgtactcctggaacccact
aatcagaaggatctgcttactggtgctatcaactgaactgcaagtgaaaccagggaagtcaaccacttactactatgaaggggacccga
tatctgcctacaaggaagtcatcggccacaatcttttttgatcttaagagaacaagcttcgagaagctggccaagttaaatctcagcatgtc
agtactcggagcctggactagacacaccagtaaaagactactacaagactgtgtcaatgtgggtgttaaagagggcaactggctagtta
atgcagatagactagtaagtagcaagactggaaataggtacatacccggagagggccacaccctgcaagggagacattatgaagaa
ctggtgttggcaagaaaacagatcaacaacttttcaagggaccgacaggtacaatctaggcccaatagtcaatatggtgttaaggaggct
gagagtcatgatgatgaccctgatagggagagggtatga;
SEQ ID NO: 322:
cggctagcctgcaaggaagattacaggtacgcaatatcatcgaccaatgagatagggctactcggggccgaaggtctcaccaccacc
tggaaagaatacaaccacgatttgcaactgaatgacgggaccgttaaggccatttgcgtggcaggttccttttaaagtcatagcacttaat
gtggtcagtaggaggtatttggcatcattgcataaggaggcttcactcacttccgtgacatttgagctcctgttcgacgggaccaacccat -continued caactgaggaaatgggagatgacttcgggttcgggctgtgcccgttcgatacgagtcctgttgtcaagggaaagtacaatacaaccttg ttgaacggtagtgcttctatcttgtctgcccaatagggtggacgggtgtcatagagtgcacagcagtgagcccaacaactctgagaaca gaagtggtaaagaccttcaggagagacaagccctttccgcacagaatggattgtgcgaccaccacagtggaaaatggagatttattcta ctgtaagttggggggcaactggacatgtgtgaaaggtgaaccagtggtctacacggggggggctagtaaaacaatgcagatggtgtgg cttcgacttcaatgagcccgacggactcccgcactaccccataggtaagtgcatcttggtaaatgagacaggttacagaatagtagattc aacggactgtaacagagatggcgttgtaatcagcacagatgggagtcatgagtgcttgatcggtaacacaactgtcaaggtgcatgcat cagatgaaagactgggccctatgccatgcagacccaaagagattgtctctagtgcaggacctgtaaggaaaacttcctgtacattcaact acgcaaaaactttgaagaacaagtactatgagcccagggacagctacttccagcaatatatgcttaagggcgagtatcagtactggtttg acctggacgtgactgaccgccactcagattacttcgcagaatttgtcgtcttggtagtggtagcactgttaggaggaagatatgtcctgtg gctaatagtgacctacatagttctaacagaacaactcgccgctggt;

SEQ ID NO: 323:
atgaacacagctggttgttttatcgctttgttgtacaccatcagagagataaaaacacgactgttttcaaggacacaggaagaaatggaat tcacactttacaacggtgagaagaagatcttctactccaggcccaacaaccacgacaactgttggctgaacgccatccttcagctgttca ggtacgtcgatgaacctttcttcgactgggtatatgaatcacctgaaaacctcacccttgaggcgatcagacaactggagaacattactg gtcttgagctgcacgagggtggtccgcccgccctcgtcatttggaacatcaaacacttgctccacaccgggatcggcaccgcctcgcg acccagcgaggtgtgcatggtggacggtacggacatgtgcctggctgacttccacgctggcatcttcctgaaaggacaggaacacgc cgtgtttgcctgcgtcacctccaacggtggtacgcgatcgacgacgaagaattctacccctggacgccagatccgtccgacgtgctg gtctttgtcccgtacgatcaagaaccacttaatggggaatggaaagcaagggttcagagacggctcaagggagccggacaatccagt ccggctactgggtcacagaaccaatcaggcaacaccgggagtatcatcaacaattactacatgcagcagtaccagaactccatggaca cccaacttggtgacaatgctatcagcggaggctccaacgagggatccacagacacaacctccacccacacaaccaacactcagaac aatgactggttttcaaagttggccagctctgtgccttcagcggtctcttcggcgccctcctcgccgataagaaaaccgaggagaccactctt ctcgaggaccgcatcctcaccacccgaaacggacacaccacctcgacaacccagtcgagtgttggcataacgcacgggtacgcaac agctgaggactttgtgaacgggccaaacacctctggtcttgagaccagagttgtccaggcggaacggttctttaaaacccacctgttcg actgggtcaccagtgatccgttcggacggtactacttgttggagctcccgactgaccacaaaggtgtctacggcagcctgaccgactca tacgcctacatgagaaacggttgggatgttgaagtcaccgctgtggggaatcagttcaacggaggctgcctactggtggccatggtgc ctgaactttgttccatcgagcggagagagttgttccagcttacgctcttcccccatcagttcatcaaccccggacgaacatgacagccc acatcaaggtgccctttgttggcgtcaaccgttacgatcagtacaaggtacacaagccgtggacccttgtggttatggtcgtagccccac tgactgtcaacaccgaaggcgctccgcaaatcaaggtgtatgccaacatcgcgcccaccaacgtgcacgtcgcgggtgagttcccttc caaagaggggattttccctgtggcatgtagccgacggttatggcggcttggtgacaactgacccaaagacggctgaccccgtttacggc aaagtgttcaaccccccccgcaacatgttgccggggcggttcaccaacctcctggacgtggctgaggcttgccccacgtttctgcactt cgatggtgacgtaccgtatgtgaccactaagacggattcggacagggtgctcgcacaatttgacttgtctttggcagcaaaacacatgtc aaacaccttccttgcaggtcttgcccagtactacacgcagtacagcggcaccgtcaacctgcacttcatgttcgcaggtcccactgacg cgaaagcgcgttacatgattgcgtatgcccctcgggcatggagccgcccaaaacacctgaggctgctgctcactgcattcacgcaga gtgggacacgggtctgaactcaatgtttaccttttccatcccctacctctcggcggctgattacgcgtacaccgcgtctgacgctgctgag accacaaatgttcagggatgggtctgcttatttcaaataacacacgggaaagctgagggtgacgctcttgtcgtgatggccagtgctgg caaagactttgagctgcgcctgcctgtggacgctcggcaacagaccacttcgacaggcgagtcggctgacccgtgactgccaccgt tgagaattacggcggcgagacacaggtccagaggcgccaccacacagacgtctcattcatattggacagatttgtgaaagtcacacca aaagactcaataaatgtattggacctgatgcagacccctcccacacccagtaggggcgctcctccgcactgccacttactatttcgct gatctagaggtggcagtgaaacacgagggggaccttacctgggtgccaaatggagcacctgaagcagccttggacaacaccaccaa cccaacggcgtaccataaggcgccgcttaccggcttgcattgccctacacggcaccacaccgtgttttggccaccgtttacaacggg aactgcaaatacgccggggctcactgcccaacgtgagaggcgatctccaagtgctggctccgaaggcagcgaggccgctgcctac -continued

```
ttctttcaactacggtgccatcaaagccactcgggtgacagaactgctgtaccgcatgaagagggccgaggcgtactgtcctcggccc ctcttggctgttcacccgagtgcggccagacacaaacagaaaatagtggcgcctgtaaagcagtccttgaactttgatctgctcaagttg gcaggggacgtggagtccaaccctgggcccttcttcttctctgacgtcaggtcaaacttcaccaaactggtggaaaccatcaaccagat gcaagaggacatgtcaacaaaacacggacccgactttaaccggttggtatccgcgtttgaggaattggccactgggtgaaagccatc aggaccggcctcgacgaggccaaaccctggtacaaactcatcaagctcctgagccgcttgtcatccatggccgctgtagcagcacgg tccaaggacccagtccttgtggccatcatgctggctgacaccggtcttgagattctggacagcacatttgtcgtgaagaaaatctccgac cccctctccagtctcttcacgtgccggcccccgtcttcagtttcggagctccgattctgctagccgggttggtcaaggtcgcttcgagctt cttccggtccacacccgaggatctcgagagagcagagaaacagctcaaagcacgtgacatcaatgacatcttcgccattctcaagaac ggcgagtggctggtcaagttgatcctagccatccgcgactggattaaagcatggatcgcctcagaagagaagtttgtcaccatgacag acttggtgcctggcatccttgaaaagcagcgggacctcaacgacccggccaagtacaaggaagccaaggaatggctcgacaacgcg cgccaaacgtgtttgaagagcgggaacgtccacattgccaacctgtgcaaagtggtcgcccagcgccgagcaagtcgagacctga acccgtggtcgtgtgcctccgcggcaaatccggtcagggtaagagtttccttgcgaacgtgctggcacaagccatctctacccactttac cggcaggactgactcagtttggtactgtccgccagaccctgaccacttcgacggttacaaccagcagaccgttgttgtgatggatgattt gggccagaatcccgacggcaaggacttcaagtacttcgctcagatggtctcgaccacggggttcatcccgcccatggcttcacttgag gacaaaggcaagcctttcaacagcaaagtcatcattgccaccaccaacctgtactcgggcttcaccccgagaaccatggtgtgccccg atgctctgaaccgaaggtttcactttgacattgacgtgagtgccaaggacgggtacaaaattaacaacaaattggacataatcaaagctc tcgaggacacccacaccaaccctgtggcaatgttccaatacgactgtgcccttctcaacggcatggccgttgaaatgaagagaatgca acaagacatgttcaaacccagccgcctttgcagaacatataccaacttgtgcaagaggtgattgacccgggtcgagctccacgagaaa gtgtcgagccacccgattttcaagcagatctcaattccttcccaaaagtcagtgctgtatttcctcattgagaaaggccaacacgaagcag caattgaattctttgaggggatggtccatgactccatcaaggaagagctccgaccccctcatccaacagacatcatttgtcaagcgcgcct tcaagcgcctgaaggaaaactttgagattgttgccctatgtttgactctcatggcaaacatagtgatcatgatccgcgaaactcgcaagag acagcagatggtggatgatgcagtgaatgagtacatcgagaaagcaaacatcaccacagatgacaagactcttgacgaggcggaaa agaaccctctagagactagcggtgccagcactgttggtttcagagagagaactctcccgggacaaggtgggtgatgacgtgaactc cgagcccgcccaccccggggatgagcaaccacaagctgaaggaccctacgccggaccactcgaccgtcagagacctctgaaagtg agagccaagctgccacagcaggagggaccttacgccggtccgatggagagacagaaaccactgaaagtgaaagcgaaagccccg gtcgtgaaggaaggaccttacgagggaccggtgaagaagcctgtcgctttgaaagtgaaagctaggaacttgatcgtcaccgagagt ggtgccccccgaccgacttgcaaaagatggtcatgggtaacaccaagcccgttgagctcatactcgacgggaagacagtagccatc tgctgtgctactggagtatttggcactgcctacctcgtgcctcgtcatcttttcgctgagaagtacgacaagatcatgttggacggtagaac catgatagacagtgactacagagtgtttgagtttgagatcaaagtaaaaggacaggacatgctctcagacgctgcgctcatggtgttgca ccgtgggaaccgcgtgagagacatcacgaaacactttcgtgacacagcaagaatgaagaaaggtaccccgtcgttggtgtgatcaa caacgctgacgtcgggagactgattttctcaggtgaggccctcacctacaaggacattgtagtgtgcatggatggagacaccatgccg ggcctatttgcctacaaagccgccaccaaggctggctactgcggggagccgtccttgctaaggatggagctgacacattcatcgttg gcactcactctgcaggtggcaatggagttgggtactgctcatgcgtatctagatccatgctccaaaaaatgaaggcacacatcgaccct gaaccacaccacgaggggttgatcgtagacaccagagatgtggaagagcgcgtgcacgtcatgcgcaaaaccaagcttgcacctac cgtggcacacggtgtgttcaaccctgagtacggccccgctgccttgtccaacaaggacccgcggctgaatgagggagttgtcctcgat gaggtcatcttctccaaacacaaggggggacacaaagatgtcaccggaagacaaagcgctgttccgccgctgcgctgccgactacgc gtcgcgtcttcacagtgtgctgggtacagcaaatgcccattgagcatctacgaggccattaaaggcgttgacggactcgacgccatg gaaccagacacagcgcctgccttccctgggcactccaggggaaacgccgcggcgcgctgattgacttcgagaacggcactgtcgg acccgaagtccaggctgccctggagctcatggagaaaagagaatacaagtttgcctgtcagaccttcctgaaggacgaaattcgcccg atggaaaaagtacgtgccggcaagacgcgcatcgtcgatgttttgcctgttgaacacattctttacaccaggatgatgattggcagatttt gtgctcaaatgcactcaaacaacggaccgcaaattggatcagcggtcggttgtaatcctgatgttgattggcaaagatttggcacacact
```

-continued tcgcccaatacagaaacgtgtgggatgtggactattcggcctttgatgctaaccactgtagtgatgcaatgagcatcatgtttgaggaggt gtttcgcacagactttggtttccacccgaatgctgagtggattctgaagaccctcgtgaacacggaacacgcctatgagaacaaacgca ttacagttgaaggtggaatgccgtccggctgttccgcaaccagcatcatcaacacaattctgaacaacatctacgtgctctacgcgctgc gtagacactatgagggagttgagctggacacttacaccatgatctcctacggagacgacatcgtggttgctagtgattatgacttggactt tgaggctctcaagccccactttaaatctcttggtcaaaccattactccagctgacaaaagcgacaaaggttttgttcttggtcactccattac cgatgtcactttcctcaaaagacacttccacatggattatggaactgggttttacaaacctgtgatggcttcgaagaccctcgaggctatcc tctcctttgcacgccgtgggaccatacaggagaagttgatctccgtggcagggctcgccgtccactctggacctgacgagtaccggcg tctcttcgagcccttccagggtctctttgagattccaagctacagatcacttacctgcgttgggtaacgccgtgtgcggtggcgcataa;

SEQ ID NO: 324:
ttgaaaggggggcgctagggtctccaccectaacatgccaacgacagctcctgcgtcgcactccacacttacgtctgtgcgcgcgcggg aaccgatggactttcgttcacccacctgcagctggactcacggcaccgcgtggccatttagctggactgagcggacgaacgtcgcttg cgcacctcgcgtgatcgactagtactctcaacactccgcctattcggtcgttagcgctgtcctgggcactcctgctggggccgttcgac gctctacggtttcccccccgcgacaaactacggtgatggggccgcttcgtgcgagccgatcgcctggtgtgtttcggttgtcactcga aacccacctttcacccccccccccccccctaagtactaccgtcgctcccgacgttaaagggaggtaaccacaagatttgcgccttctt gtccgaagttagagggctgtaaccgcaaactttgaaccgcctttcccagcgttaacgggatgtaatcacaagatggaccttcatccgga agtaaaacggcaacttacacagttttgcccgttttcatgagaaatgggacgtcagcgcacgaaacgcgcagtcgcttgaggaggacttg tacaaacacgtctcacacaggtacccacaaccgacacaaaacgtgcaacttgaaatcccgcctggtctttccaggtctagagggtga cactttgtactgtgattgactccacgctcggcccactggcgagtgttagtagtagtactgttgcttcgtagcggagcatggtggccgtggg actccctccttggtaacaaggacccacggggccgaaagccacgtctcaggacccaccatgtgtgcaaccccagcacggcaactttac cacgaaaaccatttaaggtgacactgaaactggtactcaaccactggtgacaggctaaggatgcccttcaggtaccccgaggtaaca cgcgacactcaggatctgagaaggggattggggcttctgtaaaagcgcccagtttaaaaagcttctatgcctgaataggcgaccggag gccggcgcctttccttaactattactgcttac;

SEQ ID NO: 325:
atgagtcttctaaccgaggtcgaaacgtatgttctctctattgttccgtcaggccccctcaaagccgagatagcgcagagacttgaagat gtttttgcagggaaaaacaccgatctagaggcactcatggaatggctaaagacaagaccaatcctgtcacctctgactaaggggattta ggatttgtattcacgctcaccgtgcccagtgagcgaggactgcagcgtagacgctttgtccagaatgccctcaatgggaatggtgaccc gaacaacatggacaaagcagtcaaactgtacagaaaacttaaaagggaaataacatttcacggggctaaagaagtagcgctcagttac tctgctggtgcacttgccagttgtatgggcctcatttacaacagaatggggactgtcaccactgagggcatttggcctagtatgcgcaa cctgtgaacagattgccgattcccagcatcgatctcatagacaaatggagacaacaaccaatccactaattaggcatgagaacagaatg gtattagccagcacgacagctaaagccatggaacaaatggctggatcaagtgaacaagcagcagaggctatggaaattgccagccaa gctaggcaaatggtacaggcaatgagaacaattgggactcatcctagttccagcgctggtctaaaagatgatcttcttgaaaatttacag gcctatcagaaacgaatgggagtgcagatgcaacggttcaagtga;

SEQ ID NO: 326:
atgaaggcaatactagtagtcttgctatatgcatttacaaccgcaaatgcagacacattatgtataggttaccatgcaaataattcaactga cactgttgacacagtactagaaaagaatgtaacagtaacacactctgttaaccttttagaagacagacataacgggaaactatgtaaacta aaaggggtagccccattgcatttgggtaaatgtaacattgctggatggctactgggaaacccagagtgtgaattactattcacagcaagc tcatggtcttacattgtggaaacttctaattcagacaatgggacatgttacccaggagatttcatcaattatgaagagctaagagagcagtt gagctcagtgtcatcatttgaaagatttgagatattccccaaggcaagttcatggcccaatcatgaaacgaacagaggtgtgacatcagc atgtccttattctggagcaaacagcttctacagaaacttaatatggctggtaaaaaaggaaattcatacccaaaactcagcaaatcctata ttaacaataagggggaaggaagttcttgttctatgggcattcaccatccacctaccagtactgaccaacaaagtctctaccagaatgcag atgcctatgttttttgtggggtcatcaaaatacaacaagaaattcatgccagaaatagcaacaagacccaaagtgagaggtcaagcaggg agaatgaactattactggacactaattgagcctggagacacaataacattcgaagcaactggaaatctagtggcaccaagatatgccttc -continued gcaatggaaagaggctctggatctggtattataatttcagatacaccagtctacgattgtaatacggcttgtcaaacacccaaaggtgcta taaacaccagtcttccatttcaaaatatacatccagtcacaattggagaatgtccaaaatatgtcaaaagcacaaaattgagaatggctac aggattaaggaacatcccgtctattcaatctagaggcctgtttggagccattgctggctttattgagggggggtggacaggaatgataga tggatggtatggttatcatcaccaaaatgagcaggggtcaggatatgcaccagaccgaaagagcacacagaatgccatagacgggat cactaacaaagtaaactctgttattgaaaagatgaacacacaattcacagcagtgggtaaagaattcaatcacttggagaaaagaataga gaatttaaacaaaaggttgatgatggttttctgaatgtttggacttacaatgccgaactgttggttctattggaaaatgaaagaactttggat tatcacgattcaaatgtgaagaacctatatgagaaagtaagaagccaactaaaaaacaatgccaaggaaattggaaatggctgctttga attttaccacaaatgtgatgacacgtgcatggagagcgtcaaaaatgggacttatgattatccaaaatactcagaagaagcaagactaaa cagagaagagatagatggggtaaagctggaatcaacaaggatttaccagattttggcgatctattcaactatcgccagttcattggtactg ttagtctccctgggggcaatcagtttctggatgtgctccaatgggtctttacagtgcagaatatgtattaa;

SEQ ID NO: 327:
atgaagactatcattgctttgagctacattttatgcctggttttcgctcaaaaacctcccggaaatgacaacagcacggcaacgctgtgcct ggggcaccatgcagtgccaaacggaacgctagtgaaaacaatcacgaatgaccaaattgaagtaactaatgctactgagctggttcag agttcctcaacaggtaaaatatgcgacagtcctcaccaaatccttgatggagaaaactgcacactaatagatgctctattgggagaccct cattgtgatggcttccaaaataaggaatgggacctttttgttgaacgcagcaaagcctacagcaactgttacccttatgatgtgccggatta tgtctcccttaggtcactagttgcctcatcaggcatgctggagtttaacaatgaaagcttcaattggactggagtcgctcagaatggaaca agctctgcttgcaaaaggagatctgataaaagtttctttagtagattgaattggttgcaccaattaaaatacaaatatccagcactgaacgt gaccatgccaaacaatgaaaaatttgacaaattgtacatttggggggttcaccacccgggtacagacagtgaccaaatcagcctatatg ctcaagcatcagggagagtcacagtctctaccaaaagaagccaacaaactgtaatcccgaatatcggatctagaccctgggtaagggg tgtctccagcagaataagcatctattggacaatagtaaaaccgggagacatacttttgattaacagcacagggaatctaattgctcctcgg ggttacttcaaaatacgaagtgggaaaagctcaataatgaggtcagatgcacccattggcaaatgcaattctgaatgcatcactccaaat ggaagcattcccaatgacaaaccatttcaaaatgtaaacaggatcacatatggggcctgtcccagatatgttaagcaaaacactctgaaa ttggcaacagggatgcggaatgtgccagagaaacaaactagaggcatattcggtgcaatcgcgggcttcatagaaaatggttgggag ggaatgatggacggttggtacggtttcaggcatcaaaattctgagggcacagggcaagcagcagatcttaaaagcactcaagcagca atcaaccaaatcaacgggaaactgaataggttaatcgagaaaacgaacgagaaattccatcaaattgaaaaagaattctcagaagtaga agggagaattcaggacctcgagaaatatgttgaggacactaaaatagatctctggtcgtacaatgcggagcttcttgttgccctagagaa ccaacatacaattgatctaactgactcagaaatgaacaaactgtttgaaagaacaaagaagcaactgagggaaaatgctgaggatatgg gcaatggttgtttcaaaatataccacaaatgtgacaatgcctgcatagggtcaatcagaaatggaacttatgaccatgatgtatacagaga cgaagcattgaacaaccggttccagatcaaaggtgttgagctgaagtcaggatacaaagattggatcctatggatttccttttgccatatca tgttttttgctttgtattgttttgctggggttcatcatgtgggcctgccaaaaaggcaacattaggtgcaacatttgcatttga;

SEQ ID NO: 328:
atgaataaaatatttagagttatttggagtcatgctcaacaggcttggggggttgtatctgagttagtaaagtctcataccaaaacatccgctt acacggataaaagagctcaagtatgcacctcagattatttttagataaacagcaagataaatttaaattaagtcttttaagtctagtattacta ggtatattttttagttcagtaggttcagctgcatatcttcaagatggtgctaatgagggatcgaatataggaactgacgacggtactattggt attggtcaagagagtagggcttcgtatggtgctgttgctatcggtcagaaggcaaaagctgaagctaggcataatattgcgataggttat ggagcagattcaggaacacaagtaaactctcttgcgataggctaccgcgctacagtaagtgggactggagcaattgccttaggcaaac aagccaattcgacaaatagtcaaacaattgccatcgggagtgattcaaaagcgagcggagatgaatctattgccttaggcggacaagc caattcgacaaataatcaaacaattgccatcgggagtcagtcaaaagcgagcggagaacaatctattgtcttaggcacaggggccagt gtgacaggtactcaaacaattgtaataggcgcacgtgctagtgcaagtgggcaccaatctgttgctatcggggcaaatacccaagcgc aggggtatggctccatatcaatcggtggagatgatttagctacaacgaaatatcaagatgatgctcaagactattccagcacaacaactg cggcaggtcacgcctctgttgctattgggggtcgatctaaggctcagggcgatggatctattgttgtaggtcctttagcatatgcaaggta -continued

```
tgctgaaggcattgctatcggtgcgagaagtaagtctaacaatgagtacggtattgcggttggtagtggtgcatttgctggaaagcactc cattgctgttggtaaaagtgctactgcaagtcaaacaggagcttccgcattcggtgaaagcgcacgagcaatcggacagtatacaaca gcattggggagttatgcggaagcagaaacgcaagatggcgttgctctaggttatcgatccaaaactagtcgtcggtcagggcaaagag gttggacaccagagaatacaaattattctattaacggaagtacattatctgctacgcatgcagcggtagcagtaggtgatggcaccaccg tcactcgtcaaattaccagtgttgctgcagggacagcagatactgacgcagcaaacgtggcgcaattaaaagcactgactttaaagatc agtggcgatagaaatacgcagggtcacacaacatttttataacgaaacgctctcaattgtagggctgatggtattagtacggcagttgag cagggaaatggcaattcaaaaattaccattactggctcaaaaacgtatttcatactaactataacgaacagtctcaaggtcgggagatc ctacgactaatttcggcacaattactgacaaagctggagctacaggaacctatgcaataacagcgggggtaaatgcctctgcggctgg aaattatggtattgcgatggggtataagagtaatgctagtgcttatgctgttgctcttggtagtgaatcgaaaggtgctgggcagattcca ttgcgataggtaatcttgcgagaacaacaggggtagactctgttgttgtgggtgcccatatcaatgtgacaggtcaaaaatcagtggcag ttggacgccaagcaaatgctagagattattctactgccttgggttatatggcctctgccagtggtacgtactctgttgctgtgggtgaaaat gccacgataaatgtaaatgctgctagagcaaccgcacttggtcataataccgttgtcaccgtgggtggcggtgtggcattaggttatgga tctaatgcaaatatagctggcggtgtagagggggttaaaacaagctcattctgtcacaacgggaacaagcactgaagctaacggctttaa atccacacaaaaggttgatggtaataatattggtgcagtttctgtgggtggtacaaccatcaaacgccaaatcgtcaatgtggcggctggt acacaagataccgatgcggtaaacgtggcacagcttaaatctttgacgatgaaaattggtggtaataccaatgctaatacacagccaaa agtggggttgtgggatggtattcttaaagtgctaggcacaaatggcgaaatcaagaccaatgcgtctggctcaaccattacaatatcact agacgatacgattaaaaataaattagctgatgccagagcaggaagtttgatattcaaggcgaaaaaacagataacggtacaacaaat gatgtttcgggtcaaaaatggaaggccaacgaagataagaccgttaccattacaagtaacgaaacataccaaaacggtggtgttcgata caaaggcgataacattgaaatttatcgtagaaatctagaattccatgtgttgatgaaagagacaccaacattcagcagcgttcaatatggc gataatggacctaagattaccagcaccactgacggtaatctaaaagtaacaggtacagacggcacttcctcagttaagatcaccaatttta gcacgaggtacacaaaatagcgatgcggtgaactacatgcaattttcaaatgctggttggaaacttgcaattgctccaggaacgggggg gtcaagcaactccacctggggcacatcttatcaaaataaacgataccgtaacctttaccgctggaaataatattaaattagaacaagcgg gcggaaatattacgatttctacgattggtaagttaattaaaacgactgaaagcctagaaaatggcgatctaaaaattatctatacagataatt cgcataacattatcaagaaaggtgaaaaaggagatcgtggcgagcgaggtctaagaggtgaaacaggccctgcgggtccgattggtc cagtgggtccagcaggggctaggggtgagcgaggccctgcaggtgtagctggtcctaaggtgagaaaggtgatccaggaccaga gggccctcaaggtcctagaggtgagcaaggtctaagaggtgaacgaggcctagcgggtcctagaggcgaaactggtccgaggggt ccagtgggaccacaaggagcgcaaggaatgccgggtgctcagggacagaagggtgaccgaggagaaactggccctgcgggtcct agaggcgaagctggtcctgctggagcaacaggaccacaaggtgaaaaaggagatcaaggtccgatgggtccggcaggcccagcg ggagagcgaggcgagcgggtcctaaaggagatagaggtccaaaaggtgatacaggtgagagaggtgcaactggccctgcgggt ccgatgggtccagcaggcccagcgggagagcgaggagaaactggacctgcaggtgtacctggtcctaggggtccagagggtccta gaggcgaaactggtttaacaggtccgaggggtccagtgggaccacaaggaccgcaaggaacaccgggtactccgggacagaagg gggataaaggcgatccaggacaagcgggtccagcaggacctaggggtccagtgggtccgaaaggtgaaacaggagctcaaggtc cgataggtccggcaggcccagcgggagagcgaggcgagcagggtcctagaggcgaagctggtccaacaggtccaacaggtccg aggggtccagtgggaccacaaggaccgcagggaacagcgggtgctcagggacctaaggtgagcgaggccctgcaggtgcagct ggccctgcgggtccagtaggtccagcgggaccacaaggtgaaaaaggagatcaaggtccgatgggtccggcaggcccagcgggt gctcagggcatacaaggtccaaaaggtgatagaggcgaacaagggcttccaggggtagcaggtcctaaggcgatagaggcgaag ctggtccagtgggtccagcaggaccagcgggagagcgaggcgagcagggtcctaggggggaacaaggtgcaactggccctgcg ggtccaacggggcctaggggtgaaccgggtccaacgggaccacaaggaccgcaaggaacaccgggtactccgggacagaaggg ggataaaggcgatccaggacaagcgggtccagcaggacctaggggtccagtgggtccgaaaggtgaaacaggagctcaaggtcc gataggtccggcaggcccagcgggagagcgaggcgagcagggtcctagaggcgaagctggtccaacaggtccaacaggtccga ggggtccagtgggaccacaaggaccgcagggaacagcgggtgctcagggacctaaggtgagcgaggccctgcaggtgcagct
```

-continued ggccctgcgggtccagtaggtccagcgggaccacaaggtgaaaaaggagatcaaggtccgatgggtccggcaggcccagcgggt
gctcagggcatacaaggtccaaaaggtgatagaggcgaacaagggcttccagggtagcaggtcctaagggcgatagaggcgaag
ctggtccagtgggtccagtaggaccacgaggaccacagggaacagcgggtgctcagggacctaagggtgagcgaggccctgcag
gtgaaactggacctaagggtgagaaaggtgatccaggaccaaaaggcgaaactggtccaacaggtccagtgggtccagcaggacc
agcgggagagcgaggcgagcagggtcctagggggaacaaggtgcaactggccctgcgggtccaacggggcctaggggtgaac
cgggtccaacgggaccacaaggaccgcaaggaacaccgggtactccgggacagaaggggatdaaggcgatccaggacaagcg
ggtccagcaggaccacgaggccctgcaggtgcagctggacctgcgggcccagcagggcctagggggtgaccgaggagaaactggt
cctgcgggtccaacaggggctaaggggtgaacaggcaaaaaggagatacaggtccaatgggcctgctggtccaaaaggtgatgc
aggtcctagaggcgaagctggtcctgctggagcaacaggaccacaaggtccaaaaggagataatggagctacaggtcctagggga
gagaaaggtgaacctggccctgcgggtccgattggtccagtgggtccagcaggggctgctggtccagcaggcccagcgggagagc
gaggccctacgggtcctaaaggagatgcaggtccaaaaggagatacaggtcagaaaggagaaactggccctgcgggtccagcagg
ggctaaggggtgaaccgggtcctagaggtgagcaaggtattcaaggacctacgggtccaacgggaccacaaggaccgcagggaaca
gcgggtattcagggacctaagggtgagcgaggaaatgtgagtgtcagcggtttaccgatcgagtatgcaacggaagacggcaaatca
attatcaatatgggcggtaatttctatttggaagaacctgctaaagatggttcgattaagttaattccagtggtgaatgttaaaggtaaattct
caaccaaaacgcaaaatccagatggcagtattacgcttaagtcattagcagtaaaagtgaatttggcaaatgaaactccgatggtattag
gtaatgtcgctgaaggggtagcagatacggacgctgttaatgtgaaacagttgaaatctgcgaaaactgaagtggaatctaccgatcac
agtgtggtgattaaagagcgtcagggcgataatcagcaaatcgtgtatgatttggcggttgctaaaacgaaactcactgcctctaaggat
aaacgcaccattagtgcagcagataaaggcaaccattttgcgacaggagatgaagtcgcagtagcaattaataccgcaacagcagcc
gcaagaaccgaagttgaagcgggtaaaaatgtgaaagtgacttcaaaaacgggggcaaatggtcagaatatttacaatgtgagcgtgt
ttggagatttaagcgacattacttcaattagtaatggcgatacgaaagtatctttaggtaaagataagcaaggaaatccagttgtaaatatg
aatggtgccagaattaccaacgttggagatggtagtgctgagggcgatattgtgaatgttcgtcagctcaacaaagtggtttcttctgtga
atacaggatttaatcaattatcaagagatattgttaatgcaagagcgggtattgcttctgctggggcgatggctaatttgccacaaatttctttt
accaggtaaaagtgctatttctgtttctaatgcacaatatcgcgggcaatctgcctatgctataggttattccaaaatttctgataatggcaaa
tggcttattcgagcgtctgttagcagtaatactcagcgggatactatgattggaggaggggtaggttttgtgtggtaa;

SEQ ID NO: 329:
aagcgaaagtagcagcaggtgaagctggtggtattactcagcatatcggtgcatatcacgttgaaaccgacgacggtaagatgattacc
ttcttagatacaccaggacacgcggcatttacctcaatgcgtgcgcgtggtgcgaaagcaacggatatcgttgttcttgtagtagcagct
gacgatggcgtaatgccacaaaccattgaagcaatccaacacgcgaaagcagctggtgcgccgatcgtggttgcggtaaacaaaatt
gataaaccagaagcaaacctagagcgtgtagaacaagagttattacaacacgaagtgatttctgagaaattcggtggtgatgttcaattt
gttcctgtttcagcgaaaaaaggaatggggattgacgacttacttgaagccattcttcttcaatcggaagtattagaattaagtgcggtaaa
agagggtatggcaagcggtgtggttatcgaatcttacctcgataaaggtcgtg;

SEQ ID NO: 330:
atgaaacaaatcgttttaaaaacaagcttattgatgaccctctcttcattattagttgcatgtagcggcggtggcggtagcgctggaaatcg
tgctgaccgtgtagaggaaaaagcacaaccggttcaatcaaatagtgagccttcttccgctccaatcaaaaatcctactaataccgctac
gaatgattctcttcatgacaaactttcaatgtcttctcatgacacatccaaagaaaatagtcaacaatcctcctttaaagcccctctagaaca
agaaaaaaaccaacctgcacaagaaaatctcacttggacaggttatcatgtttcagaagtgggaaatgcgagtaataatgtagataaag
ataacgttacggtattcactttcgtaaaatataattctcaatacaatgatgatccagttttttgataaaacaaaaacacaaagtaaaacaatatc
attagttgacgaaaaaatgagaataaagaggattattataactttacgttaaaagacgctttattttattatgaagttatggacaaccttca
gcagattacaaaaaagtagaaaaaaattatatttatgcaattaaaccagatgcaataaataatgagaacctcaatgcactaactgcaactt
attatcaagaagatggttttatatattccgtattaagtgatgtaaatcgagttggttcagaatatattcctcagtatggcaatgtgactcttacttt
ccgaaatggcaagatttatggtgaaatctacagatataatagaggacgtgatgatttgtttcagctctcaggagaaggacaaaacttaact -continued ataacaccacacaaggacaatccccataaactatcccctacaggacccgacaacatggcaatggagctgaattttatcaacgcagaaa aaactgataaaaaatacgttgttggtgtaggaaaagctgaaaaatattatgggttattatttgctgaaaaaagtcaccaagcacaataa;

SEQ ID NO: 331:
atgcattcaagtaaaccttattttggggaagtgtgtttcttttgttcacgttttaggtgcctatcttgcttcggcaatagatcgtgattttggtc gaattgaggtgagccatgtgagctttatgacagaagaaatgcaaccgatggtcgcgaagctatatcgtccagttctgctacggcagac acaccgaagccaggacttttggcattgcatggctatcaaagtgataaagaagcaactagtacatttggtgcgttggagctggctaagcg cggttttgtggtgctagcgatcgatcattttggacatggctattctactaagctacccgcttcaaataaaaatgagtggagcgaataatg gttatcaatatttaaaaacgttgccgtttgtagataacacacggttaggtctcttttggtcactctactggcgcgttaaatgcaattcgcgtggc aaaactcaatccagatcacaaagctgtcaatggattaagtagcaatggtggtgagatgacattgaataactacttattgacacaaggattg tacgaagaaattggtggctatcgtgaaagaaccttccctgtaaaaagtttgattcatcatcctaaccgcctgaaagcatttgggttaggcg aaaatgaaactttgcagtgggatcataccttatggtgactttaacaccggttctgcacgtcgtgcggcaatggtcgatggtacccatcttgg ggtgatgattgcttcccagagtaataaagaagccattctttggtttaatcaagcattgcaacatggcgaaaaaggtgcggattggattgat cctgaccaacagacctattggtataaagaacttacagggttatttgccttagcttgtgctttgcttgccacattatgttttgctagcggactttt aaaaacgacttattttggcgtgatgaatcaagcggtcacagaaaagacagcaatttcgagcaaacaatggtggggctttacgctgattaa tattgtgctgacattactgctctatccgctatttacccagtggggcggtgcgaatgaaccgattgcagcgaaattgagttttatgccacttga aatgggaaatggcattattttatggctcgttgtgagtgggcttgtcggtagtcttttatttggcttgtggcaaagaaaagcacagttttgttgg gcggagtttggtgtgttgagccaatctgcttccttgacaacggcgcaactgattggacgttatttattactcagcttattgttatttgccggttt atatttccttgtcaatctgatttatcaatatttccatgttgagttacgtttcttatggccattattgaagccattaacgacagagcggtttaattta tttatcgtgtattggttacctattttggtcttttttcttcgtgttcaacggtttgatcgtgtcagtccaaatgaaacaaaaagtagcgagttcgtttac ggcaacattgctgatctggagtttcaaaaccgcacttttttgctactggtggtttaatcattttatggttattccattttgttcccggttttatgcaa atcggtccgggatttgatgtggtaggactgccacaatttggtggacgttggatgatgatgttagccgtcattattccacagtttattgtcttca ccgtgatcaatcactggtgctatttaaaaacaggctatatttatttaggggtattttcacctctctgttaatgacttgggtgttagtcggaggt caagtcattgggcgattcttagcctaa;

SEQ ID NO: 332:
atgaatattgcaacaaaattaatggctagcttagtcgctagtgtagtgcttaccgcatgtagtggcggcggctcatcgggttcatcgtctaa accaaattcggaacttacacctaaggttgatatgtccgcaccaaaagcggagcagccaaaaaaagaggaagttccacaagcggataa ttcgaaagcggaagaaccaaaagagatggctccgcaagtagatagcccgaaagcggaagaaccaaaaaatatggctccacaaatgg gtaatccaaaactaaatgacccacaagtaatggctccgaaaatggataatccgcaaaaagatgccccaaaaggagaagaactaagta aggataaaagtaatgcggaaattcttaaggaattaggggttaaggatattaattcaggtatcattaataatgctgatgtagttctgaatttaaa aatagatgaaaaagatcacattacagtcgtattagataagggtaagattaatcgtaatcatctaaaagtaactaatacaatttctgctcaaga cattaaaaccttaaaagattcttcaggcaaattgtttgggttactatggatatatgcagtttaaatcaagttcgacaagatgaaaattatagcga tgaaaaagttagtttgaatgaatattatttattatcaatgaacgatgccgataaaatacgtccgactaaatctatatcatataagggagacat gttttatagttacaaagatgtaggaaatcagaaattaaaggcttctgtagaagcttcttatgatgatgtaacaaaaaaagtatcaatgaaagt atttggtgagaataatgattactggaaattaggtgagtttggtagaactaatttattagaaaatcaagtgactggagcaaaagttggcgaag atggtaccattataaatggaactttatattctaaaatagataattttccttaaaactaactcctgacgcaaacttctctgggggtattttcggta aaaatggcgaagtattagccggaagtgctattagtgaaaaatggcaaggcgtaatcggtgctacggcaaccacaaaagaagataaaa aataa;

SEQ ID NO: 333:
atgacaaaattaactatgcaagatgtgaccaatttatatttatataaaacgaaaactctacctaaagatagattggatgattcacttatttctga aataggaaaaggagatgatgatattgatagaaaagaatttatgggggccgggacgttttgtgaccgctgataactttagcgttgtaag agatttttttaatgctgggaaatcacgcattattgcgccgcaagtcccgcctattcgttcacagcaggaaaaaatcttggtcggtttaaaac cgggcaaatattccaaagcgcagatattggaaatgctgggttatacgaaaggcggagaagtggtaaatggcatgtttgccggtgaagt -continued

```
ccagacattaggcttttatgacgatggcaaaggggatttactcgaacgcgcctatatctggaataccacaggatttaaaatgagcgacaa
tgccttttttgttatagaagaatcaggcaaacgctatattgaaaactttggtattgaacctcttggtaagcaagaagattttgattttgtcggcg
gcttttggtctaacttagtgaatcgtggtttggaaagtattatcgacccatccggtatcggtggaacggtaaaccttaactttaccggcgag
gtggaaacctacacgttagacgaaacaaggtttaaagcggaagcggcgaagaaaagccattggagtttagtgaatgcggcgaaagta
tacggcggtttagaccaaattattaaaaaactatgggacagtggctcaattaagcatttatatcaagataaagatacgggcaaattaaaac
cgattatttacggcacggccggcaacgacagtaagattgaaggcactaaaatcacccgtaggattgcgggtaaagaagttacgcttgat
attgccaatcagaaaattgaaaaaggcgtgttagagaaattgggcgctgtctgttagtggttcggatatcattaaattgttgtttggagcattg
actccaactttaaatagaatgttgctatcacaacttatccagtcttttttccgatagcttggctaaacttgataatcccttagcccccttacactaa
aaatggcgtggtttatgtcaccggcaaagggaatgatgtgcttaaaggaactgaacatgaggatttgtttctcggtggtgaggggaatga
tacttattatgcgagagtaggccgatacaattgaagacgccgacggcaaaggtaaagtctattttgtgagagaaaaagggggtacctaagg
cggatcctaagcgggtagagtttagcgagtacataacgaaagaagaaataaaagaggttgaaaagggggttattaacttacgcagtttta
gaaaattataattgggaagagaaaacggcgactttcgctcatgcgactatgcttaatgagcttttttactgattatactaattatcgttatgaag
ttaaaggactaaaattgcccgccgttaaaaagttaaaaagtccgttggtggagtttacagctgatttattaactgttacgcctattgacgaaa
acggaaaagcacttagcgaaaaaagtattacggttaaaaaattttaaaaatggtgatttaggaataaggttgttggatcctaatagctattatt
atttccttgaaggccaagatacgggttttttatggtcctgcttttttatattgaacgaaaaaacggtggcggcgctaaaaataactcgtcggga
gcaggaaatagcaaagattggggcgggaacgggcatggaaatcaccgaaataatgcctccgacctgaataaaccggacggaaataa
tgggaataaccaaaataacggaagcaatcaagataatcatagcgatgtgaatgcgccaaataacccgggacgtaactatgatatttacg
atcctttagctttagatttagatggagatgggcttgaaaccgtgtcgatgaacgggcgacaaggcgcgttattcgatcatgaaggaaaag
gtattcgtaccgcaacgggctggctcgctgcggatgacggtttttagtgttagatcgtaaccaagacggcattattaatgatataagcga
gttatttagtaataaaaatcaactttccgacggcagtatttctgcacacggttttgcgacattagccgatttggatacaaaccaagatcagc
gtatcgaccaaaatgataagctgttttctaaactccaaatttggcgggatttaaatcaaaacggttttagtgaagcgaatgagctgtttagct
tagaaagtttgaatattaaatctttacataccgcctatgaagagcgtaatgattttctagcgggcaataatatccttgctcagcttgggaagt
atgaaaaaacggacggtacttttgcacaaatgggcgatttaaatttcagttttaacccgttttatagccgatttaccgaagcgttaaatttaac
cgagcaacaacgtcgcacaattaatctaaccggcaccggtcgggttcgggatttgcgtgaagccgccgcactttctgaggagttggct
gctttattacaacagtacactaaggcctccgattttcaggcacaacgagaattattgcctgccatttttagataaatgggcggcaacggattt
acagtatcaacattatgataaaacattacttaaaacggtagaaagtaccgatagtagtgcttctgtcgttagagtcacgccttctcaattaag
tagtatacgcaatgcaaagcatgatcctaccgttatgcaaaactttgaacagagtaaggcaaaaattgcgactttaaattcgctctacggg
ttaaatatcgatcaactttattacacgacggataaagacattcgctatattactgataaagtgaataatatgtatcaaacaaccgtagaactt
gcctaccgttctttacttttacaaacgcgtttgaagaaatatgtttatagcgttaatgcgaaacaattcgaagggaaatgggtaaccgattat
tctcgtactgaagccttatttaactctacttttaaacaatcgcctgaaaatgcattatatgatttaagcgaatacctttcttcttaacgatccta
cggaatggaagaagggctattactgttaagccgttatatagattatgctaaagcacaaggattttatgaaaactgggcggctacttctaa
cttaactattgcccgtttaagagaggctggagtaattttttgcagaatcgacggatttaaaaggcgatgaaaaaaataatattttgttaggtag
ccaaaaagataataacttatcgggtagtgcaggtgatgatctacttatcggcggagagggtaatgatacgttaaaaggcagctacggtg
cagacacctatatctttagcaaaggacacggacaggatatcgtttatgaagataccaataatgataaccgcgcaagagatatcgacacct
taaaatttaccgatgtgaattatgcggaagtgaagtttcgacgagtagataatgacttaatgttattcggttatcatgatacggattcggtca
cggtaaaatccttctacagccatgtagattatcaatttgacaaattggagtttgctgaccgcagtataactcgcgatgaactgattaaagca
gggcttcatctatacggcaccgatggcaatgatgatataaaggatcatgcggattgggacagcattttggaaggcggcaaaggcaacg
atattctaagaggtggctacggtgcggacacctatatctttagcaaaggacacggacaggatatcgtttatgaagataccaataatgataa
ccgcgcaagagatatcgacaccttaaaatttactgatgtgaattatgcggaagtgaaattccgacgagtagataatgacttaatgttattcg
gttatcatgatacggattcggtcacgataaaatccttctacaaccatgtagattatcaatttgacaaattggaatttgctgaccgcagtataa
ctcgtgatgaactaggtaaacaaggtatggcattatttggcactgacggtgatgataatatcaacgactggggacgtaactcggtgattg
```

-continued atgccggtgcgggtaatgatacggttaatggcggtaatggcgatgacaccctcatcggcggcaaaggtaatgatattctaagaggtgg
ctacggtgcggacacctatatctttagcaaaggacacggacaggatatcgtttatgaagataccaataatgataaccgcgcaagagatat
cgacaccttaaaatttaccgatgtgaattatgcggaagtgaaattccgacgagtagataatgacttaatgttattcggttatcatgatacgga
ttcggtcacggtaaaatccttctacagccatgtagattatcaatttgacaaattggagtttgctgaccgcagtataactcgcgatgaactgat
taaagcagggcttcatctatacggcaccgatggcaatgatgatataaaggatcatgcggattgggacagcattttggaaggggcaaa
ggcaacgatattctaagaggtggctacggtgcggacacctatatctttagcaaaggacacggacaggatatcgtttatgaagataccaat
aatgataaccgagcaagagatatcgacaccttaaaatttactgatgtgaattatgcggaagtgaaattccgacgagtagataatgacttaa
tgttattcggttatcatgatacggattcggtcacgataaaatccttctacaaccatgtagattatcaatttgacaaattggaatttgctgaccg
cagtataactcgtgatgaactaggtaaacaaggtatggcattatttggcactgacggtgatgataatatcaacgactggggacgtaactc
ggtgattgatgccggtgcgggtaatgatacggttaatggcggtaatggcgatgacaccctcatcggcggcaaaggtaatgatattctaa
gaggtggctacggtgcggacacctatatctttagcaaaggacacggacaggatatcgtttatgaagataccaataatgataaccgcgca
agagatatcgacaccttaaaatttactgatattaatttatccgaactttggtttagccgagaaaataacgatttgattattaaatcattattaagt
gaggataaagtcacggttcaaaattggtattcacaccaagatcataaaatagaaaatattcgtttatcgaatgagcaaacgttggtgagca
ctcaggtggagaagatggttgagtcgatggccggctttgctcagaagcacggaggagagatatctcttgtgtcgcttgaagaggtaaaa
caatatatcaatagcttaacagctgctttataa;

SEQ ID NO: 334:
atgtcaaatgccaaagcttacatccaagcttcttttgaagcagtcaaagcccgcaacccacatgaaacagaattcctccaagctgtagaa
gagctcttctctacacttgagcctgtttttgaagcacacccagaatacatcgaagaaaacatcttggctcgtatcgttgagcctgagcgtac
catcagcttccgtgttccatggacagataaagatggaaatgttcaagtcaaccgtggctaccgtgttcagttcaactcagctgtaggtcctt
ataaaggcggtcttcgcttccacccaactgtaaaccaatccatcttgaagttcctcggttttgagcaaatcttcaaaaacgtcttgactggtc
ttccaatcggcggtggtaaaggtggttcagactttgatcctaaaggaaaaactgatgctgaaatcatgcgcttctgccaaagcttcatgac
tgaattgcaaaaacacatcggaccttcacttgacgtccctgctggtgacatcggtgtcggtggtcgtgagatcggttacatgtacggtca
atacaaacgcctccgccagtttgatgcaggtgtcttgactggtaaacctcttggcttcggtggttcattgatccgcccagaagcaactggt
tacggtttggtttacttcactgataacatgttggcagcaaacggtaaatccttcaaagaccaaactgtccttatctcaggttctggtaacgtt
gcccaatatgctgttcaaaaagcgactgaacttggtgcaaaagttatttctgtttcagactcaaatggttacatcattgacgaaactggtatc
gacttcgacctcttggtggacatcaaagaaaaacgccgcgctcgtttgacagaatacgctgcagaaaaatcaactgctaagtacttcaa
aggttctgtatggaactacgatggcaaggctgatattgcccttccatgtgcgactcaaaatgagatcaacggcaaacaagctgctgccct
tgtaaaaaatggcgtgtactgtgtggctgaaggtgccaacatgccatctgaccttgatgccatcaaagtctacaaggaaaatggcgttct
ctacggactcgcaaaagctgccaacgctggtggtgtagctgtatctgcccttgaaatgagtcaaaacagccttcgcttgtcatggactcg
tgaagaagtagacggccgtcttaaagacatcatggccaacatcttcaacacagccaaagaaactgctgaaaaatacgaccttggtaca
gactaccttgcaggtgctaacatcgcagccttgaacaaattgcggatagcatgattgcccaaggtttggtataa;

SEQ ID NO 335:
atgttactagaagtgtccattaaaaacttcgccattattgagcaggtatcactgaattttgaaaacgggatgaccatcctatctggtgaaac
aggtgcaggtaaatccattatcattgatgccatgaacctgatgctaggggcgcgtgcgacgacagatgttatcagacatggggccgcc
aaggctgagattgaagggctcttttcctttgaaaatagcagagctctcgagcaaattttgcttgaacaggggattgaagtagctgacgaa
ctcattatccgccgtgaaatcctgcaaaatggccgttcggtcagccgtgtcaatggacaaatggtcaatttatctgtcttgaaacagattgg
gcaatatttagtagatattcatggtcaacatgaccaggaagaattgatgaaatcccagcaccatatccgtcttttggacagtttcggagaa
gatgaattttggagtcttaaagaccgttatcagacaacctttgatgcctatcgtagtcttcgcaaacgagttcttgaaaagcaaaaaaatga
gcaagaacacaaggcgcggattgagatgctagaataccaaattgctgaaatcgaagcagcggatttgaagtctggggaagatattcaa
ctcaatcaggaacgcgataaactgctcaaccacaaacaaattgcagatacactgaccaatgcctatgcactgttagacaatgaagattttt
caagcttgaacaacctacgctcagctatgagtgacttgcaaagtctggaagaatttgatccagactacaaacagctctcttctagcctgac -continued agaagcttattatgtcgttgaagatataaccaagcgtctcagcgatgtggtcgataatctagattttgacggcaatcgtctcatgcaattgg
aaagtcgtctggatttgctcaataccattacgaagaaatatggtggaactgtcgatgatgttttggactattttagtaaaatcagcgaagaat
acaatctattgacaggcaatgatttatctggagatgatttggaagttcagcttaagaacttagagaaagaattggttgaacgagcaggtca
gctcagccaatcacgccatgaattggctgttgttttagaagatattatccgccaagaattgcaagacttgtatatggagaaagctcgtttcc
aagttcgatttactaaaggaaaatttaatcgagaaggaaatgaaacagtagaattttacatctctaccaacccaggtgaagacttcaagcc
tctggttaaagtggcttctggaggagaattgtctcgcttgatgttggccattaagtcagcctttgcccgtaaagaaggcaagacttccatcg
tctttgacgaggtggatacaggggtgtctggacgtgtggcccaggccattgcccagaaaatttataaaatcggacaatatgggcaagta
ttggcgatttctcatctaccacaagtcattgctattgcagattatcagttctttattgagaaaatatccgacgaacattcgaccgtttctcgtgt
ccgtctcttgaccaaagaagagcgtattgaggaaattgccaagatgttagccggtgacaaaatcacagatgcagcccgtaatcaagca
aaagaattagtagaaaaaggttag;

SEQ ID NO: 336:
atggtagttaaagttggtattaacggtttcggacgtatcggtcgtcttgctttccgtcgtatccaaaacgtagaaggtgttgaagttactcgt
atcaacgaccttacagatccagtaatgcttgcacacttgttgaaatatgacacaactcaaggtcgtttcgacggtactgttgaagttaaaga
cggtggtttcgaagttaacggtaaattcgttaaagtttctgcagagcgcgagccaggaaacatcgactgggctactgatggcgtagatat
cgttttggaagctacaggtttctttgcttctaaagaaaaagctgagcaacacatccacgctaacggtgctaaaaaagttgttatcactgctc
ctggtggtaacgatgttaagactgttgttttcaacactaaccacgacatccttgatggtactgaaacagttatctcaggtgcttcatgtacta
caaactgtttggcaccaatggctaaagctcttcacgatgcatttggcgttcaaaaaggtttgatgactacaatccacggttacactggtga
ccaaatggttcttgacggaccacaccgtggtggtgaccttcgtcgtgcacgtgctgctgctgcaaacatcgttcctaactcaactggtgct
gctaaagctatcggcttggtaatcccagaattgaacggtaaacttgacggtgctgcacaacgtgttccagttccaacaggttctgtaactg
aattggttgcaactcttgacaagaaagtaactgctgaagaagtaaacgctgctatgaaagctgctgctactgaatcatttggttacactga
agaccaactcgtatcttcagatatcgtaggtatctcattcggttcattgtttgatgcaactcaaactaaagttatcgaagttgatggcgagca
attggttaaagttgtttcatggtacgacaacgaaatgtcttacactgcacaacttgttcgtactcttgagtacttcgcaaaaattgctaaataat;

SEQ ID NO: 337:
atgtcaaaaaataatatagtggagtgctttatagaaattgcaaagcactccaatcttaaatatgagtgtgttgatggcaaattgaaactagat
agagtactatttggttcaatggtatatccgcacaactatggatatatttctgatactctagcagaggatggagatcctctagatgtagtagtg
ctatctaatttctctgtaactccaggaacttatttggattgcaaaattcttggttctctagaaatggtagattctggagaacaagattgaaaagt
tattgcaattatggatgcggatccaagactcaagcatataaattctctagatgatgttcctcaacattgaattgctgaattgagaaacttttttg
aaagttacaagcaactagagaataagaaagtttcccttggaaactttatctctctagaatcaactctttctttaattgaagaatcaaaagcta
gatgaagaactcaagggggagaataa;

SEQ ID NO: 338:
atgacaatccacaaagtagcaatcaatggattcggaagaatcggaagattactatttagaaatcttctttcttctcaaggagttcaagttgta
gctgttaatgacgtagttgacattaaagttcttactcaccttttggtttatgacagtgctcaaggaaaactaaaagattgagaagtaagttgtg
attcagaatacataagactaaagaatgtaaatactggagaagttagagaagttagagttttcaacttcaatactgaaaagatttatcactga
ggtgaattagaaattgattgtgttgttgaatgttcaggaagattcttaactaaggaagcagttaagtgtcaccttgatgcaggagctcaaaa
agttcttatttcagctcctgcaaaggatgacactaagacagttgtttacaacgtaaaccatactcaaattaccagctcagacaatgttatttc
aggagcttcatgtacaactaatgcactagctcctatcgtaaaaattattcacagaaaatttggaattaattctggattcatgacaacagttca
cgctttcacttctgaccaaagacttcaagactctcctcactctgacctaagaagagctagagcagctgctggatcaattattcctacaacta
caggagcagctgctgcaattggaagagtaattccagaattgaatggaaaacttgatggaattgcacacagagtgcctgtattaactggtt
ctctagttgacctatgtttaaaaataaataagtctgtttctgcagaagaaatcaatgaagcaattaaggatggagaaaatgaaacccttgctt -continued atgtagaagatccaattgtatctgctgacattatcggagatacacatggttctgttttgactcatctctaactaaagtattgccaactggaga agttaagctgtatgcatgatatgataatgagtcttcttatgtaaatcaacttgcaagaactttgaaatactacatttctctttaa;

SEQ ID NO: 339:
ttcttcccagagtggatttccgttggttccgcctccttcgtccgtcgtaatatcaggccttctgttctgttcgctgtctgtctagggcacccttta ctgcaagagaagtatttgaggtcatatcgtcccatgaagtcgaccacctgtttcctctcttcactgtcacgtacgacatcgcattcaaggga agagatccagcagatctcgttcgtgtattcgagacaagagaggtccgcccccacaagacggctgaagaatgcaacattcttgtgctgc ctcctctcatggcaaatgccagaagaagggtacgtgttgcatcataacaagagctgtatttcccgctggcaaatacaggtgaaatgtacc tccagaaaagccacctagtatcgtgcggcaatgtgccacctcgcctcttgggagaaaaagaggaagagacgctgccgctgttttgcaa atgaaaaggattcattttcgcagtacaccaggagttggattttgtagagcgtctctcttcaagcagcgtattgtcgagaaaaaga;

SEQ ID NO: 340:
ctgcagggaggaagacgaaagttgttttttatttttttttcttttgttttctgattttgttttttttgactcgggcccagctgcgtctgtcg ggatgagaccgcggagccgaagtgcgttttctttttttgacttttttttgttttttcacaggcaagctcgcctgtgcttggagccacagaagggac agaagtcgaaggggactacagacgcgatgccgctcctccagccgtcttggaggagagatatcaggactgtagatgaaggcgagggtg aggatgaggggtggcgtggttgggaagcgacgagagtcggagagggagaagatgtttccggcttggctgcttttcctggagggtg gaaaagagacaccggaatgcgatccagacgagacgacgctttcctcgtggtgatggcggagagaattgaagagtggagaagagg gcgagggagacagagtcggaggcttggacgaagggaggaggaggggtaggagaggaatccagatgcactgtgtctgcag;

SEQ ID NO: 341:
ttgctcaaaaaatttaaaaattttattctattttcatctatattttcaccaatagcatttgctatatcatgttctaatacaggagtagtcaagcaa gaggatgtatcagttagtcaaggtcaatgagataaaagtataacatttggtgtttcagaagcttggttaaacaagaaaaaaggagataaaga agttaacaaagaagttattaatacattttttagaaaatttcaaaaaagaatttaataaactcaaaaatgcaaatgataaaaccaaaaacttcga tgacgttgattttaaagtaactccaattcaagactctactgtgttgttaaacaatttatctactgacaatcctgaattagattttggaattaatgct tcaggaaaattggtagaatttctaaaaaataatcctggtataataactcctgcattagaaacaacaactaattcttttgtatttgacaaagaaa aagataaattttatgttgatggtacagattcagatccacttgtaaaaattgctaaagaaattaataaaattttgttgaaactccatatgcaagtt gaactgatgaaaatcataagtgaaatggtaatgtttatcaaagtgtttacgatccaactgttcaagctaatttttatagaggaatgatttgaat aaaaggtaatgatgaaactctagctaaaattaaaaaagcttgaaatgataaagattgaaatacatttagaaattttggaattttacacggtaa agataattcttcttctaaattcaagttagaagaaactatattaaaaaaccactttcaaaataaatttacaacactaaatgaagacagaagcgc acatccaaacgcatataaacaaaaatctgcagatacattgggaacttagatgatttccatattgcttttcagaagaaggttctttttgcttga acacataacaaatcagcaacaaaaccttttgaaactaaagcaaatgaaaagatggaagcacttatagtaactaatccaattccgtatgatg ttggagtgtttagaaaaagtgttaaccaattagaacaaaatttaattgttcaaacattcattaatttagctaaaaataaacaagatacatatggt ccacttttagggtataatggttataaaaaaattgacaatttccaaaaagagattgtagaagtttatgaaaaagccattaaataa;

SEQ ID NO: 342:
gatgaacgctcgctgtgtgcctaatacatgcatgttgaacgggatgtagcaatacattcagtagcgaatgggtgagtaacacgtacctaa cctacctttaagactgggataactattggaaacaatagctaataccggatatagttatttatcgcatgatgagtaatagaaaggagcttcac agcttcacttaaaaatgggggtgcggaacattagttagttggtagggtaatggcctaccaagacgatgatgtttagccgggccgagagg ctgtacggccacactgggactgagatacggcccagactcctacgggaggcagcagtaaggaattttccacaatgagcgaaagcttga tggagcgacacagcgtgcaggatgaagttcttcggaatgtaaactgctgttataaggaagaaaaaatagaataggaaatgattttatctt gacggtaccttattagaaagcgacggcaaactatgtgccagcagccgcggtaatacataggtcgcgagcgttatccggaattattggg cgtaaagcgtccgtaggttttttgctaagtctggagttaaatgctgaagctcaacttcagtccgctttggatactggcaaaatagaattataa agaggttagcggaattcctagtgaagcggtggaatgcgtagatattaggaagaacaccaataggcgaaggcagctaactggttatatat tgacactaagggacgaaagcgtggggagcaaacaggattagataccctggtagtccacgccgtaaacgatgatcattagttggtggaa taatttcactaacgcagctaacgcgttaaatgatccgcctgagtagtatgctcgcaagagtgaaacttaaaggaattgacgggaacccg cacaagcggtggagcatgtggtttaatttgaagatacgcgtagaaccttaccccactcttgacatcttctgcaaagctatagagatatagtg gaggttaacagaatgacagatggtgcatggttgtcgtcagctcgtgtcgtgagatgttaggttaagtcctgcaacgagcgcaaccctttc -continued tttagttactaatattaagttaaggactctagagatactgcctgggtaaccaggaggaaggtggggacgacgtcaaatcatcatgcctctt acgagtggggcaacacacgtgctacaatggtcggtacaaagagaagcaatatggtgacatggagcaaatctcaaaaaaccgatctca gttcggattgaagtctgcaactcgacttcatgaagtcggaatcgctagtaatcgtagatcagctacgctacggtgaatacgttctcgggttt t;

SEQ ID NO: 343:
atgaaacctattaaaatagctctaattggtgctggaaatgtcggaaattctttcctttatgcagcaatgaatcaaggacttgcatccgagtat ggaattattgatattaaccctgattttgccgatggtaatgcttttgattttgaagatgcctcagcttctttgccttttccgattagtgtctcccgt tatgaatataaagatctaaaagatgctgattttattgtaattacagcgggaagaccacaaaaaccgggtgaaactcggcttgaattagtagct gataacatccgaattatccgggaaattgcactaaaagtcaaagaaagtggctttagtggaataagtattattgttgctaatcctgttgatata attacaagggcttaccgggatgcttctggattttccgatcaaaaagttatcggtagtggaactgttttagatacagcaaggcttcaattttgca atcgcaaaagagcaaaagtatcgcctaattcggttcaggcctacgtgatgggtgaacatggtgattcatctttttgttgcttattcaaatatt aaaattgccggtgaatgtttctgtgcttattctaaactaaccggaattgatagctcaaattacgaaaaagaacttgaatatccagtttctcgc cgggcttatgaaattattaatcgtaaaagggcaacattttatggaattggtgcagctattgccaaaatagtttctaatattatcaaagatacaa aaaatattatgattgccggagcaaatttacgaggagaatacggatttcacggagtaaatatcggagttccagttgttttaggggcaaacg gaattgaaaaaattattgagattagttttaatgataaagaaaagaaaaatttgccaaatcagttgcaatcattgataaaatttatcaggatgc aattaaaaatatttaa;

SEQ ID.NO. 344:
ttactttttaacatagtttctaatcaacccgttaattaattcacttcttttttgttaaacttcctttctctgcaaatgatttatcattaa atattgccagcgttttaatataattgtaggttcttttttagcgttttgttgtggttttttattttgttcgcctgggccgatttgataccaatcaa gatgaaatcattctaaagtaaagaaatttggcaaggtgtctttagggttaatctcgaatttaagacgttttacacgtttgggtactttgttggaa aaaataagaatttaccttaatcgaatccttgccagcaagaatttcatataaataggtaccattctcaacaatttctttggttttaggtacattat tatttgaattttgaactttaattacaagcccttttcctttctatcggctaaaagattaatccaattaccatcggaaatatttttgcatcaaaaa ctaaataaattgctccggtatataaagaagttgatatttctttttctggattagacgattttgactgtaatttcaaaggtttctttagctctaaac cttgatcagtttgaattgcatcttctgatttaaatattaatttattcacttaaatcttttaggataaaattcttttttatcttttccttgatttt gataattaattgttccatctaaaaacacatcgggattgaatttcttaattatatcataggcagatttattagaattaataatattattaagactaa ttttggactgagccaaaattagattttgattagttttatcaactaatttaaaatcaaaaaatagcttatttcctaaagttgagatctcatattcgc tttttgtattttcaagattataaatattagcgaaattaaaagctgttcaaatgcttgtcccaaatttttcattttctaatacagaatttgagctgc ttgtggaattaggaagtgaattttgactagtttgaggcgatgaagtggaaactggttgtgtttgctgactttgactttgaccttagcttcttctg caaaagtgcttaccttgactgttttgctgaattttctgttgttttagctagtgaaacctctggttttttcggttgtgtggggctatttttttctg tttttgagtatttgcctttgattttaagccctcaatcacggttttttagctcttgttttacttttttcctggtcttggtcgactaaatattttcccg tatttaataaataaatgcttttaagaacttcttcacttggattttccaaattagtcactgttttgctagttcaaaaagtcgatcaactcgctgtt ttatttcatttgaggataaagttttttgcatcttgatcttcaggcattgaaaattcttttaactgcttttatcgttccaaacatttgggcaacagcgg cttggtatttattaaaatcaactttagatcaacaaaaactggaagatcctggatgataaatttttttatcaatagcttttcgttttaaagaagcag taatttcaaagcgaatttttgattttcaactagttttttcttatcaacaacagaaatctgacttggatctaaaagtttgggaataatacttaaat agacagttccgattttggtattaagaaaaaaatttgtctcacttaaatcaaaaagatctttaaattcttacttttgttaaaatttgggatgtat ttacttttgaattcggagatccatatcaataatcagagaggctaattttatcttttactagtgccatttgcaaatcatctttggttttaatttgc cttgaagatttgtttcaagtcaggattttagaattttagaaatttcctgatttgaaatcgcgccgcgaacttcaagatttaaattcatagttttt tagttgaaatttgcactaaattaagtccaagaactaattttccatctttatttaacaaagttaataattttttcggtccaaaactgggtctaatt gataatctgggcctaaaaatacgggttctcctaaggaattataaagtgaaagactcgcttttgatgcaaccaaagctctttcaagtcgtgaaaat caattacttcctctttcattttcaaaattttgggcaagcaaaatttggaattccatcaaagttagatttgctcttgaaagatcaacaaaagacttg cttgaatcaatttgactaaaatcaaaattagttctagcttgttctgtatttccaaagcctttaagtacaatttgttttgaataagttatttgatcc -continued

```
ttatcagattttgcataaataacaacattttaattgaattttgatcaactactgcattttcaagatcaaaacttactaaataatcattgtttat tagttcacttaaatcaaaagcagaaacaagattataacgataaagatcacttttggcagcagttaaaactgttttgccgatcattttttaaaatt atctttaattttaagatttaaaacaattgaatcaaattttcctgactaattttagcattttttgctactttagctgactcgggatctgatttag ataagaataatatgatttattataagaattaattccgacaactgtaccaacagcggctgataaactaagactaattccggcaattgttgttattaa tcaaaaaggttttttaagtaattttgctaacttcat
```

Preferably, the primer group comprises a primer group 1 and a primer group 2, wherein the primer group 1 comprises primer sequences set forth in singular sequence numbers in SEQ ID NO: 1 to SEQ ID NO: 302, and the primer group 2 comprises primer sequences set forth in double sequence numbers in SEQ ID NO: 1 to SEQ ID NO: 302.

The present invention further provides a multiplex PCR reagent for simultaneous detection of 15 porcine pathogens through high-throughput targeted amplicon sequencing, comprising a PCR reagent 1 and a PCR reagent 2, wherein the PCR reagent 1 comprises the primer group 1, and the PCR reagent 2 comprises the primer group 2.

The present invention mainly aims at a specific primer of the pathogenic gene. However, because the sequencing platform requirements of each sequencing company are inconsistent, other corresponding reagents can be added according to different platforms when the primer sequence is synthesized. The PCR reagent 1 and the PCR reagent 2 further comprise necessary reagents required in the PCR amplification process, and the requirements on an amplification system are different and can be adjusted adaptively.

Preferably, each primer in the primer group 1 has a concentration of 10 nmol/μL in the PCR reagent 1, and each primer in the primer group 2 has a concentration of 10 nmol/μL in the PCR reagent 2.

The present invention further provides a kit for simultaneous detection of 15 porcine pathogens through high-throughput targeted amplicon sequencing, comprising the primer group or the multiplex PCR reagent.

The present invention further provides use of the primer group or the multiplex PCR reagent or the kit in constructing a high-throughput amplicon sequencing library for simultaneous detection of 15 porcine respiratory pathogens.

The present invention further provides use of the primer group or the multiplex PCR reagent or the kit in high-throughput amplicon sequencing for simultaneous detection of 15 porcine respiratory pathogens.

The present invention further provides use of the primer group or the multiplex PCR reagent or the kit in detecting 15 porcine respiratory pathogenic genes in a test sample.

The present invention further provides a method for detecting 15 porcine respiratory pathogenic genes in a test sample, which aims at non-disease diagnosis and treatment and comprises the following steps:
1) performing multiplex PCR reagent on a test sample by using the PCR reagent 1 and the PCR reagent 2 in the multiplex PCR reagent separately to obtain a multiplex PCR amplification product 1 and a multiplex PCR amplification product 2;
2) mixing the multiplex PCR amplification product 1 and the multiplex PCR amplification product 2 to prepare an amplicon library; and
3) sequencing the amplicon library to detect 15 porcine respiratory pathogenic genes in the test sample.

The present invention has the technical effects and advantages as follows.

The present invention provides a primer group for simultaneous detection of 15 porcine pathogens through high-throughput targeted amplicon sequencing and use thereof, wherein the pathogens comprise 7 viral pathogens, namely, African swine fever virus, porcine reproductive and respiratory syndrome virus (North American type NA/European type EU), pseudorabies virus, porcine circovirus (type 2 and type 3), swine fever virus, foot and mouth diseases virus, and swine influenza A virus; 4 bacterial pathogens, namely, haemophilus parasuis, *Pasteurella multocida*, *Actinobacillus pleuropneumoniae*, and *Streptococcus suis*; and 4 other types of pathogens, namely, Eperythrozoon suis, *Toxoplasma gondii*, *Mycoplasma hyorhinis*, and *Mycoplasma hyopneumoniae*. The present invention particularly relates to target genes corresponding to target pathogens, wherein each pathogen comprises 2 to 8 different target genes, and the total number of the target genes is 42, so that the present invention aims to implement the simultaneous and rapid detection of 15 pathogens by sequencing the target genes of the target pathogens, further implements the simultaneous and rapid detection of multiple pathogens of diseased pigs, and closely associate diseased animals, infection pathogens, and the pathogenic target genes.

The present invention comprises a primer combination that is called Primer Pool and comprises 151 pairs of primers in total, a size range of amplicon fragments corresponding to each pair of primers is 100-150 bp, which can efficiently and specifically amplify pathogenic target genes; in addition, the present invention further provides an amplicon sequencing detection analysis method for 42 target genes of 15 porcine respiratory pathogens, which has the technical advantages of rapidness, high efficiency, high targeting, strong specificity, and the like, and is suitable for rapid and accurate simultaneous diagnosis of multiple pathogens of diseased pigs in pig farms.

BRIEF DESCRIPTION OF THE DRAWINGS

FIG. 3 shows details of pathogens and target genes thereof contained in the amplicon sequencing panel.

DETAILED DESCRIPTION OF THE EMBODIMENTS

Figure 1:
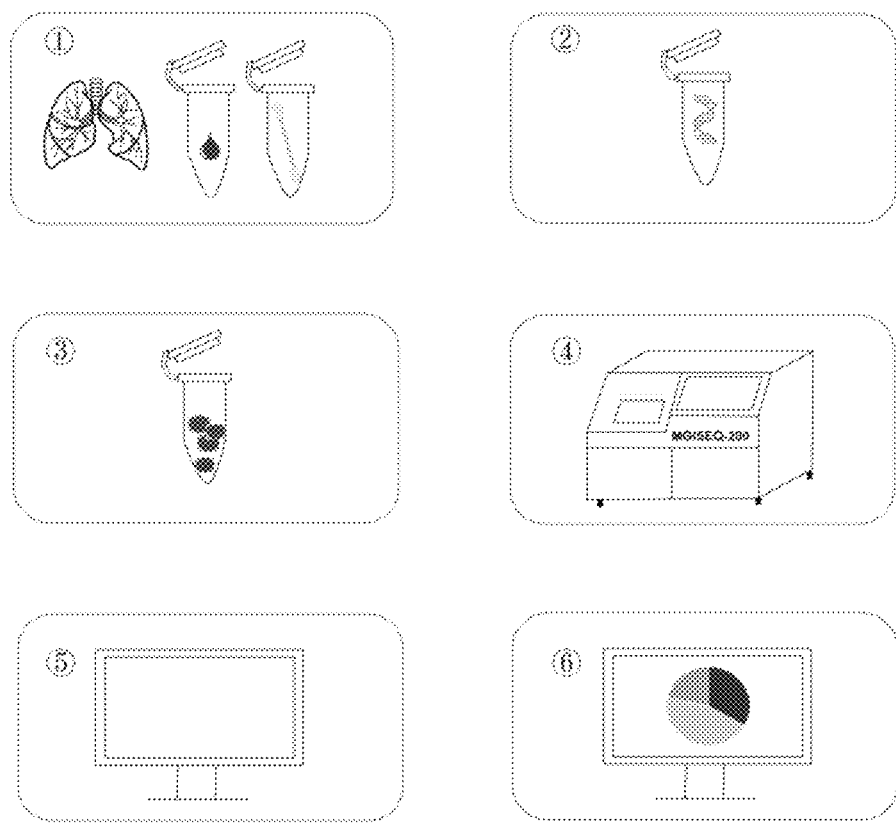
FIG. 1 is a simplified flow chart of high-throughput amplicon sequencing.
Figure 2:
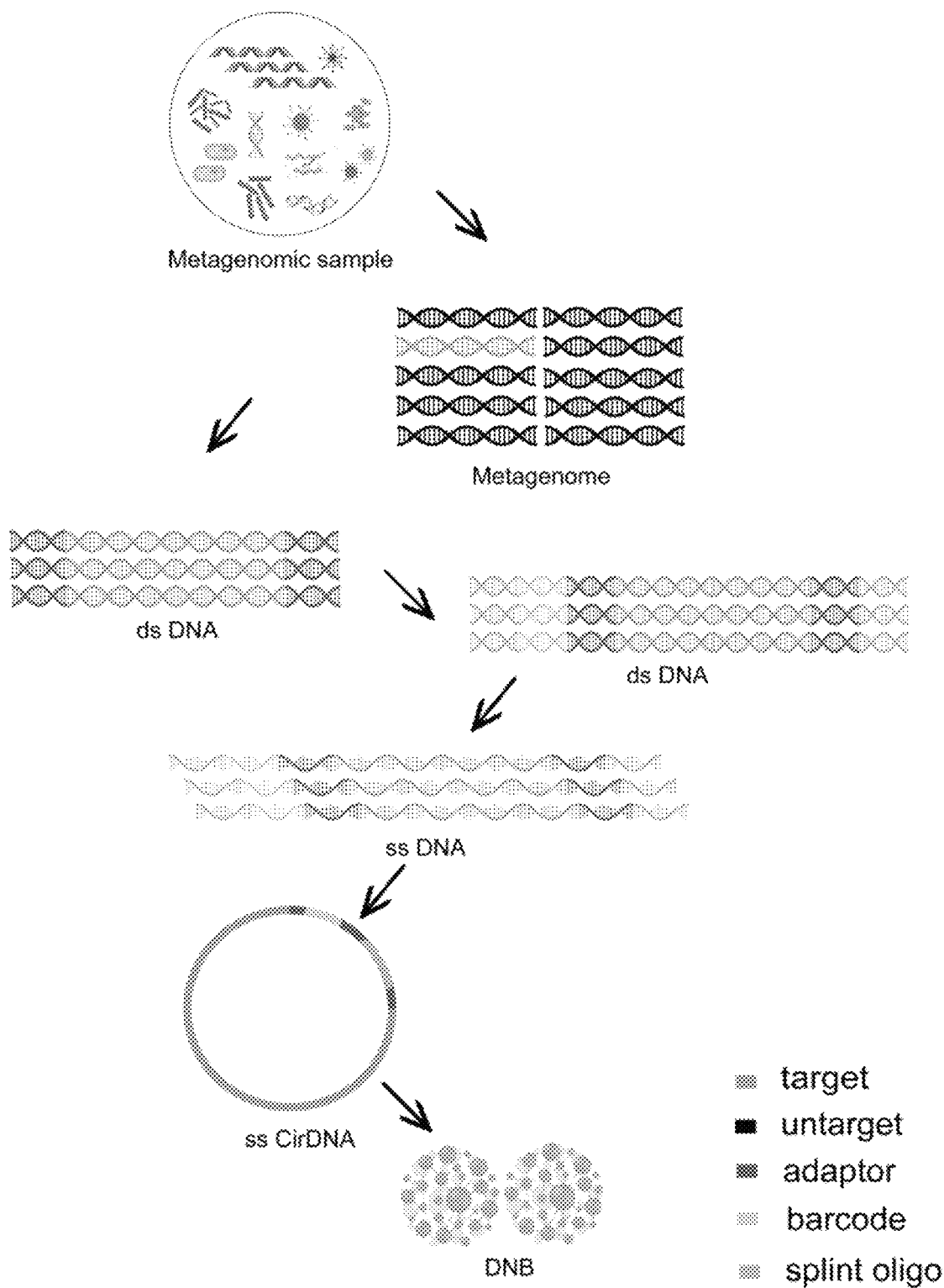
FIG. 2 is a schematic diagram of amplicon sequencing library construction.
Figure 4:
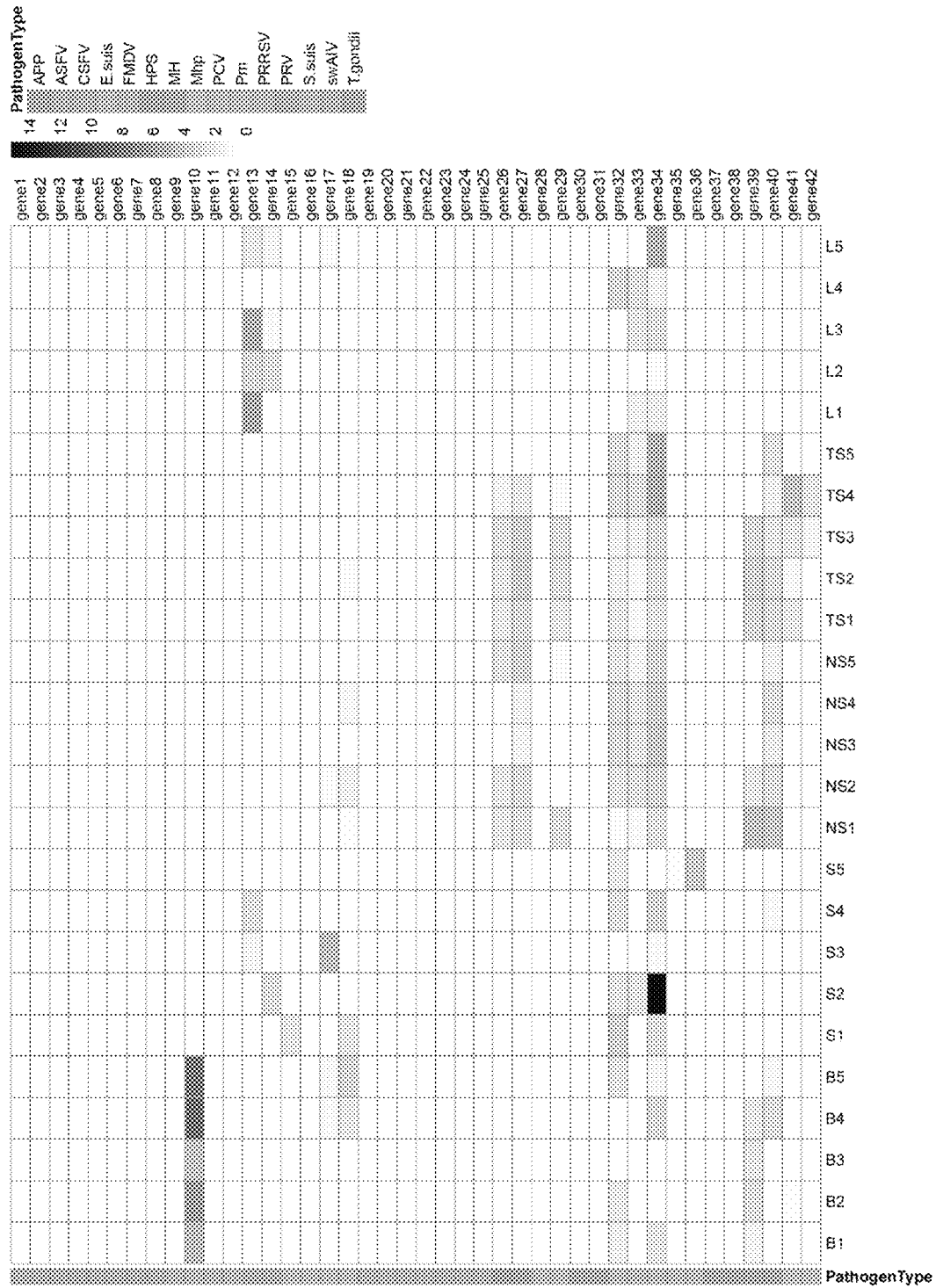
FIG. 4 shows distribution of target genes detected in Embodiment 1.
Figure 5:
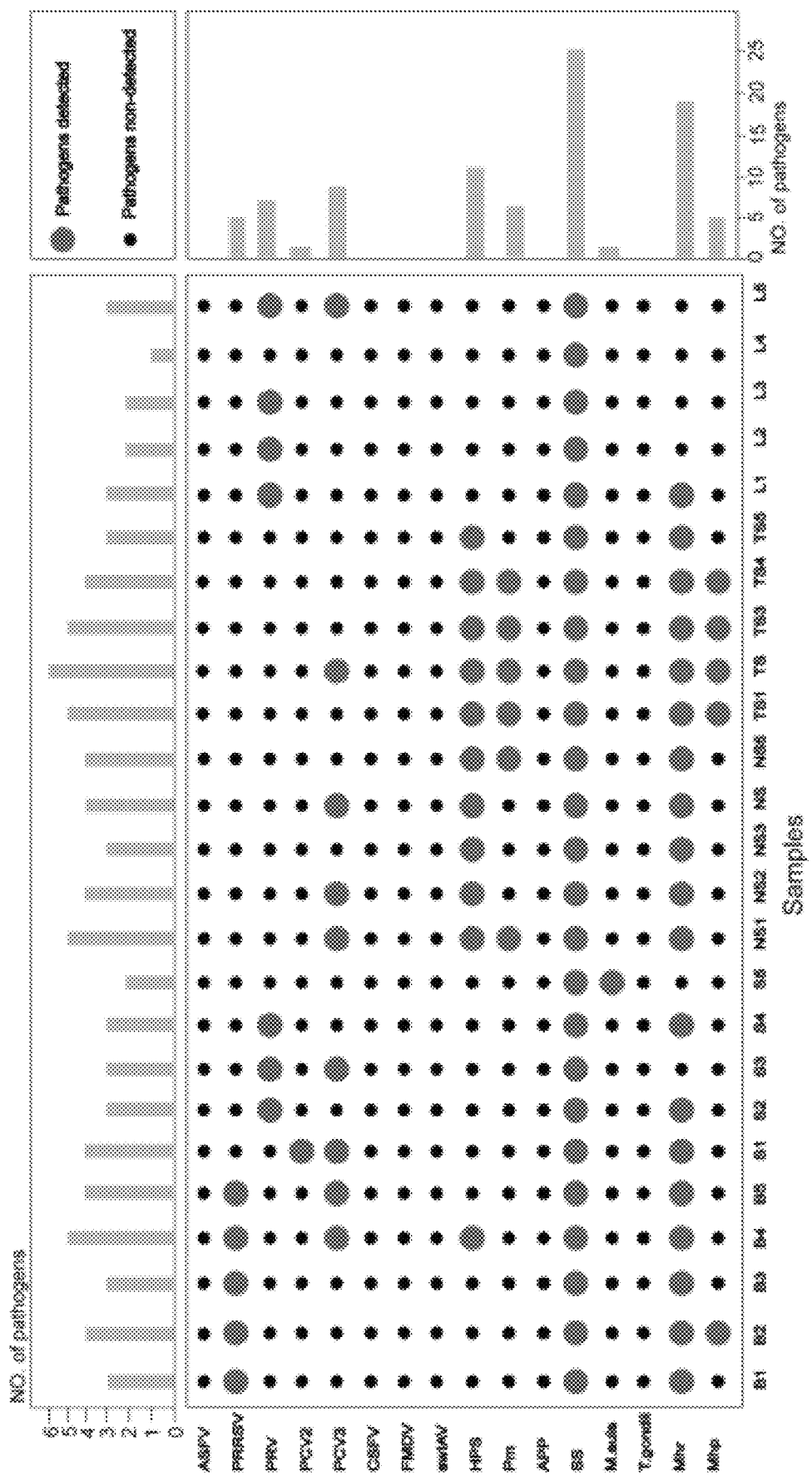
FIG. 5 shows detection results of pathogens in Embodiment 1.

Unless otherwise stated, the methods used in the following examples are conventional methods.

The materials, reagents, and the like used in the following examples can be commercially available unless otherwise stated.

The technical solutions provided by the present invention will be described in detail below with reference to the examples, which, however, should not be construed as limiting the scope of the present invention.

TABLE 1

Main reagents and instruments

Main reagents

| Name | Supplier | Cat. No. |
|---|---|---|
| HiPure MicroBiome DNA Kit | Magen | D3148-03 |
| TIANamp Virus DNA/RNA Kit | TIANGEN | DP315 |
| GoScript ™ Reverse Transcription Mix, Random Primers | Promega | A2801 |
| ATOPlex customized Panel | MGI | Customization |
| ATOPlex DNA multiplex PCR universal library constructing module | MGI | 1000021191 |
| ATOPlex single-label primer module (01-96) | MGI | 1000024934 |
| MGIEasy circularization module | MGI | 1000005260 |
| MGIEasy DNA purification magnetic bead kit | MGI | 1000007325 |
| MGISEQ-200RS high-throughput sequencing reagent set (FCS PE100) | MGI | 1000019846 |

Instruments

| NAMES | BRANDS |
|---|---|
| MGISEQ-200 | MGI |
| PCR instrument | ABI |
| Qubit ™ 4 Fluorometer | Thermo Fisher |
| NanoDrop | Thermo Fisher |
| Minute Centrifuge (MINI-6KC) | MIULAB |

TABLE 1-continued

Main reagents and instruments

| | |
|---|---|
| Vortex Mixers | MIULAB |
| DynaMag ™-2 | Invitrogen by Fisher Scientific |
| Pipettor | Eppendorf |

Embodiment 1

1. Preparation of Primer Group for Simultaneous Detection of 15 Porcine Pathogens Through High-Throughput Targeted Amplicon Sequencing According to literature reference, common porcine pathogens were selected through statistics and analysis, pathogenic target genes were determined, a complete gene sequence was downloaded on NCBI (https://www.ncbi.nlm.nih.gov/) according to the names of the target genes, a specificity of the target genes was further determined through NCBI Blast, and finally the sequences of the pathogenic target genes were obtained, wherein the nucleotide sequences of the pathogenic target genes were set forth in SEQ ID NO: 303 to SEQ ID NO: 344.

Finally, designing, analysis and comparison were performed many times according to the target gene sequences, wherein each gene was designed with 2-4 pairs of specific primers, and the total number of primers was 151 pairs of primers, and the nucleotide sequences of the primers were set forth in SEQ ID NO: 1 to SEQ ID NO: 302. The primers were synthesized by MGI Tech Co., Ltd., according to the company's library construction kit combined with this group of specific primers, the specific adapter sequence "GACATGGCTACGATCCGACTT" (SEQ ID NO: 345) was added to a 5'-end of each forward primer (F primer), the specific adapter sequence "CGCTTGGCCTCCGACTT" (SEQ ID NO: 346) was added to a 5'-end of each reverse primer (R primer), and finally the primer pool sequence for constructing the amplicon sequencing library was obtained.

TABLE 2

Sequences of a primer group for simultaneous detection of 15 porcine pathogens through high-throughput targeted amplicon sequencing

| | F ID | F seq |
|---|---|---|
| SEQ ID NO: 1 | ASFV-p72-F-1 | GACTCAAAGTGGGTTCGGG |
| SEQ ID NO: 3 | ASFV-p72-F-2 | AAAATGACTGGATATAAGCACTTGGTTG |
| SEQ ID NO: 5 | ASFV-p72-F-3 | AGCGAACGCGTTTTACAAAA |
| SEQ ID NO: 7 | ASFV-p72-F-4 | CGCAGCACAGCTGAACC |
| SEQ ID NO: 9 | ASFV-p54-F-1 | AAACTGTATATCTTCCTCCTCAATAGCA |
| SEQ ID NO: 11 | ASFV-p54-F-2 | CGTAACTGGGTTGTCCGTAA |
| SEQ ID NO: 13 | ASFV-p54-F-3 | GCAGACCGGCAACAAACAG |
| SEQ ID NO: 15 | ASFV-p54-F-4 | ATGCGTATAGGTGTTTCTTTGTCG |
| SEQ ID NO: 17 | ASFV-EP402R-F-1 | TGACATTGTTCTTCTTCATTAGATTCAG |
| SEQ ID NO: 19 | ASFV-EP402R-F-2 | GGACATGGTTTGGGTGGAG |
| SEQ ID NO: 21 | ASFV-EP402R-F-3 | TACATGCGTCCCTCAACACA |
| SEQ ID NO: 23 | ASFV-EP402R-F-4 | GTGAATAAGCGAAATATTTTGGGTAGA |
| SEQ ID NO: 25 | ASFV-MGF505-1R-F-1 | ACAGTTGTTTCCTGCTCGTTGAATA |
| SEQ ID NO: 27 | ASFV-MGF505-1R-F-2 | TGTTGCCACTTACAATTCAACAA |

TABLE 2-continued

Sequences of a primer group for simultaneous detection of 15 porcine pathogens through high-throughput targeted amplicon sequencing

| | | |
|---|---|---|
| SEQ ID NO: 29 | ASFV-MGF505-1R-F-3 | AGGTAAAAACGCTCATGATGCTA |
| SEQ ID NO: 31 | ASFV-MGF505-1R-F-4 | TTATGGGCAATAGCACATTCAAAGGTA |
| SEQ ID NO: 33 | ASFV-MGF505-2R-F-1 | TGAGATCCCGTCGTATGAGT |
| SEQ ID NO: 35 | ASFV-MGF505-2R-F-2 | GCAGAAAAATATCTTACCATCTTTTCCA |
| SEQ ID NO: 37 | ASFV-MGF505-2R-F-3 | TTGCTCAAAACGCGGCCA |
| SEQ ID NO: 39 | ASFV-MGF505-2R-F-4 | CTTTAGAACGTTTTTGTGGTGTTTCATG |
| SEQ ID NO: 41 | ASFV-MGF360-13L-F-1 | CCGCTCTCTCTGCAGACC |
| SEQ ID NO: 43 | ASFV-MGF360-13L-F-2 | TTTGGATATTTACAGCTCAGATGCTTC |
| SEQ ID NO: 45 | ASFV-MGF360-13L-F-3 | CCAAAGAAACTCTAGAGGACAACG |
| SEQ ID NO: 47 | ASFV-MGF360-13L-F-4 | GACATATCATGTCATGGACGTCT |
| SEQ ID NO: 49 | ASFV-MGF360-14L-F-1 | AGTGACTATGATTATACGTTGCAGC |
| SEQ ID NO: 51 | ASFV-MGF360-14L-F-2 | GTTTCCAAGAGTGGATTATGACAAAA |
| SEQ ID NO: 53 | ASFV-MGF360-14L-F-3 | CCCTGGCATTACGACATAATTTTACAAA |
| SEQ ID NO: 55 | ASFV-K205R-F-1 | TTGAGCCACGCGAACAGT |
| SEQ ID NO: 57 | ASFV-K205R-F-2 | AAAAACAACGATTAAGGAGGCTATGC |
| SEQ ID NO: 59 | ASFV-K205R-F-3 | CGAGAAAAGTTTTTAACACCAGAAATTC |
| SEQ ID NO: 61 | PRRSV(NA)-orf6-F-1 | CGTCTCTAGACGACTTCTGC |
| SEQ ID NO: 63 | PRRSV(NA)-orf6-F-2 | TGAAAGCCCGCGGCAC |
| SEQ ID NO: 65 | PRRSV(NA)-orf6-F-3 | CAAGGTTTACCACTCCCTGCT |
| SEQ ID NO: 67 | PRRSV(NA)-orf7-F-1 | AACAACGGCAGACAGCAAA |
| SEQ ID NO: 69 | PRRSV(NA)-orf7-F-2 | CCATTTCCCTCTAGCGACTGAAG |
| SEQ ID NO: 71 | PRRSV(EU)-orf6-F-1 | AGTCGGCCGCGTGACA |
| SEQ ID NO: 73 | PRRSV(EU)-orf6-F-2 | CTGTGGGGTATTTATAGCTTCACAGA |
| SEQ ID NO: 75 | PRRSV(EU)-orf6-F-3 | GGTAACCGAGCATACGCTGTG |
| SEQ ID NO: 77 | PRRSV(EU)-orf7-F-1 | TCAGGCTTTTCTTTTTGGCCTG |
| SEQ ID NO: 79 | PRRSV(EU)-orf7-F-2 | ACCTTCCCGCTGGATGAA |
| SEQ ID NO: 81 | PRV-gE-F-1 | CCGTCCACGTAGATCGGG |
| SEQ ID NO: 83 | PRV-gE-F-2 | GAGGGCCGAGCCGAAG |
| SEQ ID NO: 85 | PRV-gE-F-3 | CAGACGTCGAAGCGGAG |
| SEQ ID NO: 87 | PRV-gE-F-4 | GGCGAGAAGAGCTGCG |
| SEQ ID NO: 89 | PRV-gB-F-1 | TGGCGGTCTTTGGCGC |
| SEQ ID NO: 91 | PRV-gB-F-2 | ACCTCCTCGACGATGCAG |
| SEQ ID NO: 93 | PRV-gB-F-3 | CTGCAGTTCACCTACGACCAC |
| SEQ ID NO: 95 | PRV-gB-F-4 | CCGCAACCCCATGAAGG |
| SEQ ID NO: 97 | PCV2-cap-F-1 | TCCAAGGAGGCGTTACCGAA |
| SEQ ID NO: 99 | PCV2-cap-F-2 | TCAATAGTGGAATCTAGGACAGGT |
| SEQ ID NO: 101 | PCV2-cap-F-3 | TCCTACCACTCCCGGTACTTTAC |
| SEQ ID NO: 103 | PCV2-rep-F-1 | GCAAGAAGAGTGGAAGAAGCG |
| SEQ ID NO: 105 | PCV2-rep-F-2 | GCAGTATTCTGATTACCAGCAATCA |

TABLE 2-continued

Sequences of a primer group for simultaneous detection of 15 porcine pathogens through high-throughput targeted amplicon sequencing

| SEQ ID NO: 107 | PCV2-rep-F-3 | CTTACTGATAGAATGTGGAGCTCCTAGA |
| --- | --- | --- |
| SEQ ID NO: 109 | PCV2-rep-F-4 | GCCAGCCATAAAAGTCATCAATAAC |
| SEQ ID NO: 111 | PCV3-cap-F-1 | TGGTGGAGTATTTCTTTGTGTAGTATGT |
| SEQ ID NO: 113 | PCV3-cap-F-2 | GATACTAAAGATGAAAGTTACACTCAGC |
| SEQ ID NO: 115 | PCV3-cap-F-3 | CCGTAGAAGTCTGTCATTCCAGTTTT |
| SEQ ID NO: 117 | PCV3-rep-F-1 | GAGGGAAAGCCCGAAACAC |
| SEQ ID NO: 119 | PCV3-rep-F-2 | GGAGTGGTATTCATCGGAGAATATTCG |
| SEQ ID NO: 121 | PCV3-rep-F-3 | CCCGACGTCTCCGTCAG |
| SEQ ID NO: 123 | PCV3-rep-F-4 | GTAAACCGCGTGATTTTAAAACTG |
| SEQ ID NO: 125 | CSFV-5'UTR-F-1 | GCAAGTCACAGCGCACT |
| SEQ ID NO: 127 | CSFV-5'UTR-F-2 | TTGATGATATTGAGTTTTGCTCCCATAC |
| SEQ ID NO: 129 | CSFV-5'UTR-F-3 | GGACCAACTTCATCTCAAGACTTGTA |
| SEQ ID NO: 131 | CSFV-5'UTR-F-4 | TGGATTTTGTGACATGATCTCCAT |
| SEQ ID NO: 133 | CSFV-E2-F-1 | AGTGCTTGATCGGTAACACAACT |
| SEQ ID NO: 135 | CSFV-E2-F-2 | GTTCTGTTAGAACTATGTAGGTCACTAT |
| SEQ ID NO: 137 | CSFV-E2-F-3 | GAAGTGAGTGAAGCCTCCTTAT |
| SEQ ID NO: 139 | CSFV-E2-F-4 | TGTGGTGGTCGCACAATC |
| SEQ ID NO: 141 | FMDV-polyprotein-F-1 | CCCAGTGGCCAATTCCTCA |
| SEQ ID NO: 143 | FMDV-polyprotein-F-2 | TTCAAAGCGACAGGCTTCTT |
| SEQ ID NO: 145 | FMDV-polyprotein-F-3 | ACACTTCCACATGGATTATGGAACTG |
| SEQ ID NO: 147 | FMDV-polyprotein-F-4 | GGTTGTGTCTGTGGATCCC |
| SEQ ID NO: 149 | FMDV-5'UTR-F-1 | GAAAGGCGCCGGCCTC |
| SEQ ID NO: 151 | FMDV-5'UTR-F-2 | GGAACCGATGGACTTTCGTTCA |
| SEQ ID NO: 153 | FMDV-5'UTR-F-3 | TTCTTGTCCGAAGTTAGAGGGCT |
| SEQ ID NO: 155 | FMDV-5'UTR-F-4 | ACCATGCTCCGCTACGA |
| SEQ ID NO: 157 | swIAV-M-F-1 | GGATTGGTCTTGTCTTTAGCCA |
| SEQ ID NO: 159 | swIAV-M-F-2 | GACTGCAGCGTAGACGCTTT |
| SEQ ID NO: 161 | swIAV-M-F-3 | GATCCAGCCATTTGTTCCATG |
| SEQ ID NO: 163 | swIAV-M-F-4 | CATTCGTTTCTGATAGGCCTGTA |
| SEQ ID NO: 165 | swIAV-H1-F-1 | ACTGTTACATTCTTTTCTAGTACTGTGT |
| SEQ ID NO: 167 | swIAV-H1-F-2 | ATACCATCCATCTATCATTCCTGTCC |
| SEQ ID NO: 169 | swIAV-H1-F-3 | TGGTAAATCCTTGTTGATTCCAGCTTTA |
| SEQ ID NO: 171 | swIAV-H1-F-4 | TCTGGTAGAGACTTTGTTGGTCAGT |
| SEQ ID NO: 173 | swIAV-H3-F-1 | AAACTGTAATCCCGAATATCGGATCTAG |
| SEQ ID NO: 175 | swIAV-H3-F-2 | GTACGGTTTCAGGCATCAAAATTCTG |
| SEQ ID NO: 177 | swIAV-H3-F-3 | ATTCCTTATTTTGGAAGCCATCAC |
| SEQ ID NO: 179 | HPS-vtaA-F-1 | TTCTACGATAAATTTCAATGTTATCGCC |
| SEQ ID NO: 181 | HPS-vtaA-F-2 | AGAACAATCTATTGTCTTAGGCACAGG |

TABLE 2-continued

Sequences of a primer group for simultaneous detection of 15 porcine pathogens through high-throughput targeted amplicon sequencing

| SEQ ID NO: 183 | HPS-vtaA-F-3 | CTTGTCCTGGATCGCCTTTATC |
| --- | --- | --- |
| SEQ ID NO: 185 | HPS-vtaA-F-4 | ATACCCGCTCTTGCATTAACAATATC |
| SEQ ID NO: 187 | HPS-infB-F-1 | AGTAGCAGCAGGTGAAGCT |
| SEQ ID NO: 189 | HPS-infB-F-2 | ACGGATATCGTTGTTCTTGTAGTAGC |
| SEQ ID NO: 191 | HPS-infB-F-3 | AACAAGAGTTATTACAACACGAAGTGAT |
| SEQ ID NO: 193 | Pm-plpE-F-1 | AAGAAGGCTCACTATTTGATTGAACC |
| SEQ ID NO: 195 | Pm-plpE-F-2 | TTGTCGGGTCCTGTAGGG |
| SEQ ID NO: 197 | Pm-plpE-F-3 | CCTTTAAAGCCCCTCTAGAACAAGAAA |
| SEQ ID NO: 199 | Pm-kmt1-F-1 | TTCGCTGCAATCGGTTCAT |
| SEQ ID NO: 201 | Pm-kmt1-F-2 | TGATAGCCATGCAATGCCA |
| SEQ ID NO: 203 | Pm-kmt1-F-3 | TTTGATGTGGTAGGACTGCCA |
| SEQ ID NO: 205 | Pm-kmt1-F-4 | AGTTTCATTTTCGCCTAACCCA |
| SEQ ID NO: 207 | APP-om1A-F-1 | GGACATATCAACCTTAGGTGTAAGTTCC |
| SEQ ID NO: 209 | APP-om1A-F-2 | GGTATTTTCGGTAAAAATGGCGAAGTA |
| SEQ ID NO: 211 | APP-om1A-F-3 | AAAAATATGGCTCCACAAATGGGTAATC |
| SEQ ID NO: 213 | APP-om1A-F-4 | CTTCTACAGAAGCCTTTAATTTCTGATT |
| SEQ ID NO: 215 | APP-apxIVA-F-1 | AATAAACCGGACGGAAATAATGGGAATA |
| SEQ ID NO: 217 | APP-apxIVA-F-2 | CGATAAGTTATTATCTTTTTGGCTACCT |
| SEQ ID NO: 219 | APP-apxIVA-F-3 | GGATTTACTCGAACGCGCCTATA |
| SEQ ID NO: 221 | APP-apxIVA-F-4 | TGCTCATTCGATAAACGAATATTTTCT |
| SEQ ID NO: 223 | *S.suis*-gdh-F-1 | GCTTCAAAAACAGGCTCAAGTGTA |
| SEQ ID NO: 225 | *S.suis*-gdh-F-2 | GTATCGACTTCGACCTCTTGGTG |
| SEQ ID NO: 227 | *S.suis*-gdh-F-3 | GTTAGCACCTGCAAGGTAGT |
| SEQ ID NO: 229 | *S.suis*-gdh-F-4 | GATCGGTTACATGTACGGTCAATACAA |
| SEQ ID NO: 231 | *S.suis*-recN-F-1 | CCTGCTCGTTCAACCAATTCTTTC |
| SEQ ID NO: 233 | *S.suis*-recN-F-2 | AAAGGAAAAGAGCCCTTCAATCTCA |
| SEQ ID NO: 235 | *S.suis*-recN-F-3 | GAGACGGACACGAGAAACG |
| SEQ ID NO: 237 | *S.suis*-recN-F-4 | GAGCAGTTTATCGCGTTCCTGA |
| SEQ ID NO: 239 | *S.suis*-gapdh-F-1 | TATTTCAACAAGTGTGCAAGCATTACTG |
| SEQ ID NO: 241 | *S.suis*-gapdh-F-2 | GAAGTACTCAAGAGTACGAACAAGTTG |
| SEQ ID NO: 243 | *S.suis*-gapdh-F-3 | CCTGAGATAACTGTTTCAGTACCAT |
| SEQ ID NO: 245 | *S.suis*-gapdh-F-4 | ACAGAACCTGTTGGAACTGGA |
| SEQ ID NO: 247 | *E.suis*-ppa-F-1 | TACAGAGAAATTAGATAGCACTACTACA |
| SEQ ID NO: 249 | *E.suis*-ppa-F-2 | ATGGATATATTTCTGATACTCTAGCAGA |
| SEQ ID NO: 251 | *E.suis*-ppa-F-3 | AAAAGTTTCTCAATTCAGCAATTCAAT |
| SEQ ID NO: 253 | *E.suis*-g1-F-1 | TGAGTAAGAACTTTAATGTCAACTACGT |
| SEQ ID NO: 255 | *E.suis*-g1-F-2 | AATGAAACCCTTGCTTATGTAGAAGATC |
| SEQ ID NO: 257 | *E.suis*-g1-F-3 | GGTAATTTGAGTATGGTTTACGTTGTA |
| SEQ ID NO: 259 | *E.suis*-g1-F-4 | AATTAATTCTGGATTCATGACAACAGTT |

TABLE 2-continued

Sequences of a primer group for simultaneous detection of 15 porcine pathogens through high-throughput targeted amplicon sequencing

| | | |
|---|---|---|
| SEQ ID NO: 261 | T.gondii-B1-F-1 | AGGAAACAGGTGGTCGACT |
| SEQ ID NO: 263 | T.gondii-B1-F-2 | GCATTTGCCATGAGAGGAGG |
| SEQ ID NO: 265 | T.gondii-B1-F-3 | GCAGCGTCTCTTCCTCTTTT |
| SEQ ID NO: 267 | T.gondii-B1-F-4 | CACCTAGTATCGTGCGGCAAT |
| SEQ ID NO: 269 | T.gondii-RE-F-1 | TCGGCTCCGCGGTCTC |
| SEQ ID NO: 271 | T.gondii-RE-F-2 | CTTCTCCCTCTCCGACTCTC |
| SEQ ID NO: 273 | T.gondii-RE-F-3 | TGAAGGCGAGGGTGAGGAT |
| SEQ ID NO: 275 | T.gondii-RE-F-4 | CCCTCCTCCTCCCTTCG |
| SEQ ID NO: 277 | Mhr-p37-F-1 | TTCAAAAGGTTTTGTTGCTGATTTGTTA |
| SEQ ID NO: 279 | Mhr-p37-F-2 | AAAAGTGGACCATATGTATCTTGTTTAT |
| SEQ ID NO: 281 | Mhr-p37-F-3 | CATTTGGTGTTTCAGAAGCTTGGTTAA |
| SEQ ID NO: 283 | Mhr-16SrRNA-F-1 | GCTCGCTGTGTGCCTAATAC |
| SEQ ID NO: 285 | Mhr-16SrRNA-F-2 | GTCGTCCCCACCTTCCTC |
| SEQ ID NO: 287 | Mhr-16SrRNA-F-3 | CGCCTATTGGTGTTCTTCCTA |
| SEQ ID NO: 289 | Mhp-p36-F-1 | AGATCTTTATATTCATAACGGGAGACAC |
| SEQ ID NO: 291 | Mhp-p36-F-2 | GAATTATCCGGGAAATTGCACTAAAAGT |
| SEQ ID NO: 293 | Mhp-p36-F-3 | GGCGAGAAACTGGATATTCAAGTT |
| SEQ ID NO: 295 | Mhp-p102-F-1 | TGGACTGAGCCAAAATTAGATTTTG |
| SEQ ID NO: 297 | Mhp-p102-F-2 | ACTTTAGAATGATTTCATCTTGATTGGT |
| SEQ ID NO: 299 | Mhp-p102-F-3 | TTAGCCTCTCTGATTATTGATATGGATC |
| SEQ ID NO: 301 | Mhp-p102-F-4 | TTTGGCAGCAGTTAAAACTGTT |
| | R ID | R seq |
| SEQ ID NO: 2 | ASFV-p72-R-1 | GCATCAGGAGGAGCTTTTTGTCTTA |
| SEQ ID NO: 4 | ASFV-p72-R-2 | GCTGCGTATCATTTTCATCGG |
| SEQ ID NO: 6 | ASFV-p72-R-3 | GCTTTAAACCATGGTTTATCCCAGG |
| SEQ ID NO: 8 | ASFV-p72-R-4 | CCAGTGGTCATATTAACGTATCCAGAG |
| SEQ ID NO: 10 | ASFV-p54-R-1 | CCAGTCACTACACCAAGCTTCTT |
| SEQ ID NO: 12 | ASFV-p54-R-2 | ATCAGCAGTGGGTAGAAGTCACT |
| SEQ ID NO: 14 | ASFV-p54-R-3 | CGGATGAGCAGGAGCACT |
| SEQ ID NO: 16 | ASFV-p54-R-4 | ATGGCAACTGGCGGGC |
| SEQ ID NO: 18 | ASFV-EP402R-R-1 | ATATTCCATTAAGCATCATAATTGGGAT |
| SEQ ID NO: 20 | ASFV-EP402R-R-2 | CATACATGAACCATCTCCCAGAG |
| SEQ ID NO: 22 | ASFV-EP402R-R-3 | CTAGGTAGTGGTTTGGGTGGAGA |
| SEQ ID NO: 24 | ASFV-EP402R-R-4 | CCTAAACCATGTCCTTCAGCTGAAT |
| SEQ ID NO: 26 | ASFV-MGF505-1R-R-1 | GTTCTCTCTCCAGAACTTATGTCG |
| SEQ ID NO: 28 | ASFV-MGF505-1R-R-2 | GAAAATGTATCCATACATCGAACGACA |
| SEQ ID NO: 30 | ASFV-MGF505-1R-R-3 | TTAGAATAAATGGATGGATAGTCCTGTA |
| SEQ ID NO: 32 | ASFV-MGF505-1R-R-4 | GAGGATGATTTGCCCTTCACTCATT |

TABLE 2-continued

Sequences of a primer group for simultaneous detection of 15 porcine pathogens through high-throughput targeted amplicon sequencing

| SEQ ID NO: 34 | ASFV-MGF505-2R-R-1 | TTTCCCTTCAAGACCTTTGCCG |
| --- | --- | --- |
| SEQ ID NO: 36 | ASFV-MGF505-2R-R-2 | AACTACTCCGTGAAACGCAT |
| SEQ ID NO: 38 | ASFV-MGF505-2R-R-3 | AGATTTCCAGGATACTATAGCAAGATTT |
| SEQ ID NO: 40 | ASFV-MGF505-2R-R-4 | CATAGGCATGCTAGTTCAAATAGGGT |
| SEQ ID NO: 42 | ASFV-MGF360-13L-R-1 | GATTTTATTTGTATTCGGCCACGAT |
| SEQ ID NO: 44 | ASFV-MGF360-13L-R-2 | AGAATATTCCCAAATGATGGATAAGTTT |
| SEQ ID NO: 46 | ASFV-MGF360-13L-R-3 | GCCCCTTAATTGTATAACAAATTTGTTT |
| SEQ ID NO: 48 | ASFV-MGF360-13L-R-4 | GTAAGGACGCCATTTGTTTTCT |
| SEQ ID NO: 50 | ASFV-MGF360-14L-R-1 | CTTTACTAGCGCCGCTTCGA |
| SEQ ID NO: 52 | ASFV-MGF360-14L-R-2 | CTTAACGCCTGTATCCGAACCC |
| SEQ ID NO: 54 | ASFV-MGF360-14L-R-3 | TGCAAATCTCTTTTTCACGACACAAC |
| SEQ ID NO: 56 | ASFV-K205R-R-1 | TATCGTAACGTTCTATAAAGTTTTCGAA |
| SEQ ID NO: 58 | ASFV-K205R-R-2 | CGCTACGCGTGAAGAACAT |
| SEQ ID NO: 60 | ASFV-K205R-R-3 | ATCATCTCTTTGACCATTTTCTTCTGTT |
| SEQ ID NO: 62 | PRRSV(NA)-orf6-R-1 | ATTCAGAAAGATCAAAAGGTGCAG |
| SEQ ID NO: 64 | PRRSV(NA)-orf6-R-2 | CTTCTTTGGGGAGTGTACTCAGC |
| SEQ ID NO: 66 | PRRSV(NA)-orf6-R-3 | TTGTCGTCCGGCGTCC |
| SEQ ID NO: 68 | PRRSV(NA)-orf7-R-1 | GGCTTCTCCGGGTTTCTATTCTT |
| SEQ ID NO: 70 | PRRSV(NA)-orf7-R-2 | TGTAACTTATTCTCCCTGAGTCTG |
| SEQ ID NO: 72 | PRRSV(EU)-orf6-R-1 | AAGCCTAGATGATTTCTGCTTCG |
| SEQ ID NO: 74 | PRRSV(EU)-orf6-R-2 | GGAGACCTGCAGCACTTTC |
| SEQ ID NO: 76 | PRRSV(EU)-orf6-R-3 | GGCCATACTTGACGAGGTTAA |
| SEQ ID NO: 78 | PRRSV(EU)-orf7-R-1 | CGGTAAGAACCAGAGCCAGAAG |
| SEQ ID NO: 80 | PRRSV(EU)-orf7-R-2 | CTGAAGATGACATCCGGCACC |
| SEQ ID NO: 82 | PRV-gE-R-1 | CCACCTGGGACTACACGCT |
| SEQ ID NO: 84 | PRV-gE-R-2 | TCTCCGCCGAGACGAC |
| SEQ ID NO: 86 | PRV-gE-R-3 | GGGTCGTACGCGAGCC |
| SEQ ID NO: 88 | PRV-gE-R-4 | CCTCTACACGCTGCACGAC |
| SEQ ID NO: 90 | PRV-gB-R-1 | CGAGCGCCAGCAGCAG |
| SEQ ID NO: 92 | PRV-gB-R-2 | CCTGAACGCGCTCGGC |
| SEQ ID NO: 94 | PRV-gB-R-3 | CAGGCGCGACATCTCG |
| SEQ ID NO: 96 | PRV-gB-R-4 | GATGGACATGTACCGGATCATGT |
| SEQ ID NO: 98 | PCV2-cap-R-1 | GGGAGAGGCGGGTGTTGA |
| SEQ ID NO: 100 | PCV2-cap-R-2 | TAGATGATAACTTTGTAACAAAGGCCAC |
| SEQ ID NO: 102 | PCV2-cap-R-3 | TGGTCTACATTTCCAGCAGTTT |
| SEQ ID NO: 104 | PCV2-rep-R-1 | CTCCTCATTGCCTTCCTCG |
| SEQ ID NO: 106 | PCV2-rep-R-2 | GTGGATTGTTCTGTAGCATTCTTC |
| SEQ ID NO: 108 | PCV2-rep-R-3 | GCGGAAATTTCTGACAAACGT |
| SEQ ID NO: 110 | PCV2-rep-R-4 | GAAAAGCAAATGGGCTGCTAATTTTG |

TABLE 2-continued

Sequences of a primer group for simultaneous detection of 15 porcine pathogens through high-throughput targeted amplicon sequencing

| SEQ ID NO: 112 | PCV3-cap-R-1 | ATGAGACACAGAGCTATATTCAGAAG |
| --- | --- | --- |
| SEQ ID NO: 114 | PCV3-cap-R-2 | GGAGCCAAGTGTTTGTGGT |
| SEQ ID NO: 116 | PCV3-cap-R-3 | GGAACTACCAGCGCTCACC |
| SEQ ID NO: 118 | PCV3-rep-R-1 | TTCCAACCTCTTTGCCGATAATAA |
| SEQ ID NO: 120 | PCV3-rep-R-2 | TGTCTCCATGTCTTTCTTTACCC |
| SEQ ID NO: 122 | PCV3-rep-R-3 | AGGCCAGCGAGTATTGCAAG |
| SEQ ID NO: 124 | PCV3-rep-R-4 | CCCCATTATAACCATCCCACCAAG |
| SEQ ID NO: 126 | CSFV-5'UTR-R-1 | AACTATACGTGCTGTAAGTTACAGAG |
| SEQ ID NO: 128 | CSFV-5'UTR-R-2 | ATGGTACCCCTCTCACCAC |
| SEQ ID NO: 130 | CSFV-5'UTR-R-3 | CCTCACTTTGTGTTTGATGATCAG |
| SEQ ID NO: 132 | CSFV-5'UTR-R-4 | AGCGTTGTCATATTGAGTACCGC |
| SEQ ID NO: 134 | CSFV-E2-R-1 | ACAGGAAGTTTTCCTTACAGGTC |
| SEQ ID NO: 136 | CSFV-E2-R-2 | GGCGAGTATCAGTACTGGTTTGA |
| SEQ ID NO: 138 | CSFV-E2-R-3 | CAACTGAATGACGGGACCGTTA |
| SEQ ID NO: 140 | CSFV-E2-R-4 | GGTGGACGGGTGTCATAGAGT |
| SEQ ID NO: 142 | FMDV-polyprotein-R-1 | TTCTTCTCTGACGTCAGGTCAAAC |
| SEQ ID NO: 144 | FMDV-polyprotein-R-2 | GGAGGGACCTTACGCCG |
| SEQ ID NO: 146 | FMDV-polyprotein-R-3 | CGTCAGGTCCAGAGTGGA |
| SEQ ID NO: 148 | FMDV-polyprotein-R-4 | CTGGGTCACAGAACCAATCA |
| SEQ ID NO: 150 | FMDV-5'UTR-R-1 | CCCGAGGTAACACGCGAC |
| SEQ ID NO: 152 | FMDV-5'UTR-R-2 | CGACCGAATAGGCGGAGTG |
| SEQ ID NO: 154 | FMDV-5'UTR-R-3 | CCATTTCTCATGAAAACGGGC |
| SEQ ID NO: 156 | FMDV-5'UTR-R-4 | AAAACGTGCAACTTGAAATCCCG |
| SEQ ID NO: 158 | swIAV-M-R-1 | GTCTTCTAACCGAGGTCGAAACG |
| SEQ ID NO: 160 | swIAV-M-R-2 | CAGCAGAGTAACTGAGCGC |
| SEQ ID NO: 162 | swIAV-M-R-3 | CCTAGTATGCGCAACCTGTGA |
| SEQ ID NO: 164 | swIAV-M-R-4 | AGCAGCAGAGGCTATGGAAATTG |
| SEQ ID NO: 166 | swIAV-H1-R-1 | ATGAAGGCAATACTAGTAGTCTTGCTAT |
| SEQ ID NO: 168 | swIAV-H1-R-2 | TGTCCAAAATATGTCAAAAGCACAAAAT |
| SEQ ID NO: 170 | swIAV-H1-R-3 | CCACAAATGTGATGACACGTGC |
| SEQ ID NO: 172 | swIAV-H1-R-4 | TCTACAGAAACTTAATATGGCTGGT |
| SEQ ID NO: 174 | swIAV-H3-R-1 | AATTAGATTCCCTGTGCTGTTAATC |
| SEQ ID NO: 176 | swIAV-H3-R-2 | TGATGGAATTTCTCGTTCGTTTTC |
| SEQ ID NO: 178 | swIAV-H3-R-3 | TTGAAGTAACTAATGCTACTGAGCTGG |
| SEQ ID NO: 180 | HPS-vtaA-R-1 | CAGATAACGGTACAACAAATGATGTTTC |
| SEQ ID NO: 182 | HPS-vtaA-R-2 | CCCTGCGCTTGGGTATTTG |
| SEQ ID NO: 184 | HPS-vtaA-R-3 | CGAGCAGGGTCCTAGGG |
| SEQ ID NO: 186 | HPS-vtaA-R-4 | AATGGTGCCAGAATTACCAACGT |

TABLE 2-continued

Sequences of a primer group for simultaneous detection of 15 porcine pathogens through high-throughput targeted amplicon sequencing

| | | |
|---|---|---|
| SEQ ID NO: 188 | HPS-infB-R-1 | ATCCGTTGCTTTCGCACCA |
| SEQ ID NO: 190 | HPS-infB-R-2 | TTCTACACGCTCTAGGTTTGC |
| SEQ ID NO: 192 | HPS-infB-R-3 | TTACCGCACTTAATTCTAATACTTCCG |
| SEQ ID NO: 194 | Pm-plpE-R-1 | ATGAAACAAATCGTTTTAAAAACAAGCT |
| SEQ ID NO: 196 | Pm-plpE-R-2 | AATGGCAAGATTTATGGTGAAATCTACA |
| SEQ ID NO: 198 | Pm-plpE-R-3 | GAATACCGTAACGTTATCTTTATCTACA |
| SEQ ID NO: 200 | Pm-kmt1-R-1 | ATGAATCAAGCGGTCACAGAAAAGA |
| SEQ ID NO: 202 | Pm-kmt1-R-2 | GGCAATAGATCGTGATTTTGGTCG |
| SEQ ID NO: 204 | Pm-kmt1-R-3 | CAGAGAGGTGAAAAATACCCCTAAATAA |
| SEQ ID NO: 206 | Pm-kmt1-R-4 | TGACATTGAATAACTACTTATTGACACA |
| SEQ ID NO: 208 | APP-om1A-R-1 | ATGAATATTGCAACAAAATTAATGGCTA |
| SEQ ID NO: 210 | APP-om1A-R-2 | TTTTTATCTTCTTTTGTGGTTGCCGTAG |
| SEQ ID NO: 212 | APP-om1A-R-3 | TTTCCGCATTACTTTTATCCTTACTT |
| SEQ ID NO: 214 | APP-om1A-R-4 | GCGATGAAAAGTTAGTTTGAATGAATA |
| SEQ ID NO: 216 | APP-apxIVA-R-1 | CATCTAAATCTAAAGCTAAAGGATCGTA |
| SEQ ID NO: 218 | APP-apxIVA-R-2 | CAAGGATTTTATGAAAACTGGGCGG |
| SEQ ID NO: 220 | APP-apxIVA-R-3 | CCAAGAGGTTCAATACCAAAGTTTT |
| SEQ ID NO: 222 | APP-apxIVA-R-4 | ACTGATATTAATTTATCCGAACTTTGGT |
| SEQ ID NO: 224 | *S.suis*-gdh-R-1 | ATGTCAAATGCCAAAGCTTACATCC |
| SEQ ID NO: 226 | *S.suis*-gdh-R-2 | GCCATCGTAGTTCCATACAGAA |
| SEQ ID NO: 228 | *S.suis*-gdh-R-3 | CTTGTCATGGACTCGTGAAGAAGT |
| SEQ ID NO: 230 | *S.suis*-gdh-R-4 | AGTAAACCAAACCGTAACCAGT |
| SEQ ID NO: 232 | *S.suis*-recN-R-1 | ACTGTCGATGATGTTTTGGACTATTTTA |
| SEQ ID NO: 234 | *S.suis*-recN-R-2 | GAAAACGGGATGACCATCCT |
| SEQ ID NO: 236 | *S.suis*-recN-R-3 | AGGCCATTGCCCAGAAAAT |
| SEQ ID NO: 238 | *S.suis*-recN-R-4 | AAAAATGAGCAAGAACACAAGGC |
| SEQ ID NO: 240 | *S.suis*-gapdh-R-1 | ATGGTAGTTAAAGTTGGTATTAACGGT |
| SEQ ID NO: 242 | *S.suis*-gapdh-R-2 | AGTTATCGAAGTTGATGGCGAG |
| SEQ ID NO: 244 | *S.suis*-gapdh-R-3 | CATCCACGCTAACGGTGCTA |
| SEQ ID NO: 246 | *S.suis*-gapdh-R-4 | CTGCAAACATCGTTCCTAACTCA |
| SEQ ID NO: 248 | *E.suis*-ppa-R-1 | CTTAAATATGAGTGTGTTGATGGCA |
| SEQ ID NO: 250 | *E.suis*-ppa-R-2 | CTTTTCAATCTTGTTCTCCAGAATCTA |
| SEQ ID NO: 252 | *E.suis*-ppa-R-3 | TTGCAAAATTCTTGGTTCTCTAGAAAT |
| SEQ ID NO: 254 | *E.suis*-g1-R-1 | ATGACAATCCACAAAGTAGCAATCAATG |
| SEQ ID NO: 256 | *E.suis*-g1-R-2 | GAAGACTCATTATCATATCATGCATACA |
| SEQ ID NO: 258 | *E.suis*-g1-R-3 | GTTCAGGAAGATTCTTAACTAAGGAAG |
| SEQ ID NO: 260 | *E.suis*-g1-R-4 | TGCTCCTGTAGTTGTAGGAATAATT |
| SEQ ID NO: 262 | *T.gondii*-B1-R-1 | CCAGAGTGGATTTCCGTTGGT |
| SEQ ID NO: 264 | *T.gondii*-B1-R-2 | TCTCTTCACTGTCACGTACGACA |

TABLE 2-continued

Sequences of a primer group for simultaneous detection of 15 porcine pathogens through high-throughput targeted amplicon sequencing

| | | |
|---|---|---|
| SEQ ID NO: 266 | T.gondii-B1-R-3 | GAAGAAGGGTACGTGTTGCATCATA |
| SEQ ID NO: 268 | T.gondii-B1-R-4 | GAGAGACGCTCTACAAAATCCA |
| SEQ ID NO: 270 | T.gondii-RE-R-1 | AGGGAGGAAGACGAAAGTTGT |
| SEQ ID NO: 272 | T.gondii-RE-R-2 | ACAGAAGGGACAGAAGTCGAA |
| SEQ ID NO: 274 | T.gondii-RE-R-3 | TCGTCTCGTCTGGATCGCA |
| SEQ ID NO: 276 | T.gondii-RE-R-4 | GCTGCTTTTCCTGGAGGG |
| SEQ ID NO: 278 | Mhr-p37-R-1 | AATGAAGACAGAAGCGCACATC |
| SEQ ID NO: 280 | Mhr-p37-R-2 | GAAAAGATGGAAGCACTTATAGTAACTA |
| SEQ ID NO: 282 | Mhr-p37-R-3 | ACGTCATCGAAGTTTTTGGTTTTAT |
| SEQ ID NO: 284 | Mhr-16SrRNA-R-1 | GCGATAAATAACTATATCCGGTATTAGC |
| SEQ ID NO: 286 | Mhr-16SrRNA-R-2 | CTCGTGTCGTGAGATGTTAGGTTAAG |
| SEQ ID NO: 288 | Mhr-16SrRNA-R-3 | TTTTTGCTAAGTCTGGAGTTAAATGCTG |
| SEQ ID NO: 290 | Mhp-p36-R-1 | TGCAGCAATGAATCAAGGACT |
| SEQ ID NO: 292 | Mhp-p36-R-2 | ACAGTTCCACTACCGATAACTTTT |
| SEQ ID NO: 294 | Mhp-p36-R-3 | GGTGAACATGGTGATTCATCTTTTGTT |
| SEQ ID NO: 296 | Mhp-p102-R-1 | GCATTTGAACAGCTTTTAATTTCGC |
| SEQ ID NO: 298 | Mhp-p102-R-2 | AAACTTCCTTTCTCTGCAAATGATT |
| SEQ ID NO: 300 | Mhp-p102-R-3 | ACTTAAATAGACAGTTCCGATTTTGGTA |
| SEQ ID NO: 302 | Mhp-p102-R-4 | TATTCTTATCTAAATCAGATCCCGAGTC |

2. Amplicon Ds DNA Library Construction

1). Sample Processing

The sample types mainly include, but are not limited to, porcine lung tissue, whole blood or serum, nasal swab, or pharyngeal swab, and the sample microbial genome was extracted by using, but not limited to, HiPure MicroBiome DNA Kit (Magen Biotechnology Limited, http://www.magentec.com.cn/), TIANamp Virus DNA/RNA Kit (Tiangen Biochemical Technology Co., Ltd, http://www.tiangen.com.cn/), and GoScript™ Reverse Transcription Mix, Random Primer (Promega Corporation, http://www.promega.com.cn/), and the like. The microbial DNA extracted from a single sample was quantified on ds DNA by using a Qubit™ 4 Fluorometer, and the concentration of each sample was controlled to be within 100 ng/μL.

TABLE 3

Sample information

| No. | Sample No. | Sample type | Source |
|---|---|---|---|
| 1 | B1 | Whole blood | Inner Mongolia, China |
| 2 | B2 | Whole blood | Inner Mongolia, China |
| 3 | B3 | Whole blood | Inner Mongolia, China |
| 4 | B4 | Whole blood | Inner Mongolia, China |
| 5 | B5 | Whole blood | Inner Mongolia, China |
| 6 | S1 | Serum | Inner Mongolia, China |
| 7 | S2 | Serum | Inner Mongolia, China |
| 8 | S3 | Serum | Inner Mongolia, China |
| 9 | S4 | Serum | Inner Mongolia, China |
| 10 | S5 | Serum | Inner Mongolia, China |
| 11 | NS1 | Nasal swab | Inner Mongolia, China |
| 12 | NS2 | Nasal swab | Inner Mongolia, China |
| 13 | NS3 | Nasal swab | Inner Mongolia, China |
| 14 | NS4 | Nasal swab | Inner Mongolia, China |
| 15 | NS5 | Nasal swab | Inner Mongolia, China |
| 16 | TS1 | Pharyngeal swab | Inner Mongolia, China |
| 17 | TS2 | Pharyngeal swab | Inner Mongolia, China |
| 18 | TS3 | Pharyngeal swab | Inner Mongolia, China |
| 19 | TS4 | Pharyngeal swab | Inner Mongolia, China |
| 20 | TS5 | Pharyngeal swab | Inner Mongolia, China |
| 21 | L1 | Lung tissue | Inner Mongolia, China |
| 22 | L2 | Lung tissue | Inner Mongolia, China |
| 23 | L3 | Lung tissue | Inner Mongolia, China |
| 24 | L4 | Lung tissue | Inner Mongolia, China |
| 25 | L5 | Lung tissue | Inner Mongolia, China |

2). First Cycle of PCR Amplification

The total DNA of the microorganism of a single sample was taken as a template, first cycle of PCR amplification was performed by using a primer pool of an amplicon sequencing library synthesized by MGI Tech Co., Ltd., and the reaction system was as follows:

TABLE 4

First cycle of PCR reaction system

| Reaction system | |
|---|---|
| PCR Enzyme Mix | 12.5 μL |
| PCR Clean Enzyme | 0.5 μL |
| Primer pool | 2 μL |
| DNA (100 ng) | [100 ng/C (ng/μL)] μL |
| NF water | (10-DNA) μL |
| Total | 25 μL |

The first cycle of PCR reaction solution was vortexed 3 times for 3 s each time, instantaneous centrifugation was performed, the reaction solution was collected to a bottom of a tube, then first cycle of PCR amplification was performed, and the reaction procedures were as follows: heated lid at 105° C.; 37° C. for 5 min, 95° C. for 10 min, 1 cycle; 95° C. for 20 s, 64° C. for 1 min, 60° C. for 1 min, 72° C. for 30 s, 13 cycles; and 12° C. Hold. After the reaction was completed, the reaction solution was centrifuged instantaneously and collected to the bottom of the tube.

3). First Cycle of PCR Product Purification

DNA Clean Beads were taken 30 min in advance and placed at room temperature, the DNA Clean Beads were fully shaken and uniformly mixed before used, 30 μL of the DNA Clean Beads were put in 25 clean 1.5 mL centrifuge tubes according to 25 sample volumes, and sample numbers were marked; all 25 μL products corresponding to the numbers of the first cycle of PCR were transferred to centrifuge tubes, the products were gently pipetted by a pipettor at least 10 times until the products were completely mixed, and it was ensured that all liquid and magnetic beads in a suction head were injected into the tubes for the last time, and incubated at room temperature for 5 min.

After instantaneous centrifugation, a 1.5 mL centrifuge tube was placed on a magnetic rack and left to stand for 2-5 min until the liquid was clear, the liquid was carefully sucked by using a pipettor, the supernatant was discarded; a 1.5 mL centrifuge tube was kept on a magnetic rack, 200 μL of freshly prepared 80% ethanol was added to rinse the magnetic beads and the tube wall, the liquid was left to stand for 30 s and carefully sucked, the supernatant was discarded, and this process was repeated again to ensure the liquid in the tube to be thoroughly sucked for the second time; a 1.5 mL centrifuge tube was kept on a magnetic rack, a tube cover was opened and dried at room temperature until the surface of the magnetic beads had no reflection and no crack; a 1.5 mL centrifuge tube was taken and added with 6.5 μL TE Buffer for DNA elution, and the buffer was gently pipetted by a pipettor until the buffer was completely mixed, then incubated at room temperature for 5 min, and subjected to instantaneous centrifugation. In this step, the magnetic beads were not removed.

6.5 μL of the purified product (containing magnetic beads) was stored in a refrigerator at −20° C.

4). Second Cycle of PCR Amplification

The first cycle of PCR purified product was taken as a template, a customized panel provided by MGI Tech Co., Ltd. was subjected to second cycle of PCR amplification, and the reaction system was as follows:

TABLE 5

Second cycle of PCR reaction system

| Reaction system | |
|---|---|
| PCR Enzyme Mix | 12.5 μL |
| PCR Clean Enzyme | 0.5 μL |
| PCR Additive | 0.5 μL |
| Custom Panel PCR Block | 1 μL |
| PCR Barcode Primer Mix | 4 μL |
| DNA | 6.5 μL |
| Total | 25 μL |

The prepared second cycle of PCR reaction solution was vortexed 3 times for 3 s each time, instantaneous centrifugation was performed, the reaction solution was collected to a bottom of a tube, then second cycle of PCR amplification was performed, and the reaction procedures were as follows: heated lid at 105° C.; 37° C. for 5 min, 95° C. for 10 min, 1 cycle; 95° C. for 20 s, 64° C. for 1 min, 60° C. for 1 min, 72° C. for 30 s, 27 cycles; and 12° C. Hold. After the reaction was completed, the reaction solution was centrifuged instantaneously and collected to the bottom of the tube.

5). Second Cycle of PCR Product Purification

DNA Clean Beads were taken 30 min in advance and placed at room temperature, the DNA Clean Beads were fully shaken and uniformly mixed, 25 μL of the DNA Clean Beads were put in 25 clean 1.5 mL centrifuge tubes according to 25 sample volumes, and sample numbers were marked; all 25 μL products corresponding to the numbers of the second cycle of PCR in the step 4 were transferred to centrifuge tubes, the products were gently pipetted by a pipettor at least 10 times until the products were completely mixed, and it was ensured that all liquid and magnetic beads in a suction head were injected into the tubes for the last time, and incubated at room temperature for 5 min.

After instantaneous centrifugation, a 1.5 mL centrifuge tube was placed on a magnetic rack and left to stand for 2-5 min until the liquid was clear, the liquid was carefully sucked by using a pipettor, the supernatant was discarded; a 1.5 mL centrifuge tube was kept on a magnetic rack, 200 μL of freshly prepared 80% ethanol was added to rinse the magnetic beads and the tube wall, the liquid was left to stand for 30 s and carefully sucked, the supernatant was discarded, and this process was repeated again to ensure the liquid in the tube to be thoroughly sucked for the second time; a 1.5 mL centrifuge tube was kept on a magnetic rack, a tube cover was opened and dried at room temperature until the surface of the magnetic beads had no reflection and no crack; a 1.5 mL centrifuge tube was taken and added with 25 μL TE Buffer for DNA elution, and the buffer was gently pipetted by a pipettor until the buffer was completely mixed, then incubated at room temperature for 5 min, and subjected to instantaneous centrifugation; the 1.5 mL centrifuge tube was placed on the magnetic rack and left to stand for 2-5 min until the liquid was clear, and 23 μL supernatant was transferred to a new PCR tube. The magnetic beads need to be removed clean in this step.

23 μL of the purified product was stored in a refrigerator at −20° C., at this point, amplicon ds DNA library construction was completed.

3. Amplicon Ss DNA Library Construction

1). Quality Inspection of Ds DNA Library and Construction of Ds DNA Mixed Library The constructed single ds DNA library was quantified by using a Qubit™ 4 Fluorometer according to an operation instruction, wherein the library required that the yield of a final PCR product was greater than or equal to 5 ng/μL; and then according to the quantitative result of the DNA library, the samples to be sequenced were mixed according to the quality of the barcode numbers and the like, wherein the total amount of the mixed final library was required to be 400 ng, the total volume was less than or equal to 48 μL, and the sampling volume of a single library was ensured to be greater than or equal to 1 μL.

After quantification by a Qubit™ 4 Fluorometer, 25 samples all met the quality requirement, and then 25 samples were mixed by calculation. Sampling was performed, wherein the sampling quantity of a single library was enlarged by 20 times, and finally, 25 amplicon ds DNA libraries were constructed into 1 amplicon ds DNA mixed library.

2). Denaturation of Ds DNA Library to Ss DNA Library

The single ds DNA mixed library obtained in the step 1 was taken as a template, 400 ng of the ds DNA mixed library was placed in a PCR tube, the PCR tube was supplemented with a TE Buffer to a total volume of 48 μL, and a denaturation reaction was performed. The reaction conditions were as follows: heated lid at 105° C., 95° C. for 3 min, and 95° C. Hold. After the reaction was finished, the PCR tube was quickly placed on ice for an ice bath for 2 min, and then ds DNA mixed library in the tube was subjected to instantaneous centrifugation to obtain an ss DNA initial library.

3). Amplicon Ss DNA Library Circularization

The above denatured amplicon ss DNA library was taken as a template, Amplicon library circularization was performed by using MGIEasy circularization kit, and the reaction system was as follows:

TABLE 6

Reaction system for ss DNA amplicon library circularization

| Reaction system | |
| --- | --- |
| Splint Buffer | 11.5 μL |
| DNA Rapid Ligase | 0.5 μL |
| ss DNA | 48 μL |
| Total | 60 μL |

The prepared PCR reaction solution was vortexed 3 times for 3 s each time, instantaneous centrifugation was performed, the reaction solution was collected to a bottom of a tube, then PCR amplification was performed, and the reaction procedures were as follows: heated lid at 105° C.; 37° C. for 30 min, and 4° C. Hold. After the reaction was completed, the PCR tube was instantaneously centrifuged and placed on ice to immediately proceed to the reaction in step 4.

4). Ss DNA Library Enzyme Digestion

The circularized amplicon ss DNA library was taken as a template, the reaction in step 3 was followed by the reaction in step 4, and the reaction system was as follows:

TABLE 7

Reaction system for ss DNA library enzyme digestion

| Reaction system | |
| --- | --- |
| Digestion Buffer | 1.4 μL |
| Digestion Enzyme | 2.6 μL |
| ss DNA | 60 μL |
| Total | 66 μL |

The prepared enzyme digestion solution was vortexed 3 times for 3 s each time, instantaneous centrifugation was performed, the reaction solution was collected to a bottom of a tube, then PCR amplification was performed, and the reaction procedures were as follows: heated lid at 105° C.; 37° C. for 30 min, and 4° C. Hold. After the reaction was completed, the reaction solution was centrifuged instantaneously and collected to the bottom of the tube. Then 7.5 μL of Digestion Stop Buffer was immediately added to the PCR tube, vortexed 3 times for 3 s each time, the reaction solution was collected to the bottom of the tube after instantaneous centrifugation, and the whole reaction solution was sucked and transferred to a new 1.5 mL centrifuge tube.

5). Purification of Enzyme Digestion Products

The DNA Clean Beads were taken out in advance during the enzyme digestion reaction and placed at room temperature, and the DNA Clean Beads was fully shaken and mixed uniformly before use; and 170 μL of the mixture was put into the 1.5 mL centrifuge tube filled with the reaction solution and gently pipetted by a pipettor at least 10 times until the mixture was completely mixed, and it was ensured that all liquid and magnetic beads in a suction head were injected into the tubes for the last time, and incubated at room temperature for 10 min.

After instantaneous centrifugation, a 1.5 mL centrifuge tube was placed on a magnetic rack and left to stand for 2-5 min until the liquid was clear, the liquid was carefully sucked by using a pipettor, the supernatant was discarded; a 1.5 mL centrifuge tube was kept on a magnetic rack, 500 μL of freshly prepared 80% ethanol was added to rinse the magnetic beads and the tube wall, the liquid was left to stand for 30 s and carefully sucked, the supernatant was discarded, and this process was repeated again to ensure the liquid in the tube to be thoroughly sucked for the second time; a 1.5 mL centrifuge tube was kept on a magnetic rack, a tube cover was opened and dried at room temperature until the surface of the magnetic beads had no reflection and no crack; a 1.5 mL centrifuge tube was taken and added with 22 μL TE Buffer for DNA elution, and the buffer was gently pipetted by a pipettor until the buffer was completely mixed, then incubated at room temperature for 10 min, and subjected to instantaneous centrifugation; the 1.5 mL centrifuge tube was placed on the magnetic rack and left to stand for 2-5 min until the liquid was clear, and 20 μL supernatant was transferred to a new PCR tube. The magnetic beads need to be removed clean in this step.

20 μL of the purified product was stored in a refrigerator at −20° C., at this point, amplicon ss DNA library was successfully constructed.

4. Amplicon DNB Library Construction

1). Amplicon Ss DNA Equilibrium Library Construction

The conversion formula of the concentration is as follows: $C(fmol/\mu L)=3030*C(ng/\mu L)/N$.

According to the quantitative result of the Qubit™ 4 Fluorometer, the concentration of the amplicon ss DNA library constructed in this embodiment was greater than or equal to 2 fmol/μL, and the quality control requirement was met. After ss DNA quantification was performed on standard products provided in the Qubit® ssDNA Assay Kit, the standard products were calculated using the following two formulas:

$$\text{ss DNA input } (\mu L)=44/C(fmol/\mu L); \quad (1)$$

$$\text{the standard ss DNA input } (\mu L)=16/C(fmol/\mu L). \quad (1)$$

The ss DNA input and the standard ss DNA input were mixed to construct an amplicon ss DNA equilibrium library.

2). Amplicon DNB Library Construction

The amplicon ss DNA equilibrium library in the step 1 was taken as a template, DNB preparation was performed by using an MGISEQ-200RS high-throughput sequencing kit (FCS PE 100), and two cycles of reactions were performed in total, wherein the first cycle of reaction was PCR primer hybridization, and the reaction system was as follows:

TABLE 8

DNB preparation reaction system 1

| Reaction system | |
| --- | --- |
| ss DNA equilibrium library | V μL |
| TE Buffer | 20-V μL |
| DNB preparation buffer | 20 μL |
| Total | 40 μL |

The prepared DNB reaction mixed solution 1 was vortexed, uniform mixed, centrifuged for 5 s by using a mini centrifuge, and then placed in a PCR instrument for primer hybridization, wherein the reaction conditions were as follows: heated lid at 105° C., 95° C. for 1 min, 65° C. for 1 min, 40° C. for 1 min, and 4° C. Hold. After the reaction was completed, the solution was subjected to a second cycle of reaction, namely, a DNB rolling circle amplification reaction. Firstly the PCR reaction tube was taken out, centrifuged by a mini-centrifuge for 5 s, and then placed on ice to prepare a second cycle of reaction solution by DNB, wherein the second cycle of reaction system was as follows:

TABLE 9

DNB preparation reaction system 2

| Reaction system | |
| --- | --- |
| DNB reaction mixed solution 1 | 40 μL |
| DNB polymerase mixed solution I | 40 μL |
| DNB polymerase mixed solution II (LC) | 4 μL |
| Total | 84 μL |

The prepared DNB mixed reaction solution 2 was vortexed by using a vortex oscillator and uniformly mixed, centrifuged for 5 s by using a mini centrifuge, and immediately placed in a PCR instrument for DNB rolling circle amplification, wherein the reaction conditions were as follows: heated lid at 35° C., 30° C. for 25 min, 4° C. Hold. After the reaction was completed, the solution was immediately added with 20 μL of DNB termination buffer solution, and the mixture was slowly pipetted for 5 to 8 times to be well mixed by using a wide-mouthed pipette tip without vortexing or violently pipetting.

3). DNB Quality Inspection

After DNB preparation was completed, 2 μL of DNB mixed reaction solution was subjected to concentration detection by using Qubit® ssDNA Assay Kit and Qubit® Fluorometer instruments, and the concentration of the amplicon DNB=15.5 ng/μL, which met the quality control requirement. DNB was stored at 4° C. for future use and prepared for on-line sequencing.

5. On-Line Sequencing

The prepared DNB was prepared for on-line sequencing according to the instructions of the high-throughput (rapid) sequencing reagent set in MGI Tech, which was the MGISEQ-200RS high-throughput rapid sequencing reagent set (FCS PE100).

The sequencing data were extracted for analysis and comparison, a total summary report was generated after sequencing was completed, the summary report was opened by a webpage and viewed, the summary report shows that the sequencing quality is high, the data result of greater than or equal to Q30 is more than 90%, the Barcode can be normally identified, all samples can be correctly distinguished, and the capture rate of a pathogenic target gene area has certain difference according to the difference of pathogen load in the samples. The sequencing result is accurate and reliable, and the designed amplification primer has high efficiency and good specificity.

According to the sequencing results of the target gene, after data homogenization and calculation of the pathogen load, the detection of the pathogen is judged according to the calculation result of the pathogenic target gene. It has been proved by practice that the pathogenic genes in the panel are detected in the above 25 samples, thus successfully implementing the rapid, accurate, and simultaneous diagnosis of 15 pathogens in the porcine respiratory tract.

Therefore, the method for simultaneous detection of 15 porcine pathogens through high-throughput targeted amplicon sequencing provided by the present invention is successfully established.

The above descriptions are only preferred embodiments of the present invention. It should be noted that those of ordinary skill in the art can also make several improvements and modifications without departing from the principle of the present invention, and such improvements and modifications shall fall within the protection scope of the present invention.

What is claimed is:

1. A primer group for a simultaneous detection of 15 porcine pathogens through high-throughput targeted amplicon sequencing, wherein the primer group is configured to amplify pathogenic target genes, the pathogenic target genes are as follows:

| Pathogen name | Target gene | Sequence No. |
| --- | --- | --- |
| African swine fever virus | ASFV-p72 | SEQ ID NO: 303 |
| | ASFV-p54 | SEQ ID NO: 304 |
| | ASFV-EP402R | SEQ ID NO: 305 |
| | ASFV-MGF505-1R | SEQ ID NO: 306 |
| | ASFV-MGF505-2R | SEQ ID NO: 307 |
| | ASFV-MGF360-13L | SEQ ID NO: 308 |
| | ASFV-MGF360-14L | SEQ ID NO: 309 |
| | ASFV-K205R | SEQ ID NO: 310 |
| Porcine reproductive and respiratory syndrome virus | PRRSV-NA-orf6/M | SEQ ID NO: 311 |
| | PRRSV-NA-orf7/N | SEQ ID NO: 312 |
| | PRRSV-EU-orf6/M | SEQ ID NO: 313 |
| | PRRSV-EU-orf7/N | SEQ ID NO: 314 |
| Pseudorabies virus | PRV-gE | SEQ ID NO: 315 |
| | PRV-gB | SEQ ID NO: 316 |
| Porcine circovirus | PCV2-cap | SEQ ID NO: 317 |
| | PCV2-rep | SEQ ID NO: 318 |
| | PCV3-cap | SEQ ID NO: 319 |
| | PCV3-rep | SEQ ID NO: 320 |
| Classical swine fever virus | CSFV-5'UTR | SEQ ID NO: 321 |
| | CSFV-E2 | SEQ ID NO: 322 |
| Foot and mouth diseases virus | FMDV-3D-1C2B(polyprotein) | SEQ ID NO: 323 |
| | FMDV-5'UTR | SEQ ID NO: 324 |
| Swine influenza A virus | swIAV-M | SEQ ID NO: 325 |
| | swIAV-H1 | SEQ ID NO: 326 |
| | swIAV-H3 | SEQ ID NO: 327 |
| Haemophilus parasuis | HPS-vtaA | SEQ ID NO: 328 |
| | HPS-infB | SEQ ID NO: 329 |
| Pasteurella multocida | Pm-plpE | SEQ ID NO: 330 |
| | Pm-kmt1 | SEQ ID NO: 331 |
| Actinobacillus pleuropneumoniae | APP-omlA | SEQ ID NO: 332 |
| | APP-apxIVA | SEQ ID NO: 333 |
| Streptococcus suis | S.suis-gdh | SEQ ID NO: 334 |
| | S.suis-recN | SEQ ID NO: 335 |
| | S.suis-gapdh | SEQ ID NO: 336 |
| Eperythrozoon suis | E.suis-ppa | SEQ ID NO: 337 |
| | E.suis-g1 | SEQ ID NO: 338 |
| Toxoplasma gondii | T.gondii-B1 | SEQ ID NO: 339 |
| | T.gondii-RE | SEQ ID NO: 340 |
| Mycoplasma hyorhinis | Mhr-p37 | SEQ ID NO: 341 |
| | Mhr-16SrRNA | SEQ ID NO: 342 |
| Mycoplasma hyopneumoniae | Mhp-p36 | SEQ ID NO: 343 |
| | Mhp-p102 | SEQ ID NO: 344; | nucleotide sequences of the pathogenic target genes are set forth in SEQ ID NO: 303 to SEQ ID NO: 344;

the primer group comprises a first primer group and a second primer group, wherein the first primer group comprises all odd numbered sequence identifier numbers within SEQ ID NO: 1 to SEQ ID NO: 302, an adapter sequence set forth in SEQ ID NO: 345 is added at a 5'-end of each of forward primers, the second primer group comprises all even numbered sequence identifier numbers within SEQ ID NO: 1 to SEQ ID NO: 302, and an adapter sequence set forth in SEQ ID NO: 346 is added at a 5'-end of each of reverse primers.

2. A multiplex PCR reagent for a simultaneous detection of 15 porcine pathogens through high-throughput targeted amplicon sequencing, comprising a first PCR reagent and a second PCR reagent, wherein the first PCR reagent comprises the first primer group of the primer group according to claim 1, and the second PCR reagent comprises the second primer group of the primer group according to claim 1, wherein each primer in the first primer group has a concentration of 10 nmol/μL in the first PCR reagent, and each primer in the second primer group has a concentration of 10 nmol/μL in the second PCR reagent.

3. A kit for a simultaneous detection of 15 porcine pathogens through high-throughput targeted amplicon sequencing, comprising the primer group according to claim 1.

4. A method of high-throughput amplicon sequencing for a simultaneous detection of 15 porcine respiratory pathogens in non-diagnostic and therapeutic purposes with the primer group according to claim 1, comprising generating an amplicon library using the primer group of claim 1, and sequencing the amplicon library to detect 15 porcine respiratory pathogenic genes in a test sample.

5. A kit for a simultaneous detection of 15 porcine pathogens through high-throughput targeted amplicon sequencing, comprising a multiplex PCR reagent, comprising a first PCR reagent and a second PCR reagent, wherein the first PCR reagent comprises the first primer group of the primer group according to claim 1, and the second PCR reagent comprises the second primer group of the primer group according to claim 1, wherein in the multiplex PCR reagent, each primer in the first primer group has a concentration of 10 nmol/μL in the first PCR reagent, and each primer in the second primer group has a concentration of 10 nmol/μL in the second PCR reagent.

\* \* \* \* \*

SEQUENCE LISTING

```
Sequence total quantity: 346
SEQ ID NO: 1              moltype = DNA   length = 19
FEATURE                   Location/Qualifiers
source                    1..19
                          mol_type = other DNA
                          organism = synthetic construct
SEQUENCE: 1
gactcaaagt gggttcggg                                                          19

SEQ ID NO: 2              moltype = DNA   length = 25
FEATURE                   Location/Qualifiers
source                    1..25
                          mol_type = other DNA
                          organism = synthetic construct
SEQUENCE: 2
gcatcaggag gagcttttg tctta                                                    25

SEQ ID NO: 3              moltype = DNA   length = 28
FEATURE                   Location/Qualifiers
source                    1..28
                          mol_type = other DNA
                          organism = synthetic construct
SEQUENCE: 3
aaaatgactg gatataagca cttggttg                                                28

SEQ ID NO: 4              moltype = DNA   length = 21
FEATURE                   Location/Qualifiers
source                    1..21
                          mol_type = other DNA
                          organism = synthetic construct
SEQUENCE: 4
gctgcgtatc attttcatcg g                                                       21

SEQ ID NO: 5              moltype = DNA   length = 20
FEATURE                   Location/Qualifiers
source                    1..20
                          mol_type = other DNA
                          organism = synthetic construct
SEQUENCE: 5
agcgaacgcg ttttacaaaa                                                         20

SEQ ID NO: 6              moltype = DNA   length = 25
FEATURE                   Location/Qualifiers
source                    1..25
                          mol_type = other DNA
                          organism = synthetic construct
SEQUENCE: 6
gctttaaacc atggtttatc ccagg                                                   25

SEQ ID NO: 7              moltype = DNA   length = 17
FEATURE                   Location/Qualifiers
source                    1..17
                          mol_type = other DNA
                          organism = synthetic construct
SEQUENCE: 7
cgcagcacag ctgaacc                                                            17

SEQ ID NO: 8              moltype = DNA   length = 27
FEATURE                   Location/Qualifiers
source                    1..27
                          mol_type = other DNA
                          organism = synthetic construct
SEQUENCE: 8
ccagtggtca tattaacgta tccagag                                                 27

SEQ ID NO: 9              moltype = DNA   length = 28
FEATURE                   Location/Qualifiers
source                    1..28
                          mol_type = other DNA
                          organism = synthetic construct
SEQUENCE: 9
aaactgtata tcttcctcct caatagca                                                28

SEQ ID NO: 10             moltype = DNA   length = 23
FEATURE                   Location/Qualifiers
source                    1..23
                          mol_type = other DNA
                          organism = synthetic construct
```

-continued

```
SEQUENCE: 10
ccagtcacta caccaagctt ctt                                          23

SEQ ID NO: 11           moltype = DNA  length = 20
FEATURE                 Location/Qualifiers
source                  1..20
                        mol_type = other DNA
                        organism = synthetic construct
SEQUENCE: 11
cgtaactggg ttgtccgtaa                                              20

SEQ ID NO: 12           moltype = DNA  length = 23
FEATURE                 Location/Qualifiers
source                  1..23
                        mol_type = other DNA
                        organism = synthetic construct
SEQUENCE: 12
atcagcagtg ggtagaagtc act                                          23

SEQ ID NO: 13           moltype = DNA  length = 19
FEATURE                 Location/Qualifiers
source                  1..19
                        mol_type = other DNA
                        organism = synthetic construct
SEQUENCE: 13
gcagaccggc aacaaacag                                               19

SEQ ID NO: 14           moltype = DNA  length = 18
FEATURE                 Location/Qualifiers
source                  1..18
                        mol_type = other DNA
                        organism = synthetic construct
SEQUENCE: 14
cggatgagca ggagcact                                                18

SEQ ID NO: 15           moltype = DNA  length = 24
FEATURE                 Location/Qualifiers
source                  1..24
                        mol_type = other DNA
                        organism = synthetic construct
SEQUENCE: 15
atgcgtatag gtgtttctttt gtcg                                        24

SEQ ID NO: 16           moltype = DNA  length = 16
FEATURE                 Location/Qualifiers
source                  1..16
                        mol_type = other DNA
                        organism = synthetic construct
SEQUENCE: 16
atggcaactg gcgggc                                                  16

SEQ ID NO: 17           moltype = DNA  length = 28
FEATURE                 Location/Qualifiers
source                  1..28
                        mol_type = other DNA
                        organism = synthetic construct
SEQUENCE: 17
tgacattgtt cttcttcatt agattcag                                     28

SEQ ID NO: 18           moltype = DNA  length = 28
FEATURE                 Location/Qualifiers
source                  1..28
                        mol_type = other DNA
                        organism = synthetic construct
SEQUENCE: 18
atattccatt aagcatcata attgggat                                     28

SEQ ID NO: 19           moltype = DNA  length = 19
FEATURE                 Location/Qualifiers
source                  1..19
                        mol_type = other DNA
                        organism = synthetic construct
SEQUENCE: 19
ggacatggtt tgggtggag                                               19

SEQ ID NO: 20           moltype = DNA  length = 23
FEATURE                 Location/Qualifiers
source                  1..23
                        mol_type = other DNA
```

```
                         organism = synthetic construct
SEQUENCE: 20
catacatgaa ccatctccca gag                                             23

SEQ ID NO: 21            moltype = DNA  length = 20
FEATURE                  Location/Qualifiers
source                   1..20
                         mol_type = other DNA
                         organism = synthetic construct
SEQUENCE: 21
tacatgcgtc cctcaacaca                                                 20

SEQ ID NO: 22            moltype = DNA  length = 23
FEATURE                  Location/Qualifiers
source                   1..23
                         mol_type = other DNA
                         organism = synthetic construct
SEQUENCE: 22
ctaggtagtg gtttgggtgg aga                                             23

SEQ ID NO: 23            moltype = DNA  length = 27
FEATURE                  Location/Qualifiers
source                   1..27
                         mol_type = other DNA
                         organism = synthetic construct
SEQUENCE: 23
gtgaataagc gaaatatttt gggtaga                                         27

SEQ ID NO: 24            moltype = DNA  length = 25
FEATURE                  Location/Qualifiers
source                   1..25
                         mol_type = other DNA
                         organism = synthetic construct
SEQUENCE: 24
cctaaaccat gtccttcagc tgaat                                           25

SEQ ID NO: 25            moltype = DNA  length = 25
FEATURE                  Location/Qualifiers
source                   1..25
                         mol_type = other DNA
                         organism = synthetic construct
SEQUENCE: 25
acagttgttt cctgctcgtt gaata                                           25

SEQ ID NO: 26            moltype = DNA  length = 24
FEATURE                  Location/Qualifiers
source                   1..24
                         mol_type = other DNA
                         organism = synthetic construct
SEQUENCE: 26
gttctctctc cagaacttat gtcg                                            24

SEQ ID NO: 27            moltype = DNA  length = 23
FEATURE                  Location/Qualifiers
source                   1..23
                         mol_type = other DNA
                         organism = synthetic construct
SEQUENCE: 27
tgttgccact tacaattcaa caa                                             23

SEQ ID NO: 28            moltype = DNA  length = 27
FEATURE                  Location/Qualifiers
source                   1..27
                         mol_type = other DNA
                         organism = synthetic construct
SEQUENCE: 28
gaaaatgtat ccatacatcg aacgaca                                         27

SEQ ID NO: 29            moltype = DNA  length = 23
FEATURE                  Location/Qualifiers
source                   1..23
                         mol_type = other DNA
                         organism = synthetic construct
SEQUENCE: 29
aggtaaaaac gctcatgatg cta                                             23

SEQ ID NO: 30            moltype = DNA  length = 28
FEATURE                  Location/Qualifiers
source                   1..28
```

-continued

```
                        mol_type = other DNA
                        organism = synthetic construct
SEQUENCE: 30
ttagaataaa tggatggata gtcctgta                                         28

SEQ ID NO: 31           moltype = DNA   length = 27
FEATURE                 Location/Qualifiers
source                  1..27
                        mol_type = other DNA
                        organism = synthetic construct
SEQUENCE: 31
ttatgggcaa tagcacattc aaaggta                                          27

SEQ ID NO: 32           moltype = DNA   length = 25
FEATURE                 Location/Qualifiers
source                  1..25
                        mol_type = other DNA
                        organism = synthetic construct
SEQUENCE: 32
gaggatgatt tgcccttcac tcatt                                            25

SEQ ID NO: 33           moltype = DNA   length = 20
FEATURE                 Location/Qualifiers
source                  1..20
                        mol_type = other DNA
                        organism = synthetic construct
SEQUENCE: 33
tgagatcccg tcgtatgagt                                                  20

SEQ ID NO: 34           moltype = DNA   length = 22
FEATURE                 Location/Qualifiers
source                  1..22
                        mol_type = other DNA
                        organism = synthetic construct
SEQUENCE: 34
tttccctcca agacctttgc cg                                               22

SEQ ID NO: 35           moltype = DNA   length = 28
FEATURE                 Location/Qualifiers
source                  1..28
                        mol_type = other DNA
                        organism = synthetic construct
SEQUENCE: 35
gcagaaaaat atcttaccat cttttcca                                         28

SEQ ID NO: 36           moltype = DNA   length = 20
FEATURE                 Location/Qualifiers
source                  1..20
                        mol_type = other DNA
                        organism = synthetic construct
SEQUENCE: 36
aactactccg tgaaacgcat                                                  20

SEQ ID NO: 37           moltype = DNA   length = 18
FEATURE                 Location/Qualifiers
source                  1..18
                        mol_type = other DNA
                        organism = synthetic construct
SEQUENCE: 37
ttgctcaaaa cgcggcca                                                    18

SEQ ID NO: 38           moltype = DNA   length = 28
FEATURE                 Location/Qualifiers
source                  1..28
                        mol_type = other DNA
                        organism = synthetic construct
SEQUENCE: 38
agatttccag gatactatag caagattt                                         28

SEQ ID NO: 39           moltype = DNA   length = 28
FEATURE                 Location/Qualifiers
source                  1..28
                        mol_type = other DNA
                        organism = synthetic construct
SEQUENCE: 39
ctttagaacg tttttgtggt gtttcatg                                         28

SEQ ID NO: 40           moltype = DNA   length = 26
FEATURE                 Location/Qualifiers
```

```
source                  1..26
                        mol_type = other DNA
                        organism = synthetic construct
SEQUENCE: 40
cataggcatg ctagttcaaa tagggt                                          26

SEQ ID NO: 41           moltype = DNA   length = 18
FEATURE                 Location/Qualifiers
source                  1..18
                        mol_type = other DNA
                        organism = synthetic construct
SEQUENCE: 41
ccgctctctc tgcagacc                                                   18

SEQ ID NO: 42           moltype = DNA   length = 25
FEATURE                 Location/Qualifiers
source                  1..25
                        mol_type = other DNA
                        organism = synthetic construct
SEQUENCE: 42
gattttattt gtattcggcc acgat                                           25

SEQ ID NO: 43           moltype = DNA   length = 27
FEATURE                 Location/Qualifiers
source                  1..27
                        mol_type = other DNA
                        organism = synthetic construct
SEQUENCE: 43
tttggatatt tacagctcag atgcttc                                         27

SEQ ID NO: 44           moltype = DNA   length = 28
FEATURE                 Location/Qualifiers
source                  1..28
                        mol_type = other DNA
                        organism = synthetic construct
SEQUENCE: 44
agaatattcc caaatgatgg ataagttt                                        28

SEQ ID NO: 45           moltype = DNA   length = 24
FEATURE                 Location/Qualifiers
source                  1..24
                        mol_type = other DNA
                        organism = synthetic construct
SEQUENCE: 45
ccaaagaaac tctagaggac aacg                                            24

SEQ ID NO: 46           moltype = DNA   length = 28
FEATURE                 Location/Qualifiers
source                  1..28
                        mol_type = other DNA
                        organism = synthetic construct
SEQUENCE: 46
gccccttaat tgtataacaa atttgttt                                        28

SEQ ID NO: 47           moltype = DNA   length = 23
FEATURE                 Location/Qualifiers
source                  1..23
                        mol_type = other DNA
                        organism = synthetic construct
SEQUENCE: 47
gacatatcat gtcatggacg tct                                             23

SEQ ID NO: 48           moltype = DNA   length = 22
FEATURE                 Location/Qualifiers
source                  1..22
                        mol_type = other DNA
                        organism = synthetic construct
SEQUENCE: 48
gtaaggacgc catttgtttt ct                                              22

SEQ ID NO: 49           moltype = DNA   length = 25
FEATURE                 Location/Qualifiers
source                  1..25
                        mol_type = other DNA
                        organism = synthetic construct
SEQUENCE: 49
agtgactatg attatacgtt gcagc                                           25

SEQ ID NO: 50           moltype = DNA   length = 20
```

```
FEATURE                 Location/Qualifiers
source                  1..20
                        mol_type = other DNA
                        organism = synthetic construct
SEQUENCE: 50
ctttactagc gccgcttcga                                               20

SEQ ID NO: 51           moltype = DNA   length = 26
FEATURE                 Location/Qualifiers
source                  1..26
                        mol_type = other DNA
                        organism = synthetic construct
SEQUENCE: 51
gtttccaaga gtggattatg acaaaa                                        26

SEQ ID NO: 52           moltype = DNA   length = 22
FEATURE                 Location/Qualifiers
source                  1..22
                        mol_type = other DNA
                        organism = synthetic construct
SEQUENCE: 52
cttaacgcct gtatccgaac cc                                            22

SEQ ID NO: 53           moltype = DNA   length = 28
FEATURE                 Location/Qualifiers
source                  1..28
                        mol_type = other DNA
                        organism = synthetic construct
SEQUENCE: 53
ccctggcatt acgacataat tttacaaa                                      28

SEQ ID NO: 54           moltype = DNA   length = 26
FEATURE                 Location/Qualifiers
source                  1..26
                        mol_type = other DNA
                        organism = synthetic construct
SEQUENCE: 54
tgcaaatctc ttttcacga cacaac                                         26

SEQ ID NO: 55           moltype = DNA   length = 18
FEATURE                 Location/Qualifiers
source                  1..18
                        mol_type = other DNA
                        organism = synthetic construct
SEQUENCE: 55
ttgagccacg cgaacagt                                                 18

SEQ ID NO: 56           moltype = DNA   length = 28
FEATURE                 Location/Qualifiers
source                  1..28
                        mol_type = other DNA
                        organism = synthetic construct
SEQUENCE: 56
tatcgtaacg ttctataaag ttttcgaa                                      28

SEQ ID NO: 57           moltype = DNA   length = 26
FEATURE                 Location/Qualifiers
source                  1..26
                        mol_type = other DNA
                        organism = synthetic construct
SEQUENCE: 57
aaaaacaacg attaaggagg ctatgc                                        26

SEQ ID NO: 58           moltype = DNA   length = 19
FEATURE                 Location/Qualifiers
source                  1..19
                        mol_type = other DNA
                        organism = synthetic construct
SEQUENCE: 58
cgctacgcgt gaagaacat                                                19

SEQ ID NO: 59           moltype = DNA   length = 28
FEATURE                 Location/Qualifiers
source                  1..28
                        mol_type = other DNA
                        organism = synthetic construct
SEQUENCE: 59
cgagaaaagt ttttaacacc agaaattc                                      28
```

| | | |
|---|---|---|
| SEQ ID NO: 60 | moltype = DNA length = 28 | |
| FEATURE | Location/Qualifiers | |
| source | 1..28<br>mol_type = other DNA<br>organism = synthetic construct | |
| SEQUENCE: 60 | | |
| atcatctctt tgaccatttt cttctgtt | | 28 |
| | | |
| SEQ ID NO: 61 | moltype = DNA length = 20 | |
| FEATURE | Location/Qualifiers | |
| source | 1..20<br>mol_type = other DNA<br>organism = synthetic construct | |
| SEQUENCE: 61 | | |
| cgtctctaga cgacttctgc | | 20 |
| | | |
| SEQ ID NO: 62 | moltype = DNA length = 24 | |
| FEATURE | Location/Qualifiers | |
| source | 1..24<br>mol_type = other DNA<br>organism = synthetic construct | |
| SEQUENCE: 62 | | |
| attcagaaag atcaaaaggt gcag | | 24 |
| | | |
| SEQ ID NO: 63 | moltype = DNA length = 16 | |
| FEATURE | Location/Qualifiers | |
| source | 1..16<br>mol_type = other DNA<br>organism = synthetic construct | |
| SEQUENCE: 63 | | |
| tgaaagcccg cggcac | | 16 |
| | | |
| SEQ ID NO: 64 | moltype = DNA length = 23 | |
| FEATURE | Location/Qualifiers | |
| source | 1..23<br>mol_type = other DNA<br>organism = synthetic construct | |
| SEQUENCE: 64 | | |
| cttctttggg gagtgtactc agc | | 23 |
| | | |
| SEQ ID NO: 65 | moltype = DNA length = 21 | |
| FEATURE | Location/Qualifiers | |
| source | 1..21<br>mol_type = other DNA<br>organism = synthetic construct | |
| SEQUENCE: 65 | | |
| caaggtttac cactccctgc t | | 21 |
| | | |
| SEQ ID NO: 66 | moltype = DNA length = 16 | |
| FEATURE | Location/Qualifiers | |
| source | 1..16<br>mol_type = other DNA<br>organism = synthetic construct | |
| SEQUENCE: 66 | | |
| ttgtcgtccg gcgtcc | | 16 |
| | | |
| SEQ ID NO: 67 | moltype = DNA length = 19 | |
| FEATURE | Location/Qualifiers | |
| source | 1..19<br>mol_type = other DNA<br>organism = synthetic construct | |
| SEQUENCE: 67 | | |
| aacaacggca gacagcaaa | | 19 |
| | | |
| SEQ ID NO: 68 | moltype = DNA length = 23 | |
| FEATURE | Location/Qualifiers | |
| source | 1..23<br>mol_type = other DNA<br>organism = synthetic construct | |
| SEQUENCE: 68 | | |
| ggcttctccg ggtttctatt ctt | | 23 |
| | | |
| SEQ ID NO: 69 | moltype = DNA length = 23 | |
| FEATURE | Location/Qualifiers | |
| source | 1..23<br>mol_type = other DNA<br>organism = synthetic construct | |
| SEQUENCE: 69 | | |
| ccatttccct ctagcgactg aag | | 23 |

```
SEQ ID NO: 70          moltype = DNA   length = 24
FEATURE                Location/Qualifiers
source                 1..24
                       mol_type = other DNA
                       organism = synthetic construct
SEQUENCE: 70
tgtaacttat tctccctgag tctg                                              24

SEQ ID NO: 71          moltype = DNA   length = 16
FEATURE                Location/Qualifiers
source                 1..16
                       mol_type = other DNA
                       organism = synthetic construct
SEQUENCE: 71
agtcggccgc gtgaca                                                       16

SEQ ID NO: 72          moltype = DNA   length = 23
FEATURE                Location/Qualifiers
source                 1..23
                       mol_type = other DNA
                       organism = synthetic construct
SEQUENCE: 72
aagcctagat gatttctgct tcg                                               23

SEQ ID NO: 73          moltype = DNA   length = 26
FEATURE                Location/Qualifiers
source                 1..26
                       mol_type = other DNA
                       organism = synthetic construct
SEQUENCE: 73
ctgtggggta tttatagctt cacaga                                            26

SEQ ID NO: 74          moltype = DNA   length = 19
FEATURE                Location/Qualifiers
source                 1..19
                       mol_type = other DNA
                       organism = synthetic construct
SEQUENCE: 74
ggagacctgc agcactttc                                                    19

SEQ ID NO: 75          moltype = DNA   length = 21
FEATURE                Location/Qualifiers
source                 1..21
                       mol_type = other DNA
                       organism = synthetic construct
SEQUENCE: 75
ggtaaccgag catacgctgt g                                                 21

SEQ ID NO: 76          moltype = DNA   length = 21
FEATURE                Location/Qualifiers
source                 1..21
                       mol_type = other DNA
                       organism = synthetic construct
SEQUENCE: 76
ggccatactt gacgaggtta a                                                 21

SEQ ID NO: 77          moltype = DNA   length = 23
FEATURE                Location/Qualifiers
source                 1..23
                       mol_type = other DNA
                       organism = synthetic construct
SEQUENCE: 77
tcaggctttt tcttttggc ctg                                                23

SEQ ID NO: 78          moltype = DNA   length = 22
FEATURE                Location/Qualifiers
source                 1..22
                       mol_type = other DNA
                       organism = synthetic construct
SEQUENCE: 78
cggtaagaac cagagccaga ag                                                22

SEQ ID NO: 79          moltype = DNA   length = 18
FEATURE                Location/Qualifiers
source                 1..18
                       mol_type = other DNA
                       organism = synthetic construct
SEQUENCE: 79
```

```
accttcccgc tggatgaa                                                    18

SEQ ID NO: 80            moltype = DNA   length = 21
FEATURE                  Location/Qualifiers
source                   1..21
                         mol_type = other DNA
                         organism = synthetic construct
SEQUENCE: 80
ctgaagatga catccggcac c                                                21

SEQ ID NO: 81            moltype = DNA   length = 18
FEATURE                  Location/Qualifiers
source                   1..18
                         mol_type = other DNA
                         organism = synthetic construct
SEQUENCE: 81
ccgtccacgt agatcggg                                                    18

SEQ ID NO: 82            moltype = DNA   length = 19
FEATURE                  Location/Qualifiers
source                   1..19
                         mol_type = other DNA
                         organism = synthetic construct
SEQUENCE: 82
ccacctggga ctacacgct                                                   19

SEQ ID NO: 83            moltype = DNA   length = 16
FEATURE                  Location/Qualifiers
source                   1..16
                         mol_type = other DNA
                         organism = synthetic construct
SEQUENCE: 83
gagggccgag ccgaag                                                      16

SEQ ID NO: 84            moltype = DNA   length = 16
FEATURE                  Location/Qualifiers
source                   1..16
                         mol_type = other DNA
                         organism = synthetic construct
SEQUENCE: 84
tctccgccga gacgac                                                      16

SEQ ID NO: 85            moltype = DNA   length = 18
FEATURE                  Location/Qualifiers
source                   1..18
                         mol_type = other DNA
                         organism = synthetic construct
SEQUENCE: 85
cagacgtcga agccggag                                                    18

SEQ ID NO: 86            moltype = DNA   length = 16
FEATURE                  Location/Qualifiers
source                   1..16
                         mol_type = other DNA
                         organism = synthetic construct
SEQUENCE: 86
gggtcgtacg cgagcc                                                      16

SEQ ID NO: 87            moltype = DNA   length = 16
FEATURE                  Location/Qualifiers
source                   1..16
                         mol_type = other DNA
                         organism = synthetic construct
SEQUENCE: 87
ggcgagaaga gctgcg                                                      16

SEQ ID NO: 88            moltype = DNA   length = 19
FEATURE                  Location/Qualifiers
source                   1..19
                         mol_type = other DNA
                         organism = synthetic construct
SEQUENCE: 88
cctctacacg ctgcacgac                                                   19

SEQ ID NO: 89            moltype = DNA   length = 16
FEATURE                  Location/Qualifiers
source                   1..16
                         mol_type = other DNA
                         organism = synthetic construct
```

```
SEQUENCE: 89
tggcggtctt tggcgc                                                          16

SEQ ID NO: 90         moltype = DNA  length = 16
FEATURE               Location/Qualifiers
source                1..16
                      mol_type = other DNA
                      organism = synthetic construct
SEQUENCE: 90
cgagcgccag cagcag                                                          16

SEQ ID NO: 91         moltype = DNA  length = 18
FEATURE               Location/Qualifiers
source                1..18
                      mol_type = other DNA
                      organism = synthetic construct
SEQUENCE: 91
acctcctcga cgatgcag                                                        18

SEQ ID NO: 92         moltype = DNA  length = 16
FEATURE               Location/Qualifiers
source                1..16
                      mol_type = other DNA
                      organism = synthetic construct
SEQUENCE: 92
cctgaacgcg ctcggc                                                          16

SEQ ID NO: 93         moltype = DNA  length = 21
FEATURE               Location/Qualifiers
source                1..21
                      mol_type = other DNA
                      organism = synthetic construct
SEQUENCE: 93
ctgcagttca cctacgacca c                                                    21

SEQ ID NO: 94         moltype = DNA  length = 16
FEATURE               Location/Qualifiers
source                1..16
                      mol_type = other DNA
                      organism = synthetic construct
SEQUENCE: 94
caggcgcgac atctcg                                                          16

SEQ ID NO: 95         moltype = DNA  length = 17
FEATURE               Location/Qualifiers
source                1..17
                      mol_type = other DNA
                      organism = synthetic construct
SEQUENCE: 95
ccgcaacccc atgaagg                                                         17

SEQ ID NO: 96         moltype = DNA  length = 17
FEATURE               Location/Qualifiers
source                1..17
                      mol_type = other DNA
                      organism = synthetic construct
SEQUENCE: 96
ccgcaacccc atgaagg                                                         17

SEQ ID NO: 97         moltype = DNA  length = 20
FEATURE               Location/Qualifiers
source                1..20
                      mol_type = other DNA
                      organism = synthetic construct
SEQUENCE: 97
tccaaggagg cgttaccgaa                                                      20

SEQ ID NO: 98         moltype = DNA  length = 18
FEATURE               Location/Qualifiers
source                1..18
                      mol_type = other DNA
                      organism = synthetic construct
SEQUENCE: 98
gggagaggcg ggtgttga                                                        18

SEQ ID NO: 99         moltype = DNA  length = 24
FEATURE               Location/Qualifiers
source                1..24
                      mol_type = other DNA
```

```
                        organism = synthetic construct
SEQUENCE: 99
tcaatagtgg aatctaggac aggt                                              24

SEQ ID NO: 100          moltype = DNA  length = 28
FEATURE                 Location/Qualifiers
source                  1..28
                        mol_type = other DNA
                        organism = synthetic construct
SEQUENCE: 100
tagatgataa ctttgtaaca aaggccac                                          28

SEQ ID NO: 101          moltype = DNA  length = 23
FEATURE                 Location/Qualifiers
source                  1..23
                        mol_type = other DNA
                        organism = synthetic construct
SEQUENCE: 101
tcctaccact cccggtactt tac                                               23

SEQ ID NO: 102          moltype = DNA  length = 22
FEATURE                 Location/Qualifiers
source                  1..22
                        mol_type = other DNA
                        organism = synthetic construct
SEQUENCE: 102
tggtctacat ttccagcagt tt                                                22

SEQ ID NO: 103          moltype = DNA  length = 21
FEATURE                 Location/Qualifiers
source                  1..21
                        mol_type = other DNA
                        organism = synthetic construct
SEQUENCE: 103
gcaagaagag tggaagaagc g                                                 21

SEQ ID NO: 104          moltype = DNA  length = 19
FEATURE                 Location/Qualifiers
source                  1..19
                        mol_type = other DNA
                        organism = synthetic construct
SEQUENCE: 104
ctcctcattg ccttcctcg                                                    19

SEQ ID NO: 105          moltype = DNA  length = 25
FEATURE                 Location/Qualifiers
source                  1..25
                        mol_type = other DNA
                        organism = synthetic construct
SEQUENCE: 105
gcagtattct gattaccagc aatca                                             25

SEQ ID NO: 106          moltype = DNA  length = 24
FEATURE                 Location/Qualifiers
source                  1..24
                        mol_type = other DNA
                        organism = synthetic construct
SEQUENCE: 106
gtggattgtt ctgtagcatt cttc                                              24

SEQ ID NO: 107          moltype = DNA  length = 28
FEATURE                 Location/Qualifiers
source                  1..28
                        mol_type = other DNA
                        organism = synthetic construct
SEQUENCE: 107
cttactgata gaatgtggag ctcctaga                                          28

SEQ ID NO: 108          moltype = DNA  length = 21
FEATURE                 Location/Qualifiers
source                  1..21
                        mol_type = other DNA
                        organism = synthetic construct
SEQUENCE: 108
gcggaaattt ctgacaaacg t                                                 21

SEQ ID NO: 109          moltype = DNA  length = 25
FEATURE                 Location/Qualifiers
source                  1..25
```

```
                            mol_type = other DNA
                            organism = synthetic construct
SEQUENCE: 109
gccagccata aaagtcatca ataac                                              25

SEQ ID NO: 110              moltype = DNA  length = 27
FEATURE                     Location/Qualifiers
source                      1..27
                            mol_type = other DNA
                            organism = synthetic construct
SEQUENCE: 110
gaaaaagcaa atgggctgct aattttg                                            27

SEQ ID NO: 111              moltype = DNA  length = 28
FEATURE                     Location/Qualifiers
source                      1..28
                            mol_type = other DNA
                            organism = synthetic construct
SEQUENCE: 111
tggtggagta tttctttgtg tagtatgt                                           28

SEQ ID NO: 112              moltype = DNA  length = 26
FEATURE                     Location/Qualifiers
source                      1..26
                            mol_type = other DNA
                            organism = synthetic construct
SEQUENCE: 112
atgagacaca gagctatatt cagaag                                             26

SEQ ID NO: 113              moltype = DNA  length = 28
FEATURE                     Location/Qualifiers
source                      1..28
                            mol_type = other DNA
                            organism = synthetic construct
SEQUENCE: 113
gatactaaag atgaaagtta cactcagc                                           28

SEQ ID NO: 114              moltype = DNA  length = 19
FEATURE                     Location/Qualifiers
source                      1..19
                            mol_type = other DNA
                            organism = synthetic construct
SEQUENCE: 114
ggagccaagt gtttgtggt                                                     19

SEQ ID NO: 115              moltype = DNA  length = 26
FEATURE                     Location/Qualifiers
source                      1..26
                            mol_type = other DNA
                            organism = synthetic construct
SEQUENCE: 115
ccgtagaagt ctgtcattcc agtttt                                             26

SEQ ID NO: 116              moltype = DNA  length = 19
FEATURE                     Location/Qualifiers
source                      1..19
                            mol_type = other DNA
                            organism = synthetic construct
SEQUENCE: 116
ggaactacca gcgctcacc                                                     19

SEQ ID NO: 117              moltype = DNA  length = 19
FEATURE                     Location/Qualifiers
source                      1..19
                            mol_type = other DNA
                            organism = synthetic construct
SEQUENCE: 117
gagggaaagc ccgaaacac                                                     19

SEQ ID NO: 118              moltype = DNA  length = 24
FEATURE                     Location/Qualifiers
source                      1..24
                            mol_type = other DNA
                            organism = synthetic construct
SEQUENCE: 118
ttccaacctc tttgccgata ataa                                               24

SEQ ID NO: 119              moltype = DNA  length = 27
FEATURE                     Location/Qualifiers
```

```
source                   1..27
                         mol_type = other DNA
                         organism = synthetic construct
SEQUENCE: 119
ggagtggtat tcatcggaga atattcg                                            27

SEQ ID NO: 120           moltype = DNA   length = 23
FEATURE                  Location/Qualifiers
source                   1..23
                         mol_type = other DNA
                         organism = synthetic construct
SEQUENCE: 120
tgtctccatg tctttctttta ccc                                               23

SEQ ID NO: 121           moltype = DNA   length = 17
FEATURE                  Location/Qualifiers
source                   1..17
                         mol_type = other DNA
                         organism = synthetic construct
SEQUENCE: 121
cccgacgtct ccgtcag                                                       17

SEQ ID NO: 122           moltype = DNA   length = 20
FEATURE                  Location/Qualifiers
source                   1..20
                         mol_type = other DNA
                         organism = synthetic construct
SEQUENCE: 122
aggccagcga gtattgcaag                                                    20

SEQ ID NO: 123           moltype = DNA   length = 24
FEATURE                  Location/Qualifiers
source                   1..24
                         mol_type = other DNA
                         organism = synthetic construct
SEQUENCE: 123
gtaaaccgcg tgattttaaa actg                                               24

SEQ ID NO: 124           moltype = DNA   length = 24
FEATURE                  Location/Qualifiers
source                   1..24
                         mol_type = other DNA
                         organism = synthetic construct
SEQUENCE: 124
ccccattata accatcccac caag                                               24

SEQ ID NO: 125           moltype = DNA   length = 17
FEATURE                  Location/Qualifiers
source                   1..17
                         mol_type = other DNA
                         organism = synthetic construct
SEQUENCE: 125
gcaagtcaca gcgcact                                                       17

SEQ ID NO: 126           moltype = DNA   length = 26
FEATURE                  Location/Qualifiers
source                   1..26
                         mol_type = other DNA
                         organism = synthetic construct
SEQUENCE: 126
aactatacgt gctgtaagtt acagag                                             26

SEQ ID NO: 127           moltype = DNA   length = 28
FEATURE                  Location/Qualifiers
source                   1..28
                         mol_type = other DNA
                         organism = synthetic construct
SEQUENCE: 127
ttgatgatat tgagttttgc tcccatac                                           28

SEQ ID NO: 128           moltype = DNA   length = 19
FEATURE                  Location/Qualifiers
source                   1..19
                         mol_type = other DNA
                         organism = synthetic construct
SEQUENCE: 128
atggtacccc tctcaccac                                                     19

SEQ ID NO: 129           moltype = DNA   length = 26
```

```
FEATURE                 Location/Qualifiers
source                  1..26
                        mol_type = other DNA
                        organism = synthetic construct
SEQUENCE: 129
ggaccaactt catctcaaga cttgta                                          26

SEQ ID NO: 130          moltype = DNA   length = 24
FEATURE                 Location/Qualifiers
source                  1..24
                        mol_type = other DNA
                        organism = synthetic construct
SEQUENCE: 130
cctcactttg tgtttgatga tcag                                            24

SEQ ID NO: 131          moltype = DNA   length = 24
FEATURE                 Location/Qualifiers
source                  1..24
                        mol_type = other DNA
                        organism = synthetic construct
SEQUENCE: 131
tggattttgt gacatgatct ccat                                            24

SEQ ID NO: 132          moltype = DNA   length = 23
FEATURE                 Location/Qualifiers
source                  1..23
                        mol_type = other DNA
                        organism = synthetic construct
SEQUENCE: 132
agcgttgtca tattgagtac cgc                                             23

SEQ ID NO: 133          moltype = DNA   length = 23
FEATURE                 Location/Qualifiers
source                  1..23
                        mol_type = other DNA
                        organism = synthetic construct
SEQUENCE: 133
agtgcttgat cggtaacaca act                                             23

SEQ ID NO: 134          moltype = DNA   length = 23
FEATURE                 Location/Qualifiers
source                  1..23
                        mol_type = other DNA
                        organism = synthetic construct
SEQUENCE: 134
acaggaagtt ttccttacag gtc                                             23

SEQ ID NO: 135          moltype = DNA   length = 28
FEATURE                 Location/Qualifiers
source                  1..28
                        mol_type = other DNA
                        organism = synthetic construct
SEQUENCE: 135
gttctgttag aactatgtag gtcactat                                        28

SEQ ID NO: 136          moltype = DNA   length = 23
FEATURE                 Location/Qualifiers
source                  1..23
                        mol_type = other DNA
                        organism = synthetic construct
SEQUENCE: 136
ggcgagtatc agtactggtt tga                                             23

SEQ ID NO: 137          moltype = DNA   length = 22
FEATURE                 Location/Qualifiers
source                  1..22
                        mol_type = other DNA
                        organism = synthetic construct
SEQUENCE: 137
gaagtgagtg aagcctcctt at                                              22

SEQ ID NO: 138          moltype = DNA   length = 22
FEATURE                 Location/Qualifiers
source                  1..22
                        mol_type = other DNA
                        organism = synthetic construct
SEQUENCE: 138
caactgaatg acgggaccgt ta                                              22
```

| | | |
|---|---|---|
| SEQ ID NO: 139 | moltype = DNA length = 18 | |
| FEATURE | Location/Qualifiers | |
| source | 1..18 | |
| | mol_type = other DNA | |
| | organism = synthetic construct | |
| SEQUENCE: 139 | | |
| tgtggtggtc gcacaatc | | 18 |
| | | |
| SEQ ID NO: 140 | moltype = DNA length = 21 | |
| FEATURE | Location/Qualifiers | |
| source | 1..21 | |
| | mol_type = other DNA | |
| | organism = synthetic construct | |
| SEQUENCE: 140 | | |
| ggtggacggg tgtcatagag t | | 21 |
| | | |
| SEQ ID NO: 141 | moltype = DNA length = 19 | |
| FEATURE | Location/Qualifiers | |
| source | 1..19 | |
| | mol_type = other DNA | |
| | organism = synthetic construct | |
| SEQUENCE: 141 | | |
| cccagtggcc aattcctca | | 19 |
| | | |
| SEQ ID NO: 142 | moltype = DNA length = 24 | |
| FEATURE | Location/Qualifiers | |
| source | 1..24 | |
| | mol_type = other DNA | |
| | organism = synthetic construct | |
| SEQUENCE: 142 | | |
| ttcttctctg acgtcaggtc aaac | | 24 |
| | | |
| SEQ ID NO: 143 | moltype = DNA length = 20 | |
| FEATURE | Location/Qualifiers | |
| source | 1..20 | |
| | mol_type = other DNA | |
| | organism = synthetic construct | |
| SEQUENCE: 143 | | |
| ttcaaagcga caggcttctt | | 20 |
| | | |
| SEQ ID NO: 144 | moltype = DNA length = 17 | |
| FEATURE | Location/Qualifiers | |
| source | 1..17 | |
| | mol_type = other DNA | |
| | organism = synthetic construct | |
| SEQUENCE: 144 | | |
| ggagggacct tacgccg | | 17 |
| | | |
| SEQ ID NO: 145 | moltype = DNA length = 26 | |
| FEATURE | Location/Qualifiers | |
| source | 1..26 | |
| | mol_type = other DNA | |
| | organism = synthetic construct | |
| SEQUENCE: 145 | | |
| acacttccac atggattatg gaactg | | 26 |
| | | |
| SEQ ID NO: 146 | moltype = DNA length = 18 | |
| FEATURE | Location/Qualifiers | |
| source | 1..18 | |
| | mol_type = other DNA | |
| | organism = synthetic construct | |
| SEQUENCE: 146 | | |
| cgtcaggtcc agagtgga | | 18 |
| | | |
| SEQ ID NO: 147 | moltype = DNA length = 19 | |
| FEATURE | Location/Qualifiers | |
| source | 1..19 | |
| | mol_type = other DNA | |
| | organism = synthetic construct | |
| SEQUENCE: 147 | | |
| ggttgtgtct gtggatccc | | 19 |
| | | |
| SEQ ID NO: 148 | moltype = DNA length = 20 | |
| FEATURE | Location/Qualifiers | |
| source | 1..20 | |
| | mol_type = other DNA | |
| | organism = synthetic construct | |
| SEQUENCE: 148 | | |
| ctgggtcaca gaaccaatca | | 20 |

```
SEQ ID NO: 149         moltype = DNA   length = 16
FEATURE                Location/Qualifiers
source                 1..16
                       mol_type = other DNA
                       organism = synthetic construct
SEQUENCE: 149
gaaaggcgcc ggcctc                                                        16

SEQ ID NO: 150         moltype = DNA   length = 18
FEATURE                Location/Qualifiers
source                 1..18
                       mol_type = other DNA
                       organism = synthetic construct
SEQUENCE: 150
cccgaggtaa cacgcgac                                                      18

SEQ ID NO: 151         moltype = DNA   length = 22
FEATURE                Location/Qualifiers
source                 1..22
                       mol_type = other DNA
                       organism = synthetic construct
SEQUENCE: 151
ggaaccgatg gactttcgtt ca                                                 22

SEQ ID NO: 152         moltype = DNA   length = 19
FEATURE                Location/Qualifiers
source                 1..19
                       mol_type = other DNA
                       organism = synthetic construct
SEQUENCE: 152
cgaccgaata ggcggagtg                                                     19

SEQ ID NO: 153         moltype = DNA   length = 23
FEATURE                Location/Qualifiers
source                 1..23
                       mol_type = other DNA
                       organism = synthetic construct
SEQUENCE: 153
ttcttgtccg aagttagagg gct                                                23

SEQ ID NO: 154         moltype = DNA   length = 21
FEATURE                Location/Qualifiers
source                 1..21
                       mol_type = other DNA
                       organism = synthetic construct
SEQUENCE: 154
ccatttctca tgaaaacggg c                                                  21

SEQ ID NO: 155         moltype = DNA   length = 17
FEATURE                Location/Qualifiers
source                 1..17
                       mol_type = other DNA
                       organism = synthetic construct
SEQUENCE: 155
accatgctcc gctacga                                                       17

SEQ ID NO: 156         moltype = DNA   length = 23
FEATURE                Location/Qualifiers
source                 1..23
                       mol_type = other DNA
                       organism = synthetic construct
SEQUENCE: 156
aaaacgtgca acttgaaatc ccg                                                23

SEQ ID NO: 157         moltype = DNA   length = 22
FEATURE                Location/Qualifiers
source                 1..22
                       mol_type = other DNA
                       organism = synthetic construct
SEQUENCE: 157
ggattggtct tgtctttagc ca                                                 22

SEQ ID NO: 158         moltype = DNA   length = 23
FEATURE                Location/Qualifiers
source                 1..23
                       mol_type = other DNA
                       organism = synthetic construct
SEQUENCE: 158
```

```
gtcttctaac cgaggtcgaa acg                                              23

SEQ ID NO: 159         moltype = DNA   length = 20
FEATURE                Location/Qualifiers
source                 1..20
                       mol_type = other DNA
                       organism = synthetic construct
SEQUENCE: 159
gactgcagcg tagacgcttt                                                  20

SEQ ID NO: 160         moltype = DNA   length = 19
FEATURE                Location/Qualifiers
source                 1..19
                       mol_type = other DNA
                       organism = synthetic construct
SEQUENCE: 160
cagcagagta actgagcgc                                                   19

SEQ ID NO: 161         moltype = DNA   length = 21
FEATURE                Location/Qualifiers
source                 1..21
                       mol_type = other DNA
                       organism = synthetic construct
SEQUENCE: 161
gatccagcca tttgttccat g                                                21

SEQ ID NO: 162         moltype = DNA   length = 21
FEATURE                Location/Qualifiers
source                 1..21
                       mol_type = other DNA
                       organism = synthetic construct
SEQUENCE: 162
cctagtatgc gcaacctgtg a                                                21

SEQ ID NO: 163         moltype = DNA   length = 23
FEATURE                Location/Qualifiers
source                 1..23
                       mol_type = other DNA
                       organism = synthetic construct
SEQUENCE: 163
cattcgtttc tgataggcct gta                                              23

SEQ ID NO: 164         moltype = DNA   length = 23
FEATURE                Location/Qualifiers
source                 1..23
                       mol_type = other DNA
                       organism = synthetic construct
SEQUENCE: 164
agcagcagag gctatggaaa ttg                                              23

SEQ ID NO: 165         moltype = DNA   length = 28
FEATURE                Location/Qualifiers
source                 1..28
                       mol_type = other DNA
                       organism = synthetic construct
SEQUENCE: 165
actgttacat tcttttctag tactgtgt                                         28

SEQ ID NO: 166         moltype = DNA   length = 28
FEATURE                Location/Qualifiers
source                 1..28
                       mol_type = other DNA
                       organism = synthetic construct
SEQUENCE: 166
atgaaggcaa tactagtagt cttgctat                                         28

SEQ ID NO: 167         moltype = DNA   length = 26
FEATURE                Location/Qualifiers
source                 1..26
                       mol_type = other DNA
                       organism = synthetic construct
SEQUENCE: 167
ataccatcca tctatcattc ctgtcc                                           26

SEQ ID NO: 168         moltype = DNA   length = 28
FEATURE                Location/Qualifiers
source                 1..28
                       mol_type = other DNA
                       organism = synthetic construct
```

```
SEQUENCE: 168
tgtccaaaat atgtcaaaag cacaaaat                                             28

SEQ ID NO: 169          moltype = DNA   length = 28
FEATURE                 Location/Qualifiers
source                  1..28
                        mol_type = other DNA
                        organism = synthetic construct
SEQUENCE: 169
tggtaaatcc ttgttgattc cagcttta                                             28

SEQ ID NO: 170          moltype = DNA   length = 22
FEATURE                 Location/Qualifiers
source                  1..22
                        mol_type = other DNA
                        organism = synthetic construct
SEQUENCE: 170
ccacaaatgt gatgacacgt gc                                                   22

SEQ ID NO: 171          moltype = DNA   length = 25
FEATURE                 Location/Qualifiers
source                  1..25
                        mol_type = other DNA
                        organism = synthetic construct
SEQUENCE: 171
tctggtagag actttgttgg tcagt                                                25

SEQ ID NO: 172          moltype = DNA   length = 25
FEATURE                 Location/Qualifiers
source                  1..25
                        mol_type = other DNA
                        organism = synthetic construct
SEQUENCE: 172
tctacagaaa cttaatatgg ctggt                                                25

SEQ ID NO: 173          moltype = DNA   length = 28
FEATURE                 Location/Qualifiers
source                  1..28
                        mol_type = other DNA
                        organism = synthetic construct
SEQUENCE: 173
aaactgtaat cccgaatatc ggatctag                                             28

SEQ ID NO: 174          moltype = DNA   length = 25
FEATURE                 Location/Qualifiers
source                  1..25
                        mol_type = other DNA
                        organism = synthetic construct
SEQUENCE: 174
aattagattc cctgtgctgt taatc                                                25

SEQ ID NO: 175          moltype = DNA   length = 26
FEATURE                 Location/Qualifiers
source                  1..26
                        mol_type = other DNA
                        organism = synthetic construct
SEQUENCE: 175
gtacggtttc aggcatcaaa attctg                                               26

SEQ ID NO: 176          moltype = DNA   length = 24
FEATURE                 Location/Qualifiers
source                  1..24
                        mol_type = other DNA
                        organism = synthetic construct
SEQUENCE: 176
tgatggaatt tctcgttcgt tttc                                                 24

SEQ ID NO: 177          moltype = DNA   length = 24
FEATURE                 Location/Qualifiers
source                  1..24
                        mol_type = other DNA
                        organism = synthetic construct
SEQUENCE: 177
attccttatt ttggaagcca tcac                                                 24

SEQ ID NO: 178          moltype = DNA   length = 27
FEATURE                 Location/Qualifiers
source                  1..27
                        mol_type = other DNA
```

```
                         organism = synthetic construct
SEQUENCE: 178
ttgaagtaac taatgctact gagctgg                                         27

SEQ ID NO: 179           moltype = DNA  length = 28
FEATURE                  Location/Qualifiers
source                   1..28
                         mol_type = other DNA
                         organism = synthetic construct
SEQUENCE: 179
ttctacgata aatttcaatg ttatcgcc                                        28

SEQ ID NO: 180           moltype = DNA  length = 28
FEATURE                  Location/Qualifiers
source                   1..28
                         mol_type = other DNA
                         organism = synthetic construct
SEQUENCE: 180
cagataacgg tacaacaaat gatgtttc                                        28

SEQ ID NO: 181           moltype = DNA  length = 27
FEATURE                  Location/Qualifiers
source                   1..27
                         mol_type = other DNA
                         organism = synthetic construct
SEQUENCE: 181
agaacaatct attgtcttag gcacagg                                         27

SEQ ID NO: 182           moltype = DNA  length = 19
FEATURE                  Location/Qualifiers
source                   1..19
                         mol_type = other DNA
                         organism = synthetic construct
SEQUENCE: 182
ccctgcgctt gggtatttg                                                  19

SEQ ID NO: 183           moltype = DNA  length = 22
FEATURE                  Location/Qualifiers
source                   1..22
                         mol_type = other DNA
                         organism = synthetic construct
SEQUENCE: 183
cttgtcctgg atcgccttta tc                                              22

SEQ ID NO: 184           moltype = DNA  length = 17
FEATURE                  Location/Qualifiers
source                   1..17
                         mol_type = other DNA
                         organism = synthetic construct
SEQUENCE: 184
cgagcagggt cctaggg                                                    17

SEQ ID NO: 185           moltype = DNA  length = 26
FEATURE                  Location/Qualifiers
source                   1..26
                         mol_type = other DNA
                         organism = synthetic construct
SEQUENCE: 185
atacccgctc ttgcattaac aatatc                                          26

SEQ ID NO: 186           moltype = DNA  length = 23
FEATURE                  Location/Qualifiers
source                   1..23
                         mol_type = other DNA
                         organism = synthetic construct
SEQUENCE: 186
aatggtgcca gaattaccaa cgt                                             23

SEQ ID NO: 187           moltype = DNA  length = 19
FEATURE                  Location/Qualifiers
source                   1..19
                         mol_type = other DNA
                         organism = synthetic construct
SEQUENCE: 187
agtagcagca ggtgaagct                                                  19

SEQ ID NO: 188           moltype = DNA  length = 19
FEATURE                  Location/Qualifiers
source                   1..19
```

```
                        mol_type = other DNA
                        organism = synthetic construct
SEQUENCE: 188
atccgttgct ttcgcacca                                              19

SEQ ID NO: 189          moltype = DNA   length = 26
FEATURE                 Location/Qualifiers
source                  1..26
                        mol_type = other DNA
                        organism = synthetic construct
SEQUENCE: 189
acggatatcg ttgttcttgt agtagc                                      26

SEQ ID NO: 190          moltype = DNA   length = 21
FEATURE                 Location/Qualifiers
source                  1..21
                        mol_type = other DNA
                        organism = synthetic construct
SEQUENCE: 190
ttctacacgc tctaggtttg c                                           21

SEQ ID NO: 191          moltype = DNA   length = 28
FEATURE                 Location/Qualifiers
source                  1..28
                        mol_type = other DNA
                        organism = synthetic construct
SEQUENCE: 191
aacaagagtt attacaacac gaagtgat                                    28

SEQ ID NO: 192          moltype = DNA   length = 27
FEATURE                 Location/Qualifiers
source                  1..27
                        mol_type = other DNA
                        organism = synthetic construct
SEQUENCE: 192
ttaccgcact taattctaat acttccg                                     27

SEQ ID NO: 193          moltype = DNA   length = 26
FEATURE                 Location/Qualifiers
source                  1..26
                        mol_type = other DNA
                        organism = synthetic construct
SEQUENCE: 193
aagaaggctc actatttgat tgaacc                                      26

SEQ ID NO: 194          moltype = DNA   length = 28
FEATURE                 Location/Qualifiers
source                  1..28
                        mol_type = other DNA
                        organism = synthetic construct
SEQUENCE: 194
atgaaacaaa tcgttttaaa aacaagct                                    28

SEQ ID NO: 195          moltype = DNA   length = 18
FEATURE                 Location/Qualifiers
source                  1..18
                        mol_type = other DNA
                        organism = synthetic construct
SEQUENCE: 195
ttgtcgggtc ctgtaggg                                               18

SEQ ID NO: 196          moltype = DNA   length = 28
FEATURE                 Location/Qualifiers
source                  1..28
                        mol_type = other DNA
                        organism = synthetic construct
SEQUENCE: 196
aatggcaaga tttatggtga aatctaca                                    28

SEQ ID NO: 197          moltype = DNA   length = 27
FEATURE                 Location/Qualifiers
source                  1..27
                        mol_type = other DNA
                        organism = synthetic construct
SEQUENCE: 197
cctttaaagc ccctctagaa caagaaa                                     27

SEQ ID NO: 198          moltype = DNA   length = 28
FEATURE                 Location/Qualifiers
```

```
                               -continued source                  1..28
                        mol_type = other DNA
                        organism = synthetic construct
SEQUENCE: 198
gaataccgta acgttatctt tatctaca                                    28

SEQ ID NO: 199          moltype = DNA   length = 19
FEATURE                 Location/Qualifiers
source                  1..19
                        mol_type = other DNA
                        organism = synthetic construct
SEQUENCE: 199
ttcgctgcaa tcggttcat                                              19

SEQ ID NO: 200          moltype = DNA   length = 25
FEATURE                 Location/Qualifiers
source                  1..25
                        mol_type = other DNA
                        organism = synthetic construct
SEQUENCE: 200
atgaatcaag cggtcacaga aaaga                                       25

SEQ ID NO: 201          moltype = DNA   length = 19
FEATURE                 Location/Qualifiers
source                  1..19
                        mol_type = other DNA
                        organism = synthetic construct
SEQUENCE: 201
tgatagccat gcaatgcca                                              19

SEQ ID NO: 202          moltype = DNA   length = 24
FEATURE                 Location/Qualifiers
source                  1..24
                        mol_type = other DNA
                        organism = synthetic construct
SEQUENCE: 202
ggcaatagat cgtgattttg gtcg                                        24

SEQ ID NO: 203          moltype = DNA   length = 21
FEATURE                 Location/Qualifiers
source                  1..21
                        mol_type = other DNA
                        organism = synthetic construct
SEQUENCE: 203
tttgatgtgg taggactgcc a                                           21

SEQ ID NO: 204          moltype = DNA   length = 28
FEATURE                 Location/Qualifiers
source                  1..28
                        mol_type = other DNA
                        organism = synthetic construct
SEQUENCE: 204
cagagaggtg aaaaataccc ctaaataa                                    28

SEQ ID NO: 205          moltype = DNA   length = 22
FEATURE                 Location/Qualifiers
source                  1..22
                        mol_type = other DNA
                        organism = synthetic construct
SEQUENCE: 205
agtttcattt tcgcctaacc ca                                          22

SEQ ID NO: 206          moltype = DNA   length = 28
FEATURE                 Location/Qualifiers
source                  1..28
                        mol_type = other DNA
                        organism = synthetic construct
SEQUENCE: 206
tgacattgaa taactactta ttgacaca                                    28

SEQ ID NO: 207          moltype = DNA   length = 28
FEATURE                 Location/Qualifiers
source                  1..28
                        mol_type = other DNA
                        organism = synthetic construct
SEQUENCE: 207
ggacatatca accttaggtg taagttcc                                    28

SEQ ID NO: 208          moltype = DNA   length = 28
```

```
FEATURE                 Location/Qualifiers
source                  1..28
                        mol_type = other DNA
                        organism = synthetic construct
SEQUENCE: 208
atgaatattg caacaaaatt aatggcta                                              28

SEQ ID NO: 209          moltype = DNA   length = 27
FEATURE                 Location/Qualifiers
source                  1..27
                        mol_type = other DNA
                        organism = synthetic construct
SEQUENCE: 209
ggtattttcg gtaaaaatgg cgaagta                                               27

SEQ ID NO: 210          moltype = DNA   length = 28
FEATURE                 Location/Qualifiers
source                  1..28
                        mol_type = other DNA
                        organism = synthetic construct
SEQUENCE: 210
tttttatctt cttttgtggt tgccgtag                                              28

SEQ ID NO: 211          moltype = DNA   length = 28
FEATURE                 Location/Qualifiers
source                  1..28
                        mol_type = other DNA
                        organism = synthetic construct
SEQUENCE: 211
aaaaatatgg ctccacaaat gggtaatc                                              28

SEQ ID NO: 212          moltype = DNA   length = 26
FEATURE                 Location/Qualifiers
source                  1..26
                        mol_type = other DNA
                        organism = synthetic construct
SEQUENCE: 212
tttccgcatt acttttatcc ttactt                                                26

SEQ ID NO: 213          moltype = DNA   length = 28
FEATURE                 Location/Qualifiers
source                  1..28
                        mol_type = other DNA
                        organism = synthetic construct
SEQUENCE: 213
cttctacaga agcctttaat ttctgatt                                              28

SEQ ID NO: 214          moltype = DNA   length = 28
FEATURE                 Location/Qualifiers
source                  1..28
                        mol_type = other DNA
                        organism = synthetic construct
SEQUENCE: 214
gcgatgaaaa agttagtttg aatgaata                                              28

SEQ ID NO: 215          moltype = DNA   length = 28
FEATURE                 Location/Qualifiers
source                  1..28
                        mol_type = other DNA
                        organism = synthetic construct
SEQUENCE: 215
aataaaccgg acggaaataa tgggaata                                              28

SEQ ID NO: 216          moltype = DNA   length = 28
FEATURE                 Location/Qualifiers
source                  1..28
                        mol_type = other DNA
                        organism = synthetic construct
SEQUENCE: 216
catctaaatc taaagctaaa ggatcgta                                              28

SEQ ID NO: 217          moltype = DNA   length = 28
FEATURE                 Location/Qualifiers
source                  1..28
                        mol_type = other DNA
                        organism = synthetic construct
SEQUENCE: 217
cgataagtta ttatctttt ggctacct                                               28
```

| | | |
|---|---|---|
| SEQ ID NO: 218 | moltype = DNA  length = 25 | |
| FEATURE | Location/Qualifiers | |
| source | 1..25<br>mol_type = other DNA<br>organism = synthetic construct | |
| SEQUENCE: 218 | | |
| caaggatttt atgaaaactg ggcgg | | 25 |
| | | |
| SEQ ID NO: 219 | moltype = DNA  length = 23 | |
| FEATURE | Location/Qualifiers | |
| source | 1..23<br>mol_type = other DNA<br>organism = synthetic construct | |
| SEQUENCE: 219 | | |
| ggatttactc gaacgcgcct ata | | 23 |
| | | |
| SEQ ID NO: 220 | moltype = DNA  length = 25 | |
| FEATURE | Location/Qualifiers | |
| source | 1..25<br>mol_type = other DNA<br>organism = synthetic construct | |
| SEQUENCE: 220 | | |
| ccaagaggtt caataccaaa gtttt | | 25 |
| | | |
| SEQ ID NO: 221 | moltype = DNA  length = 27 | |
| FEATURE | Location/Qualifiers | |
| source | 1..27<br>mol_type = other DNA<br>organism = synthetic construct | |
| SEQUENCE: 221 | | |
| tgctcattcg ataaacgaat attttct | | 27 |
| | | |
| SEQ ID NO: 222 | moltype = DNA  length = 28 | |
| FEATURE | Location/Qualifiers | |
| source | 1..28<br>mol_type = other DNA<br>organism = synthetic construct | |
| SEQUENCE: 222 | | |
| actgatatta atttatccga actttggt | | 28 |
| | | |
| SEQ ID NO: 223 | moltype = DNA  length = 24 | |
| FEATURE | Location/Qualifiers | |
| source | 1..24<br>mol_type = other DNA<br>organism = synthetic construct | |
| SEQUENCE: 223 | | |
| gcttcaaaaa caggctcaag tgta | | 24 |
| | | |
| SEQ ID NO: 224 | moltype = DNA  length = 25 | |
| FEATURE | Location/Qualifiers | |
| source | 1..25<br>mol_type = other DNA<br>organism = synthetic construct | |
| SEQUENCE: 224 | | |
| atgtcaaatg ccaaagctta catcc | | 25 |
| | | |
| SEQ ID NO: 225 | moltype = DNA  length = 23 | |
| FEATURE | Location/Qualifiers | |
| source | 1..23<br>mol_type = other DNA<br>organism = synthetic construct | |
| SEQUENCE: 225 | | |
| gtatcgactt cgacctcttg gtg | | 23 |
| | | |
| SEQ ID NO: 226 | moltype = DNA  length = 22 | |
| FEATURE | Location/Qualifiers | |
| source | 1..22<br>mol_type = other DNA<br>organism = synthetic construct | |
| SEQUENCE: 226 | | |
| gccatcgtag ttccatacag aa | | 22 |
| | | |
| SEQ ID NO: 227 | moltype = DNA  length = 20 | |
| FEATURE | Location/Qualifiers | |
| source | 1..20<br>mol_type = other DNA<br>organism = synthetic construct | |
| SEQUENCE: 227 | | |
| gttagcacct gcaaggtagt | | 20 |

```
SEQ ID NO: 228          moltype = DNA  length = 24
FEATURE                 Location/Qualifiers
source                  1..24
                        mol_type = other DNA
                        organism = synthetic construct
SEQUENCE: 228
cttgtcatgg actcgtgaag aagt                                              24

SEQ ID NO: 229          moltype = DNA  length = 27
FEATURE                 Location/Qualifiers
source                  1..27
                        mol_type = other DNA
                        organism = synthetic construct
SEQUENCE: 229
gatcggttac atgtacggtc aatacaa                                           27

SEQ ID NO: 230          moltype = DNA  length = 22
FEATURE                 Location/Qualifiers
source                  1..22
                        mol_type = other DNA
                        organism = synthetic construct
SEQUENCE: 230
agtaaaccaa accgtaacca gt                                                22

SEQ ID NO: 231          moltype = DNA  length = 24
FEATURE                 Location/Qualifiers
source                  1..24
                        mol_type = other DNA
                        organism = synthetic construct
SEQUENCE: 231
cctgctcgtt caaccaattc tttc                                              24

SEQ ID NO: 232          moltype = DNA  length = 28
FEATURE                 Location/Qualifiers
source                  1..28
                        mol_type = other DNA
                        organism = synthetic construct
SEQUENCE: 232
actgtcgatg atgttttgga ctatttta                                          28

SEQ ID NO: 233          moltype = DNA  length = 25
FEATURE                 Location/Qualifiers
source                  1..25
                        mol_type = other DNA
                        organism = synthetic construct
SEQUENCE: 233
aaaggaaaag agcccttcaa tctca                                             25

SEQ ID NO: 234          moltype = DNA  length = 20
FEATURE                 Location/Qualifiers
source                  1..20
                        mol_type = other DNA
                        organism = synthetic construct
SEQUENCE: 234
gaaaacggga tgaccatcct                                                   20

SEQ ID NO: 235          moltype = DNA  length = 19
FEATURE                 Location/Qualifiers
source                  1..19
                        mol_type = other DNA
                        organism = synthetic construct
SEQUENCE: 235
gagacggaca cgagaaacg                                                    19

SEQ ID NO: 236          moltype = DNA  length = 19
FEATURE                 Location/Qualifiers
source                  1..19
                        mol_type = other DNA
                        organism = synthetic construct
SEQUENCE: 236
aggccattgc ccagaaaat                                                    19

SEQ ID NO: 237          moltype = DNA  length = 22
FEATURE                 Location/Qualifiers
source                  1..22
                        mol_type = other DNA
                        organism = synthetic construct
SEQUENCE: 237
```

```
gagcagttta tcgcgttcct ga                                          22

SEQ ID NO: 238          moltype = DNA   length = 23
FEATURE                 Location/Qualifiers
source                  1..23
                        mol_type = other DNA
                        organism = synthetic construct
SEQUENCE: 238
aaaaatgagc aagaacacaa ggc                                         23

SEQ ID NO: 239          moltype = DNA   length = 28
FEATURE                 Location/Qualifiers
source                  1..28
                        mol_type = other DNA
                        organism = synthetic construct
SEQUENCE: 239
tatttcaaca agtgtgcaag cattactg                                    28

SEQ ID NO: 240          moltype = DNA   length = 27
FEATURE                 Location/Qualifiers
source                  1..27
                        mol_type = other DNA
                        organism = synthetic construct
SEQUENCE: 240
atggtagtta agttggtat taacggt                                      27

SEQ ID NO: 241          moltype = DNA   length = 27
FEATURE                 Location/Qualifiers
source                  1..27
                        mol_type = other DNA
                        organism = synthetic construct
SEQUENCE: 241
gaagtactca agagtacgaa caagttg                                     27

SEQ ID NO: 242          moltype = DNA   length = 22
FEATURE                 Location/Qualifiers
source                  1..22
                        mol_type = other DNA
                        organism = synthetic construct
SEQUENCE: 242
agttatcgaa gttgatggcg ag                                          22

SEQ ID NO: 243          moltype = DNA   length = 25
FEATURE                 Location/Qualifiers
source                  1..25
                        mol_type = other DNA
                        organism = synthetic construct
SEQUENCE: 243
cctgagataa ctgtttcagt accat                                       25

SEQ ID NO: 244          moltype = DNA   length = 20
FEATURE                 Location/Qualifiers
source                  1..20
                        mol_type = other DNA
                        organism = synthetic construct
SEQUENCE: 244
catccacgct aacggtgcta                                             20

SEQ ID NO: 245          moltype = DNA   length = 21
FEATURE                 Location/Qualifiers
source                  1..21
                        mol_type = other DNA
                        organism = synthetic construct
SEQUENCE: 245
acagaacctg ttggaactgg a                                           21

SEQ ID NO: 246          moltype = DNA   length = 23
FEATURE                 Location/Qualifiers
source                  1..23
                        mol_type = other DNA
                        organism = synthetic construct
SEQUENCE: 246
ctgcaaacat cgttcctaac tca                                         23

SEQ ID NO: 247          moltype = DNA   length = 28
FEATURE                 Location/Qualifiers
source                  1..28
                        mol_type = other DNA
                        organism = synthetic construct
```

```
SEQUENCE: 247
tacagagaaa ttagatagca ctactaca                                         28

SEQ ID NO: 248          moltype = DNA   length = 25
FEATURE                 Location/Qualifiers
source                  1..25
                        mol_type = other DNA
                        organism = synthetic construct
SEQUENCE: 248
cttaaatatg agtgtgttga tggca                                            25

SEQ ID NO: 249          moltype = DNA   length = 28
FEATURE                 Location/Qualifiers
source                  1..28
                        mol_type = other DNA
                        organism = synthetic construct
SEQUENCE: 249
atggatatat ttctgatact ctagcaga                                         28

SEQ ID NO: 250          moltype = DNA   length = 27
FEATURE                 Location/Qualifiers
source                  1..27
                        mol_type = other DNA
                        organism = synthetic construct
SEQUENCE: 250
cttttcaatc ttgttctcca gaatcta                                          27

SEQ ID NO: 251          moltype = DNA   length = 27
FEATURE                 Location/Qualifiers
source                  1..27
                        mol_type = other DNA
                        organism = synthetic construct
SEQUENCE: 251
aaaagtttct caattcagca attcaat                                          27

SEQ ID NO: 252          moltype = DNA   length = 27
FEATURE                 Location/Qualifiers
source                  1..27
                        mol_type = other DNA
                        organism = synthetic construct
SEQUENCE: 252
ttgcaaaatt cttggttctc tagaaat                                          27

SEQ ID NO: 253          moltype = DNA   length = 28
FEATURE                 Location/Qualifiers
source                  1..28
                        mol_type = other DNA
                        organism = synthetic construct
SEQUENCE: 253
tgagtaagaa ctttaatgtc aactacgt                                         28

SEQ ID NO: 254          moltype = DNA   length = 28
FEATURE                 Location/Qualifiers
source                  1..28
                        mol_type = other DNA
                        organism = synthetic construct
SEQUENCE: 254
atgacaatcc acaaagtagc aatcaatg                                         28

SEQ ID NO: 255          moltype = DNA   length = 28
FEATURE                 Location/Qualifiers
source                  1..28
                        mol_type = other DNA
                        organism = synthetic construct
SEQUENCE: 255
aatgaaaccc ttgcttatgt agaagatc                                         28

SEQ ID NO: 256          moltype = DNA   length = 28
FEATURE                 Location/Qualifiers
source                  1..28
                        mol_type = other DNA
                        organism = synthetic construct
SEQUENCE: 256
gaagactcat tatcatatca tgcataca                                         28

SEQ ID NO: 257          moltype = DNA   length = 27
FEATURE                 Location/Qualifiers
source                  1..27
                        mol_type = other DNA
```

```
                        organism = synthetic construct
SEQUENCE: 257
ggtaatttga gtatggttta cgttgta                                          27

SEQ ID NO: 258          moltype = DNA  length = 27
FEATURE                 Location/Qualifiers
source                  1..27
                        mol_type = other DNA
                        organism = synthetic construct
SEQUENCE: 258
gttcaggaag attcttaact aaggaag                                          27

SEQ ID NO: 259          moltype = DNA  length = 28
FEATURE                 Location/Qualifiers
source                  1..28
                        mol_type = other DNA
                        organism = synthetic construct
SEQUENCE: 259
aattaattct ggattcatga caacagtt                                         28

SEQ ID NO: 260          moltype = DNA  length = 25
FEATURE                 Location/Qualifiers
source                  1..25
                        mol_type = other DNA
                        organism = synthetic construct
SEQUENCE: 260
tgctcctgta gttgtaggaa taatt                                            25

SEQ ID NO: 261          moltype = DNA  length = 19
FEATURE                 Location/Qualifiers
source                  1..19
                        mol_type = other DNA
                        organism = synthetic construct
SEQUENCE: 261
aggaaacagg tggtcgact                                                   19

SEQ ID NO: 262          moltype = DNA  length = 21
FEATURE                 Location/Qualifiers
source                  1..21
                        mol_type = other DNA
                        organism = synthetic construct
SEQUENCE: 262
ccagagtgga tttccgttgg t                                                21

SEQ ID NO: 263          moltype = DNA  length = 20
FEATURE                 Location/Qualifiers
source                  1..20
                        mol_type = other DNA
                        organism = synthetic construct
SEQUENCE: 263
gcatttgcca tgagaggagg                                                  20

SEQ ID NO: 264          moltype = DNA  length = 23
FEATURE                 Location/Qualifiers
source                  1..23
                        mol_type = other DNA
                        organism = synthetic construct
SEQUENCE: 264
tctcttcact gtcacgtacg aca                                              23

SEQ ID NO: 265          moltype = DNA  length = 20
FEATURE                 Location/Qualifiers
source                  1..20
                        mol_type = other DNA
                        organism = synthetic construct
SEQUENCE: 265
gcagcgtctc ttcctctttt                                                  20

SEQ ID NO: 266          moltype = DNA  length = 25
FEATURE                 Location/Qualifiers
source                  1..25
                        mol_type = other DNA
                        organism = synthetic construct
SEQUENCE: 266
gaagaagggt acgtgttgca tcata                                            25

SEQ ID NO: 267          moltype = DNA  length = 21
FEATURE                 Location/Qualifiers
source                  1..21
```

```
                        mol_type = other DNA
                        organism = synthetic construct
SEQUENCE: 267
cacctagtat cgtgcggcaa t                                              21

SEQ ID NO: 268          moltype = DNA   length = 22
FEATURE                 Location/Qualifiers
source                  1..22
                        mol_type = other DNA
                        organism = synthetic construct
SEQUENCE: 268
gagagacgct ctacaaaatc ca                                             22

SEQ ID NO: 269          moltype = DNA   length = 16
FEATURE                 Location/Qualifiers
source                  1..16
                        mol_type = other DNA
                        organism = synthetic construct
SEQUENCE: 269
tcggctccgc ggtctc                                                    16

SEQ ID NO: 270          moltype = DNA   length = 21
FEATURE                 Location/Qualifiers
source                  1..21
                        mol_type = other DNA
                        organism = synthetic construct
SEQUENCE: 270
agggaggaag acgaaagttg t                                              21

SEQ ID NO: 271          moltype = DNA   length = 20
FEATURE                 Location/Qualifiers
source                  1..20
                        mol_type = other DNA
                        organism = synthetic construct
SEQUENCE: 271
cttctccctc tccgactctc                                                20

SEQ ID NO: 272          moltype = DNA   length = 21
FEATURE                 Location/Qualifiers
source                  1..21
                        mol_type = other DNA
                        organism = synthetic construct
SEQUENCE: 272
acagaaggga cagaagtcga a                                              21

SEQ ID NO: 273          moltype = DNA   length = 19
FEATURE                 Location/Qualifiers
source                  1..19
                        mol_type = other DNA
                        organism = synthetic construct
SEQUENCE: 273
tgaaggcgag ggtgaggat                                                 19

SEQ ID NO: 274          moltype = DNA   length = 19
FEATURE                 Location/Qualifiers
source                  1..19
                        mol_type = other DNA
                        organism = synthetic construct
SEQUENCE: 274
tcgtctcgtc tggatcgca                                                 19

SEQ ID NO: 275          moltype = DNA   length = 17
FEATURE                 Location/Qualifiers
source                  1..17
                        mol_type = other DNA
                        organism = synthetic construct
SEQUENCE: 275
ccctcctcct cccttcg                                                   17

SEQ ID NO: 276          moltype = DNA   length = 18
FEATURE                 Location/Qualifiers
source                  1..18
                        mol_type = other DNA
                        organism = synthetic construct
SEQUENCE: 276
gctgcttttc ctggaggg                                                  18

SEQ ID NO: 277          moltype = DNA   length = 28
FEATURE                 Location/Qualifiers
```

```
source                  1..28
                        mol_type = other DNA
                        organism = synthetic construct
SEQUENCE: 277
ttcaaaaggt tttgttgctg atttgtta                                           28

SEQ ID NO: 278          moltype = DNA   length = 22
FEATURE                 Location/Qualifiers
source                  1..22
                        mol_type = other DNA
                        organism = synthetic construct
SEQUENCE: 278
aatgaagaca gaagcgcaca tc                                                 22

SEQ ID NO: 279          moltype = DNA   length = 28
FEATURE                 Location/Qualifiers
source                  1..28
                        mol_type = other DNA
                        organism = synthetic construct
SEQUENCE: 279
aaaagtggac catatgtatc ttgtttat                                           28

SEQ ID NO: 280          moltype = DNA   length = 28
FEATURE                 Location/Qualifiers
source                  1..28
                        mol_type = other DNA
                        organism = synthetic construct
SEQUENCE: 280
gaaaagatgg aagcacttat agtaacta                                           28

SEQ ID NO: 281          moltype = DNA   length = 27
FEATURE                 Location/Qualifiers
source                  1..27
                        mol_type = other DNA
                        organism = synthetic construct
SEQUENCE: 281
catttggtgt ttcagaagct tggttaa                                            27

SEQ ID NO: 282          moltype = DNA   length = 25
FEATURE                 Location/Qualifiers
source                  1..25
                        mol_type = other DNA
                        organism = synthetic construct
SEQUENCE: 282
acgtcatcga agtttttggt tttat                                              25

SEQ ID NO: 283          moltype = DNA   length = 20
FEATURE                 Location/Qualifiers
source                  1..20
                        mol_type = other DNA
                        organism = synthetic construct
SEQUENCE: 283
gctcgctgtg tgcctaatac                                                    20

SEQ ID NO: 284          moltype = DNA   length = 28
FEATURE                 Location/Qualifiers
source                  1..28
                        mol_type = other DNA
                        organism = synthetic construct
SEQUENCE: 284
gcgataaata actatatccg gtattagc                                           28

SEQ ID NO: 285          moltype = DNA   length = 18
FEATURE                 Location/Qualifiers
source                  1..18
                        mol_type = other DNA
                        organism = synthetic construct
SEQUENCE: 285
gtcgtcccca ccttcctc                                                      18

SEQ ID NO: 286          moltype = DNA   length = 26
FEATURE                 Location/Qualifiers
source                  1..26
                        mol_type = other DNA
                        organism = synthetic construct
SEQUENCE: 286
ctcgtgtcgt gagatgttag gttaag                                             26

SEQ ID NO: 287          moltype = DNA   length = 21
```

```
FEATURE                 Location/Qualifiers
source                  1..21
                        mol_type = other DNA
                        organism = synthetic construct
SEQUENCE: 287
cgcctattgg tgttcttcct a                                                    21

SEQ ID NO: 288          moltype = DNA   length = 28
FEATURE                 Location/Qualifiers
source                  1..28
                        mol_type = other DNA
                        organism = synthetic construct
SEQUENCE: 288
tttttgctaa gtctggagtt aaatgctg                                             28

SEQ ID NO: 289          moltype = DNA   length = 28
FEATURE                 Location/Qualifiers
source                  1..28
                        mol_type = other DNA
                        organism = synthetic construct
SEQUENCE: 289
agatctttat attcataacg ggagacac                                             28

SEQ ID NO: 290          moltype = DNA   length = 21
FEATURE                 Location/Qualifiers
source                  1..21
                        mol_type = other DNA
                        organism = synthetic construct
SEQUENCE: 290
tgcagcaatg aatcaaggac t                                                    21

SEQ ID NO: 291          moltype = DNA   length = 28
FEATURE                 Location/Qualifiers
source                  1..28
                        mol_type = other DNA
                        organism = synthetic construct
SEQUENCE: 291
gaattatccg ggaaattgca ctaaaagt                                             28

SEQ ID NO: 292          moltype = DNA   length = 24
FEATURE                 Location/Qualifiers
source                  1..24
                        mol_type = other DNA
                        organism = synthetic construct
SEQUENCE: 292
acagttccac taccgataac tttt                                                 24

SEQ ID NO: 293          moltype = DNA   length = 24
FEATURE                 Location/Qualifiers
source                  1..24
                        mol_type = other DNA
                        organism = synthetic construct
SEQUENCE: 293
ggcgagaaac tggatattca agtt                                                 24

SEQ ID NO: 294          moltype = DNA   length = 27
FEATURE                 Location/Qualifiers
source                  1..27
                        mol_type = other DNA
                        organism = synthetic construct
SEQUENCE: 294
ggtgaacatg gtgattcatc ttttgtt                                              27

SEQ ID NO: 295          moltype = DNA   length = 25
FEATURE                 Location/Qualifiers
source                  1..25
                        mol_type = other DNA
                        organism = synthetic construct
SEQUENCE: 295
tggactgagc caaaattaga ttttg                                                25

SEQ ID NO: 296          moltype = DNA   length = 25
FEATURE                 Location/Qualifiers
source                  1..25
                        mol_type = other DNA
                        organism = synthetic construct
SEQUENCE: 296
gcatttgaac agcttttaat ttcgc                                                25
```

```
SEQ ID NO: 297          moltype = DNA   length = 28
FEATURE                 Location/Qualifiers
source                  1..28
                        mol_type = other DNA
                        organism = synthetic construct
SEQUENCE: 297
actttagaat gatttcatct tgattggt                                         28

SEQ ID NO: 298          moltype = DNA   length = 25
FEATURE                 Location/Qualifiers
source                  1..25
                        mol_type = other DNA
                        organism = synthetic construct
SEQUENCE: 298
aaacttcctt tctctgcaaa tgatt                                            25

SEQ ID NO: 299          moltype = DNA   length = 28
FEATURE                 Location/Qualifiers
source                  1..28
                        mol_type = other DNA
                        organism = synthetic construct
SEQUENCE: 299
ttagcctctc tgattattga tatggatc                                         28

SEQ ID NO: 300          moltype = DNA   length = 28
FEATURE                 Location/Qualifiers
source                  1..28
                        mol_type = other DNA
                        organism = synthetic construct
SEQUENCE: 300
acttaaatag acagttccga ttttggta                                         28

SEQ ID NO: 301          moltype = DNA   length = 22
FEATURE                 Location/Qualifiers
source                  1..22
                        mol_type = other DNA
                        organism = synthetic construct
SEQUENCE: 301
tttggcagca gttaaaactg tt                                               22

SEQ ID NO: 302          moltype = DNA   length = 28
FEATURE                 Location/Qualifiers
source                  1..28
                        mol_type = other DNA
                        organism = synthetic construct
SEQUENCE: 302
tattcttatc taaatcagat cccgagtc                                         28

SEQ ID NO: 303          moltype = DNA   length = 1941
FEATURE                 Location/Qualifiers
source                  1..1941
                        mol_type = other DNA
                        organism = synthetic construct
SEQUENCE: 303
atggcatcag gaggagcttt ttgtcttatt gctaacgatg ggaaggccga caagattata        60
ttggcccaag acttgctgaa tagcaggatc tctaacatta aaaatgtgaa caaaagttat       120
gggaaacccg atcccgaacc cactttgagt caaatcgaag aaacacattt ggtgcatttt       180
aatgcgcatt ttaagcctta tgttccagta gggtttgaat acaataaagt acgcccgcat       240
acgggtaccc ccaccttggg aaacaagctt acctttgtta ttccccagta cggagacttt       300
ttccatgata tggtgggcca tcatatattg ggtgcatgtc attcatcctg gcaggatgct       360
ccgattcagg gcacgtccca gatgggggcc catgggcagc ttcaaacgtt tcctcgcaac       420
ggatatgact gggacaacca aacacccta gagggcgccg tttacacgct tgtagatcct       480
tttggaagac ccattgtacc cggcacaaag aatgcgtacc gaaacttggt ttactactgc       540
gaatacccccg gagaacgact ttatgaaaac gtaagattcg atgtaaatgg aaatttccta       600
gacgaatata gttcgatgt cacaacgctt gtgcgcaaat tttgcatccc agggatcaaa       660
atgactggat ataagcactt ggttggccag gaggtatcgg tggagggaac cagtggccct       720
ctcctatgca acattcatga tttgcacaag ccgcaccaaa gcaaacctat tcttaccgat       780
gaaaatgata cgcagcgaac gtgtagccat accaaacccga aatttctttc acagcattt       840
cccgagaact ctcacaatat ccaaacagca ggtaaacaag atattactcc tatcacggac       900
gcaacgtatc tggacataag acgtaatgtt cattacagct gtaatggacc tcaaacccct       960
aaatactatc agccccctct tgcgctctgg attaagttgc gcttttggtt taatgagaac      1020
gtgaaccttg ctattccctc agtatccatt ccctttcggcg agcgctttat caccataaag      1080
cttgcatcgc aaaaggattt ggtgaatgaa tttcctggac ttttttgtacg ccagtcacgt      1140
tttatagctg gacgcccag tagacgcaat atacgcttta aaccatggtt tatcccagga      1200
gtcattaatg aaatctcgct cacgaataat gaacttttaca tcaataacct gtttgtaacc      1260
cctgaaatac acaaccttttt tgtaaaacgc gttcgctttt cgctgatacg tgtccataaa      1320
acgcaggtga cccacaccaa caataaccac cacgatgaaa aactaatgtc tgctcttaaa      1380
tgggccattg aatatatgtt tataggatta aaacctacct ggaacatctc cgatcaaat      1440
cctcatcaac accgagattg gcacaagttc ggacatgttc ttaacgccat tatgcagccc      1500
```

```
actcaccacg cagagataag cttctcaggat agagatacag ctcttccaga cgcatgttca   1560
tctatatctg atattagccc cgttacgtat ccgatcacat tacctattat taaaaacatt   1620
tccgtaactg ctcatggtat caatcttatc gataaatttc catcaaagtt ctgcagctct   1680
tacataccct tccactacgg aggcaatgcg attaaaaccc ccgatgatcc gggtgcgatg   1740
atgattacct ttgctttgaa gccacggag gaataccaac ccagtggtca ttattaacgta   1800
tccagagcaa gagaattta tattagttgg gacacggatt acgtgggtc tatcactacg   1860
gctgatcttg tggtatcggc atctgctatt aactttcttc ttcttcagaa cggttcagct   1920
gtgctgcgtt acagtaccta a                                             1941

SEQ ID NO: 304           moltype = DNA   length = 555
FEATURE                  Location/Qualifiers
source                   1..555
                         mol_type = other DNA
                         organism = synthetic construct
SEQUENCE: 304
atggattctg aatttttca accggtttat ccgcggcatt atggtgagtg tttgtcacca    60
gtcactacac caagcttctt ctccacacat atgtatacta ttctcattgc tatcgtggtc   120
ttagtcatca ttatcatcgt tctaatctat ctattctctt caagaaagaa aaaagctgct   180
gctattgagg aggaagatat acagtttata aatccttatc aagatcagca gtgggtagaa   240
gtcactccac aaccaggtac ctctaaacca gctggagcga ctacagcaag tgtaggcaag   300
ccagtcacgg gcagaccggc aacaaacaga ccagcaacaa caaaccagt tacggacaac   360
ccagttacgg acagactagt catggcaact ggcgggccgg cggccgcaac tgccgccgcg   420
agtgctcctg ctcatccggc tgagccttac acgacagtca ctactcagaa cactgcttca   480
caaacaatgt cggctattga aaatttacga caaagaaaca cctatacgca taaagaccta   540
gaaaactcct tgtaa                                                    555

SEQ ID NO: 305           moltype = DNA   length = 1083
FEATURE                  Location/Qualifiers
source                   1..1083
                         mol_type = other DNA
                         organism = synthetic construct
SEQUENCE: 305
atgataaatac ttatttttt aatattttct aacatagttt taagtattga ttattgggtt    60
agttttaata aaacaataat tttagatagt aatattacta atgataataa tgatataaat   120
ggagtatcat ggaattttt taataattct tttaatacac tagctacatg tggaaaagca   180
ggtaactttt gtgaatgttc taattatagt acatcaatat ataatataac aaataattgt   240
agcttaacta ttttttcctca taatgatgta tttgatacaa catatcaagt agtatggaat   300
caaataatta attatacaat aaaattatta acacctgcta ctccccccaaa tatcacatat   360
aattgtacta attttttaat aacatgtaaa aaaaataatg gaacaaacac taatatatat   420
ttaaatataa atgatacttt tgttaaatat actaatgaaa gtatacttga ataaactgg   480
aataatagta acattaacaa ttttacagct acatgtataa ttaataatac aattagtaca   540
tctaatgaaa caacacttat aaattgtact tatttaacat tgtcatctaa ctatttttat   600
acttttttta aattatatta tattccatta agcatcataa ttgggataac ataagtatt   660
cttcttatat ccatcataac ttttttatct ttacgaaaaa gaaaaaaaca tgttgaagaa   720
atagaaagtc caccacctga atcaatgaaa gaagaacaat gtcagcatga tgacaccact   780
tccatacatg aaccatctcc cagagaacca ttacttccta agcctacag tcgttatcag   840
tataatacac ctatttacta catgcgtccc tcaacacaac cactcaaccc atttccctta   900
cctaaaccgt gtcctccacc caaaccatgt ccgccaccca aaccatgtcc tccacctaaa   960
ccatgtcctt cagctgaatc ctattctcca cccaaaccac tacctagtat cccgctacta  1020
cccaatatcc cgccattatc tacccaaaat atttcgctta ttcacgtaga tagaattatt  1080
taa                                                                1083

SEQ ID NO: 306           moltype = DNA   length = 1596
FEATURE                  Location/Qualifiers
source                   1..1596
                         mol_type = other DNA
                         organism = synthetic construct
SEQUENCE: 306
atgttctctc tccagaactt atgtcgaaaa acattaccta accgtaaact tcctgaattt    60
tttgacgaat atatattaca actgctggga ttatactggg aaaaccatgg aactattcaa   120
cgagcaggaa acaactgtgt gcttatacag caacataccc tcattcccgt aaatgaagcc   180
ctgagaacag cagcatctga agaaaattat gagatcgtga gccttttatt agcgtgggag   240
gggaaccttt actatgctat tatagggggct ctagagggca accgcacga cttaattcgt   300
aaatatgatg accaaatcaa ggaccatcat gaaattctgc cattcattga cgatccagtc   360
atattttcaca aatgccatat catgcggcaa tgctttttttg attgtatttt atatcaagct   420
gtaaaatata gtaagtttcg cgttcttctt tactttaaac atagattaga ggatgatttg   480
cccttcactc atttacttat tgaaaaggca tgtaaagatc ataattatga agttattaaa   540
tggatatata aaaacctaca tatctacaat atgatagata cctttgaatg tgctattgcc   600
cataaggatc tacatctata ttgtttgggg tatagattta tatataacag aatcgtaccc   660
gataagtatc atcatttaga tattcgcatg ctttcaagcc tacaactcct acataaggtg   720
gcagccaaag gatacttaga ttttatccta gaaaccttaa agtatgatca taataaagat   780
aatataaata ttattctaac acaagctgca acctataacc atagaaaaat ttaatctat   840
ttcattcctc aatcaaccca cgcacagata gaacaatgtt tactagtggc gataaaagca   900
aatcaaaaaa ggaaaacctt gaacttacta ctgtctcaac catcaaccttc catcaacctc   960
atcaaaaaaa taagccatta tgttgccact tacaattcaa caaatataat aggcattctg  1020
agtatgcggc ggaaaagaa gatatattta gatatcatat tgacaaatt tgtaaaaaaa  1080
gctatttta ataagtttgt cgttcgatgt atggatacat tttctataaa cccgaaagaa  1140
atccttaaaa tagccgcgcg aataaatagg atgatgttag tgaaaaaaat atctgaacat  1200
gtttggaaaa atcatgcgcgt tagacttaaa taccttaaac atgcggtaca cacgatgaag  1260
```

```
cataaagatg ggaaaaatag actcatgaac tttatctatg atcgctgtta ttaccatatg  1320
caaggggaag aaatctttag cctcgcaaga ttttatgcaa tccatcatgc accaaagttg  1380
tttgacgttt tttatgattg ttgtatccta gatacgatac gattcaaaag ccttctttta  1440
gattgttcac atatcatagg taaaaacgct catgatgcta ccaatatcaa catcgtgaac  1500
aagtatatcg gcaacctgtt tgttatggga gttcttagca aaaagaaat cttacaggac  1560
tatccatcca tttattctaa acaatacatg ccttag                            1596

SEQ ID NO: 307          moltype = DNA   length = 1581
FEATURE                 Location/Qualifiers
source                  1..1581
                        mol_type = other DNA
                        organism = synthetic construct
SEQUENCE: 307
atgttttccc ttcaagacct tgccgaaag catctttta ttcttcccga tgttttggc      60
gagcatgtac tacaacgatt aggactgtat tggagatgtc acggctccct tcaacgcata  120
ggagacgacc acatactcat acgacgggat ctcatccttt ccaccaacga ggccttaaga  180
atggcgggag aggaaggaaa caatgaagta gtaaagctct tgttactgtg aagggaaat   240
cttcattacg ccgtcatagg agccttgcag ggtgatcaat atgacctgat cctataagtat 300
gaaaaccaaa tcggcgactt tcatttatc ttaccattga ttcaagacgc gaatacgttt   360
gaaaaatgcc acgctttaga acgttttttgt ggtgtttcat gtctgctaaa acatgctaca 420
aaatacaaca tgctccctat tctccaaaaa taccaagaag agctgtctat gagagcgtat  480
cttcacgaaa ccctatttga actagcatgc ctatgcgaga ggtatgatgt ccttaaatgg  540
atagagcaaa ccatacatgt ttacgaccta aagattatgt ttaatattgc catctccaag  600
agggatctga ctatgtactc cttaggatat attttccttt ttgatagagg aacaccgaa   660
gctacgttgc taacgcaaca tctcaagaag acagcggcca aagggctcct ccactttgtg  720
ctagaaacgt taaatacgg cggcaacata gatccgtcc tgacccaagc cgtaaagtac   780
aatcatagaa aacttttaga ttattttctg cgtcaactac ctcgtaaaca tattgaaaaa  840
cttttgttgc tggccgtgca ggaaaaggct tctaaaaaa cattgaactt actgttgtca  900
catttaaaact actccgtgaa acgcatcaaa aaactaccgc gctatgtgat agagtacgag 960
tccaccttgg tgataaagat tttattaaaa aaagagtga acctgataga tgccatgttg 1020
gaaaagatgg taagatatt ttctgcgacg aaagtgagga cgatcatgga tgagctttcg  1080
attagtccgg aaagagtcat taagatggct atacagaaaa tgagaacgga tatcgtaatc 1140
catacttctt atgtttggga ggatgatcta gaacgtctta ctcgtcttaa aaatatggta  1200
tacaccataa agtacgaaca tgggaaaaaa atgttaatta aagtcatgca cggacatatac 1260
aaaaacttat tatacggcga aagggaaaaa gtcatgtttt atttagccaa gctctatgt  1320
gctcaaaacg cggccaccca attcagagac atttgtaagg actgttacaa actggatgtg 1380
gcacggttta aaccgcggtt taagcaacta atattagact gtttagaaat tattactaaa 1440
aaatcttgct atagtatcct ggaaatctta gaaaaacata ttatttccct gtttactatg 1500
aaagtttatga ctgaagaaga aaaaaaccta tgtttagaaa tattatataa agtaattcat 1560
tataaaacaa tacaatgtta a                                            1581

SEQ ID NO: 308          moltype = DNA   length = 1062
FEATURE                 Location/Qualifiers
source                  1..1062
                        mol_type = other DNA
                        organism = synthetic construct
SEQUENCE: 308
atgtcgttgc cgctctctct gcagaccctc gtcaaaaaga cgatagccag ccagtgtttg  60
tcaatagatg aacactgcat tttgaaatat tgtggcctat ggtggcatga tgctcctctc  120
aagctttgta tggatcgtgg ccgaatacaa ataaatcag gattttttagg agaagatata  180
gaccttcgtg tggcattaat aatagctgtt aaggaaaaca actatagtct gataaagctc  240
tttacagagt ggggcgcaaa tatcaactat ggtttgcttt ctatcaatac gaagcacatc  300
cgagagttgt gtagacagct aggcgccaaa gaaactctag aggacaacga tattttccgt  360
attttttacca ggataatgca caataaaacc agcggcagta ttattttgtg ccatgaaatt  420
tttatgaata atcctatttt agaaaacaaa tttgttatac aattaagggg cttaatttat  480
aaaagactat gggggctcat agaaataaaa gaaacggacg agttaaatgg tttactagtg  540
aagtattggt acgccaaagc agtacaatac gattgtaagg acgccatttg ttttctagat  600
gagaaatata cggatcttaa tgaatggcga ttaaaatgtc tcctgtatta aacaaaata   660
tatgaggttc atgagatgta ccacaaggaa aatatccaaa tagacgtcca tgacatgata  720
tgtctggctt ctaccaagga taacaatcca ttaacaatat attactgtta cgcgctgggg  780
ggcaacatca accaagctat gcttacttca gtacaatatt ataacatcgg taatatatttt  840
ttctgtatag atttgggtgg taatgccttt gaagagggtc gtgccatagc ggaacaaaaa  900
ggttataatt ttctgagcca tagtttggct ttggatattt acagctcaga tgcttccttg  960
ccactaaact taaggacccc gaagaaata agcagtttat taaagatta taaatcaaaa 1020
aacttatcca tcatttggga atattctcat aatatactat ag                    1062

SEQ ID NO: 309          moltype = DNA   length = 864
FEATURE                 Location/Qualifiers
source                  1..864
                        mol_type = other DNA
                        organism = synthetic construct
SEQUENCE: 309
atgttgtctt tacaaacgtt ggccaaaaaa gttgtggcat gcaattatct ttcaagtgac  60
tatgattata cgttgcagcg ttttggtttg tggtgggatt taggtcctat tcacctatgt  120
aacaattgta agcaagtttt ttcgtataaa catttacagt gttttttctga ggatgatctt  180
tgtctcgaag cggcgctagt aaaggccgtg aagagcgata tcttgaaact tatacgttta  240
tttgtggatt ggggcgcaaa tcctgaatat gggcttatac gtgttcctgc cgtgtatcta  300
aagcggctgt gtgcggaact gggaggctta acgcctgtat ccgaacccg tcttctgaa   360
attttaaaag aagtggccag gctaaaatcc tgtgcaggag ttctgctggg ttatgacatg  420
```

```
ttttgtcata atccactctt ggaaaccgta actagaacca ctttagacac agttacgtac    480
acctgttcaa acattccgtt gacggggat acgcgcacc acctattaac aaagttttgg      540
tttgccctgg cattacgaca taattttaca aaggctattc actatttcta taaaaggcat    600
aaaaatcacc tctattggcg ggtagcttgt agcctttatt ttaataacat ttttgacata    660
cacgagttgt gtcgtgaaaa agagatttgc atcagcccta atctgatgat gaaatttgct    720
tgcttgcggg aaaaaaatta cgcggccatt tattactgtc ataggttggg ggctagtctc    780
gattatggca tgaatctttc tatctataac aataatactt taaacatgtt tttctgtatt    840
gatttggggg gctgccgatt ttga                                           864

SEQ ID NO: 310           moltype = DNA  length = 618
FEATURE                  Location/Qualifiers
source                   1..618
                         mol_type = other DNA
                         organism = synthetic construct
SEQUENCE: 310
atggttgagc cacgcgaaca gttttttcaa gacctgcttt cagcagtgga tcaacaaatg    60
gacactgtaa aaaatgacat aaaagacatc atgaaagaaa aacatctttt tatggtgtca    120
ttcgaaaact ttatagaacg ttacgatacc atggaaaaaa atattcaaga ccttcagaat    180
aagtacgaag aaatggcggc caaccttatg accgtcatga cggatacaaa aattcagctt    240
ggagccatta tcgcccaact tgagattctg atgataaatg gcactccact tccggcaaaa    300
aaaacaacga ttaaggaggc tatgcccta ccttcatcaa acacgaacaa tgatcaaacg     360
agtcctcccg cctcaggcaa aacaagtgaa acacctcaaa aaaatcccac gaatgcaaatg   420
ttcttcacgc gtagcgaatg ggcatcctcg aaaacttttc gagaaaagtt tttaacacca   480
gaaattcagg ccatattgga tgagcagttt gcaacaagaa ccgggatcga aagattgcat    540
gccgagggtc tttacatgtg gagaacccaa ttctctgacg aacagaagaa aatggtcaaa    600
gagatgatga agaagtaa                                                  618

SEQ ID NO: 311           moltype = DNA  length = 525
FEATURE                  Location/Qualifiers
source                   1..525
                         mol_type = other DNA
                         organism = synthetic construct
SEQUENCE: 311
atggggtcgt ctctagacga cttctgcaat gatagcacag ctccacagaa ggtgcttttg    60
gcgttttcca ttacctacac gccagtgatg atatatgctc taaaggtaag tcgcggccga   120
ctgctagggc ttctgcacct tttgatcttt ctgaattgtg cttttacctt cgggtacatg   180
acattcgtgc actttgagag cacaaatagg gtcgcgctca ctatgggagc agtagttgca    240
cttctttggg gagtgtactc agccatagaa acctggaaat tcatcacctc cagatgtcgt   300
ttgtgcttgc taggccgcaa gtacattctg gccctgccc accacgtcga aagtgccgcg    360
ggctttcatc cgattgcggc aaatgataac cacgcatttg tcgtccggcg tcccggctcc    420
actacggtca acgcgcatt ggtgcccggg ttgaaaagcc tcgtgttggg tggcagaaaa    480
gctgttaagc agggagtggt aaaccttgtt aaatatgcca aataa                   525

SEQ ID NO: 312           moltype = DNA  length = 372
FEATURE                  Location/Qualifiers
source                   1..372
                         mol_type = other DNA
                         organism = synthetic construct
SEQUENCE: 312
atgccaaata caacggcag acagcaaaat aaaagaagg gggatggcca gccagtcaat     60
cagctgtgcc agatgctggg caaaattatc gcccagcaga accagtccag aggtaaggga    120
ccggggaaga agaataagaa tagaaacccg gagaagcccc atttccctct agcgactgaa    180
gatgacgtca gacatcactt caaccccagt gaacgacaat tgtgcctgtc gtcaatccgg   240
actgccttta accaaggcgc tgggacttgc acctgtcag actcagggag aataagttac    300
actgtggagt ttagtttgcc tactcatcac actgtgcgct tgattcgcgc cacagcgtca   360
ccctcagcat ga                                                        372

SEQ ID NO: 313           moltype = DNA  length = 522
FEATURE                  Location/Qualifiers
source                   1..522
                         mol_type = other DNA
                         organism = synthetic construct
SEQUENCE: 313
atgggaagcc tagatgattt ctgcttcgat cacaccgccg cacaaaagct tgtgctagcc    60
tttagcatca catatacacc tataatgata tacgccctca aggtgtcacg cggccgactc    120
ctggggctgt tgcacatcct gatatttctg aactgtgcct tcacgttcgg atacatgaca   180
tatgtgcatt ttgaatccac caaccgtgtc gcactcacta tggggctgt tgttgccctt    240
ctgtggggta tttatagctt cacagagtca tggaagttca ttacttccag atgcagattg    300
tgttgcctag gccggcgata cattctggcc cctgcccacc acgtagaaag tgctgcaggt   360
ctccattcaa tcccagcgtc tggtaaccga gcatacgctg tgagaaagcc cggactaaca   420
tcagtgaacg gcaccctagt accagggctt cggagcctcg tgttgggcgg caaacgagct  480
gttaaacgag gagtggttaa cctcgtcaag tatggccggt aa                      522

SEQ ID NO: 314           moltype = DNA  length = 387
FEATURE                  Location/Qualifiers
source                   1..387
                         mol_type = other DNA
                         organism = synthetic construct
SEQUENCE: 314
```

```
atggccggta agaaccagag ccagaagaaa aggaaaaaca cagctccaat ggggaatggc    60
cagccagtca atcaactgtg tcagttgctg ggtgcaatga taaagtccca gcgccagcaa   120
tctaggggag gacaggccaa aaagaaaaag cctgagaagc cgcatttcc cctgccgct    180
gaagatgaca tccggcacca tctcacccag accgaacgat cccttttgctt gcaatcgatc   240
cagacggctt ttaatcaagg cgcaggaact gcgtcgcttt catccagcgg gaaggttggt   300
tttcaggttg agtttatgct gccggttgct catacagtgc gcctgattcg cgtgacttct   360
acatccgcca gtcagggtgc aagttaa                                       387

SEQ ID NO: 315         moltype = DNA  length = 1677
FEATURE                Location/Qualifiers
source                 1..1677
                       mol_type = other DNA
                       organism = synthetic construct
SEQUENCE: 315
atgcggccct ttctgctgcg cgccgcgcag ctcctggcgc tgctggccct ggcgctctcc    60
accgaggccc cgagcctctc cgccgagacg accccgggcc ccgtcaccga ggtcccgagt   120
ccctcggccg aggtctggga cgacctctcc accgaggccg cgacgatga cctcaacggc   180
gacctcgacg gcgacgaccg ccgtcgcggc ttcggctcgg ccctcgcctc cctgagggag   240
gcgcccccgg cccatctggt gaacgtgtcc gagggcgcca acttcaccct cgacgcgcgc   300
ggcgacggcg ccgtgctggc cgggatctgg acgttcctgc ccgtccgcgg ctgcgacgcc   360
gtgtcggtga ccacggtgtg cttcgagacc gcgtgccacc cggacctggt gctggggccga   420
gcctcgtcc ccgaggcccc ggagatgggc atcgccgcc acctgccgcc cgaggtgccga   480
cggctccggc gcgagccgcc catcgtcacc ccggagcggt ggtcgccgca cctgagcgtc   540
ctgcgggcca cgcccaacga cacgggcctc tacacgctgc acgacgcctc ggggccgcgg   600
gccgtgttct tgtgcggt gggcgaccgg ccgcccgcgc cggcggaccc ggtgggcccc   660
gcgcgccacg agccccgctt ccacgcgctc ggcttccact cgcttctctt ctcgcccggg   720
gacacgttcg acctgatgcc gcgcgtggtc tcgacatgg cgactgcgcg cgagaacttt   780
accgccacgc tggactggta ctacgcgcgc gcgccccgc ggtgcctgct gtactacgtg   840
tacgagccct gcatctacca cccgcgcgcg cccgagtgcc tgcgcccggt ggacccggcg   900
tgcagcttca cctcgccggc gcgcgcgcgg ctggtggcgcg ta cgcctcgtgc    960
agccccgctgc tcgggaccgg gtggctgacc gcctgcccct tcgacgcctt cggcgaggag  1020
gtgcacacga acgccaccgc ggacgagtcg gggctgtacg tgctcgtgat gacccacaac  1080
ggccacgtcg ccacctggga ctacacgctc gtcgccaccg cggccgagta cgtcacggtc  1140
atcaaggagc tgacggcccc ggccggggcc ccgggccggc cgtggggccc cggcggcggc  1200
gacgacccga tctacgtgga cggcgtcacg acgccgcgcg cccgtgaac  1260
ccgtacggcc ggacgacgcc cgggcggctg tttgtgctgg cgctgggctc cttcgtgatg  1320
acgtgcgtcg tcgggggcc gtctggctct gcgtgctgtg ctcccggcgc cgggcggcct  1380
cgcggccgtt ccgggtgccg acgcgggcgc ggacgcacat gctctctccg gtgtacacca  1440
gcctgcccac gcacgaggac tactacgacg gcgacgacga cggaggag gcgggcgtca  1500
tccgccggcg gcccgcctcc cccggcgag acagcggcta cgaggggtcg tacgcgagcc  1560
tggaccccga ggacgagttc agcagcgacg gaagacacgg gctgtacgtg cgccccgagg  1620
aggcgccccg ctccggcttc gacgtctggt tccgcgatcc ggagaaaccg gaagtga     1677

SEQ ID NO: 316         moltype = DNA  length = 2745
FEATURE                Location/Qualifiers
source                 1..2745
                       mol_type = other DNA
                       organism = synthetic construct
SEQUENCE: 316
atgcccgctg gtggcggtct ttggcgcggg cccgcgggc atcggcccgg gcaccacggc    60
ggtgcggcc tcggacgtct ttggcctgct ccacaccacg ctgcagctgc gcggggcgg   120
gtcgcgctag cgctgctgct gctggcgctc gccgcgaccc gacgtgcgg cgcggcggcc   180
gtgacgcggg ccgcctcggc ctcgccgcg ccgggacgg cgccaccc agacggcttc   240
tccgcggagg agtccctcga ggagatcgac ggggccgtca ccccccggcccc ctcgaacgcc   300
cccgacgcg agtacggcga cctggtcgcg cgcacggcg tgcgcggc cgcgaccgag   360
cgggaccgct tctacgtctg ccgccgccg tccggctcca cggtggtgcg cctgcgagccc   420
gagcaggcct gccccgagta ctcgcagggg cgcaacttca cggaggggat cgccgtgctc   480
ttcaaggaga acatcgcccc gcacaagttc aaggcccaca tctactacaa gaacgtcatc   540
gtcacgaccg tgtggtccgg gagcacgtac gcggccatca cgaaccgctt cacggaccgc   600
gtgcccgtcc ccgtgcagga gatcacggac gtgatcgacc gccgacgcaa gtgcgtctcc   660
aaggccgagt acgtgcgcaa caccacaag gtgaccgcct tcgactgcga cgagaacccc   720
gtcgaggtgg gcctgcgccc ctcgcgcctg aacgcgctcg gcaccgcggg ctggcacacc   780
accaacgaca cctacaccaa gatcggcgcc gcgggcttct accacacggg cacctccgtc   840
aactgcatcg tcgaggaggt ggaggcgcgc tccgtgtaccc cctacgactc cttcgccctg   900
tccacgggg acatcgtgta catgtccccc ttctacgcc tgcgcgaggg ggcccacggg   960
gagcacatcg gctacgcgcc cgggcgcttc cagcaggtgg agcactacta ccccatcgac  1020
ctggactcgc gcctccgcgc tccgagagc gtgacgcgca actttctgcg cacgccgcac  1080
ttcacggtgg cctgggactg gccccccaag acgcggcgcg tgtgcagcct ggccaagtgg  1140
cgcgaggcg aggagatgat ccgcgacgag acgccgacga ggtccttccg cttcacgtcg  1200
cgggccctgg gcgcctcctt cgtcagcgac gtcacgcagc tcgacctccg gcgcgtcac  1260
ctgggcgact cgtgcctccg cgaggcctcg gaggccatcg acgccatcta ccgcggcgc  1320
tacaacaaca cgcacgtgct ggcggcgac aagcccgagg tgtacctcgc ccgcggggc  1380
ttcgtggtgg ccttccgccc gctgatcctg aacgagctgc cgcagctgta cgcgcgcgag  1440
ctcgagcgcc tcggccgtgg tgccccgcgt cggcccgtcgg cccgtcgg  1500
gcccgcgct cccccggccc ggcgggacg cccgagccgc cggccgtcga cggcacgggg  1560
cacctgcgca tcaccacggg ctcggccgag tttcgcgcc tgcagttcac ctacgaccac  1620
atccaggcgc acgtgaacga catgctgagc cgcatcgcgg ccgcctggtg cgagctgcag  1680
aacaaggacc gcacctgtg gggcgagatg tcgcgcctga ccccagcgc cgtggccacg  1740
gccgcgctgg ccagcgcgt ctcggcgcgc atgctcggcc acgtgatggc catctcgcgg  1800
```

```
tgcgtggagg tgcgcggcgg cgtgtacgtt cagaactcca tgcgcgtgcc cggcgagcgc  1860
ggcacgtgct acagccgccc gctggtgacc ttcgagcaca acggcacggg cgtgatcgag  1920
ggccagctcg cgacgacaa cgagctcctc atctcgcgcg acctcatcga gccctgcacc  1980
ggcaaccacc ggcgctactt taagctgggc ggcgggtacg tgtactacga ggactactgc  2040
tacgtcgca tggtggaggt gcccgagacg atcagccgc gggtgaccct gaacctgacg  2100
ctgctcaagg accgcgagtt cctgccccc gaggtgtaca cgcgcgagga gctcgccgac  2160
acgggcctcc tggactacag cgagatccag cgccgcaacc agctgcacgc gctcaagttc  2220
tacgacattg accgcgtggt caaggtggac acaacgtgg tgctgctgcg cggcatcgcc  2280
aacttcttcc agggcctcgg cgacgtgggc gccgccgtcg gcaaggtggt cctgggcgcc  2340
acggggccg tgatctcggc cgtcggcggc atggtgtcct tcccgtccaa ccccttcggg  2400
gcgctcgcca tcgggctgct ggtgctggcc ggcctggtcg cggccttcct ggcctaccgg  2460
cacatctcgc gcctgcgccg caaccccatg aaggccctgt accccgtcac gacgaaggcg  2520
ctcaaggagg acggcgtcga agaggacggc gtggacgagg ccaagctgga ccaggccgg  2580
gacatgatcc ggtacatgtc catcgtgtcg gccctgacgg gcaggagca caaggcgcc  2640
aagaagaaca gcgggcccgc gctgctggcc agccgcgtcg gggcgatggc cacgcgccgc  2700
cggcactacc agcgcctcga gaacgaggac cccgacgccc tgtag              2745

SEQ ID NO: 317          moltype = DNA   length = 702
FEATURE                 Location/Qualifiers
source                  1..702
                        mol_type = other DNA
                        organism = synthetic construct
SEQUENCE: 317
atgacgtatc caaggaggcg ttaccgaaga agaagacacc gccccgcag ccatcttggc   60
cagatcctcc gccgccgccc ctggctcgtc caccccgcc accgttaccg ctggagaagg  120
aaaaatggca tcttcaacac ccgcctctcc cgcaccttcg gatatactgt caagcgaacc  180
acagtcagaa cgccctcctg ggcggtggac atgatgagat tcaatattaa tgactttctt  240
cccccaggag ggggctcaaa ccccgctct gtgccctttg aatactacag aataagaaag  300
gttaaggtta aattctggcc ctgctccccg atcacccagg gtgacagggg agtgggctcc  360
agtgctgtta ttttagatga taactttgta acaaaggcca cagccctcac ctatgacccc  420
tatgtaaact actcctcccg ccataccata acccagccct tctcctacca ctcccggtac  480
tttacccca aacctgtcct agattccact attgattact tccaaccaaa caacaaaaga  540
aaccagctgt ggctgagact acaaactgct ggaaatgtag accacgtagg cctcggcact  600
gcgttcgaaa acagtatata cgaccaggaa tacaatatcc gtgtaaccat gtatgtacaa  660
ttcagagaat ttaattttaa agaccccca cttaacccct aa                    702

SEQ ID NO: 318          moltype = DNA   length = 945
FEATURE                 Location/Qualifiers
source                  1..945
                        mol_type = other DNA
                        organism = synthetic construct
SEQUENCE: 318
atgcccagca agaagagtgg aagaagcgga ccccaaccac ataaaaggtg ggtgttcacg   60
ctgaataatc cttccgaaga cgagcgcaag aaaatacggg agctcccaat ctccctattt  120
gattatttta ttgttggcga ggaaggcaat gaggagggcc gaacaccca cctacagggg  180
ttcgctaatt ttgtgaagaa gcaaactttt aataaagtga agtggtattt tggtgcccgc  240
tgccacatcg agaaagcgaa aggaacagat cagcagaata aagaatattg cagtaaagaa  300
ggcaacttac tgatagaatg tggagctcct agatctcaag gacaacggag cgacctctct  360
accgctgtga gtaccttgtt ggagagcggg agtctggtga ccgttgcaga gcagcaccct  420
gtaacgtttg tcagaaattt ccgcgggctg gctgaacttt tgaaagtgag cgggaaaatg  480
cagaagcgta attggaagac gaatgtacac gtcattatgg ggccacctgg tgtgtggaaa  540
agcaaatggg ctgctaattt tgcagacccg gaaaccacat actgaaaacc acctagaaac  600
aagtggtggg atggttacca tggtgaagaa gtggttgtta ttgatgactt ttatggctgg  660
ctgccgtggg atgatctact gagactctgt gatcgatatc ctttgactgt tgagactaaa  720
ggtgaactg taccttttt ggcccgcagt atttctgatta ccagcaatca gaccccgttg  780
gaatggtact cctccaactgc tgtcccagct gtagaagctc tctatcggag gattacttcc  840
ttggtatttt ggaagaatgc tacagaacaa tccacggagg aagggggcca gttcgtcacc  900
ctttccccc catgccctga atttccatat gaaataaatt actga                 945

SEQ ID NO: 319          moltype = DNA   length = 645
FEATURE                 Location/Qualifiers
source                  1..645
                        mol_type = other DNA
                        organism = synthetic construct
SEQUENCE: 319
atgagacaca gagctatatt cagaagaaga ccccgcccaa ggagacgacg acgccacaga   60
aggcgctatg tcagaagaaa actattcatt aggaggccca cagctggcac atactacaca  120
aagaaatact ccaccatgaa tcatttcc gttggaaccc ctcagaataa caagccctgg  180
cacgccaacc acttcattac ccgcctaaac gaatgggaaa ctgcaattag ctttgaatat  240
tataagatac taaagatgaa agttacactc agccctgtaa tttctccggc tcagcaaaca  300
aaaactatgt tcgggcacac agccatagat ctagacggcg cctggaccac aaacacttgg  360
ctccaagacg acccttatgc ggaaagttcc actcgtaaag ttatgacttc taaaaaaaa   420
cacagccgtt acttcacccc caaaccaatt ctggcgggaa ctaccagcgc tcacccagga  480
ccatctct tcttttctc cagacccacc ccatggctca acacatatga cccaccgtt   540
caatggggag cactgctttg gagcatttat gtcccggaaa aaactggaat gacagacttc  600
tacggcacca aagaagtttg gattcgttac aagtccgttc tctaa                645

SEQ ID NO: 320          moltype = DNA   length = 891
FEATURE                 Location/Qualifiers
```

| source | 1..891 |
| --- | --- |
| | mol_type = other DNA |
| | organism = synthetic construct |

SEQUENCE: 320

```
gtccggaggg aaagcccgaa acacaggtgg tgttttacga taaacaactg gaccccgacc    60
gagtgggaat ctattgtgga gtgtggaggc agtatagcga gataccttat tatcggcaaa   120
gaggttggaa aaagcggtac cccacacttg caagggtacg tgaatttcaa gaacaaaagg   180
cgactcagct cggtgaagcg cttacccgga tttggtcggg cccatctgga gccggcgagg   240
gggagccaca aagaggccag cgagtattgc aagaaagagg gggattacct cgagattggc   300
gaagattcct cttcgggtac cagatcggat cttcaagcag cagctcggat tctgacggag   360
acgtcgggaa atctgactga agttgcggag aagatgcctg cagtatttat acgctatggg   420
cggggtttgc gtgattttg cggggtgatg gggttgggta aaccgcgtga ttttaaaact    480
gaagtttatg ttttttattgg tcctccagga tgcgggaaaa cgcgggaagc ttgtgcggat   540
gcggctgcgc gggaattgca gttgtatttc aagccacggg ggccttggtg ggatggttat   600
aatggggagg gtgctgttat tctgatgat ttttatgggt gggttccatt tgatgaattg    660
ctgagaattg gggacaggta ccctctgagg gttcctgtta agggtgggtt tgttaatttt   720
gtggctaagg tattatatat tactagtaat gttgtaccgg aggagtggta ttcatcggag   780
aatattcgtg gaaagttgga ggccttgttt aggaggttca ctaaggttgt ttgttggggg   840
gaggggggg taaagaaaga catggagaca gtgtatccaa taaactattg a              891
```

| SEQ ID NO: 321 | moltype = DNA  length = 11697 |
| --- | --- |
| FEATURE | Location/Qualifiers |
| source | 1..11697 |
| | mol_type = other DNA |
| | organism = synthetic construct |

SEQUENCE: 321

```
atggagttga atcattttga acttttatac aaaacaaaca aacaaaaacc aatgggagtg    60
gaggaaccgg tatacgatgc cacggggagg ccattgtttg gagacccgag tgaggtacac   120
ccacaatcaa cactgaagct accacatgat agggggagag gtaacatcaa acaacactg    180
aagaacctac ctaggaaagg cgactgcagg agtggcaacc atctaggccc ggttagtggg   240
atatatgtaa agcccggccc tgtctttat caggactaca tgggcccggt ctaccataga   300
gcccctctag agttttttaa cgaagcgcag ttttgcgagg tgaccaaag gataggtagg    360
gtgacaggta gtgacggaaa gctttaccat atatatgtgt gcatcgatgg ttgcatactg    420
ctgaagctag ccaagaggga cgagccaaga accctgaagt ggattagaaa tttcaccgac    480
tgtccattgt gggttaccag ttgctctgat gatggcgcaa gtggaagtaa agagaagaag    540
ccagatagga tcaacaaagg caaattaaaa atagccccaa aagagcatga gaaggacagc    600
agaactaagc cacctgacgc tacgattgta gtggaaggaa taaatacca ggttaaaaag    660
aagggtaaag ttaaggaaa gagtacccaa gacggctgt accacaacaa gaataaacca    720
ccagaatcta ggaagaaatt agaaaaagcc ctattgcat gggcggtaat agcaattatg    780
ttgtaccaac cagttgaagc cgaaaatata actcaatgga acctgagtga caacggcact    840
aatggtatcc agcatgctat gtaccttaga ggggttagca ggagcttgca tgggatctgg    900
ccggaaaaaa tatgcaaagg agtccccacc tacctggcca cagacacgga actgaaagaa    960
atacagggaa tgatgatgc cagcgagggg acaaactata cgtgctgtaa gttacagaga   1020
catgaatgga acaaacatgg atggtgtaac tggtacaata tagaccctg gatacagttg   1080
atgaataaga cccaagcaaa cttggcagaa ggccctccgg ccaaggagtg cgctgtgact   1140
tgcaggtacg ataaagatgc tgacatcaac gtggtcaccc aggccagaaa caggccaaca   1200
accctgaccg gttgcaagaa aggaaaaaat ttttcttttg cgggtacgat tatagagggc   1260
ccatgtaatt tcaatgtttc cgtggaggat atcttgtatg gggatcatga gtgcggcagt   1320
ttgcttcagg acacggctct gtaccagtg gatggaatga ccaacactat agagaatgcc   1380
agacaggagg cagcgagggt aacatcttgg ctcgggaggc aactcagcac tgccgggaag   1440
aggttgggga gtagaagcaa aacctggttt gtgcctatg ccctatcgcc ttactgtaat   1500
gtaacaagca aataggta catatggtac actaacaact gcaccccgc ttgcctcccc   1560
aaaaatacaa agataatagg ccccggaaaa tttgacacta cgcgcgaaga cggaaagatt   1620
ctccatgaga tggggggtca cctatcagaa tttctgctgc tctctctggt tgttctgtct   1680
gacttcgccc ctgaaacagc cagcgcgtta tacctcattt tgcactacat gattcctcaa   1740
tcccatgaag aacctgaagg ctgcgacaca aaccagctga atctaacagt ggaactcagg   1800
actgaagacg taataccgtc atcagtctgg aatgttggca aatatgtgtg tgttagacca   1860
gactggtggc catatgaaac caaggtggct ttgtatttg aagaggcagg acaggtcgta   1920
aaattagcct tacgagcgct gagggattta accagggtct ggatagcgc atcaaccacg   1980
gcattcctca tctgcttgat aaaagtatta agaggacaga tcgtgcaagg tgtgatatgg   2040
ctgctactag taactgggc acaaggccgg ctagcctgca aggaagatta caggtacgca   2100
atatcatcga ccaatgagat agggctactc ggggccgaag tctcaccac cacctggaaa   2160
gaatacaacc acgatttgca actgaatgac gggaccgtta aggccatttg cgtggcaggt   2220
tccttaaag tcatagcact taatgtggtc agtaggagt atttggcatc attgcataag   2280
gaggcttcac tcacttccgt gacatttgag ctcctgttcg acgggaccaa cccatcaact   2340
gaggaaatgg gagtgactt cggttcggg ctgtgcccgt cgatacgag tcctgttgtc   2400
aagggaaagt acaatacaac cttgttgaac ggtagtgctt tctatcttgt ctgcccaata   2460
gggtggacgg tgtcataga gtgcagca gtgagcccaa caactctgag aacagaagtg   2520
gtaaagacct tcaggagaga caagcccttt ccgcacagaa tggattgtgc gaccaccaca   2580
gtggaaaatg gagattatt ctactgtaag ttgggggca actgagacatg tgtgaaaggt   2640
gaaccagtgg tctacacggg ggcgtagta aacaatgca gatggtgtgg cttcgacttc   2700
aatgagcccg acgactccc gcactacccc ataggtaagt gcatcttggt aaatgagaca   2760
ggttacagaa tagtagattc aacggactgt acagagatg cgttgtaat cagcacagat   2820
ggagtcatg agtgctgat cggtaacaca ctgtcaagt cgatgaaga   2880
ctgggcccta tgccatgcag acccaaagag attgtctcta gtgcaggacc tgtaaggaaa   2940
acttcctgta cattcaacta cgcaaaaact tgaagaaca agtactatga gcccagggac   3000
agctacttcc agcaatatat gcttaagggc gagtatcagt actggtttga cctgacgtg   3060
actgaccgcc actcagatta cttcgcagaa tttgtcgtct tggtagtggt agcactgtta   3120
ggaggaagat atgtcctgtg gctaatagtg acctacatag ttcctaacag acaactcgcc   3180
```

```
gctggtttac cattgggcca gggtgaggta gtgttgatag ggaacttaat tacccacaca   3240
gacattgagg tcgtagtata tttcttacta ctctatttgg tcatgaggga tgagcctata   3300
aagaaatgga tactgctgct gttccatgct atgactaaca atccagtcaa gaccataaca   3360
gtggcattgc ttatgGttag tggggttgcc aagggtggaa agatagacgg cggttggcag   3420
cggctgccag agaccagctt tgacatccaa ctcgcgctga cagttatagt agtcgctgtg   3480
atgttactgg caaagagaga tccaactact gtcccCttgg ttataacagt ggcaaccctg   3540
agaacggcta agatgactaa tggacttagc acggatatag ccatagctac agtgtcaaca   3600
gcgttgctaa cctggaccta cattagtgac tattatagat acaagacttg gctacagtac   3660
cttattagca cagtgacagg tatcttctta ataagggtac tgaagggaat aggtgagttg   3720
gatttacaca ctccaacctt gccatcttac agaccCCtct tcttcattct cgtgtacctc   3780
atttccactg cagtggtaac aagatggaat ctggacatag ccggattgct gttgcagtgt   3840
gtcccaaccc ttttgatggt ttttacgatg tgggcagaca ttctcaccct gatcctcata   3900
ctgcccactt acgagctaac aaaactatat tacctcaagg aagtgaagac tggggcagaa   3960
aagggctggt tatggaagac caacttcaag agggtaaacg acatatacga agttgaccaa   4020
tctggtgaag gggtttacct ttttccgtca aaacaaaaga caagttcaat aacaggtacc   4080
atgttgccat tgatcaaagc catactcatc agctgcatca gtaataagtg gcagttcata   4140
tatctattgt acttgatatt tgaagtgtct tactacctcc acaagaagat catagatgaa   4200
atagcaggag ggaccaactt catctcaaga cttgtagccg cttTgatcga agccaattgg   4260
gcctttgaca acgaagaagt taggggttta aagaagttct tcctgttgtc tagtagggtt   4320
aaagaactga tcatcaaaca caaagtgagg aatgaagtaa tggtccactg gtttggtgac   4380
gaagaggttt atgggatgcc aaagttggtt ggcttagtca aggcagcaac attgagtaaa   4440
aataaacatt gtattttgtg caccgtctgt gaagacagag agtggagagg agaaacctgc   4500
ccaaaatgcg ggcgttttgg gccaccaatg acctgtggta tgaccctagc cgactttgaa   4560
gaaaaacatt ataagaggat ctttttttaga gaggatcaat cagaagggcc ggttagagag   4620
gagtacgcag ggtatctgca atatagagcc agagggcaat tattcctgag gaatctcccg   4680
gtgctagcaa caaaagtcaa gatgctcctg gtcggaaatc ttgggacgga ggtgggagac   4740
ttggaacacc ttggctgggt ccttaggggg cctgccgttt gcaagaaggt taccgaacat   4800
gagaaatgca ccacatccat aatgacaaaa ttgactgctt ttttcggtgt tatgccaagg   4860
ggcaccacac ctagagcccc tgtgagattc cccacctctc tcttaaagat aagaaggggg   4920
ttggaaactg gctgggcgta cacacaccaa ggtggcatta gttcagtgga ccatgtcact   4980
tgtgggaaag acttgctggt atgtgacact atgggccgga caagggtcgt ttgccaatca   5040
aataataaga tgacagatga gtctgagtat ggagttaaaa ctgactccgg atgcccggaa   5100
ggagctaggt gttatgtgtt caacccagag gcagttaaca tatcagggac taaggagcc    5160
atggtccact tacaaaaaac tggaggagaa ttcacctgtg tgacagcatc aggaactccg   5220
gccttctttg atctcaagaa cctcaaaggc tggtcagggc taccgatatt tgaggcatca   5280
agtgaaggg tagtcggcag ggtcaaggtc gggaagaatg aggactctaa accaaccaag   5340
cttatgagtg gaatacaaac agtctccaaa gtaccacag acttgacaga aatggtaaag   5400
aaaataacga ccatgaacag gggagaattc agacaaataa cccttgctac aggtgccgga   5460
aaaaccacgg aactccctag gtcagtcata gaagagatag ggaggcataa ggagtcttg   5520
gtcttgatcc ctctgaggg ggcagcagag tcagtatacc aatatatgag acaaaaacat    5580
ccaagcatcg catttaacct gaggataggg gagatgaagg aagggacat ggccacaggg    5640
ataacctatg cttcatacgg ttacttctgt cagatgccac aacctaagtt gcgagccgcg   5700
atggttgagt actccttcat atttcttgac gagtaccact gtgccacccc agaacaattg   5760
gccatcatgg gaaagatcca cagattttca gagaacctgc gggtagtagc catgaccgca   5820
acaccagcag gcacagtaac aaccacaggg cagaaacacc ctatagaaga attcatagcc   5880
ccagaagtga tgaagggga agacttaggc tcagagtact ggacattgc tggactaaag   5940
ataccagtag aggagataa gagcaacatg ctggtttttg tgcccactag gaacatggcg    6000
gtggagacag caaagaaatt gaaagctaag ggttacaact caggctacta ttatagtgga   6060
gaggatccat ctaacctgag ggtggtaacg tcgcagtccc cgtacgtggt ggtggcaacc   6120
aacgcgatag aatcaggtgt tactctcccg gacttggatg tggttgtcga tacgggcttc   6180
aagtgtgaa agagaatacg gctgtcaCCT aagtgccct tcatagtgac gggcctgaag   6240
agaatggctg tcacgattgg ggaacaagcc cagagaaggg ggagagttgg gagagtaaag   6300
cctgggagat actacaggag tcaagaaact cccgttggtt ctaaagatta ccattatgat   6360
ctactgcaag cacagaggta cggtattgaa gatgggataa acatcaccaa atcctttaga   6420
gagatgaact atgattggag cctttatgag gaggacagtc tgatgattac acaattggaa   6480
atcctcaata atttgttgat atcagaagaa ctaccgatgg cagtaaaaaa tataatggcc   6540
aggactgacc acccagaacc aattcagctg gcgtacaaca gctacgaaac acaagtgcca   6600
gtgctattcc caaaaataaa gaatggagag gtgactgata gttacgataa ctataccttc   6660
ctcaacgcaa gaaaattggg ggatgatgta ccccccttacg tgtatgccac agaggatgag   6720
gacttagcgg tagagctact ggggcttgac tggccagacc ctggaaacca aggaaccgta   6780
gaggctggca gagcactaaa acaagtagtt ggtctatcaa cagctgagaa tgccctgtta   6840
gtagcctat tcggctatgt aggatatcag gcactttcaa agaggcatat accagtagtc   6900
acagatatat attcaattga agatcacagg ttggaagaca ccacacacct acagtacgcc   6960
ccaaatgcta tcaagacgga ggggaaggag acagaattga aggagctagc caggggggat   7020
gtgcagagat gtgtggaagc tatgaccaat tatgcaagag agggtatcca attcatgaag   7080
tctcaggcac tgaaggtgaa agaaacccc acttacaaag agacaatgaa cactgtgact   7140
gactatgtaa agaaattcat ggaggcgctg cagacagta agaagacat cttaagtatt   7200
gggttgtggg ggacgcacac agcctatat aagagcacac gtgccaggtc tgggagtgag   7260
actgcgttcg ctaccctggt cgtgaggtgg ctggcatttg ggggaatc aatagcagac   7320
catgtcaaac aagcggccac agacttggtc gtctactata tcatcaacag acctcagttc   7380
ccaggagaca cagagacaca acaggaagga aggaaattg tggccagcct actggtctca   7440
gctctagcta cttacacata caaaagctgg aattacaata atctgtccaa gatagttgaa   7500
ccggcttgg ccactctgcc ctatgccgcc acagctctca aactattcgc ccccactcga   7560
ttggagacg ttgtcatatt gagtaccgca atctacagaa cctacctatc aatcaggcgc   7620
ggaaaaagcg atggtttgct aggcacaggg gttagtgcgg ctatgagat catgtcacaa   7680
aatcagtat ccgtgggcat agcagtcatg ctaggggtag gggccgtggc agcccacaat   7740
gcaatcgagg ccagtgagca aagagaaca ctactcatga aagttttgt aaagaacttc   7800
ttggaccaag cagccactga tgaattagtc aaggagagtc ctgagaaaat aataatggct   7860
ttgtttgaag cagtgcagac agtcggtaac cctcttagac tagtataccca cctttatgga   7920
```

```
gttttctata agggtggga ggcaaaagag ttggcccaaa ggacagccgg taggaacctt  7980
ttcactttga taatgttcga ggctgtggaa ctactgggag tagatagtga aggaaagatc  8040
cgccagctat caagtaatta catactagag ctcctgtata agttccgtga cagtatcaag  8100
tctagcgtga gggagatggc aatcagctgg cccctgccc ctttcagctg tgattggaca  8160
ccgacggatg acagaatagg gctccccca gacaatttcc tccaagtgga gacgaaatgc  8220
ccctgtggtt acaagatgaa ggcagttaag aattgtgctg gagagctgag actcttggag  8280
gaggaaggct catttctctg cagaaataaa ttcgggagag gttcacggaa ctacagggtg  8340
acaaatact atgatgacaa tctatcagaa ataaagccag tgataagaat ggaagggcat  8400
gtggaactct actacaaggg agccaccatc aaactggact tcaacaacag taaaacaata  8460
ctggcaaccg ataaatggga gattgatcac tccactctgg tcagggtgct caagaggcac  8520
acaggggctg gatatcatgg ggcatacctg ggcgagaaac cgaactacaa acatctgata  8580
gagagggact gtgcaaccat caccaaagat aaggtttgtt ttctcaaaat gaagagaggg  8640
tgtgcattta cttatgactt atcccttcac aaccttaccc gactgattga attggtacac  8700
aagaataact tggaagacaa agagattcct gctgttacgg ttacaacctg gctggcttac  8760
acgtttgtaa atgaagatat agggaccata aaaccagcct tcggggagaa agtaacaccg  8820
gagatgcagg aggaaataac cttgcagcct gctgtagtgg tggatacaac tgacgtgacc  8880
gtgactgtgg taggggaagc ccctactatg actcagggg agactccgac agcgttcacc  8940
agctcaggtt cagacccgaa aggccaacaa gttttaaaac tggggtagg tgaaggccaa  9000
taccccggga ctaatccaca gagggcaagc ctgcacgaag ccatacaagg tgcagatgag  9060
agaccctcgg tgctgatatt agggtctgat aaagccacct ctaatagagt gaaaactgca  9120
aagaatgtaa aggtatacag aggcagggac ccactgaaag tgagagatat gatgaggagg  9180
ggaaagatcc tggtcatagc cctgtctagg gttgataatg ctctattgaa atttgttgac  9240
tacaaaggca cctttctaac tagagagacc ctagaggcat taagtttggg taggcctaaa  9300
aagaaaaaca taaccaaggc agaagcgcag tggttgctgt gcctcgaaga ccaaatggaa  9360
gagctacccg attggttcgc agccgggaaa cccatttttc tagaggctaa cattaaacat  9420
gacaggtacc atctggtggg ggatatagcc aatatcagag aaaaagccaa acagttggga  9480
gctacagact ccacaaagat atctaaggag gttggtgcaa aagtgtattc tatgaaactg  9540
agtaattggg tgatgcaaga agaaaataaa cagggcaacc tgacccccctt gtttgaaag  9600
ctcctgcaac agtgtccacc cggaggccag aacaaaactg cacatatggt ctctgcttac  9660
caactagctc aagggaactg gatgccaacc agctgccatg ttttatggg gaccatatct  9720
gccaggagga ccaagaccca tccatatgaa gcatacgtca agttaaggga gttggtagag  9780
gaacacaaga tgaaaacatt gtgtcctgga tcaagcctgg gtaagcacaa cgaatggata  9840
attggtaaaa tcaaatacca gggaaacctg aggaccaaac acatgttgaa cccccggcaag  9900
gtggcagagc aactgtgcag agagggacac agacacaatg tgtataacaa gacaatagc  9960
tcagtaatga cagctactgg tatcaggttg gagaagttgc ccgtggttag ggcccagaca  10020
gacacaacca acttccacca agcaataagg gataagatac acaaggaaga gaacctacaa  10080
accccggt tacataagaa actaatgaa gttttcaatg cattgaaacg acccgagtta  10140
gagtcctcct acgatgccgt ggaatgggag gaactggaga gaggaataaa caggaagggt  10200
gctgctgtt tctttgaacg caaaaatata ggggaaatat tggattcaga gaaaaacaaa  10260
gtcgaagaga ttattgacaa tctgaaaaaa ggcagaaaca tcaaatacta tgaaaccgcg  10320
atcccaaaga atgagaagag ggacgtcaat gatgactgga ctgctggtga cttcgtggaa  10380
gagaagaaac ccagagtcat acaataccct gaagcaaaaa caaggctggc catcaccaag  10440
gtgatgtata agtgggtgaa gcagaagcca gtagttatac ccgggtatga agggaagaca  10500
cctctattcc aaatttttga caaagtaaag aaggaatggg atcaattcca aaatccagtg  10560
gcagtggatt ttgacactaa ggcgtgggac acccaggtaa ccacaaaaga tttggagttg  10620
ataaaggaca tacaaagta ctatttcaag aagaaatggc ataaattat tgacaccctg  10680
accatgcaac atgcaagt acccgtaatc agtgctgatg gggaagtata caggaaa  10740
gggcaaagag gcagtggaca acctgacaca agcgcaggca atagcatgct aaatgtgtta  10800
acaatgattt acgccttctg cgaggccacg ggagtaccct acaagagctt cgacaggtg  10860
gcaaaaattc atgtgtgtgg ggatgatggt ttcctgatca cagaaagagc tctccggtgag  10920
aaattcgcga gtaagggagt ccagatccta tatgaagctg ggaagcccca agaagatcct  10980
gaagggaca agatgaaagt ggcctaccaa tttgatgata ttgagttttg ctccccataca  11040
ccaatacaag taaggtggtc agataacact tctagttaca tgccggggag aaatacaacc  11100
acaatcctgg ctaaaatggc cacaaggtta gattccagtg gtgagagggg accatagca  11160
tatgaaaag cagtagcatt cagcttcctg ctgatgtact cctggaaccc actaatcaga  11220
aggatctgct tactggtgct atcaactgaa ctgcaagtga aaccaggaa gtcaaccact  11280
tactactatg aagggacccc gatatctgcc tacaaggaag tcatcggcca caatcttttt  11340
gatcttaaga gaacaagctt cgagaagctg gccaagttaa atctcagcat gtcagtactc  11400
ggagcctgga ctagacacac cagtaaaaga ctactacaag actgtgtcaa tgtgggtgtt  11460
aaagagggca actggctagt taatgcagat agactagtaa gtagcaagac tggaaataag  11520
tacataccg gagagggcca cacccctgcaa gggagacatt atgaagaact ggtgttggca  11580
agaaaacaga tcaacaactt tcaagggacc gacaggtaca atctaggccc aatagtcaat  11640
atggtgttaa ggaggctgag agtcatgatg atgacctga tagggagggg ggtatga      11697
SEQ ID NO: 322         moltype = DNA   length = 1119
FEATURE                Location/Qualifiers
source                 1..1119
                       mol_type = other DNA
                       organism = synthetic construct
SEQUENCE: 322
cggctagcct gcaaggaaga ttacaggtac gcaatatcat cgaccaatga gatagggcta  60
ctcgggccc aaggtctcac caccacctgg aaagaataca accacgattt gcaactgaat  120
gacgggaccg ttaaggccat ttgcgtggca ggttcccttta aagtcatagc acttaatgtg  180
gtcagtagga ggtatttggc atcattgcat aaggaggctt cactcacttc cgtgacattt  240
gagctcctgt tcgacgggac caacccatca actgaggaaa tgggagatga cttcgggttc  300
gggctgtgcc cgttcgatac gagtcctgtt gtcaagggaa agtacaatac aaccttgttg  360
aacggtagtg ctttctatct tgtctgccca ataggtggga cgggtgtcat agagtgcaca  420
gcagtgagcc caacaactct gagaacagaa gtggtaaaga ccttcaggag agacaagccc  480
tttccgcaca gaatggattg tgcgaccacc acagtggaaa atgagatttt attctactgt  540
```

```
aagttgggggg gcaactggac atgtgtgaaa ggtgaaccag tggtctacac ggggggggcta    600
gtaaaacaat gcagatggtg tggcttcgac ttcaatgagc ccgacggact cccgcactac    660
cccataggta agtgcatctt ggtaaatgag acaggttaca gaatagtaga ttcaacggac    720
tgtaacagag atgcgttgt aatcagcaca gatgggagtc atgagtgctt gatcggtaac    780
acaactgtca aggtgcatgc atcagatgaa agactgggcc ctatgccatg cagacccaaa    840
gagattgtct ctagtgcagg acctgtaagg aaaacttcct gtacattcaa ctacgcaaaa    900
actttgaaga acaagtacta tgagcccagg gacagctact tccagcaata tatgcttaag    960
ggcgagtatc agtactggtt tgacctggac gtgactgacc gccactcaga ttacttcgca   1020
gaatttgtcg tcttggtagt ggtagcactg ttaggaggaa gatatgtcct gtggctaata   1080
gtgacctaca tagttctaac agaacaactc gccgctggt                          1119

SEQ ID NO: 323          moltype = DNA   length = 6999
FEATURE                 Location/Qualifiers
source                  1..6999
                        mol_type = other DNA
                        organism = synthetic construct
SEQUENCE: 323
atgaacacag ctggttgttt tatcgctttg ttgtacacca tcagagagat aaaaacacga     60
ctgttttcaa ggacacagga agaaatgaaa ttcacacttt acaacggtga aagaagatc    120
ttctactcca ggcccaacaa ccacgacaac tgttggctga acgccatcct tcagctgttc    180
aggtacgtcg atgaaccttt cttcgactgg gtatatgaat cacctgaaaa cctcacccttt   240
gaggcgatca gacaactgga gaacattact ggtcttgagc tgcacgaggg tggtccgccc    300
gccctcgtca tttggaacat caaacacttg ctccacaccg ggatcggcac cgcctcgcga    360
cccagcgagg tgtgcatggt ggacggtacg gacatgtgcc tggctgactt ccacgctggc    420
atcttcctga aggacagga acacgccgtg tttgcctgcg tcacctccaa cggtggtac    480
gcgatcgacg acgaagaatt ctaccccctgg gcgccagatc cgtccgacgt gctggtcttt    540
gtcccgtacg atcaagaacc acttaatggg gaatgaaag caagggttca gagacggctc    600
aagggagccg gacaatccag tccggctact gggtcacaga accaatcagg caacaccggg    660
agtatcatca acaattacta catgcagcag taccagaact ccatgacac ccaacttggt    720
gacaatgcta tcagcggagg ctccaacgag ggatccacga acacaacctc cacccacaca    780
accaacactc agaacaatga ctggttttca aagttggcca gctctgcctt cagcggtctc    840
ttcggcgccc tcctgccga taagaaaacc gaggagacca ctcttctcga ggaccgcatc    900
ctcaccaccc gaaacggaca caccacctcg acaacccagt cgagtgttgg cataacgcac    960
gggtacggca cagctgagga ctttgtgaac gggccaaaca cctctggtct tgagaccaga   1020
gttgtccagg cggaacggtt cttttaaaacc cacctgttcg actgggtcac cagtgatccg   1080
ttcggacggt actacttgtt ggagctcccg actgaccaca aagtgtcta cggcagcctg   1140
accgactcat acgcctacat gagaaacggt tgggatgttg aagtcaccgc tgtggggaat   1200
cagttcaacg gaggctgcct actggtggcc atggtgcctg aactttgttc catcgagcgg   1260
agagagttgt tccagcttac gctcttccc catcagttca tcaaccccg gacgaacatg   1320
acagcccaca tcaaggtgcc ctttgttggc gtcaaccgtt acgatcagta caaggtacac   1380
aagccgtgga cccttgtggt tatggtcgta gccccactga ctgtcaacac cgaaggcgct   1440
ccgcaaatca aggtgtatgc caacatcgcg cccaccaacg tgcacgtcgc gggtgagttc   1500
ccttccaaag aggggatttt ccctgtggca tgtagcgacg gttatgcggg cttggtgaca   1560
actgacccaa agacggctga ccccgtttac ggcaaagtgt tcaacccccc ccgcaacatg   1620
ttgccggggc ggttcaccaa cctcctggac gtggctgagg cttgcccccac gtttctgcac   1680
ttcgatggtg acgtaccgta tgtgaccact aagacggatt cggacagggt gctcgcacaa   1740
tttgacttgt ctttggcagc aaaaacacatg tcaaacacct tccttgcagg tcttgcccag   1800
tactacacgc agtacagcgg caccgtcaac ctgcacttca tgttcgcagg tcccactgac   1860
gcgaaagcgc gttacatgat tgcgtatgcc cctccgggca tggagccgcc caaaacacct   1920
gaggctgctg ctcactgcat tcacgcagag tgggacacgg tctgaactc aatgtttacc   1980
ttttccatcc cctacctctc ggcggctgat tacgcgtaca ccgcgtctga cgctgctgag   2040
accacaaatg ttcagggatg gtctgctta tttcaaataa cacacgggaa agctgaggggt   2100
gacgctcttg tcgtgatggc cagtgctggc aaagactttg agctgcgcct gcctgtggac   2160
gctcggcaac agaccacttc gacaggcgag tcggctgacc ccgtgactgc caccgttgag   2220
aattacggcg gcgagacaca ggtccagagg cgccaccaca cagacgtctc attcatattg   2280
gacagatttg tgaaagtcac accaaaagac tcaataaatg tattggaccct gatgcagacc   2340
ccctccacat cctagtaagg ggcgctcctc cgcactgcca cttactatttt cgctgatcta   2400
gaggtggcag tgaaacacga gggggacctt acctgggtgc caaatggagc acctgaagca   2460
gccttggaca acaccaccaa cccaacggcg taccataagg cgccgcttac ccggcttgca   2520
ttgccctaca cggcaccaca ccgtgttttg gccaccgttt acaacgggaa ctgcaaatac   2580
gccgggggct cactgcccaa cgtgagaggc gatctccaag tgctggctcc gaaggcagcg   2640
aggccgctgc ctacttcttt caactacggt gccatcaaag ccactcgggt gacagaactg   2700
ctgtaccgca tgaagagggc cgaggcgtac tgtcctcggc ccctcttggc tgttcacccg   2760
agtgcggcca gacacaaaca gaaaatagtg gcgcctgtaa gcagtgcctt gaacttgat    2820
ctgctcaagt tggcagggga cgtggagtcc aaccctgggc ccttcttctt ctctgacgtc   2880
aggtcaaact tcaccaaact ggtggaaacc atcaaccaga tgcaagagga catgtcaaca   2940
aaacacggac ccgactttaa ccggttggta tccgcgtttg aggaattggc cactgggggtg   3000
aaagccatca ggacggggcct cgacgaggcc aaacccggt acaaactcat caagctcctg   3060
agccgcttgt catccatggc cgctgtagca gcacgggtaca aggacccagt ccttgtgggca   3120
atcatgctgg ctgacaccgg tcttgagatt ctggacagca catttgtcgt gaagaaaatc   3180
tccgacccc tctccagtct cttttacgtg ccggcccccg tcttcagttt cggagctccg   3240
attctgctag ccgggttggt caaggtcgct tcgagcttct tccggtccac acccgaggat   3300
ctcgagagag cagagaaaca gctcaaagca cgtgacatca atgacatctt cgccattctc   3360
aagaaccgcg agtggctggt caagttgatc ctagccatcc gacctggat taagcatgg   3420
atcgcctcag aagagaagtt tgtcaccatg acagactttgg tgcctggcat ccttgaaaag   3480
cagcgggacc tcaacgaccc ggccaagtac aaggaagcca aggaatggct cgacaacgcg   3540
cgccaaacgt gtttgaagag cgggaacgtc cacattgcca acctgtgcaa agtggtcgcc   3600
ccagcgccga gcaagtcgag acctgaaccc gtggtcgtgt gcctccgcgg caaatccggt   3660
cagggtaaga gtttccttgc gaacgtgctg gcacaagcca tctctaccca ctttaccggc   3720
```

```
aggactgact cagtttggta ctgtccgcca gaccctgacc acttcgacgg ttacaaccag   3780
cagaccgttg ttgtgatgga tgatttgggc cagaatcccg acggcaagga cttcaagtac   3840
ttcgctcaga tggtctcgac cacggggttc atcccgccca tggcttcact tgaggacaaa   3900
ggcaagcctt tcaacagcaa agtcatcatt gccaccacca acctgtactc gggcttcacc   3960
ccgaaaacca tggtgtgccc cgatgctctg aaccgaaggt ttcactttga cattgacgtg   4020
agtgccaagg acgggtacaa aattaacaca aaattggaca taatcaaagc tctcggaggc   4080
acccacacca accctgtggc aatgttccaa tacgactgtg cccttctcaa cggcatggcc   4140
gttgaaatga agagaatgca acaagacatg ttcaaacccc agccgccttt gcagaacata   4200
taccaacttg tgcaagaggt gattgaccgg gtcgagctcc acgagaaagt gtcgagccac   4260
ccgattttca agcagatctc aattccttcc caaaagtcag tgctgtattt cctcattgag   4320
aaaggccaac acgaagcagc aattgaattc tttgagggga tggtccatga ctccatcaag   4380
gaagagctcc gacccctcat ccaacagaca tcatttgtca agcgcgcctt caagcgcctg   4440
aaggaaaact ttgagattgt tgccctatgt ttgactctca tggcaaacat agtgatcatg   4500
atccgcgaaa ctcgcaagag acagcagatg gtggatgatg cagtgaatga gtacatcgag   4560
aaagcaaaca tcaccacaga tgacaagact cttgacgagg cggaaaagaa ccctctagag   4620
actagcggtg ccagcactgt tggtttcaga gagagaactc tcccgggaca caaggtgggt   4680
gatgacgtga actccgagcc cgcccacccc ggggatgagc aaccacaagc tgaaggaccc   4740
tacgccggac cactcgaccg tcagagacct ctgaaagtga gagccaagct gccacagcag   4800
gagggacctt acgccggtcc gatggagaga cagaaaccac tgaaagtgaa agcgaaagcc   4860
ccggtcgtga aggaaggacc ttacgaggga ccggtgaaga agcctgtcgc tttgaaagtg   4920
aaagctagga acttgatcgt caccgagagt ggtgcccccc cgaccgactt gcaaaagatg   4980
gtcatgggta acaccaagcc cgttgagctc atactcgacg ggaagacagt agccatctgc   5040
tgtgctactg gagtatttgg cactgcctac ctcgtgcctc gtcatctttt cgctgagaag   5100
tacgacaaga tcatgttgga cggtagaacc atgatagaca gtgactacag agtgtttgag   5160
tttgagatca aagtaaaagg acaggacatg ctctcagacg ctgcgctcat ggtgttgcac   5220
cgtgggaacc gcgtgagaga catcacgaaa cactttcgtg acacagcaag aatgaagaaa   5280
ggtaccccg tcgttggtgt gatcaacaac gctgacgtcg ggagactgat tttctcaggt   5340
gaggccctca cctacaagga cattgtagtg tgcatggatg gagacaccat gccgggccta   5400
tttgcctaca agccgccac caaggctggc tactgcgggg gagccgtcct tgctaaggat   5460
ggagctgaca cattcatcgt tggcactcac tctgcaggtg gcaatggagt tgggtactgc   5520
tcatgcgtat ctagatccat gctccaaaaa atgaaggca acatcgaccc tgaaccacac   5580
cacgaggggt tgatcgtaga caccagagat gtggaagagc gcgtgcacgt catgcgcaaa   5640
accaagcttg cacctaccgt ggcacacggt gtgttcaacc ctgagtacgg ccccgctgcc   5700
ttgtccaaca aggacccgcg gctgaatgag ggagttgcc tcgatgaggt catcttctcc   5760
aaacacaagg gggacacaaa gatgtcaccg gaagacaaag cgctgttccg ccgctgcgct   5820
gccgactacg cgtcgcgtct tcacagtgtg ctgggtacag caaatgcccc attgagcatc   5880
tacgaggcca ttaaaggcgt tgacggactc gacgccatgg aaccagacac agcgcctggc   5940
cttccctggg cactccaggg gaaacgccgc ggcgcgctga ttgacttcga gaacggcact   6000
gtcggacccg aagtccaggc tgccctggag ctcatggaga aaagagaata caagtttgcc   6060
tgtcagacct tcctgaagga cgaaattcgc ccgatggaaa agtacgtgc cggcaagacg   6120
cgcatcgtcg atgttttgcc tgttgaacac attctttaca ccaggatgat gattggcaga   6180
ttttgtgctc aaatgcactc aaacaacgga ccgcaaattg gatcagcggt cggttgtaat   6240
cctgatgttg attggcaaag atttggcaca cacttcgcca aatacagaaa cgtgtgggat   6300
gtggactatt cggcctttga tgctaaccac tgtagtgatg caatgagcat catgtttgag   6360
gaggtgtttc gcacagactt tggtttccac ccgaatgctg agtggattct gaagaccctc   6420
gtgaacacgg aacacgccta tgaaacaaa cgcattacag ttgaaggtgg aatgccgtcc   6480
ggctgttccg caaccagcat catcaacaca atttctgaca acatctacgt gctctacgcg   6540
ctgcgtagac actatgaggg agttgagctg gacacttaca ccatgatctc ctacggagac   6600
gacatcgtgt tgctagtga ttatgacttg gactttgagg ctctcaagcc ccactttaaa   6660
tctcttggtc aaaccattac tccagctgac aaaagcgaca aggttttgt tcttggtcac   6720
tccattaccg atgtcacttt cctcaaaaga cacttccaca tggattatgg aactgggttt   6780
tacaaacctg tgatggcttc gaagaccctc gaggctatcc tctccttgc acgccgtggg   6840
accatacagg agaagttgat ctccgtggca gggctgccg tccactctgg acctgacgag   6900
taccggcgtc tcttcgagcc cttccagggt ctctttgaga ttccaagcta cagatcactt   6960
tacctgcgtt gggtgaacgc cgtgtgcggt ggcgcataa                          6999
SEQ ID NO: 324         moltype = DNA   length = 1097
FEATURE                Location/Qualifiers
source                 1..1097
                       mol_type = other DNA
                       organism = synthetic construct
SEQUENCE: 324
ttgaaagggg gcgctagggt ctcaccccta acatgccaac gacagctcct gcgtcgcact     60
ccacacttac gtctgtgcgc gcgcgggaac cgatggactt tcgttcaccc acctgcagct    120
ggactcacgg caccgcgtgg ccatttagc tggactgagc ggacgaacgt cgcttgcgca    180
cctcgcgtga tcgactagta ctctcaacac tccgccatt cggtcgttag cgctgtcctg    240
ggcactcctg ctgggggccg ttcgacgctc tacggtttcc cccccgcga caaactacgg    300
tgatggggcc gcttcgtgcg agccgatcgc ctggtgtgtt tcggttgtca ctcgaaaccc    360
acctttcacc ccccccccc cccccctaag tactaccgtc gctcccgacg ttaaagggag    420
gtaaccacaa gatttgcgcc ttcttgtccg aagttagagg gctgtaaccg caaactttga    480
accgcctttc ccagcgttaa cgggatgtaa tcacaagatg gaccttcatc cggaagtaaa    540
acggcaactt acacagtttt gcccgttttc atgagaaatg gacgtcagc gcacgaaacg    600
cgcagtcgct tgaggaggac ttgtacaaac acgtctcaca caggtaccca caaccgacac    660
aaaacgggtg acttgaaatc tgcctggtc tttcaggtc tagaggggtg acactttgta    720
ctgtgattga ctccacgctc ggcccactgg cgagtgttag tagtagtact gttgcttcgt    780
agcggagcat ggtggcgtg ggactccctc cttggtaaca aggacccacg gggccgaaag    840
ccacgtctca ggacccacca tgtgtgcaac cccagcacgg caactttacc acgaaaacca    900
tttttaaggtg acactgaaac tggtactcaa ccactggtga caggctaagg atgcccttca    960
ggtaccccga ggtaacacgc gacactcagg atctgagaag gggattgggg cttctgtaaa   1020
```

```
agcgcccagt ttaaaaagct tctatgcctg aataggcgac cggaggccgg cgcctttcct    1080
taactattac tgcttac                                                   1097

SEQ ID NO: 325          moltype = DNA   length = 759
FEATURE                 Location/Qualifiers
source                  1..759
                        mol_type = other DNA
                        organism = synthetic construct
SEQUENCE: 325
atgagtcttc taaccgaggt cgaaacgtat gttctctcta ttgttccgtc aggcccctc     60
aaagccgaga tagcgcagag acttgaagat gtttttgcag ggaaaaacac cgatctagag   120
gcactcatgg aatggctaaa gacaagacca atcctgtcac ctctgactaa ggggatttta   180
ggatttgtat tcacgctcac cgtgcccagt gagcgaggac tgcagcgtag acgctttgtc   240
cagaatgccc tcaatgggaa tggtgacccg aacaacatgg acaaagcagt caaactgtac   300
agaaaactta aagggaaat aacatttcac ggggctaaag aagtagcgct cagttactct    360
gctggtgcac ttgccagttg tatgggcctc atttacaaca gaatggggac tgtcaccact   420
gaggtggcat ttggcctagt atgcgcaacc tgtgaacaga ttgccgattc ccagcatcga   480
tctcatagac aaatggagac aacaaccaat ccactaatta ggcatgagaa cagaatggta   540
ttagccagca cgacagctaa agccatggaa caaatggctg atcaagtga acaagcagca   600
gaggctatga aaattgccag ccaagctagg caaatggtac aggcaatgag aacaattggg   660
actcatccta gttccagcgc tggtctaaaa gatgatcttc ttgaaaattt acaggcctat   720
cagaaacgaa tgggagtgca gatgcaacgg ttcaagtga                          759

SEQ ID NO: 326          moltype = DNA   length = 1701
FEATURE                 Location/Qualifiers
source                  1..1701
                        mol_type = other DNA
                        organism = synthetic construct
SEQUENCE: 326
atgaaggcaa tactagtagt cttgctatat gcatttacaa ccgcaaatgc agacacatta    60
tgtataggtt accatgcaaa taattcaact gacactgttg acacagtact agaaaagaat   120
gtaacagtaa cacactctgt taaccttta gaagacagac ataacgggaa actatgtaaa   180
ctaaaagggg tagccccatt gcatttgggt aaatgtaaca ttgctggatg ctactggga   240
aacccagagt gtgaattact attcacagca agctcatggt cttacattgt ggaaacttct   300
aattcagaca tgggacatg ttacccagga gatttcatca attatgaaga gctaagagag   360
cagttgagct cagtgtcatc atttgaaaga tttgagatat tccccaaggc aagttcatgg   420
cccaatcatg aaacgaacag aggtgtgaca tcagcatgtc cttattctgg agcaaacagc   480
ttctacagaa acttaatatg gctggtaaaa aaggaaatt catacccaaa actcagcaaa   540
tcctatatta acaataaggg gaaggaagtt cttgttctat ggggcattca ccatccacct   600
accagtactg accaacaaag tctctaccag aatgcagatg cctatgtttt tgtggggtca   660
tcaaaataca caagaaatt catgccagaa atagcaacaa gacccaaagt gagaggtcaa   720
gcagggagaa tgaactatta ctggacacta attgagcctg agacacaat aacattcgaa   780
gcaactggaa atctagtggc accaagatat gccttcgcaa tggaaagagc tctggatct   840
ggtattataa tttcagatac accagtctac gattgtaata cggcttgtca aacacccaaa   900
ggtgctataa acaccagtct tccatttcaa aatatacatc cagtcacaat tggagaatgt   960
ccaaaatatg tcaaaagcac aaaattgaga atggctacag gattaaggaa catcccgtct  1020
attcaatcta gaggcctgtt tggagccatt gctggcttca ttgaggggg gtggacagga  1080
atgatagatg gatggtatgg ttatcatcac caaaatgagc aggggtcagg atatgcacca  1140
gaccgaaaga gcacacagaa tgccatagac gggatcacta caaagtaaa ctctgttatt   1200
gaaaagatga acacacaatt cacagcagtg gtaaagaat tcaatcactt ggagaaaaga  1260
ataagaaatt taaacaaaaa ggttgatgat ggttttctga atgtttggac ttacaatgcc  1320
gaactgttgg ttctattgga aaatgaaaga actttggatt atcacgattc aaatgtgaag  1380
aacctatatg agaagtaag aagccaacta aaaacaatg ccaaggaaat ggaaatggc   1440
tgctttgaat tttaccacaa atgtgatgac acgtgcatgg agagcgtcaa aaatgggact  1500
tatgattatc caaaatactc agaagaagca agactaaga agactgggta                1560
aagctggaat caacaaggat ttaccagatt ttggcgatct attcaactat cgccagttca  1620
ttggtactgt tagtctccct gggggcaatc agtttctgga tgtgctccaa tgggtcttta  1680
cagtgcagaa tatgtatttt a                                             1701

SEQ ID NO: 327          moltype = DNA   length = 1701
FEATURE                 Location/Qualifiers
source                  1..1701
                        mol_type = other DNA
                        organism = synthetic construct
SEQUENCE: 327
atgaagacta tcattgcttt gagctacatt ttatgcctgg ttttcgctca aaaacctccc    60
ggaaatgaca acagcacggc aacgctgtgc ctggggcacc atgcagtgcc aaacggaacg   120
ctagtgaaaa caatcacgaa tgaccaaatt gaagtaacta atgctactga gctggttcag   180
agttcctcaa caggtaaaat atgcgacagt cctcaccaaa tccttgatgg agaaactgga   240
acactaatag atgctctatt gggagaccct cattgtgatg gcttccaaaa taaggaatgg   300
gaccttttg ttgaacgcag caaagcctac agcaactgtt acccttatga tgtgccggat   360
tatgtctccc ttaggtcact agttgcctca tcaggcatgc tggagtttaa caatgaaagc   420
ttcaattgga ctggagtcgc tcagaatgga acaagctctg cttgcaaaag agatctgat   480
aaaagtttct ttagtagatt gaattggttc accaattaa aatacaaata tccagcactg   540
aacgtgacca tgccaaacaa tgaaaaattt gacaaattgt acatttgggg ggttcaccac   600
ccgggtacag acagtgacca atcagcctat atgctcaag catcaggag agtcacagtc   660
tctaccaaaa gaagccaaca aactgtaatc cgaatatcg atctagacc ctgggtaagg   720
ggtgtctcca gcagaataag catctattgg acaaatgtaa aaccgggaga catacttttg   780
attaacagca caggaatct aattgctcct cggggttact tcaaaatacg aagtgggaaa   840
```

```
agctcaataa tgaggtcaga tgcacccatt ggcaaatgca attctgaatg catcactcca   900
aatggaagca ttcccaatga caaaccattt caaaatgtaa acaggatcac atatggggcc   960
tgtcccagat atgttaagca aaacactctg aaattggcaa cagggatgcg gaatgtgcca  1020
gagaaacaaa ctagaggcat attcggtgca atcgcgggct tcatagaaaa tggttgggag  1080
ggaatgatgg acggttggta cggtttcagg catcaaaatt ctgagggcac agggcaagca  1140
gcagatctta aaagcactca agcagcaatc aaccaaatca acgggaaact gaataggtta  1200
atcgagaaaa cgaacgagaa attccatcaa attgaaaaag aattctcaga gtagaagggg  1260
agaattcagg acctcgagaa atatgttgag gacactaaaa tagatctctg gtcgtacaat  1320
gcggagcttc ttgttgccct agagaaccaa catacaattg atctaactga ctcagaaatg  1380
aacaaactgt ttgaaagaac aaagaagcaa ctgagggaaa atgctgagga tatgggcaat  1440
ggttgtttca aaatataccca caaatgtgac aatgcctgca tagggtcaat cagaaatgga  1500
acttatgacc atgatgtata cagagacgaa gcattgaaca accggttcca gatcaaaggt  1560
gttgagctga agtcaggata caaagattgg atcctatgga tttcctttgc catatcatgt  1620
tttttgcttt gtattgtttt gctggggttc atcatgtggg cctgccaaaa aggcaacatt  1680
aggtgcaaca tttgcatttg a                                             1701

SEQ ID NO: 328       moltype = DNA  length = 6573
FEATURE              Location/Qualifiers
source               1..6573
                     mol_type = other DNA
                     organism = synthetic construct
SEQUENCE: 328
atgaataaaa tatttagagt tatttggagt catgctcaac aggcttgggt ggttgtatct   60
gagttagtaa agtctcatac caaaacatcc gcttacacgg ataaaagagc tcaagtatgc  120
acctcagatt attttttaga taaacagcaa gataaattta attaagtct tttaagtcta  180
gtattactag gtatatttt tagttcagta ggttcagctg catatcttca agatgtgct   240
aatgagggat cgaatatagg aactgacgac ggtactattg gtattggtca agagagtagg  300
gcttcgtatg gtgctgttgc tatccggtcag aaggcaaaag ctgaagctag cataatatt   360
gcgatagtt atggagcaga ttcaggaaca caagtaaact ctcttgcgat aggctaccgc   420
gctacagtaa gtgggactgg agcaattgcc ttaggcaaaa aagccaattc gacaaatagt   480
caaacaattg ccatcgggag tgattcaaaa gcgagcggag atgaatctat tgccttaggc   540
ggacaagcca attcgacaaa taatcaaaca attgccatcg ggagtcagtc aaaagcgagc   600
ggagaacaat ctattgtctt aggcacaggg gccagtgtga caggtactca aacaattgta   660
ataggcgcac gtgctagtgc aagtgggcac caatctgttc ctatcgggc aaatacccaa   720
gcgcagggg atggctccat atcaatcggt ggagatgatt tagctacaac gaaatatcaa   780
gatgatgctc aagactattc cagcacaaca actgcggcag gtcacgcctc tgttgctatt   840
gggggtcgat ctaaggctca gggcgatgga tctattgttg taggtccttt agcatatgca   900
aggtatgctg aaggcattgc tatcggtgcg agaagtaagt ctaacaatga gtacggtatt   960
gcggttggta gtggtgcatt tgctggaaag cactccattg ctgttggtaa aagtgctact  1020
gcaagtcaaa caggagcttc cgcattcggt gaaagcgcac gagcaatcgg acagtataca  1080
acagcattgg ggagttatgc ggaagcagaa acgaagatgg cgttgctct aggtttatcga  1140
tccaaaacta gtcgtcggtc agggcaaaga ggttggacac agagaatac aaattattct  1200
attaacggaa gtacattatc tgctacgcat gcagcggtag cagtaggtga tggcaccacc  1260
gtcactcgtc aaattaccag tgttgctgca gggacagcga atactgacgc agcaaacgtg  1320
gcgcaattaa aagcactgac tttaaagatc agtggcgata gaaatacgca gggtcacaca  1380
acattttata acgaaacgct ctcaattgta ggggctgatg gtattagtac ggcagttgag  1440
cagggaaatg gcaattcaaa aaattaccatt actggctcaa agtgtatttt tcatactaac  1500
tataacgaac agtctcaagg tcggggagat cctacgacta atttcggcac aattactgac  1560
aaagctggag ctacaggaac ctatgcaata acagcggggg taaatgcctc tgcggctgga  1620
aattatggta ttgcgatggg gtataagagt aatgctagtg cttatgctgt tgctcttggt  1680
agtgaatcga aaggtgctgg ggcagattcc attgcgatag gtaatcttgc gagaacaaca  1740
ggggtagact ctgttgttgt gggtgcccat atcaatgtga caggtcaaaa atcagttgca  1800
gttgacgcc aagcaaatgc tagagattat tctactgcct tgggttatat ggcctctgcc  1860
agtggtacgt actctgttgc tgtgggtgaa aatgccacga taaatgtaaa tgctgctaga  1920
gcaaccgcac ttggtcataa taccgttgtc accgtggtgc gcggtgtggc attaggttat  1980
ggatctaatg caaatatagc tggcggtgta gaggggttaa aacaagctca ttctgtcaca  2040
acgggaacaa gcactgaagc taacggcttt aaatccacac aaaagttga tggtaataat  2100
attggtgcag tttctgtggg tggtacaacc atcaaacgcc aaatcgtcaa tgtggcggct  2160
ggtacacaag ataccgatgc ggtaaacgtg gcacagctta aatctttgau gatgaaaatt  2220
ggtggtaata ccaatgctaa tacacagcca aaagtggggt tgtgggatgg tattcttaaa  2280
gtgctaggca caaatggcga aatcaagacc aatgcgtctg gctcaaccat tacaatatca  2340
ctagacgata cgattaaaaa taaattagct gatgccagag caggaagttt gatattcaag  2400
ggcgaaaaaa cagataacgg tacaacaaat gatgtttcgg gtcaaaaatg gaaggccaac  2460
gaagataaga ccgttaccat tacaagtaac gaaacataaa aaacggttgg tgttcgatac  2520
aaaggcgata acattgaaat ttatcgtaga aatctagaat tccatgtgtt gatgaaaagg  2580
acaccaacat tcagcagcgt tcaatatggc gataatggac ctaagattac cagcaccact  2640
gacggtaatc taaagtaac aggtacagac ggcacttcct cagttaagat caccaattta  2700
gcacgaggta cacaaaatag cgatgcggtg aactacatgc aattttcaaa tgctggttgg  2760
aaacttgcaa ttgctccagg aacggggggt caagcaactc cacctgggc acatccttatc  2820
aaaataaacg ataccgtaac ctttaccgct ggaataataa ttaaattaga caagcgggc   2880
ggaaatatta cgatttctac gattggtaag ttaattaaaa cgactgaaag cctagaaaat  2940
ggcgatctaa aaattatcta tacagataat tcgcataaca ttatcaagaa aggtgaaaaa  3000
ggagatcgtg gcgagcgagg tctaagaggt gaaacaggcc ctgcgggtcc gattggtcca  3060
gtgggtccag caggggcag gggtgagcga ggccctgcta gtggctgg tcctaagggt  3120
gagaaaggtg atccaggacc agagggccct caaggtccta gaggtgagca aggtctaaga  3180
ggtgaacgag gctagcggg tcctagaggc gaaactggtc gaggggtcc agtgggacca  3240
caaggagcgc aaggaatgcc gggtgctcag ggacagaagg gtgaccgagg agaaactggc  3300
cctgcgggtc ctagaggcga agctggtcct gctggagcaa caggaccaca aggtgaaaaa  3360
ggagatcaag gtccgatggg tccggcaggc ccagcggag agcgaggcga gcggggtcct  3420
```

```
aaaggagata gaggtccaaa aggtgataca ggtgagagag gtgcaactgg ccctgcggt      3480
ccgatgggtc cagcaggccc agcgggagag cgaggagaaa ctggacctgc aggtgtacct      3540
ggtcctaggg gtccagaggg tcctagaggc gaaactggtt taacaggtcc gagggtcca      3600
gtgggaccac aaggaccgca aggaacaccg ggtactccgg gacagaaggg ggataaaggc      3660
gatccaggac aagcgggtcc agcaggacct aggggtccag tgggtccgaa aggtgaaaca      3720
ggagctcaag gtccgatagg tccggcaggc ccagcgggag agcgaggcga gcagggtcct      3780
agaggcgaag ctggtccaac aggtccaaca ggtccgaggg gtccagtggg accacaagga      3840
ccgcagggaa cagcgggtgc tcagggacct aaggggtgagc gaggccctgc aggtgcagct      3900
ggccctgcgg gtccagtagg tccagcggga ccacaaggtg aaaaaggaga tcaaggtccg      3960
atgggtccgg caggcccagc gggtgctcag ggcatacaag gtccaaaagg tgatagaggc      4020
gaacaagggc ttccaggggt agcaggtcct aagggcgata gaggcgaagc tggtccagtg      4080
ggtccagcag gaccagcggg agagcgaggc gagcagggtc ctaggggga acaaggtgca      4140
actggccctg cgggtccaac ggggcctagg ggtgaaccgg gtcaacggg accacaagga      4200
ccgcaaggaa caccgggtac tccgggacag aaggggaata aggcgatcc aggacaagcg      4260
ggtccagcag gacctagggg tccagtgggt ccgaaaggtg aaacaggagc tcaaggtccg      4320
ataggtccgg caggcccagc gggagagcga ggcgagcagg gtcctagagg cgaagctggt      4380
ccaacaggtc caacaggtcc gagggtcca gtggaccac aaggaccgca gggaacagcg      4440
ggtgctcagg gacctaaggg tgagcgaggc cctgcaggtc agctggccc gggtcca      4500
gtaggtccag cgggaccaca aggtgaaaaa ggagatcaag gtccgatggg tccggcaggc      4560
ccagcgggtg ctcagggcat acaaggtcca aaggtgata gaggcgaaca agggcttcca      4620
ggggtagcag gtcctaaggg cgatagaggc gaagctggtc cagtgggtcc agtaggacca      4680
cgaggaccac agggaacagc gggtgctcag ggacctaagg gtgagcgagg ccctgcaggt      4740
gaaactggac ctaagggtga aaggtgat ccaggaccaa aaggcgaaac tggtccaaca      4800
ggtccagtgg gtccagcagg accagcggga gagcgaggcg agcagggtcc tagggggga      4860
caaggtgcaa ctggccctgc gggtccaacg gggcctaggg gtgaaccggg tccaacggga      4920
ccacaaggac cgcaaggaac accgggtact ccgggacaga aggggataa aggcgatcca      4980
ggacaagcgg gtccagcagg accacgaggc cctgcaggtg cagctggacc tgcgggccca      5040
gcagggccta ggggtgaccg aggagaaact ggtcctgcgg gtccaacagg gctaagggt      5100
gaacagggtc aaaaggaga tacaggtcca atggggcctg ctggtccaaa aggtgatgca      5160
ggtcctagag gcgaaggctg tcctgctgga gcaacaggtcc cacaaggtcc aaaaggagat      5220
aatggagcta caggtcctag gggagagaaa ggtgaacctg gccctgcggg tccgattggt      5280
ccagtgggtc cagcagggc tgctggtcca gcaggcccag cggagagcg aggccctacg      5340
ggtcctaaag gagatgcagg tccaaaagga gatacaggtc agaaggaga aactggccct      5400
gcgggtccag caggggctaa gggtgaaccg ggtcctagag gtgagcaagg tattcaagga      5460
cctacgggtc caacgggacc acaaggaccg cagggaacag cgggtattca gggacctaag      5520
ggtgagcgag gaaatgtgag tgtcagcggt ttaccgatcg agtatgcaac ggaagacggc      5580
aaatcaatta tcaatatggg cggtaatttc tattggaag aacctgctaa agatggttcg      5640
attaagttaa ttccagtggt gaatgttaaa ggtaaattct caaccaaaac gcaaaatcca      5700
gatgcagta ttacgcttaa gtcattagca gtaaagtga atttggcaaa tgaaactcga      5760
atggtattag gtaatgtcgc tgaagggta gcagatacgg acgctgttaa tgtgaaacag      5820
ttgaaatctg cgaaaactga agtggaatct accgatcaca gtgtggtgat taagagcgt      5880
cagggcgata atcagcaaat cgtgtatgat ttggcggttg ctaaaacgaa actcactgcc      5940
tctaaggata aacgaccat tagtcagca gataaaggca accattttgc gacaggagat      6000
gaagtcgcag tagcaattaa taccgcaaca gcagccgcaa gaaccgaagt tgaagcgggt      6060
aaaaatgtga aagtgacttc aaaaacgggg gcaaatggtc agaatattta caatgtgagc      6120
gtgtttggag atttaagcga cattacttca attagtaatg gcgatacgaa agtatcttta      6180
ggtaaagata agcaaggaaa tccagttgta aatatgaatg gtgccagaat taccaacgtt      6240
gggagatggta gtgctgaggg cgatattgtg aatgttcgtc agctcaacaa agtggttctt      6300
tctgtgaata caggatttaa tcaattatca agagatattg ttaatgcaag agcgggtatt      6360
gcttctgctg ggcgatggc taatttgcca caaatttctt taccaggtaa aagtgctatt      6420
tctgttttcta atgcacaata tcgcgggcaa tctgcctatg ctataggtta ttccaaaatt      6480
tctgataatg gcaaatggct tattcgagcg tctgttagca gtaatactca gcgggatact      6540
atgattggag gaggggtagg ttttgtgtgg taa                                   6573

SEQ ID NO: 329          moltype = DNA  length = 501
FEATURE                 Location/Qualifiers
source                  1..501
                        mol_type = other DNA
                        organism = synthetic construct
SEQUENCE: 329
aagcgaaagt agcagcaggt gaagctggtg gtattactca gcatatcggt gcatatcacg      60
ttgaaaccga cgacggtaag atgattacct tcttagatac accaggacac gcggcattta      120
cctcaatgcg tgcgcgtggt gcgaaagcaa cggatatcgt tgttcttgta gtagcagctg      180
acgatcgcgt aatgccacaa accattgaag caatccaaca cgcgaaagcc ggaaagtcg      240
cgatcgtggt tgcggtaaac aaaattgata aaccagaagc aaacctagag cgtgtagaac      300
aagagttatt acaacacgaa gtgatttctg agaaattcgg tggtgatgtt caatttgttc      360
ctgtttcagc gaaaaagga atggggattg acgacttact tgaagccatt cttcttcaat      420
cggaagtatt agaattaagt gcggtaaaag agggtatggc aagcggtgtg ttatcgaat      480
cttacctcga taaaggtcgt g                                                501

SEQ ID NO: 330          moltype = DNA  length = 1008
FEATURE                 Location/Qualifiers
source                  1..1008
                        mol_type = other DNA
                        organism = synthetic construct
SEQUENCE: 330
atgaaacaaa tcgttttaaa acaagcttta ttgatgaccc tctcttcatt attagttgca      60
tgtagcggcg gtgcggtag cgctggaaat cgtgctgacc gtgtagagga aaaagcacaa      120
ccggttcaat caaatagtga gccttcttcc gctccaatca aaaatcctac taataccgct      180
```

```
acgaatgatt ctcttcatga caaactttca atgtcttctc atgcacatc caaagaaaat    240
agtcaacaat cctcctttaa agcccctcta gaacaagaaa aaaaccaacc tgcacaagaa    300
aatctcactt ggacaggtta tcatgtttca gaagtgggaa atgcgagtaa taatgtagat    360
aaagataacg ttacggtatt cactttcgta aaatataatt ctcaatacaa tgatgatcca    420
gttttgata aaacaaaaac acaaagtaaa acaatatcat tagttgacgg aaaaaatgag    480
aataaagagg attattataa ctttacgtta aaagacgctt tattttatta tggaagttat    540
ggacaacctt cagcagatta caaaaaagta gaaaaaaatt atatttatgc aattaaacca    600
gatgcaataa ataatgagaa cctcaatgca ctaactgcaa cttattatca agaagatggt    660
tttatatatt ccgtattaag tgatgtaaat cgagttggt cagaatatat tcctcagtat     720
ggcaatgtga ctcttacttt ccgaaatggc aagatttatg gtgaaatcta cagatataat    780
agaggacgtg atgatttgtt tcagctctca ggagaaggac aaaacttaac tataacacca    840
cacaaggaca atccccataa actatcccct acaggacccg acaacatggc aatggagctg    900
aattttatca acgcagaaaa aactgataaa aaatacgttg ttggtgtagg aaaagctgaa    960
aaatattatg ggttattatt tgctgaaaaa agtcaccaag cacaataa                1008

SEQ ID NO: 331         moltype = DNA   length = 1800
FEATURE                Location/Qualifiers
source                 1..1800
                       mol_type = other DNA
                       organism = synthetic construct
SEQUENCE: 331
atgcattcaa gtaaacctta ttttttgggga agtgtgtttc ttttgttcac gttttttaggt    60
gcctatcttg cttcggcaat agatcgtgat tttggtcgaa ttgaggtgag ccatgtgagc    120
tttatgacag aagaaatgca accgatggtc gcgaagctat atcgtccagt ttctgctacg    180
gcagacacac cgaagccagg acttttggca ttgcatggct atcaaagtga taagaagca     240
actagtacat ttggtgcgtt ggagctggct aagcgcgtt ttgtggtgtc agcgatcgat      300
cattttggac atggctattc tactaagcta cccgcttcaa ataaaaatat gagtggagcg    360
aataatggtt atcaatattt aaaaacgttg ccgtttgtag ataacacacg ttaggtctc     420
tttggtcact ctactggcgc gttaaatgca attcgcgtgg caaaactcaa tccagatcac    480
aaagctgtca atggattaag tagcaatggt ggtgagatga cattgaataa ctacttattg    540
acacaaggat tgtacgaaga aattggtggc tatcgtgaaa gaaccttccc tgtaaaaagt    600
ttgattcatc atcctaaccg cctgaaagca tttgggttag cgaaaatga aactttgcag     660
tgggatcata cctatggtga ctttaacacc ggttctgcac gtcgtgcggc aatggtcgat    720
ggtacccatc ttgggggtgat gattgcttcc cagagtaata aagaagccat tctttggttt    780
aatcaagcat tgcaacatgg cgaaaaaggt gcggattgga ttgatcctga ccaacagacc    840
tattggtata aagaacttac agggttattt gccttagctt gtgctttgct tgccacatta    900
tgttttgcta gcggactttt aaaaacgact tattttggcg tgatgaatca agcggtcaca    960
gaaaagacag caatttcgag caaacaatgg tgggggcttta cgctgattaa tattgtgctg   1020
acattactgc tctatccgct atttacccag tgggcgggtg cgaatgaacc gattgcacg    1080
aaattgagtt ttatgccact tgaaatggga aatggcatta ttttatggct cgttgtgagt   1140
gggcttgtcg gtagtctttt atttggcttg tgcaaagaa aagcacagtt ttgttgggcg    1200
gagtttggtg tgttgagcca atctgcttcc ttgacaacgg cgcaactgat tggacgttat   1260
ttattactca gcttattgtt attgccggtt ttatatttcc ttgtcaatct gatttatcaa   1320
tatttccatg ttgagttacg tttcttatgg ccattattga agccattaac gacagagcgg   1380
tttaatttat ttatcgtgta ttggttacct attttggtct ttttcttcgt gttcaacggt   1440
ttgatcgtgt cagtccaaat gaaacaaaaa gtagcgagtc gtttacggc aacattgctg    1500
atctggagtt tcaaaaccgc actttttgct actggtggtt taatcatttt atggttattc   1560
cattttgttc ccggttttat gcaaatcggt ccgggatttg atgtggtagg actgccacaa   1620
tttggtggac gttggatgat gatgttagcc gtcattattc cacagtttat tgtcttcacc   1680
gtgatcaatc actggtgcta tttaaaaaca ggctatattt atttagggg atttttcacc    1740
tctctgttaa tgacttgggt gttagtcgga ggtcaagtca ttgggcgatt cttagcctaa   1800

SEQ ID NO: 332         moltype = DNA   length = 1098
FEATURE                Location/Qualifiers
source                 1..1098
                       mol_type = other DNA
                       organism = synthetic construct
SEQUENCE: 332
atgaatattg caacaaaatt aatggctagc ttagtcgcta gtgtagtgct taccgcatgt    60
agtggcggcg gctcatcggg ttcatcgtct aaaccaaatt cggaacttac acctaaggtt   120
gatatgtccg caccaaaagc ggagcagcca aaaaagagg aagttccaca agcggataat    180
tcgaaagcg aagaaccaaa agagatggct ccgcaagtag atagcccgaa agcggaagaa    240
ccaaaaaata tggctccaca aatgggtaat ccaaaactaa atgacccaca agtaatggct    300
ccgaaaatgg ataatccgca aaaagatgcc ccaaaaggag aagaactaag taaggataaa    360
agtaatgcgc aaattcttaa ggaattaggg gttaaggata ttaattcagg tatcattaat    420
aatgctgatg tagttctgaa tttaaaaata gatgaaaaag atcacattac agtcgtatta    480
gataagggta agattaatcg taatcatcta aaagtaacta atacaattt ctgctcaagac    540
attaaaaacct taaaagattc ttcaggcaaa ttgttggt actatggata tatgcagtta    600
aatcaagttc gacaagtaga aaattatagc gatgaaaaag ttagtttga tgaatattat    660
ttattatcaa tgaacgatgc cgataaaata cgtccgacta aatctatatc atataaggga    720
gacatgtttt atagttacaa agatgtagga aatcagaaat taaaggcttc tgtagaagct    780
tcttatgatg atgtaacaaa aaagtatca atgaaagtat tggtgagaa taatgattac     840
tggaaattag gtgagtttgg tagaactaat ttattagaaa atcaagtgac tggagcaaaa    900
gttggcgaag atggtaccat tataaatgga acttatatt ctaaaaatga taattttcct     960
ttaaaactaa ctcctgacgc aaacttctct gggggtattt tcggtaaaaa tggcgaagta   1020
ttagccggaa gtgctattag tgaaaaatgg caaggcgtaa tcggtgctac ggcaaccaca   1080
aaagaagata aaaaataa                                                  1098

SEQ ID NO: 333         moltype = DNA   length = 5418
```

```
FEATURE              Location/Qualifiers
source               1..5418
                     mol_type = other DNA
                     organism = synthetic construct
SEQUENCE: 333
atgacaaaat taactatgca agatgtgacc aatttatatt tatataaaac gaaaactcta   60
cctaaagata gattggatga ttcacttatt tctgaaatag gaaaaggaga tgatgatatt  120
gatagaaaag aatttatggt ggggccggga cgttttgtga ccgctgataa ctttagcgtt  180
gtaagagatt tttttaatgc tgggaaatca cgcattattg cgccgcaagt cccgcctatt  240
cgttcacagc aggaaaaaat cttggtcggt ttaaaaccgg gcaaatattc caaagcgcag  300
atattggaaa tgctgggtta tacgaaaggc ggagaagtgg taaatggcat gtttgccggt  360
gaagtccaga cattaggctt ttatgacgat ggcaaagggg atttactcga acgcgcctat  420
atctggaata ccacaggatt taaaatgagc gacaatgcct tttttgttat agaagaatca  480
ggcaaacgct atattgaaaa ctttggtatt gaacctcttg gtaagcaaga agattttgat  540
tttgtcggcg gcttttggtc taacttagtg aatcgtggtt tggaaagtat tatcgaccca  600
tccggtatcg gtgaacggt aaaccttaac tttaccggcg aggtgaaaac ctacacgtta  660
gacgaaacaa ggtttaaagc ggaagcggcg aagaaaagcc attggagttt agtgaatgcg  720
gcgaaagtat acggcggttt agaccaaatt attaaaaaac tatgggacag tggctcaatt  780
aagcatttat atcaagataa agatacgggc aaattaaaac cgattattta cggcacggcc  840
ggcaacgaca gtaagattga aggcactaaa atcacccgta ggattgcggg taaagaagtt  900
acgcttgata ttgccaatca gaaaattgaa aaggcgtgt tagagaaatt ggggctgtct  960
gttagtggtt cggatatcat taaattgttg tttggagcat tgactccaac tttaaataga 1020
atgttgctat cacaacttat ccagtctttt tccgatagct tggctaaaact tgataatccc 1080
ttagccccctt acactaaaaa tggcgtggtt tatgtcaccg gcaaagggaa tgatgtgctt 1140
aaaggaactg aacatgagga tttgtttctc ggtggtgagg gaatgatac ttattatgcg 1200
agagtagcg atacaattga agacgccgac ggcaaagta aagtctattt tgtgagagaa 1260
aaaggggtac ctaaggcgga tcctaagcgg gtagagttta gcgagtacat aacgaaagaa 1320
gaaataaaag aggttgaaaa gggggttatta acttacgcag ttttagaaaa ttataattgg 1380
gaagagaaaa cggcgacttt cgctcatgcg actatgctta atgagctttt tactgattat 1440
actaattatc gttatgaagt taaaggacta aaattgcccg ccgttaaaaa gttaaaaagt 1500
ccgttggtgg agtttacagc tgatttatta actgttacgc ctattgacga aaacggaaaa 1560
gcacttagcg aaaaaagtat tacggttaaa aatttttaaaa atggtgattt aggaataagg 1620
ttgttggatc ctaatagcta ttattatttc cttgaaggcc aagatacggg ttttatggt 1680
cctgcttttt atattgaacg aaaaaacggt ggcggcgcta aaaataactc gtcgggacga 1740
ggaaatagca aagattgggg cgggaacggg catggaaatc accgaaataa tgcctccgac 1800
ctgaataaac cggacggaaa taatgggaat aaccaaaata acggaagcaa tcaagataat 1860
catagcgatg tgaatgcgcc aaataacccg ggacgtaact atgatattta cgatcctttca 1920
gctttagatt tagatggaga tgggcttgaa accgtgtcga tgaacgggcg acaaggcgcg 1980
ttattcgatc atgaaggaaa aggtattcgt accgcaacgg gctggctcgc tgcggatgac 2040
ggttttttag tgttagatcg taaccaagac ggcattatta atgatataag cgagttattt 2100
agtaataaaa atcaactttc cgacggcagt atttctgcac acggttttgc gacattagcc 2160
gatttggata caaaccaaga tcagcgtatc gaccaaaatg ataagctgtt ttctaaactc 2220
caaatttggc gggatttaaa tcaaaacggt tttagtgaag tgagtgagct gtttagctta 2280
gaaagtttga atattaaatc tttacatacc gcctatgaag agcgtaatga ttttctagcg 2340
ggcaataata tccttgctca gcttgggaag tatgaaaaaa cggacggtac ttttgcacaa 2400
atgggcgatt taaatttcag ttttaacccg ttttatagcc gatttaccga agcgttaaat 2460
ttaaccgagc aacaactcg cacaattaat ctaaccggca cggctcgggt tcgggatttg 2520
cgtgaagccg ccgcactttc tgaggagttg gctgctttat acaacagta cactaaggcc 2580
tccgatttc aggcacaacg agaattattg cctgccattt tagataaatg ggcggcaacg 2640
gatttacagt atcaacatta tgataaaaca ttacttaaaa cggtagaaag taccgatagt 2700
agtgcttctg tcgttagagt cacgccttct caattaagta gtatacgcaa tgcaaagcat 2760
gatcctaccg ttatgcaaaa cttgaacag agtaaggcaa aaattgcgac tttaaattcg 2820
ctctacgggt taaatatcga tcaacttat tacacgacgg ataaagacat cgctatatt 2880
actgataaag tgaataatat gtatcaaaca accgtagaac ttgcctaccg ttctttactt 2940
ttacaaacgc gtttgaagaa atatgtttat agcgttaagt cgaaacaatt cgaagggaaa 3000
tgggtaaccg attattctcg tactgaagcc ttatttaact ctacttttaa acaatcgcct 3060
gaaaatgcat tatatgattt aagcgaatac ctttctttct taacgatcc tacggaatgg 3120
aaagaagggc tattactgtt aagccgttat atagattatg ctaaagcaca aggattttat 3180
gaaaactggg cggctacttc taacttaact attgcccgtt taagagaggc tggagtaatt 3240
tttgcagaat cgacggattt aaaaggcgat gaaaaaaata atattttgtt aggtagccaa 3300
aaagataata acttatcggg tagtgcaggt gatgatctac ttatcggcgg agagggtaat 3360
gatacgttaa aaggcagcta cggtcagac acctatatct ttagcaaagg cacggacag 3420
gatatcgttt atgaagatac caataatgat aaccgcgcaa gagatatcga caccttaaaa 3480
tttaccgatg tgaattatgc ggaagtgaag tttcgacgag tagataatga cttaatgtta 3540
ttcggttatc atgatacgga ttcggtcacg gtaaaatcct tctacagcca tgtagattat 3600
caatttgaca aattggagtt tgctgaccgc agtataactc gcgatgaact gattaaagca 3660
gggcttcatc tatacggcac cgatggcaat gatgatataa aggatcatgc ggattgggac 3720
agcatttttgg aaggcggcaa aggcacaggat attcaaagag gtggctacgg tgcggacacg 3780
tatatcttta gcaaaggaca cggacaggat atcgtttatg aagatatt 3840
cgcgcaagag atatcgacac cttaaaattt actgatgtga attatgcgga agtgaaattc 3900
cgacgagtag ataatgactt aatgttattc ggttatcatg atacggattc ggtcacgata 3960
aaatccttct acaccatgt agattatcaa tttgacaaat tggaatttgc tgaccgcagt 4020
ataactcgtg atgaactagg taaacaaggt atggcattat ttggcactga cggtgatgat 4080
aatatcaacg actggggacg taactcggtg attgatgccg gtgcggtaa tgatacggtt 4140
aatggcggta atggcgatga caccctcatc ggcggcaaag gtaatgatat tctaagaggt 4200
ggctacggta cggacaccta tatctttagc aaaggcacg gacaggatat cgtttatgaa 4260
gataccaata tgataaccg cgcaagagat atcgacacct taaaatttac cgatgtgaat 4320
tatgcggaag tgaaattccg acgagtagat aatgacttaa tgttattcgg ttatcatgat 4380
acggattcgg tcacggtaaa atccttctac agccatgtag attatcaatt tgacaaattg 4440
```

```
gagtttgctg accgcagtat aactcgcgat gaactgatta aagcagggct tcatctatac   4500
ggcaccgatg gcaatgatga tataaaggat catgcggatt gggacagcat tttggaaggc   4560
ggcaaaggca acgatattct aagaggtggc tacggtgcgg acacctatat ctttagcaaa   4620
ggacacggac aggatatcgt ttatgaagat accaataatg ataaccgagc aagagatatc   4680
gacaccttaa aatttactga tgtgaattat gcggaagtga aattccgacg agtagataat   4740
gacttaatgt tattcggtta tcatgatacg gattcggtca cgataaaatc cttctacaac   4800
catgtagatt atcaatttga caaattggaa tttgctgacc gcagtataac tcgtgatgaa   4860
ctaggtaaac aaggtatggc attatttggc actgacggtg atgataatat caacgactgg   4920
ggacgtaact cggtgattga tgccggtgcg ggtaatgata cggttaatgg cggtaatggc   4980
gatgacaccc tcatcggcgg caaaggtaat gatattctaa gaggtggcta cggtgcgac    5040
acctatatct ttagcaaagg acacggacag gatatcgttt atgaagatac caataatgat   5100
aaccgcgcaa gagatatcga caccttaaaa tttactgata taattttatc cgaactttgg   5160
tttagccgag aaaataacga tttgattatt aaatcattat taagtgagga taaagtcacg   5220
gttcaaaatt ggtattcaca ccaagatcat aaaatagaaa atattcgttt atcgaatgag   5280
caaacgttgg tgagcactca ggtgagaag atggttgagt cgatggccgg ctttgctcag    5340
aagcacggag gagagatatc tcttgtgtcg cttgaagagg taaaacaata tatcaatagc   5400
ttaacagctg ctttataa                                                 5418

SEQ ID NO: 334         moltype = DNA  length = 1347
FEATURE                Location/Qualifiers
source                 1..1347
                       mol_type = other DNA
                       organism = synthetic construct
SEQUENCE: 334
atgtcaaatg ccaaagctta catccaagct tcttttgaag cagtcaaagc ccgcaaccca   60
catgaaacag aattcctcca agctgtagaa gagctcttct ctacacttga gcctgttttt   120
gaagcacacc cagaatacat cgaagaaaac atcttggctc gtatcgttga gcctgagcgt   180
accatcagct tccgtgttcc atggacagat aaagatggaa atgttcaagt caaccgtggc   240
taccgtgttc agttcaactc agctgtaggt cctatataaag cggtcttcg cttccaccca    300
actgtaaacc aatccatctt gaagttcctc ggttttgagc aaatcttcaa aaacgtcttg   360
actggtcttc caatcggcgg tggtaaaggt ggttcagact ttgatcctaa aggaaaaact   420
gatgctgaaa tcatgcgctt ctgccaaagc ttcatgactg aattgcaaaa acacatcgga   480
ccttcacttg acgtccctgc tggtgacatc ggtgtcggtg tcgtgagat cggttacatg    540
tacggtcaat acaaacgcct ccgccagttt gatgcaggtc tcttgactgg taaacctct    600
ggcttcggtg ttcattgat ccgcccagaa gcaactgctt acggtttggt ttacttcact    660
gataacatgt tggcagcaaa cggtaaatcc ttcaaagacc aaactgtcct tatctcaggt   720
tctggtaacg ttgcccaata tgctgttcaa aagcgactg aacttggtgc aaaagttatt    780
tctgtttcag actcaaatgg ttacatcatt gacgaaactg gtatcgactt cgacctcttg   840
gtggacatca aagaaaaacg ccgcgctcgt ttgacagaat acgtcgcaaa aaatcaact   900
gctaagtact tcaaaggttc tgtatggaac tacgatggca aggctgatat tgcccttcca   960
tgtgcgactc aaaatgagat caacggcaaa caagctgctg ccccttgtaaa aatggcgtg  1020
tactgtgtgg ctgaaggtgc caacatgcca tctgaccttg atgccatcaa agtctacaag   1080
gaaaatggcg ttctctacgg actcgcaaaa gctgccaaac ctggtggtgt agctgtatct   1140
gcccttgaaa tgagtcaaaa cagccttcgc ttgtcatgga ctcgtgaaga agtagacggc   1200
cgtcttaaag acatcatggc caacatcttc aacacagcca agaaactgc tgaaaaatac   1260
gaccttggta cagactacct tgcaggtgct aacatcgcag ccttgaaca aattgcggat   1320
agcatgattg cccaaggttt ggtataa                                      1347

SEQ ID NO: 335         moltype = DNA  length = 1662
FEATURE                Location/Qualifiers
source                 1..1662
                       mol_type = other DNA
                       organism = synthetic construct
SEQUENCE: 335
atgttactag aagtgtccat taaaaacttc gccattattg agcaggtatc actgaatttt    60
gaaaacggga tgaccatcct atctggtgaa acaggtgcag gtaaatccat tatcattgat   120
gccatgaacc tgatgctagg ggcgcgtgcg acgacagatg ttatcagaca tggggccgcc   180
aaggctgaga ttgaagggct cttttccttt gaaaatagca gagctctcga gcaaattttg   240
cttgaacagg ggattgaagt agctgacgaa ctcattatcc gccgtgaaat cctgcaaaat   300
ggccgttcgg tcagccgtgt caatggacaa atggtcaatt tatctgtctt gaaacagatt   360
gggcaatatt tagtagatat tcatggtcaa catgaccagg aagaattgat gaaatcccag   420
caccatatcc gtcttttgga cagtttcgga gaagatgaat tttggagtct taagaccgt    480
tatcagacaa cccttttgat gctatcgtagt cttcgcaaac gagttcttga aaagcaaaaa   540
aatgagcaag aacacaaggc gcggattgag atgctagaat accaaattgc tgaaatcgaa   600
gcagcggatt tgaagtctgg ggaagatatt caactcaatc aggaacgcga taactgctc   660
aaccacaaac aaattgcaga tacactgacc aatgcctatg cactgttaga caatgaagat   720
tttttcaagct tgaacaacct acgctcagct atgagtgact tgcaaagtct ggaagaattt   780
gatccagact acaaacagct ctcttctagc ctgacagaag cttattatgt cgttgaagat   840
ataaccaagc gtctcagcga tgtggtcgat aatctagatt ttgacggcaa tcgtctcatg   900
caattggaaa gtcgtctgga tttgctcaat accattacga agaaatatgg tggaactgtc   960
gatgatgttt tggactattt tagtaaaatc agcgaagaat acaatctatt gacaggcaat  1020
gatttatctg gagatgattt ggaagttcag cttaagaact tagagaaaga attggttgaa  1080
cgagcaggtc agctcagcca atcacgccat gaattggctg ttgttttaga agatattatc  1140
cgccaagaat tgcaagcttt gtatatggag aagcttcgtt tccaagttcg atttactaaa  1200
ggaaatttta tcgagaagg aaatgaaaca gtagaatttt acatctctac caacccaggt  1260
gaagacttca ggcctctggt taaagtggct tctggaggag aattgtcccg cttgatgttg  1320
gccattaagt cagcctttgc ccgtaaagaa ggcaagactt ccatcgtctt tgacgaggtg  1380
gatacagggg tgtctggacg tgtggcccag gccattgccc agaaaattta aaaatcgga   1440
caatatgggc aagtattggc gatttctcat ctaccacaag tcattgctat tgcagattat  1500
```

```
cagttcttta ttgagaaaat atccgacgaa cattcgaccg tttctcgtgt ccgtctcttg   1560
accaaagaag agcgtattga ggaaattgcc aagatgttag ccggtgacaa aatcacagat   1620
gcagcccgta atcaagcaaa agaattagta gaaaaaggtt ag                      1662

SEQ ID NO: 336          moltype = DNA  length = 1012
FEATURE                 Location/Qualifiers
source                  1..1012
                        mol_type = other DNA
                        organism = synthetic construct
SEQUENCE: 336
atggtagtta aagttggtat taacggtttc ggacgtatcg gtcgtcttgc tttccgtcgt     60
atccaaaacg tagaaggtgt tgaagttact cgtatcaacg accttacaga tccagtaatg    120
cttgcacact tgttgaaata tgacacaact caaggtcgtt tcgacggtac tgttgaagtt    180
aaagacggtg gtttcgaagt taacggtaaa ttcgttaaga tttctgcaga gcgcgagcca    240
ggaaacatcg actgggctac tgatggcgta gatatcgttt tggaagctac aggtttcttt    300
gcttctaaag aaaaagctga gcaacacatc cacgctaacg gtgctaaaaa agttgttatc    360
actgctcctg gtggtaacga tgttaagact gttgttttca acactaacca cgacatcctt    420
gatggtactg aaacagttat ctcaggtgct tcatgtacta caaactgttt ggcaccaatg    480
gctaaagctc ttcacgatgc atttggcgtt caaaaaggtt tgatgactac aatccacggt    540
tacactggtg accaaaatgg tcttgacgga ccacaccgtg gtggtgacct tcgtcgtgca    600
cgtgctgctg ctgcaaacat cgttcctaac tcaactggtg ctgctaaagc tatcggcttg    660
gtaatcccag aattgaacgg taaacttgac ggtgctgcac aacgtgttcc agttccaaca    720
ggttctgtaa ctgaattggt tgcaactctt gacaagaaag taactgctga agaagtaaac    780
gctgctatga aagctgctgc tactgaatca tttggttaca ctgaagacca actcgtatct    840
tcagatatcg taggtatctc attcggttca ttgtttgatg caactcaaac taaagttatc    900
gaagttgatg gcgagcaatt ggttaaagtt gtttcatggt acgacaacga aatgtcttac    960
actgcacaac ttgttcgtac tcttgagtac ttcgcaaaaa ttgctaaata at           1012

SEQ ID NO: 337          moltype = DNA  length = 495
FEATURE                 Location/Qualifiers
source                  1..495
                        mol_type = other DNA
                        organism = synthetic construct
SEQUENCE: 337
atgtcaaaaa ataatatagt ggagtgcttt atagaaattg caagcactc caatcttaaa     60
tatgagtgtg ttgatggcaa attgaaacta gatagagtac tatttggttc aatggtatat    120
ccgcacaact atggatatat ttctgatact ctagcagagg atggagatcc tctagatgta    180
gtagtgctat ctaatttctc tgtaactcca ggaacttatt tggattgcaa aattcttggt    240
tctctagaaa tggtagattc tggagaacaa gattgaaaag ttattgcaat tatggatgcg    300
gatccaagac tcaagcatat aaattctcta gatgatgttc ctcaacattg aattgctgaa    360
ttgagaaact ttttttgaaag ttacaagcaa ctagagaata agaaagtttc ccttggaaac    420
tttatctctc tagaatcaac tctttcttta attgaagaat caaaagctag atgaagaact    480
caaggggag aataa                                                      495

SEQ ID NO: 338          moltype = DNA  length = 1011
FEATURE                 Location/Qualifiers
source                  1..1011
                        mol_type = other DNA
                        organism = synthetic construct
SEQUENCE: 338
atgacaatcc acaaagtagc aatcaatgga ttcggaagaa tcggaagatt actatttaga    60
aatcttcttt cttctcaagg agttcaagtt gtagctgtta atgacgtagt tgacattaaa    120
gttcttactc acctttttggt ttatgacagt gctcaaggaa aactaaaaga ttgagaagta    180
agttgtgatt cagaatacat aagactaaag aatgtaaata ctggagaagt tagagaagtt    240
agagttttca acttcaatac tgaaaagatt atcactgag gtgaattgaa aattgattgt    300
gttgttgaat gttcaggaag attcttaact aaggaagcag ttaagtgtca ccttgatgca    360
ggagctcaaa aagttcttat ttcagctcct gcaaaggatg cactaagac agttgtttac    420
aacgtaaacc atactcaaat taccagctca gacaatgtta tttcaggagc ttcatgtaca    480
actaatgcac tagctcctat cgtaaaaatt attcacagaa aatttggaat taattctgga    540
ttcatgacaa cagttcacgc tttcacttct gaccaaagac ttcaagactc tcctcactct    600
gacctaagaa gagctagagc agctgctgga tcaattattc ctacaactac aggagcagct    660
gctgcaattg aagagtaat tccagaattg aatggaaaac ttgatggaat tgcacacaga    720
gtgcctgtat taactggttc tctagttgac ctatgtttaa aaataaataa gtctgtttct    780
gcagaagaaa tcaatgaagc aattaaggat ggagaaacaa aaacccttgc ttatgtagaa    840
gatccaattg tatctgctga cattatcgga gatacacatg gttctgtttt tgactcatct    900
ctaactaaag tattgccaac tggagaagtt aagctgtatg catgatatga taatgagtct    960
tcttatgtaa atcaacttgc aagaactttg aaatactaca tttctcttta a            1011

SEQ ID NO: 339          moltype = DNA  length = 538
FEATURE                 Location/Qualifiers
source                  1..538
                        mol_type = other DNA
                        organism = synthetic construct
SEQUENCE: 339
ttcttcccag agtggatttc cgttggttcc gcctccttcg tccgtcgtaa tatcaggcct     60
tctgttctgt tcgctgtctg tctagggcac ccttactgca agagaagtat ttgaggtcat    120
atcgtcccat gaagtcgacc acctgttccc tctcttcact gtcacgtacg acatcgcatt    180
caagggaaga gatccagcag atctcgttcg tgtattcgag acaagagagg tccgccccca    240
caagacggct gaagaatgca acattcttgt gctgcctcct ctcatggcaa atgccagaag    300
```

```
aagggtacgt gttgcatcat aacaagagct gtatttcccg ctggcaaata caggtgaaat  360
gtacctccag aaaagccacc tagtatcgtg cggcaatgtg ccacctcgcc tcttgggaga  420
aaaagaggaa gagacgctgc cgctgttttg caaatgaaaa ggattcattt tcgcagtaca  480
ccaggagttg gattttgtag agcgtctctc ttcaagcagc gtattgtcga gaaaaaga    538

SEQ ID NO: 340          moltype = DNA   length = 529
FEATURE                 Location/Qualifiers
source                  1..529
                        mol_type = other DNA
                        organism = synthetic construct
SEQUENCE: 340
ctgcagggag gaagacgaaa gttgtttttt tattttttt tcttttgtt tttctgattt     60
ttgtttttt tgactcgggc ccagctgcgt ctgtcgggat gagaccgcgg agccgaagtg   120
cgttttcttt ttttgacttt ttttgtttt ttcacaggca agctcgcctg tgcttggagc   180
cacagaaggg acagaagtcg aaggggacta cagacgcgat gccgctcctc cagccgtctt  240
ggaggagaga tatcaggact gtagatgaag gcgagggtga ggatgagggg gtggcgtggt  300
tgggaagcga cgagagtcgg agaggagaa gatgtttccg gcttggctgc ttttcctgga   360
gggtggaaaa agagacaccg gaatgcgatc cagacgaagc gacgctttcc tcgtggtgat  420
ggcgagaga attgaagagt ggagaagagg gcgagggaga cagagtcgga ggcttggacg   480
aagggaggag gaggggtagg agaggaatcc agatgcactg tgtctgcag              529

SEQ ID NO: 341          moltype = DNA   length = 1212
FEATURE                 Location/Qualifiers
source                  1..1212
                        mol_type = other DNA
                        organism = synthetic construct
SEQUENCE: 341
ttgctcaaaa aatttaaaaa ttttattcta ttttcatcta tattttcacc aatagcattt    60
gctatatcat gttctaatac aggagtagtc aagcaagagg atgtatcagt tagtcaaggt  120
caatgagata aaagtataac atttggtgtt tcagaagctt ggttaaacaa gaaaaaagga  180
gataaagaag ttaacaaaga agttattaat acatttttag aaaatttcaa aaaagaattt  240
aataaactca aaaatgcaaa tgataaaacc aaaaacttcg atgacgttga ttttaaagta  300
actccaattc aagactctac tgtgttgtta acaatttat ctactgacaa tcctgaatta   360
gatttggaa ttaatgcttc aggaaaattg gtagaatttc taaaaaataa tcctggtata  420
ataactcctg cattagaaac aacaactaat tcttttgtat ttgacaaaga aaagataaa   480
ttttatgttg atggtacaga ttcagatcca cttgtaaaaa ttgctaaaga aattaataaa  540
attttgttg aaactccata tgcaagttga actgatgaaa atcataagtg aaatggtaat  600
gtttatcaaa gtgtttacga tccaactgtt caagctaatt tttatagagg aatgatttga  660
ataaaaggta atgatgaaac tctagctaaa attaaaaaag cttgaaatga taagattga   720
aatacattta gaaattttgg aattttacac ggtaaagata attcttcttc taaattcaag  780
ttagaagaaa ctatattaaa aaaccacttt caaaataaat ttacaacact aaatgaagac  840
agaagcgcac atccaaacgc atataaacaa aaatctgcag atacattggg aactttagat  900
gatttccata ttgctttttc gaagaaggt tcttttgctt gaacacataa caaatcagca   960
acaaaacctt tgaaactaaa gcaaatgaa aagatggaag cacttatagt aactaatcca  1020
attccgtatg atgttggagt gtttagaaaa agtgttaacc aattagaaca aaatttaatt  1080
gttcaaacat tcattaattt agctaaaaat aaacaagata catatggtcc acttttaggg  1140
tataatggtt ataaaaaaat tgacaatttc caaaagagaa ttgtagaagt ttatgaaaaa  1200
gccattaaat aa                                                      1212

SEQ ID NO: 342          moltype = DNA   length = 1349
FEATURE                 Location/Qualifiers
source                  1..1349
                        mol_type = other DNA
                        organism = synthetic construct
SEQUENCE: 342
gatgaacgct cgctgtgtgc ctaatacatg catgttgaac gggatgtagc aatacattca    60
gtagcgaatg ggtgagtaac acgtacctaa cctaccttta agactgggat aactattgga   120
aacaatagct aataccggat atagttattt atcgcatgat gagtaataga aaggagcttc   180
acagcttcac ttaaaaatgg gggtgcggaa cattagttag ttggtagggt aatggcctac   240
caagacgatg atgtttagcc gggccgagag gctgtacggc cacactggga ctgagatacg   300
gcccagactc ctacgggagg cagcagtaag gaattttcca caatgagcga agcttgatg    360
gagcgacaca gcgtgcagga tgaagttctt cggaatgtaa actgctgtta tagggaaga    420
aaaaatagaa taggaaatga tttatcttg acggtacctt attagaaagc gacggcaaac   480
tatgtgccag cagccgcggt aatacatagg tcgcagcgtt atccggaat tattgggcgt   540
aaagcgtccg taggtttttt gctaagtctg gagttaaatg ctgaagctca acttcagtcc  600
gctttggata ctgcaaaat agaattataa agaggttagc ggaattccta gtgaagcggt   660
ggaatgcgta gatattagga agaacaccaa taggcgaagg cagctaactg gttatatatt   720
gacactaagg gacgaaagcg tggggagcaa acaggattag ataccctggt agtccacgcc  780
gtaaacgatg atcattagtt ggtggaataa tttcactaac gcagctaacg cgttaaatga   840
tccgcctgag tagtatgctc gcaagagtga aacttaaagg aattgacggg aacccgcaca   900
agcggtggag catgtggttt aattgaaga tacgcgtaga accttaccca ctcttgacat    960
cttctgcaaa gctatagaga tatagtggag gttaacagaa tgacagatgg tgcatggttg  1020
tcgtcagctc gtgtcgtgag atgttaggtt aagtcctgca acgagcgcaa cccttttctt  1080
tagttactaa tattaagtta aggactctag agatactgcc tgggtaacca ggaggaaggt  1140
ggggacgacg tcaaatcatc atgcctctta cgagtgggc aacacacgtg ctacaatggt   1200
cggtacaaag agaagcaata tggtgacatg gagcaaatct caaaaaaccg atctcagttc  1260
ggattgaagt ctgcaactcg acttcatgaa gtcggaatcg ctagtaatcg tagatcagct  1320
acgctacggt gaatacgttc tcgggttt                                     1349
```

SEQ ID NO: 343        moltype = DNA   length = 948
FEATURE               Location/Qualifiers
source                1..948
                      mol_type = other DNA
                      organism = synthetic construct
SEQUENCE: 343
atgaaaccta ttaaaatagc tctaattggt gctggaaatg tcggaaattc tttcctttat    60
gcagcaatga atcaaggact tgcatccgag tatggaatta ttgatattaa ccctgatttt   120
gccgatggta atgcttttga ttttgaagat gcctcagctt ctttgccttt tccgattagt   180
gtctcccgtt atgaatataa agatctaaaa gatgctgatt ttattgtaat tacagcggga   240
agaccacaaa aaccgggtga aactcggctt gaattagtag ctgataacat ccgaattatc   300
cgggaaattg cactaaaagt caaagaaagt ggctttagtg gaataagtat tattgttgct   360
aatcctgttg atataattac aagggcttac cgggatgctt ctggattttc cgatcaaaaa   420
gttatcggta gtggaactgt tttagataca gcaaggcttc aatttgcaat cgcaaaaaga   480
gcaaaagtat cgcctaattc ggttcaggcc tacgtgatgg gtgaacatgg tgattcatct   540
tttgttgctt attcaaatat taaaattgcc ggtgaatgtt tctgtgctta ttctaaaacta  600
accggaattg atagctcaaa ttcgaaaaaa gaacttgaat atccagtttc tcgccgggct   660
tatgaaatta ttaatcgtaa aagggcaaca ttttatggaa ttggtgcagt tattgccaaa   720
atagtttcta atattatcaa agatacaaaa aatattatga ttgccggagc aaatttacga   780
ggagaatacg gatttcacgg agtaaatatc ggagttccag ttgttttagg ggcaaacgga   840
attgaaaaaa ttattgagat tagttttaat gataaagaaa agaaaaaatt tgccaaatca   900
gttgcaatca ttgataaaat ttatcaggat gcaattaaaa atatttaa                948

SEQ ID NO: 344        moltype = DNA   length = 2715
FEATURE               Location/Qualifiers
source                1..2715
                      mol_type = other DNA
                      organism = synthetic construct
SEQUENCE: 344
ttacttttta acatagtttc taatcaaccc gttaattaat tcacttcttt ttgttaaact    60
tcctttctct gcaaatgatt tatcattaaa tattgccagc gttttaata taattgtagg    120
ttctttttta gcgttttgtt gtggtttttt atttgttcg cctgggccga tttgatacca   180
atcaagatga aatcattcta aagtaaagaa atttggcaag tgtctttag ggttaatctc   240
gaatttaaga cgttttacac gttttgggta cttttgttgga aaaaaataag aatttacctt   300
aaatcgaatcc ttgccagcaa gaatttcata taaaataggca ccattctcaa caatttcttt   360
ggttttaggt acattattat ttgaattttg aactttaatt acaagcccct ttcctttttct   420
atcggctaaa agattaatcc aattaccatc ggaaatattt tttgcatcaa aaactaaata   480
aattgctccg gtatataaag aagttgatat ttcttttct ggattagacg attttgactg    540
taatttcaaa ggtttcttta gctctaaacc ttgatcagtt tgaattgcat cttctgattt    600
aaatattaat ttattatcac ttaaatcttt taggataaat tctttttttat cttttccttg   660
attttgataa ttaattgttc catctaaaaa cacatcggga ttgaatttct taattatatc    720
ataggcagat ttattagaat taataatatt attaagacta attttggact gagccaaaat    780
tagattttga ttagttttat caactaattt aaaatcaaaa aatagcttat ttcctaaagt    840
tgagatctca tattcgcttt ttgtattttc aagattataa atattagcga aattaaaagc    900
tgttcaaatg cttgtcccaa attttcatt ttctaataca gaatttgagc tgcttgtgga    960
attaggaagt gaatttgac tagtttgagg cgatgaagtg gaaactggtt gtgtttgctg   1020
actttgactt tgacccttag cttcttctgc aaaagtgctt accttgactg tttttgctga  1080
attttctgtt gttttagcta gtgaaacctc tggtttttc ggttgtgtgg gctattttt    1140
ttctgttttt tgagtatttg cctttgattt taagccctca atcacggttt ttagctcttg   1200
ttttacttttt tcctggtctt ggtcgactaa atattttccc gtatttaata aataaatgct  1260
tttaagaact tcttcacttg gattttccaa attagtcact gttttttgcta gttcaaaaag   1320
tcgatcaact cgctgttta tttcatttga ggataaagtt tttgcatctt gatcttcagg   1380
cattgaaaat tctttaactg cttttatcgt tccaaacatt tgggcaacag cggcttggta   1440
tttattaaaa tcaactttta gatcaacaaa aactggaaga tcctgatga taaattttt    1500
atcaatagct tttcgtttta aagaagcagt aatttcaaag cgaatttttt gatttcaac    1560
tagttttttc ttatcaacaa cagaaatctg acttggatct aaaagttttgg gaataatact  1620
taaatagaca gttccgattt tggtattaag aaaaaaattt gtctcactta aatcaaaaag   1680
atctttaaat tctttacttt ttgttaaaat ttgggatgta tttactttttg aattcggaga  1740
tccatatcaa taatcagaga ggctaatttt atctttact agtgccattt gcaaatcatc   1800
tttggttttt aatttgcctt gaagatttgt ttcaagtcag gattttagaa ttttagaaat  1860
ttcctgatttt gaaatcgcgc cgcgaacttc aagatttaaa ttcatagttt tttttagttga 1920
aatttgcact aaattaagtc caagaactaa ttttccatct ttatttaaca agttaataa    1980
tttttttcgg tccaaaactg ggtctaattg ataatctggg cctaaaaata cgggttctcc    2040
taaggaatta taaagtgaaa gactcgcttt tgatgcaaac aaagctcttt caagtcgtga   2100
aaatcaatta cttcctctttt cattttcaaa atttttggca agcaaatttt ggaattccat   2160
caaagttaga tttgctcttg aaagatcaac aaaagacttg cttgaatcaa tttgactaaa   2220
atcaaaatta gttctagctt gttctgtatt tccaaagcct ttaagtacaa tttgtttttga  2280
ataagttatt tgatccttat cagatttttgc ataataaca acatttttaa ttgaatttttg  2340
atcaactact gcattttcaa gatcaaaact tactaaataa tcattgttta ttagttcact   2400
taaatcaaaa gcagaaacaa gattataacg ataaagatca cttttggcag cagttaaaac   2460
tgttttttgcc gatcattttt taaaattatc tttaatttta agatttaaaa caattgaatc  2520
aaatttttcc tgactaattt tagcattttt tgctactttt agctgactcg ggatctgatt   2580
tagataagaa taatatgatt tattataaga attaattccg acaactgtac caacagcggc    2640
tgataaacta agactaattc cggcaattgt tgttattaat caaaaaggtt ttttaagtaa   2700
ttttgctaac ttcat                                                   2715

SEQ ID NO: 345        moltype = DNA   length = 21
FEATURE               Location/Qualifiers
source                1..21

-continued

```
                        mol_type = other DNA
                        organism = synthetic construct
SEQUENCE: 345
gacatggcta cgatccgact t                                                    21

SEQ ID NO: 346          moltype = DNA   length = 17
FEATURE                 Location/Qualifiers
source                  1..17
                        mol_type = other DNA
                        organism = synthetic construct
SEQUENCE: 346
cgcttggcct ccgactt                                                         17
```